United States Patent
Claremon et al.

(10) Patent No.: US 9,845,308 B2
(45) Date of Patent: Dec. 19, 2017

(54) ISOINDOLINE INHIBITORS OF ROR-GAMMA

(71) Applicant: Vitae Pharmaceuticals, Inc., Fort Washington, PA (US)

(72) Inventors: David A. Claremon, Maple Glen, PA (US); Lawrence Wayne Dillard, Yardley, PA (US); Chengguo Dong, Staten Island, NY (US); Yi Fan, Doylestown, PA (US); Lanqi Jia, Horsham, PA (US); Stephen D. Lotesta, Burlington, NJ (US); Andrew Marcus, Media, PA (US); Suresh B. Singh, Kendall Park, NJ (US); Colin M. Tice, Maple Glen, PA (US); Jing Yuan, Lansdale, PA (US); Wei Zhao, Germantown, MD (US); Yajun Zheng, Hockessin, DE (US); Linghang Zhuang, Chalfont, PA (US)

(73) Assignee: Vitae Pharmaceuticals, Inc., Parsippany, NJ (US)

( * ) Notice: Subject to any disclaimer, the term of this patent is extended or adjusted under 35 U.S.C. 154(b) by 0 days.

(21) Appl. No.: 14/933,468

(22) Filed: Nov. 5, 2015

(65) Prior Publication Data
US 2016/0122318 A1 May 5, 2016

Related U.S. Application Data

(60) Provisional application No. 62/075,612, filed on Nov. 5, 2014.

(51) Int. Cl.
| | | |
|---|---|---|
| *C07D 401/12* | (2006.01) |
| *C07D 209/44* | (2006.01) |
| *C07D 403/12* | (2006.01) |
| *C07D 413/14* | (2006.01) |
| *C07D 405/14* | (2006.01) |

(52) U.S. Cl.
CPC ......... *C07D 401/12* (2013.01); *C07D 209/44* (2013.01); *C07D 403/12* (2013.01); *C07D 405/14* (2013.01); *C07D 413/14* (2013.01)

(58) Field of Classification Search
None
See application file for complete search history.

(56) References Cited

U.S. PATENT DOCUMENTS

| | | |
|---|---|---|
| 5,238,950 A | 8/1993 | Clader et al. |
| 5,272,158 A | 12/1993 | Hartman et al. |
| 5,326,760 A | 7/1994 | McElroy et al. |
| 5,364,869 A | 11/1994 | De |
| 5,389,631 A | 2/1995 | Claremon et al. |
| 5,571,774 A | 11/1996 | Hamprecht et al. |
| 5,719,144 A | 2/1998 | Hartman et al. |
| 5,770,590 A | 6/1998 | Natsugari et al. |
| 5,786,352 A | 7/1998 | Natsugari et al. |
| 6,103,659 A | 8/2000 | Pasenok et al. |
| 6,177,443 B1 | 1/2001 | Madsen et al. |
| 6,417,207 B1 | 7/2002 | Garvey et al. |
| 6,444,617 B1 | 9/2002 | Takaishi et al. |
| 6,489,315 B1 | 12/2002 | Natsugari et al. |
| 6,512,117 B1 | 1/2003 | Harclerode et al. |
| 6,770,666 B2 | 8/2004 | Hashimoto et al. |
| 7,112,600 B1 | 9/2006 | Hashimoto et al. |
| 7,115,752 B2 | 10/2006 | Lesieur et al. |
| 7,183,318 B2 | 2/2007 | Lesieur et al. |
| 7,244,730 B2 | 7/2007 | Suzuki et al. |
| 7,732,616 B2 | 6/2010 | Marlow et al. |
| 7,750,021 B2 | 7/2010 | Mi et al. |
| 7,807,706 B2 * | 10/2010 | Van Wagenen ...... C07D 209/34 514/416 |
| 8,148,402 B2 * | 4/2012 | Cho ..................... A61K 31/454 514/323 |

(Continued)

FOREIGN PATENT DOCUMENTS

| | | |
|---|---|---|
| CA | 2031684 A1 | 6/1991 |
| CA | 2134192 A1 | 5/1995 |
| CA | 2352612 A1 | 6/2000 |
| CA | 2524027 A1 | 12/2004 |
| CN | 1424770 A | 6/2003 |
| CN | 1869036 A | 11/2006 |
| CN | 101225070 A | 7/2008 |
| CN | 101455661 A | 6/2009 |
| CN | 102180780 A | 9/2011 |
| DE | 4343922 A1 | 6/1995 |

(Continued)

OTHER PUBLICATIONS

Maddur et al., "Biology, Pathogenesis of Automimmune and Inflammatory Diseases, and Therapeutic Strategies", The American Journal of Pathology, 181(1):8-18 (2012).

(Continued)

*Primary Examiner* — Heidi Reese
(74) *Attorney, Agent, or Firm* — McCarter & English, LLP; Steven G. Davis; Michael J. DeGrazia

(57) ABSTRACT

Provided are novel compounds of Formula (I):

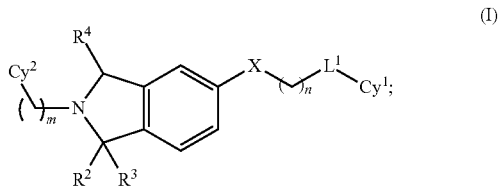

pharmaceutically acceptable salts thereof, and pharmaceutical compositions thereof, which are useful in the treatment of diseases and disorders mediated by RORγ. Also provided are pharmaceutical compositions comprising the novel compounds of Formula (I) and methods for their use in treating one or more inflammatory, metabolic, autoimmune and other diseases or disorders.

12 Claims, No Drawings

(56) References Cited

U.S. PATENT DOCUMENTS

| | | |
|---|---|---|
| 8,389,739 B1 | 3/2013 | Thacher et al. |
| 8,415,351 B2 | 4/2013 | Wagner et al. |
| 9,266,886 B2 | 2/2016 | Lotesta et al. |
| 2002/0132817 A1 | 9/2002 | Natsugari et al. |
| 2003/0050320 A1 | 3/2003 | Hashimoto et al. |
| 2004/0002424 A1 | 1/2004 | Minn et al. |
| 2004/0038973 A1 | 2/2004 | Nahra et al. |
| 2005/0004204 A1 | 1/2005 | Suzuki et al. |
| 2005/0020593 A1 | 1/2005 | Mailliet et al. |
| 2005/0234065 A1 | 10/2005 | Hulin et al. |
| 2006/0135557 A1 | 6/2006 | Nan et al. |
| 2007/0032497 A1 | 2/2007 | Hashimoto et al. |
| 2007/0112038 A1 | 5/2007 | Marlow et al. |
| 2007/0258887 A1 | 11/2007 | Tamagnan et al. |
| 2008/0277622 A1 | 11/2008 | Deshpande et al. |
| 2008/0287462 A1 | 11/2008 | Chessari et al. |
| 2009/0036423 A1 | 2/2009 | Pan et al. |
| 2009/0076275 A1 | 3/2009 | Bolin et al. |
| 2009/0233945 A9 | 9/2009 | Chessari et al. |
| 2009/0258871 A1 | 10/2009 | Jitsuoka et al. |
| 2009/0270405 A1 | 10/2009 | Cook, II et al. |
| 2010/0099684 A1 | 4/2010 | Cook, II et al. |
| 2011/0070193 A1 | 3/2011 | Wagner et al. |
| 2011/0189167 A1 | 8/2011 | Flynn et al. |
| 2011/0313003 A1 | 12/2011 | Shi et al. |
| 2012/0077840 A1 | 3/2012 | Turner et al. |
| 2012/0115903 A1 | 5/2012 | Frank et al. |
| 2012/0245163 A1 | 9/2012 | Gomtsyan et al. |
| 2012/0322837 A1 | 12/2012 | Maeba et al. |
| 2013/0143870 A1 | 6/2013 | Grauert et al. |
| 2013/0150347 A1 | 6/2013 | Rudolf et al. |
| 2014/0163001 A1 | 6/2014 | Yamamoto et al. |
| 2014/0228409 A1 | 8/2014 | Yamamoto et al. |

FOREIGN PATENT DOCUMENTS

| | | |
|---|---|---|
| DE | 4446396 A1 | 7/1995 |
| EP | 254951 A2 | 2/1988 |
| EP | 321368 A1 | 6/1989 |
| EP | 468187 A2 | 1/1992 |
| EP | 520277 A2 | 12/1992 |
| EP | 520573 A1 | 12/1992 |
| EP | 540334 A1 | 5/1993 |
| EP | 655439 A2 | 5/1995 |
| EP | 733632 A1 | 9/1996 |
| EP | 1178048 A1 | 2/2002 |
| FR | 2725946 A1 | 4/1996 |
| FR | 2926554 A1 | 7/2009 |
| GB | 2276384 A | 9/1994 |
| JP | H06236056 A | 8/1994 |
| JP | H1143489 A | 2/1999 |
| JP | 2000007661 A | 1/2000 |
| JP | 2003171380 A | 6/2003 |
| JP | 2003531894 A | 10/2003 |
| JP | 2004203791 A | 7/2004 |
| WO | 90/09787 A1 | 9/1990 |
| WO | 94/00119 A1 | 1/1994 |
| WO | 94/24712 A1 | 10/1994 |
| WO | 95/11680 A1 | 5/1995 |
| WO | 95/17397 A1 | 6/1995 |
| WO | 96/26187 A1 | 8/1996 |
| WO | 97/32832 A1 | 9/1997 |
| WO | 98/40385 A1 | 9/1998 |
| WO | 98/42666 A1 | 10/1998 |
| WO | 99/47132 A2 | 9/1999 |
| WO | 99/58495 A1 | 11/1999 |
| WO | 99/58496 A1 | 11/1999 |
| WO | 00/32192 A1 | 6/2000 |
| WO | 00/67754 A1 | 11/2000 |
| WO | 01/05790 A1 | 1/2001 |
| WO | 01/47883 A1 | 7/2001 |
| WO | 01/51128 A1 | 7/2001 |
| WO | 01/83445 A1 | 11/2001 |
| WO | 01/85722 A1 | 11/2001 |
| WO | 02/24650 A2 | 3/2002 |
| WO | 02/38107 A2 | 5/2002 |
| WO | 02/081443 A1 | 10/2002 |
| WO | 02/081447 A1 | 10/2002 |
| WO | 02/081463 A1 | 10/2002 |
| WO | 02/085855 A1 | 10/2002 |
| WO | 03/008421 A1 | 1/2003 |
| WO | 03/029252 A1 | 4/2003 |
| WO | 03/029254 A1 | 4/2003 |
| WO | 03/070710 A1 | 8/2003 |
| WO | 03/076440 A1 | 9/2003 |
| WO | 03/104216 A1 | 12/2003 |
| WO | 2004/014365 A1 | 2/2004 |
| WO | 2004/042029 A2 | 5/2004 |
| WO | 2004/065351 A1 | 8/2004 |
| WO | 2004/089897 A1 | 10/2004 |
| WO | 2004/103309 A2 | 12/2004 |
| WO | 2004/108133 A2 | 12/2004 |
| WO | 2004/111010 A1 | 12/2004 |
| WO | 2004/113330 A1 | 12/2004 |
| WO | 2005/005392 A1 | 1/2005 |
| WO | 2005/011601 A2 | 2/2005 |
| WO | 2005/023806 A2 | 3/2005 |
| WO | 2005/025504 A2 | 3/2005 |
| WO | 2005/028480 A2 | 3/2005 |
| WO | 2005/039564 A1 | 5/2005 |
| WO | 2005/051301 A2 | 6/2005 |
| WO | 2005/060958 A1 | 7/2005 |
| WO | 2005/063296 A2 | 7/2005 |
| WO | 2005/100334 A1 | 10/2005 |
| WO | 2006/032631 A1 | 3/2006 |
| WO | 2006/062981 A2 | 6/2006 |
| WO | 2006/065842 A2 | 6/2006 |
| WO | 2006/074428 A2 | 7/2006 |
| WO | 2006/082001 A1 | 8/2006 |
| WO | 2006/092731 A1 | 9/2006 |
| WO | 2006/109085 A1 | 10/2006 |
| WO | 2007/007054 A1 | 1/2007 |
| WO | 2007/036733 A1 | 4/2007 |
| WO | 2007/036734 A1 | 4/2007 |
| WO | 2007/050124 A1 | 5/2007 |
| WO | 2007/084451 A1 | 7/2007 |
| WO | 2007/084455 A1 | 7/2007 |
| WO | 2007/097931 A2 | 8/2007 |
| WO | 2007/101224 A1 | 9/2007 |
| WO | 2007/107545 A1 | 9/2007 |
| WO | 2007/109596 A2 | 9/2007 |
| WO | 2007/131982 A2 | 11/2007 |
| WO | 2008/013963 A1 | 1/2008 |
| WO | 2008/044027 A2 | 4/2008 |
| WO | 2008/044029 A1 | 4/2008 |
| WO | 2008/044041 A1 | 4/2008 |
| WO | 2008/044045 A1 | 4/2008 |
| WO | 2008/044054 A1 | 4/2008 |
| WO | 2008/048991 A2 | 4/2008 |
| WO | 2008/073865 A2 | 6/2008 |
| WO | 2008/083070 A1 | 7/2008 |
| WO | 2008/086161 A1 | 7/2008 |
| WO | 2008/132155 A2 | 11/2008 |
| WO | 2008/135524 A2 | 11/2008 |
| WO | 2008/135526 A1 | 11/2008 |
| WO | 2008/149163 A2 | 12/2008 |
| WO | 2009/004496 A1 | 1/2009 |
| WO | 2009/013299 A2 | 1/2009 |
| WO | 2009/026248 A2 | 2/2009 |
| WO | 2009/050228 A2 | 4/2009 |
| WO | 2009/052319 A1 | 4/2009 |
| WO | 2009/052320 A1 | 4/2009 |
| WO | 2009/068463 A2 | 6/2009 |
| WO | 2009/073788 A1 | 6/2009 |
| WO | 2009/097972 A1 | 8/2009 |
| WO | 2009/112445 A1 | 9/2009 |
| WO | 2009/112678 A2 | 9/2009 |
| WO | 2009/112826 A1 | 9/2009 |
| WO | 2009/112839 A1 | 9/2009 |
| WO | 2009/124755 A1 | 10/2009 |
| WO | 2009/131926 A1 | 10/2009 |
| WO | 2009/144450 A1 | 12/2009 |
| WO | 2010/003022 A1 | 1/2010 |
| WO | 2010/021878 A1 | 2/2010 |

(56) References Cited

FOREIGN PATENT DOCUMENTS

| | | |
|---|---|---|
| WO | 2010/033350 A1 | 3/2010 |
| WO | 2010/056194 A1 | 5/2010 |
| WO | 2010/056195 A1 | 5/2010 |
| WO | 2010/077680 A2 | 7/2010 |
| WO | 2010/086311 A1 | 8/2010 |
| WO | 2011/078143 A1 | 6/2011 |
| WO | 2011/090473 A1 | 7/2011 |
| WO | 2011/094545 A2 | 8/2011 |
| WO | 2011/107248 A1 | 9/2011 |
| WO | 2011/140936 A1 | 11/2011 |
| WO | 2011/146358 A1 | 11/2011 |
| WO | 2011/159297 A1 | 12/2011 |
| WO | 2012/019015 A2 | 2/2012 |
| WO | 2012/027965 A1 | 3/2012 |
| WO | 2012/028100 A1 | 3/2012 |
| WO | 2012/031197 A1 | 3/2012 |
| WO | 2012/043505 A1 | 4/2012 |
| WO | 2012/062462 A1 | 5/2012 |
| WO | 2012/064744 A2 | 5/2012 |
| WO | 2012/100732 A1 | 8/2012 |
| WO | 2012/100734 A1 | 8/2012 |
| WO | 2012/106995 A1 | 8/2012 |
| WO | 2012/125521 A1 | 9/2012 |
| WO | 2012/136296 A1 | 10/2012 |
| WO | 2012/139775 A1 | 10/2012 |
| WO | 2013/000994 A1 | 1/2013 |
| WO | 2013/019621 A1 | 2/2013 |
| WO | 2013/019626 A1 | 2/2013 |
| WO | 2013/019635 A1 | 2/2013 |
| WO | 2013/019653 A1 | 2/2013 |
| WO | 2013/019682 A1 | 2/2013 |
| WO | 2013/029338 A1 | 3/2013 |
| WO | 2013/045431 A1 | 4/2013 |
| WO | 2013/064231 A1 | 5/2013 |
| WO | 2013/067036 A1 | 5/2013 |
| WO | 2013/079223 A1 | 6/2013 |
| WO | 2013/083741 A1 | 6/2013 |
| WO | 2013/087739 A1 | 6/2013 |
| WO | 2013/092460 A1 | 6/2013 |
| WO | 2013/092939 A1 | 6/2013 |
| WO | 2013/092941 A1 | 6/2013 |
| WO | 2013/096496 A2 | 6/2013 |
| WO | 2013/100027 A1 | 7/2013 |
| WO | 2013/159095 A1 | 10/2013 |
| WO | 2013/160418 A1 | 10/2013 |
| WO | 2013/160419 A1 | 10/2013 |
| WO | 2013/166013 A1 | 11/2013 |
| WO | 2013/169588 A1 | 11/2013 |
| WO | 2013/169704 A2 | 11/2013 |
| WO | 2013/169864 A2 | 11/2013 |
| WO | 2013/171729 A2 | 11/2013 |
| WO | 2013/178362 A1 | 12/2013 |
| WO | 2014/008214 A1 | 1/2014 |
| WO | 2014/009447 A1 | 1/2014 |
| WO | 2014/026327 A1 | 2/2014 |
| WO | 2014/026328 A1 | 2/2014 |
| WO | 2014/026329 A1 | 2/2014 |
| WO | 2014/026330 A1 | 2/2014 |
| WO | 2014/028589 A2 | 2/2014 |
| WO | 2014/028591 A2 | 2/2014 |
| WO | 2014/028597 A2 | 2/2014 |
| WO | 2014/028600 A2 | 2/2014 |
| WO | 2014/028669 A1 | 2/2014 |
| WO | 2014/062938 A1 | 4/2014 |
| WO | 2014/086894 A1 | 6/2014 |
| WO | 2015/116904 A1 | 8/2015 |

OTHER PUBLICATIONS

Marcoux, et al., "Annulation of Ketones with Vinamidinium Hexafluorophosphate Salts: An Efficient Preparation of Trisubstituted Pyridines," Organic Letters, 2000, vol. 2, No. 15, 2339-2341.

Schlecker, et al., "Regioselective Metalation of Pyridinylcarbamates and Pyridinecarboxamides with (2,2,6,6-Tetramethylpiperidino)magnesium Chloride," J. Org. Chem., 1995, 60, 8414-8416.

Schlecker, et al., "Regioselective Monometalation of 2,5-Pyridinedicarboxamides with (2,2,6,6-Tetramethylpiperidino) magnesium Chloride (TMPMgCl)," Liebigs Annalen, 1995, vol. 8, pp. 1441-1446.

* cited by examiner

ISOINDOLINE INHIBITORS OF ROR-GAMMA

RELATED APPLICATIONS

This application claims the benefit of U.S. Provisional Application No. 62/075,612, filed Nov. 5, 2014, the entire contents of which is incorporated herein by reference.

TECHNICAL FIELD OF THE INVENTION

The present invention is directed to novel retinoic acid receptor-related orphan receptor gamma ("RORγ" or "ROR-gamma") inhibitors, processes for their preparation, pharmaceutical compositions containing these inhibitors, and their use in the treatment of inflammatory, metabolic, autoimmune and other diseases mediated by RORγ.

BACKGROUND OF THE INVENTION

Retinoic acid receptor-related orphan receptors (RORs) are a subfamily of transcription factors in the steroid hormone nuclear receptor superfamily (Jetten & Joo (2006) Adv. Dev. Biol. 2006, 16, 313-355). The ROR family consists of ROR alpha (RORα), ROR beta (RORβ) and ROR gamma (RORγ), each encoded by a separate gene (in human: RORA, RORB and RORC, respectively; in mouse: rora, rorb and rorc, respectively). RORs contain four principal domains shared by the majority of nuclear receptors: an N-terminal domain, a highly conserved DNA-binding domain (DBD) consisting of two zinc finger motifs, a hinge domain, and a ligand binding domain (LBD). Each ROR gene generates several isoforms, differing only in their N-terminal domains. RORγ has two isoforms: RORγ1 and RORγ2 (also known as RORγt). RORγ refers to RORγ1 and/or RORγt. RORγ1 is expressed in a variety of tissues including thymus, muscle, kidney and liver, but RORγt is exclusively expressed in the cells of the immune system, has a critical role in thymopoiesis and the development of several secondary lymphoid tissues, and is a key regulator of Th17 cell differentiation (Jetten, 2009, Nucl. Recept. Signal., 7:e003, doi:10.1621/nrs.07003, Epub 2009 Apr. 3).

Th17 cells are a subset of T helper cells which preferentially produce the pro-inflammatory cytokines IL-17A, IL-17F, IL-21 and IL-22. Th17 cells and their effector molecules, such as IL-17, IL-21, IL-22, GM-CSF and CCL20, are associated with the pathogenesis of several autoimmune and inflammatory diseases, such as rheumatoid arthritis, systemic lupus erythematosus, multiple sclerosis, psoriasis, inflammatory bowel disease, allergy and asthma (Maddur et al., 2012, Am. J. Pathol., 181:8-18). Recent findings support a role for IL17 and Th17 cells in the pathogenesis of acne (Thiboutot et al., 2014, J. Invest. Dermatol., 134(2):307-10, doi: 10.1038/jid.2013.400; Agak et al., 2014, J. Invest. Dermatol., 134(2):366-73, doi: 10.1038/jid.2013.334, Epub 2013 Aug. 7). Th17 cells are also potent inducers of inflammation associated with endometriosis, a chronic inflammatory disease (Hirata et al., 2010, Endocrinol., 151:5468-5476; Hirata et al., 2011, Fertil Steril., July; 96(1):113-7, doi: 10.1016/j.fertns-tert.2011.04.060, Epub 2011 May 20). Additionally, Th17 cells have a key role in the mouse autoimmune models of experimental autoimmune encephalomyelitis (EAE), collagen-induced arthritis (CIA) and adjuvant-induced arthritis (AIA) (Bedoya et al., 2013, Clin. Dev. Immunol., 2013: 986789. Epub 2013 Dec. 26. Th17 cells are activated during inflammatory and autoimmune disease processes and are responsible for recruiting other inflammatory cell types, particularly neutrophils, to mediate pathology in target tissues (Miossec & Kolls, 2012, Nature Rev., 11:763-776; Korn et al., 2009, Annu. Rev. Immunol., 27:485-517). Aberrant Th17 cell function has been implicated in a variety of autoimmune diseases, including multiple sclerosis and rheumatoid arthritis. Autoimmune disease is believed to arise from the disruption of the equilibrium between effector and regulatory T cells (Solt et al., 2012, ACS Chem. Biol., 7:1515-1519, Epub 2012 Jul. 9). The importance of RORγt to Th17 cell differentiation and the pathogenic role of Th17 cells is evidenced by the fact that RORγt-deficient mice have very few Th17 cells and have a reduction in severity of EAE (Ivanov et al., 2006, Cell, 126:1121-1133).

Circadian rhythms are daily cycles of behavioral and physiological changes that are regulated by endogenous circadian clocks. A number of studies have established links between nuclear receptor (including RORγ) function and expression, the circadian regulatory circuitry, and the regulation of various physiological processes (Jetten (2009) op. cit.).

Obstructive sleep apnea syndrome (OSAS) is a chronic inflammatory disease regulated by T lymphocytes. OSAS patients have a significant increase in peripheral Th17 cell frequency, IL-17 and RORγt levels (Ye et al., 2012, Mediators Inflamm., 815308, doi: 10.1155/2012/815308, Epub 2012 Dec. 31).

A number of studies have provided evidence of a role of RORs in cancer. Mice deficient in the expression of RORγ exhibit a high incidence of thymic lymphomas that metastasize frequently to liver and spleen. High expression of Th17-associated genes (including RORγ) and high levels of Th17 cells in the tumor microenvironment has been shown to correlate with a poor prognosis in various cancers, including lung, gastric, breast and colon cancer (Tosolini et al., 2011, Cancer Res., 71:1263-1271, doi: 10.1158/0008-5472.CAN-10-2907, Epub 2011 Feb. 8; Su et al., 2014, Immunol. Res., 58:118-124, doi: 10.1007/s12026-013-8483-y, Epub 2014 Jan. 9; Carmi et al., 2011, J. Immunol., 186:3462-3471, doi: 10.4049/jimmunol.1002901, Epub 2011 Feb. 7; Chen et al., 2013, Histopathology, 63:225-233, doi: 10.1111/his.12156, Epub 2013 Jun. 6).

RORγ has also been identified to have a regulatory role in lipid/glucose homeostasis, and has been implicated in metabolic syndrome, obesity (Meissburger et al., 2011, EMBO Mol. Med., 3:637-651), hepatosteatosis, insulin resistance and diabetes.

Further support for the role of RORγ in the pathogenesis of inflammatory, metabolic, circadian effect, cancer, and autoimmune diseases and disorders can be found in the following references: Chang et al., 2012, J. Exp. Pharmacol., 4:141-148; Jetten et al., 2013, Frontiers Endocrinol., 4:1-8; Huh & Littman, 2012, Eur. J. Immunol., 42:2232-2237; Martinez et al., 2008, Ann. N.Y. Acad. Sci., 1143:188-211; Pantelyushin et al., 2012, J. Clin. Invest., 122:2252-2256; Jetten & Ueda, 2002, Cell Death Differen., 9:1167-1171; Solt et al., 2010, Curr. Opin. Lipidol., 21:204-211.

In light of the role that RORγ plays in disease pathogenesis, inhibition of RORγ activity and Th17 cell differentiation and activity, including IL17 production, will be of significant therapeutic benefit. It is therefore desirable to prepare compounds that inhibit RORγ activity and hence have utility in the treatment of inflammatory, autoimmune, metabolic, circadian effect, cancer, and other diseases mediated by RORγ, such as e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus, scleroderma, psoriasis, psoriatic arthritis, steroid resistant asthma and rheumatoid arthritis.

SUMMARY OF THE INVENTION

It has now been found that compounds described herein, and pharmaceutically acceptable compositions thereof, are effective inhibitors of RORγ (see e.g., Table 4). Such compounds include those of Formula (I):

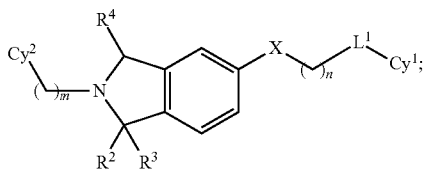

(I)

or a pharmaceutically acceptable salt thereof, wherein each of $R^2$, $R^3$, $R^4$, X, $L^1$, n, m, $Cy^1$, and $Cy^2$ are as defined and described herein.

The provided compounds, and pharmaceutically acceptable compositions thereof, are inverse agonists or antagonists of RORγ and are useful for treating a variety of diseases, disorders or conditions. Such diseases, disorders, or conditions include those described herein.

The provided compounds can be used alone (i.e., as a monotherapy) or in combination with one or more other therapeutic agent effective for treating any of the indications described herein.

DETAILED DESCRIPTION OF CERTAIN EMBODIMENTS

1. General Description of Compounds of the Invention

In certain embodiments, the present invention provides a compound of Formula (I):

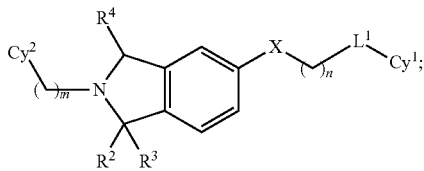

(I)

or a pharmaceutically acceptable salt thereof, wherein:

$R^2$ is hydroxy, monocyclic cycloalkyl, monocyclic heterocyclyl, or $(C_1-C_6)$alkyl, wherein the $(C_1-C_6)$alkyl is optionally substituted with 1 to 2 groups independently selected from hydroxy, halo, $(C_1-C_3)$alkoxy, and cyano;

$R^3$ is hydrogen, monocyclic cycloalkyl, monocyclic heterocyclyl, or $(C_1-C_6)$alkyl, wherein the $(C_1-C_6)$alkyl is optionally substituted with 1 to 2 groups independently selected from hydroxy, halo, and cyano;

$R^4$ is hydrogen, $(C_1-C_3)$alkyl, or =O;

X is —C(O)NH— or —NHC(O)—;

m is 0, 1, or 2;

n is 0, 1, 2, or 3;

$L^1$ is absent or is $SO_2$ or $CR^7R^8$;

$Cy^1$ is aryl, heteroaryl, heterocyclyl, or cycloalkyl, each of which is optionally substituted with 1 to 3 groups independently selected from $R^5$;

$Cy^2$ is aryl, heteroaryl, monocyclic cycloalkyl, monocyclic heterocyclyl, or bicyclic heterocyclyl, each of which is optionally substituted with 1 to 3 groups independently selected from $R^6$;

$R^5$ and $R^6$ are each independently selected from halo, cyano, nitro, amino, hydroxy, carboxy, $(C_1-C_6)$alkyl, heterocyclyl, hydroxy$(C_1-C_6)$alkyl, $CO_2H$, $(CH_2)_{1-3}COOH$, $(C_1-C_3)$alkylcarbonyloxy, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkylsulfinyl, $(C_3-C_6)$cycloalkylsulfinyl, $(C_4-C_7)$cycloalkylalkylsulfinyl, halo$(C_1-C_6)$alkylsulfinyl, halo$(C_3-C_6)$cycloalkylsulfinyl, halo$(C_4-C_7)$cycloalkylalkylsulfinyl, $(C_1-C_6)$alkylsulfonyl, $(C_3-C_6)$cycloalkylsulfonyl, $(C_4-C_7)$cycloalkylalkylsulfonyl, halo$(C_1-C_6)$alkylsulfonyl, hydroxy$(C_2-C_6)$alkylsulfonyl, halo$(C_3-C_6)$cycloalkylsulfonyl, halo$(C_4-C_7)$cycloalkylalkylsulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylamino sulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, aryl, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, hydroxy$(C_1-C_6)$alkylcarbonyl, $(C_1-C_6)$alkylhydroxycarbonyl, $(C_1-C_6)$alkylhydroxy$(C_1-C_6)$alkyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$amino sulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl, $[(C_1-C_6)$alkyl$(C_4-C_6)$heterocyclyl$](C_1-C_6)$alkyl, and di$(C_3-C_6)$cycloalkylaminocarbonyl$(C_1-C_6)$alkyl; and $R^7$ and $R^8$ are each independently hydrogen, hydroxy, $(C_1-C_3)$alkyl, hydroxy$(C_1-C_3)$alkyl, $(C_1-C_3)$alkoxy$(C_1-C_3)$alkyl, aminocarbonyl-O$(C_1-C_3)$alkyl, hydroxycarbonyl$(C_1-C_3)$alkoxy$(C_1-C_3)$alkyl, $(C_1-C_3)$alkylcarbonylamino$(C_1-C_3)$alkyl, $(C_1-C_3)$alkoxycarbonylamino$(C_1-C_3)$alkyl, di$(C_1-C_3)$alkylamino$(C_1-C_3)$alkyl, di$(C_1-C_3)$alkylaminocarbonyl$(C_1-C_3)$alkyl, $(C_1-C_3)$alkylaminocarbonyl$(C_1-C_3)$alkyl, aminocarbonyl$(C_1-C_3)$alkyl, aminocarbonyl, mono$(C_1-C_3)$alkylamino, di$(C_1-C_3)$alkylamino, $CO_2H$, $(CH_2)_{1-3}COOH$, moncyclic heterocyclyl, $(C_1-C_3)$alkoxycarbonyl, halophenyl, halophenyl$(C_1-C_3)$alkyl, or quinolin-2(1H)one-4ylmethyl; or $R^7$ and $R^8$, together with the carbon atom to which they are attached, form a 3- to 6-membered cycloalkyl or heterocyclyl.

2. Compounds and Definitions

The terms "halo" and "halogen" as used herein refer to an atom selected from fluorine (fluoro, F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The term "haloalkyl" or "halocycloalkyl" include mono, poly, and perhaloalkyl groups where the halogens are independently selected from fluorine, chlorine, iodine, and bromine.

The term "cycloalkyl" used alone or as part of a larger moiety, refer to a saturated aliphatic monocyclic or bicyclic ring system, as described herein, having from, unless otherwise specified, 3 to 10 carbon ring atoms. Monocyclic cycloalkyl groups include, without limitation, cyclopropyl, cyclobutyl, cyclopentyl, cyclohexyl, cycloheptyl, and cyclooctyl. It will be understood that when specified, optional substituents on a cycloalkyl group may be present on any substitutable position and, include, e.g., the position at which the cycloalkyl group is attached.

The term "cycloaliphatic" used alone or as part of a larger moiety refer to unsaturated non-aromatic monocyclic or bicyclic ring system, as described herein, having from, unless otherwise specified, 3 to 10 carbon ring atoms. Monocyclic cycloaliphatic groups include, without limitation, cyclopentenyl, cyclohexenyl, and cycloheptenyl. It will be understood that when specified, optional substituents on a cycloaliphatic group may be present on any substitutable position and, include, e.g., the position at which the cycloaliphatic group is attached.

The term "carbocycle", "carbocyclyl", "carbocyclo", or "carbocyclic" used alone or as part of a larger moiety refer to saturated, partially saturated, or aromatic ring systems comprising all carbon atoms having, unless otherwise specified, a total of 3 to 10 ring members. It will be understood that when specified, optional substituents on a carbocycle, carbocyclyl, carbocyclo, or carbocyclic may be present on any substitutable position and, include, e.g., the position at which the carbocycle is attached.

The term "aryl" used alone or as part of a larger moiety as in "aralkyl", "aralkoxy", or "aryloxyalkyl", refers to an aromatic carbocyclic ring system having, unless otherwise specified, a total of 6 to 10 ring members. The term "aryl" may be used interchangeably with the term "aryl ring", "aryl group", "aryl moiety," or "aryl radical". In certain embodiments of the present disclosure, "aryl" refers to an aromatic ring system which includes, but is not limited to, phenyl (abbreviated as "Ph"), naphthyl and the like. It will be understood that when specified, optional substituents on an aryl group may be present on any substitutable position and, include, e.g., the position at which the aryl is attached.

The term "heteroaryl" used alone or as part of a larger moiety as in "heteroarylalkyl", "heteroarylalkoxy", or "heteroarylaminoalkyl", refers to a 5-10-membered aromatic radical containing 1-4 heteroatoms selected from N, O, and S and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". The terms "heteroaryl" and "heteroar-", as used herein, also include groups in which a heteroaromatic ring is fused to one or more aryl rings, where the radical or point of attachment is on the heteroaromatic ring. Nonlimiting examples include indolyl, indazolyl, benzimidazolyl, benzthiazolyl, quinolyl, quinazolinyl, imidazopyrimidinyl and quinoxalinyl. A heteroaryl group may be mono- or bicyclic. It will be understood that when specified, optional substituents on a heteroaryl group may be present on any substitutable position and, include, e.g., the position at which the heteroaryl is attached.

The term "heterocyclyl" means a 4-, 5-, 6- and 7-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, tetrahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. A heterocyclyl group may be mono- or bicyclic. Unless otherwise specified, bicyclic heterocyclyl groups include, e.g., unsaturated heterocyclic radicals fused to another unsaturated heterocyclic radical or aromatic, cycloalkyl, or heteroaryl ring, such as for example, tetrahydronaphthyridine, 4,5,6,7-tetrahydrobenzo[d]oxazolyl, indolinone, dihydropyrrolotriazole, quinolinone, dioxaspirodecane. It will also be understood that when specified, optional substituents on a heterocyclyl group may be present on any substitutable position and, include, e.g., the position at which the heterocyclyl is attached.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity, i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "St," "R*," "E," "Z," "cis," and "trans," indicate configurations relative to the core molecule.

The compounds of the invention may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and e.g., the compound has at least two chiral centers, it is to be understood that the name or structure encompasses one stereoisomer free of other stereoisomers, mixtures of stereoisomers, and mixtures of stereoisomers in which one or more stereoisomers is enriched relative to the other stereoisomer(s). For example, the name or structure may encompass one stereoisomer free of other diastereomers, mixtures of stereoisomers, and mixtures of stereoisomers in which one or more diastereomers is enriched relative to the other diastereomer(s).

The compounds of the invention may be present in the form of pharmaceutically acceptable salts. For use in medicines, the salts of the compounds of the invention refer to nontoxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

3. Description of Exemplary Compounds

In a first embodiment, the present invention provides a compound of Formula (I),

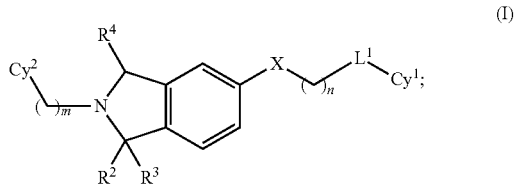

or a pharmaceutically acceptable salt thereof, wherein the variables are as described above.

In a second embodiment, the compound of Formula (I) is of Formula (II):

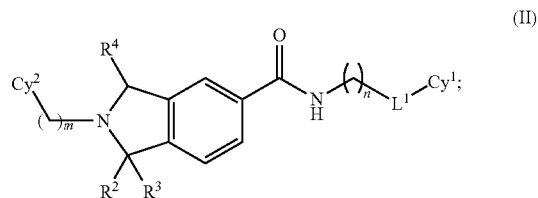

or a pharmaceutically acceptable salt thereof, wherein the variables in structural Formula (II) are as described for Formula (I).

In a third embodiment, the compound of Formula (I) is of Formula (III):

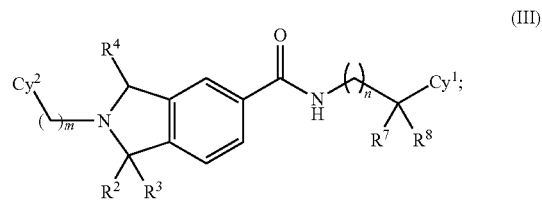

or a pharmaceutically acceptable salt thereof, wherein the variables in structural Formula (III) are as described for Formula (I).

In a fourth embodiment, the compound of Formula (I) is of Formula (IV):

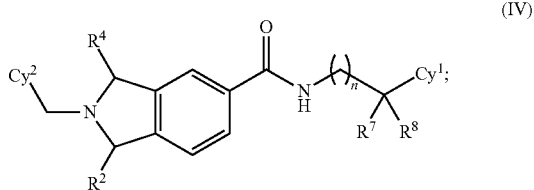

or a pharmaceutically acceptable salt thereof, wherein the variables in structural Formula (IV) are as described for Formula (I).

In a fifth embodiment, the compound of Formula (I) is of Formula (V):

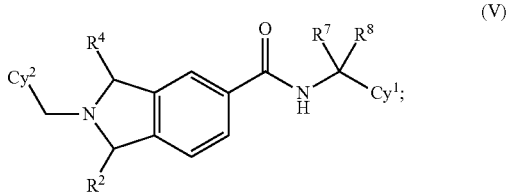

or a pharmaceutically acceptable salt thereof, wherein the variables in structural Formula (V) are as described for Formula (I).

In a sixth embodiment, the compound of Formula (I) is of Formula (VI):

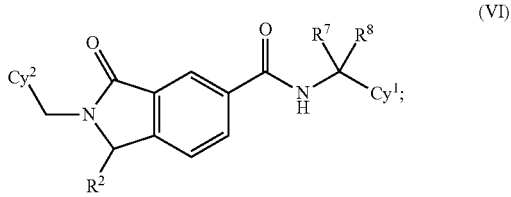

or a pharmaceutically acceptable salt thereof, wherein the variables in structural Formula (VI) are as described for Formula (I).

In a seventh embodiment, the compound of Formula (I) is of Formula (VII) or (VIIa):

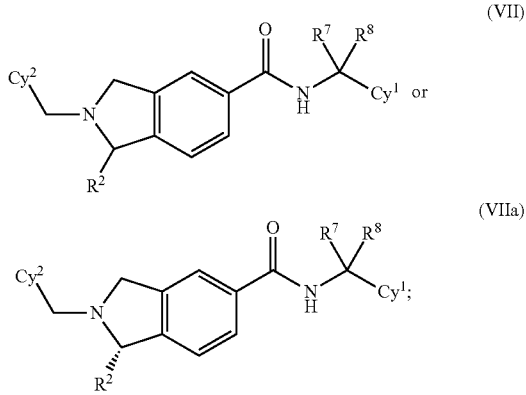

or a pharmaceutically acceptable salt thereof, wherein the variables in structural Formula (VII) and structural Formula (VIIa) are as described for Formula (I).

In an eighth embodiment, $R^2$ in Formulas (I) to (VIIa) is $(C_1-C_3)$alkyl, wherein the remainder of the variables are as described in Formula (I).

In a ninth embodiment, $Cy^2$ in Formulas (I) to (VIIa) is selected from aryl, monocyclic cycloalkyl, monocyclic heterocyclyl, and bicyclic heterocyclyl, each of which is optionally substituted with 1 to 2 groups independently selected from $R^6$, wherein the remainder of the variables are as described in Formula (I) or the eighth embodiment.

In a tenth embodiment, $Cy^2$ in Formulas (I) to (VIIa) is phenyl, cyclohexyl, dioxanyl, tetrahydropyranyl or 4,5,6,7-tetrahydrobenzo[d]oxazolyl, each of which is optionally substituted with 1 to 2 groups independently selected from $R^6$, wherein the remainder of the varables are as described in Formula (I) or the eighth or ninth embodiment.

In an eleventh embodiment, $Cy^1$ in Formulas (I) to (VIIa) is phenyl, piperidinyl, or pyridinyl, each of which is optionally substituted with 1 to 2 groups independently selected from $R^5$, wherein the remainder of the varables are as described in Formula (I) or the eighth, ninth, or tenth embodiment.

In a twelfth embodiment, $Cy^1$ in Formulas (I) to (VIIa) is phenyl or pyridinyl, each of which is optionally substituted with 1 to 2 groups independently selected from $R^5$; and $Cy^2$ is cyclohexyl or phenyl, each of which is optionally substituted with 1 to 2 groups independently selected from $R^6$, wherein the remainder of the varables are as described in Formula (I) or the eighth, ninth, tenth, or eleventh embodiment.

In a thirteenth embodiment, $R^7$ in Formulas (I) to (VIIa) is hydrogen; and $R^8$ is hydrogen, hydroxy$(C_1-C_3)$alkyl, $(C_1-C_3)$alkoxy$(C_1-C_3)$alkyl, aminocarbonyl-O$(C_1-C_3)$alkyl, hydroxycarbonyl$(C_1-C_3)$alkoxy$(C_1-C_3)$alkyl, $(C_1-C_3)$alkylcarbonylamino$(C_1-C_3)$alkyl, $(C_1-C_3)$alkoxycarbonylamino$(C_1-C_3)$alkyl, di$(C_1-C_3)$alkylamino$(C_1-C_3)$alkyl, di$(C_1-C_3)$alkylaminocarbonyl$(C_1-C_3)$alkyl, $(C_1-C_3)$alkylaminocarbonyl$(C_1-C_3)$alkyl, aminocarbonyl$(C_1-C_3)$alkyl, or aminocarbonyl, wherein the remainder of the varables are as described in Formula (I) or the eighth, ninth, tenth, eleventh, or twelfth embodiment. Alternatively, $R^7$ is hydrogen; and $R^8$ is hydrogen, —$CH_2OH$, —$(CH_2)_2OH$, —$CH_2OCH_3$, —$CH_2OC(O)NH_2$, —$CH_2OCH_2COOH$, —$CH_2NHC(O)CH_3$, —$CH_2NHC(O)OCH_3$, —$(CH_2)_2N(CH_3)_2$, —$CH_2C(O)N(CH_3)_2$, —$CH_2C(O)NHCH_3$, —$CH_2C(O)NH_2$, or $CONH_2$, wherein the remainder of the varables are as described in Formula (I) or the eighth, ninth, tenth, eleventh, or twelfth embodiment. In another alternative, $R^7$ is hydrogen; and $R^8$ is hydrogen, —$CH_2OH$, —$(CH_2)_2OH$, or —$CH_2OCH_3$, wherein the remainder of the varables are as described in Formula (I) or the eighth, ninth, tenth, eleventh, or twelfth embodiment.

In a fourteenth embodiment, $R^5$ in Formulas (I) to (VIIa) is selected from halo, $(C_1-C_3)$alkyl, halo$(C_1-C_3)$alkyl, cyano, hydroxy$(C_1-C_3)$alkyl, $(C_1-C_3)$alkoxycarbonyl, $(C_1-C_3)$alkylsulfonyl, $(C_1-C_3)$alkoxy, halo$(C_1-C_3)$alkoxy, oxo, hydroxy, $(C_1-C_3)$alkylcarbonyl, hydroxy$(C_1-C_3)$alkylcarbonyl, $(C_1-C_3)$alkylhydroxycarbonyl, $(C_1-C_3)$alkylaminosulfonyl, $(C_1-C_3)$alkylaminocarbonyl, di$(C_1-C_3)$alkylamino$(C_2-C_6)$alkoxy, $(C_1-C_6)$alkoxycarbonyl, [$(C_1-C_3)$alkyl($C_4-C_6$)heterocyclyl]$(C_1-C_3)$alkyl, and $(C_1-C_3)$alkylhydroxy$(C_1-C_3)$alkyl; and $R^6$ is selected from halo, $(C_1-C_3)$alkyl, halo$(C_1-C_3)$alkyl, cyano, hydroxy$(C_1-C_3)$alkyl, $(C_1-C_3)$alkoxycarbonyl, $(C_1-C_3)$alkylsulfonyl, $(C_1-C_3)$alkoxy, halo$(C_1-C_3)$alkoxy, oxo, hydroxy, aryl$(C_1-C_3)$alkoxycarbonyl, $(C_1-C_3)$alkylhydroxy$(C_1-C_3)$alkyl, heteroaryl, and $(C_1-C_3)$alkoxycarbonyl, wherein the remainder of the varables are as described in Formula (I) or the eighth, ninth, tenth, eleventh, twelfth, or thirteenth embodiment. Alternatively, $R^5$ is $(C_1-C_3)$alkylsulfonyl, wherein the remainder of the varables are as described in Formula (I) or the eighth, ninth, tenth, eleventh, twelfth, or thirteenth embodiment. In another alternative, $R^6$ is selected from $(C_1-C_3)$alkyl, halo$(C_1-C_3)$alkyl, hydroxy, and $(C_1-C_3)$alkoxy, wherein the remainder of the varables are as described in Formula (I) or the eighth, ninth, tenth, eleventh, twelfth, or thirteenth embodiment. In another alternative, $R^5$ is $-SO_2CH_2CH_3$ or $-SO_2CH_3$, wherein the remainder of the varables are as described in Formula (I) or the eighth, ninth, tenth, eleventh, twelfth, or thirteenth embodiment. In another alternative, $R^6$ is $CF_3$, wherein the remainder of the varables are as described in Formula (I) or the eighth, ninth, tenth, eleventh, twelfth, or thirteenth embodiment.

In a fifteenth embodiment, $R^2$ in Formulas (I) to (VIIa) is ethyl or isopropyl, wherein the remainder of the varables are as described in Formula (I) or the eighth, ninth, tenth, eleventh, twelfth, thirteenth, or fourteenth embodiment.

In a sixteenth embodiment, the compound of Formula (I) is of Formula (VIII):

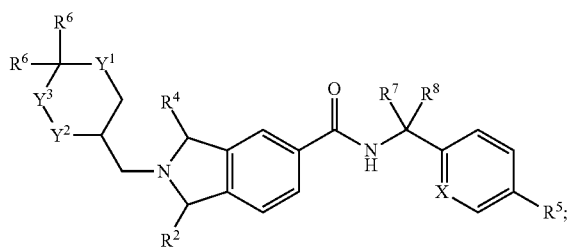

(VIII)

or a pharmaceutically acceptable salt thereof, wherein
X is CH or N;
$Y^1$ is O and $Y^2$ and $Y^3$ are each $CH_2$, $Y^1$ and $Y^3$ are each $CH_2$ and $Y^2$ is O, $Y^1$ and $Y^3$ are each O and $Y^2$ is $CH_2$, $Y^1$ and $Y^2$ are each O and $Y^3$ is $CH_2$, or $Y^1$, $Y^2$ and $Y^3$ are each $CH_2$;
$R^2$ is $(C_1-C_3)$alkyl;
$R^4$ is hydrogen, $(C_1-C_3)$alkyl, or =O;
$R^7$ and $R^8$ are each independently selected from hydrogen, $(C_1-C_3)$alkyl, $(C_1-C_3)$alkoxy$(C_1-C_3)$alkyl, halo$(C_1-C_3)$alkyl, hydroxy$(C_1-C_3)$alkyl, $(C_1-C_3)$alkoxy, aminocarbonyl-O$(C_1-C_3)$alkyl, $(C_1-C_3)$alkyl-aminocarbonyl-O$(C_1-C_3)$alkyl, and di$(C_1-C_3)$alkyl-aminocarbonyl-O$(C_1-C_3)$alkyl;
each $R^6$ is independently selected from halo$(C_1-C_3)$alkyl, $(C_1-C_3)$alkoxy, and hydroxy; and
$R^5$ is $(C_1-C_3)$alkylsulfonyl.

In a seventeenth embodiment, the compound of Formula (I) is of Formula (IX):

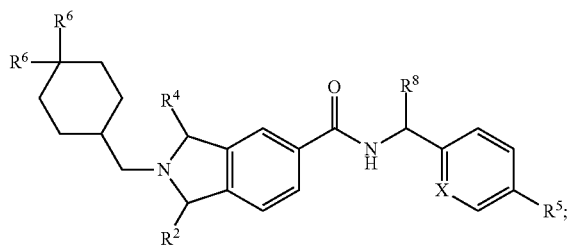

(IX)

or a pharmaceutically acceptable salt thereof, wherein variables in structural Formula (IX) are as described for Formula (VIII).

In an eighteenth embodiment, the compound of Formula (I) is of Formula (X):

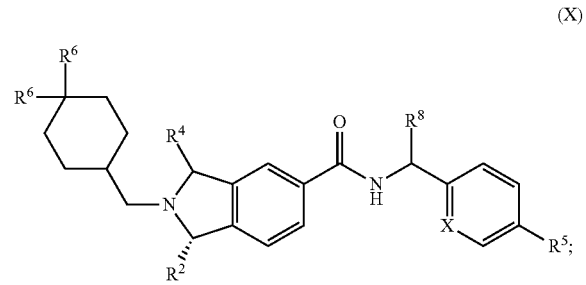

(X)

or a pharmaceutically acceptable salt thereof, wherein the variables in structural Formula (X) are as described for Formula (VIII).

In a nineteenth embodiment, $R^4$ in compounds of Formulas (VIII) to (X) is hydrogen or =O; and $R^8$ is hydrogen, hydroxy$(C_1-C_3)$alkyl, $(C_1-C_3)$alkoxy$(C_1-C_3)$alkyl, or aminocarbonyl-O$(C_1-C_3)$alkyl, wherein the remaining variables are as described in Formula (VIII).

In a twentieth embodiment, the compound of Formula (I) is of Formula (XI):

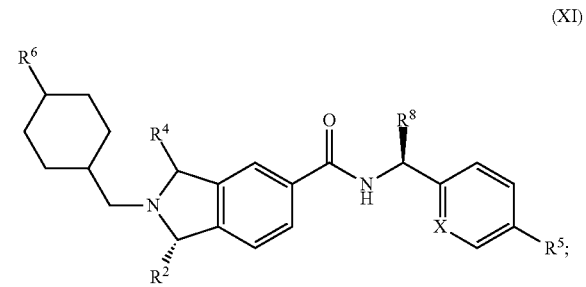

(XI)

or a pharmaceutically acceptable salt thereof, wherein the variables in structural Formula (XI) are as described for Formula (VIII) or the nineteenth embodiment.

In a twenty-first embodiment, the compound of Formula (I) is of Formula (XII):

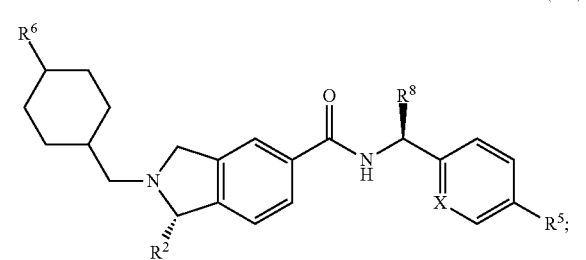

(XII)

or a pharmaceutically acceptable salt thereof, wherein the variables in structural Formula (XII) are as described for Formula (VIII) or the nineteenth embodiment.

In a twenty-second embodiment, $R^6$ in compounds of Formulas (VIII) to (XII) is $CF_3$; and $R^5$ is $-SO_2(C_1-C_3)$alkyl, wherein the remaining variables are as described for Formula (VIII) or the nineteenth embodiment. Alternatively, $R^6$ in compounds of Formulas (VIII) to (XII) is $CF_3$; $R^5$ is $-SO_2(C_1-C_3)$alkyl and X is N, wherein the remaining variables are as described for Formula (VIII) or the nineteenth embodiment In a twenty-third embodiment, the compound of Formula (I) is of Formula (XIII)

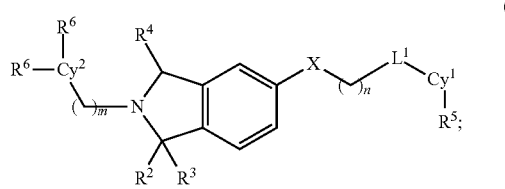

(XIII)

or a pharmaceutically acceptable salt thereof, wherein each $R^6$ is independently selected from halo($C_1-C_3$)alkyl, ($C_1-C_3$)alkoxy, and hydroxy; and $R^5$ is ($C_1-C_3$)alkylsulfonyl, wherein the remaining variables are as described in Formula (I).

In a twenty-fourth embodiment, the compound of Formula (I) is of Formula (XIV):

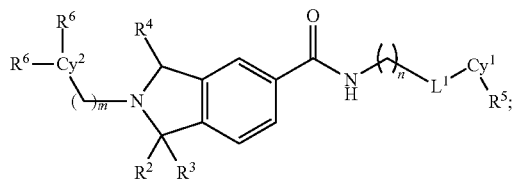

(XIV)

or a pharmaceutically acceptable salt thereof, wherein the variables in structural Formula (XIV) are as described in Formula (I) or the twenty-third embodiment.

In a twenty-fifth embodiment, the compound of Formula (I) is of Formula (XV):

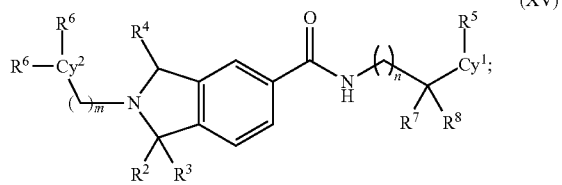

(XV)

or a pharmaceutically acceptable salt thereof, wherein the variables in structural Formula (XV) are as described in Formula (I) or the twenty-third embodiment.

In a twenty-sixth embodiment, the compound of Formula (I) is of Formula (XVI):

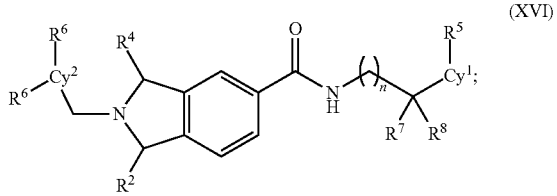

(XVI)

or a pharmaceutically acceptable salt thereof, wherein the variables in structural Formula (XVI) are as described in Formula (I) or the twenty-third embodiment.

In a twenty-seventh embodiment, the compound of Formula (I) is of Formula (XVII):

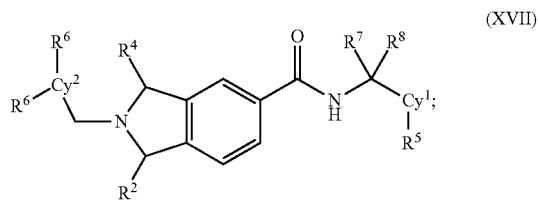

(XVII)

or a pharmaceutically acceptable salt thereof, wherein the variables in structural Formula (XVII) are as described in Formula (I) or the twenty-third embodiment.

In a twenty-eighth embodiment, the compound of Formula (I) is of Formula (XVIII) or (XIX):

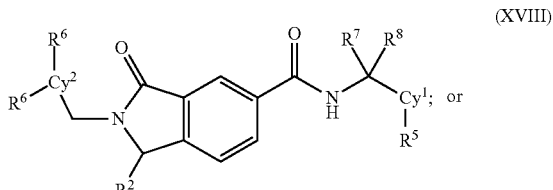

(XVIII)

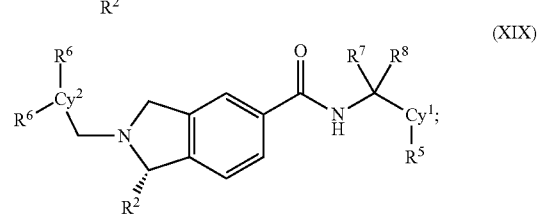

(XIX)

or a pharmaceutically acceptable salt thereof, wherein the variables in structural Formulas (XVIII) and (XIX) are as described in Formula (I) and the twenty-third embodiment.

In a twenty-ninth embodiment, $R^2$ in Formulas (XIII) to (XIX) is ($C_1-C_3$)alkyl, wherein the remainder of the variables are as described in Formula (I) or the twenty-third embodiment.

In a thirtieth embodiment, $Cy^2$ in Formulas (XIII) to (XIX) is selected from aryl, monocyclic cycloalkyl, monocyclic heterocyclyl, and bicyclic heterocyclyl, wherein the remainder of the variables are as described in Formula (I) or the twenty-third or twenty-ninth embodiment.

In a thirty-first embodiment, $Cy^2$ in Formulas (XIII) to (XIX) is phenyl, cyclohexyl, or 4,5,6,7-tetrahydrobenzo[d]oxazolyl, wherein the remainder of the variables are as described in Formula (I) or the twenty-third, twenty-ninth, or thirtieth embodiment.

In a thirty-second embodiment, $Cy^1$ in Formulas (XIII) to (XIX) is phenyl, piperidinyl, or pyridinyl, wherein the remainder of the variables are as described in Formula (I) or the twenty-third, twenty-ninth, thirtieth, or thirty-first embodiment.

In a thirty-third embodiment, $Cy^1$ in Formulas (XIII) to (XIX) is phenyl or pyridinyl; and $Cy^2$ is cyclohexyl or phenyl, wherein the remainder of the variables are as described in Formula (I) or the twenty-third, twenty-ninth, thirtieth, thirty-first, or thirty-second embodiment.

In a thirty-fourth embodiment, $R^7$ in Formulas (XIII) to (XIX) is hydrogen; and $R^8$ is hydrogen, hydroxy($C_1-C_3$)alkyl, ($C_1-C_3$)alkoxy($C_1-C_3$)alkyl, aminocarbonyl-O($C_1-C_3$)alkyl, hydroxycarbonyl($C_1-C_3$)alkoxy($C_1-C_3$)alkyl, ($C_1-C_3$)alkylcarbonylamino($C_1-C_3$)alkyl, ($C_1-C_3$)

alkoxycarbonylamino($C_1$-$C_3$)alkyl, di($C_1$-$C_3$)alkylamino($C_1$-$C_3$)alkyl, di($C_1$-$C_3$)alkylaminocarbonyl($C_1$-$C_3$)alkyl, ($C_1$-$C_3$)alkylaminocarbonyl($C_1$-$C_3$)alkyl, aminocarbonyl($C_1$-$C_3$)alkyl, or aminocarbonyl, wherein the remainder of the variables are as described in Formula (I) or the twenty-third, twenty-ninth, thirtieth, thirty-first, or thirty-second, or thirty-third embodiment.

In a thirty-fifth embodiment, $R^7$ in Formulas (XIII) to (XIX) is hydrogen; and $R^8$ is hydrogen, —$CH_2OH$, —$(CH_2)_2OH$, —$CH_2OCH_3$, —$CH_2OC(O)NH_2$, —$CH_2OCH_2COOH$, —$CH_2NHC(O)CH_3$, —$CH_2NHC(O)OCH_3$, —$(CH_2)_2N(CH_3)_2$, —$CH_2C(O)N(CH_3)_2$, —$CH_2C(O)NHCH_3$, —$CH_2C(O)NH_2$, or $CONH_2$, wherein the remainder of the variables are as described in Formula (I) or the twenty-third, twenty-ninth, thirtieth, thirty-first, or thirty-second, thirty-third, or thirty-fourth embodiment.

In a thirty-sixth embodiment, $R^7$ in Formulas (XIII) to (XIX) is hydrogen; and $R^8$ is hydrogen, —$CH_2OH$, —$(CH_2)_2OH$, or —$CH_2OCH_3$, wherein the remainder of the variables are as described in Formula (I) or the twenty-third, twenty-ninth, thirtieth, thirty-first, or thirty-second, thirty-third, thirty-fourth, or thirty-fifth embodiment.

In a thirty-seventh embodiment, $R^5$ in Formulas (XIII) to (XIX) is —$SO_2CH_2CH_3$ or —$SO_2CH_3$; and $R^6$ is $CF_3$, wherein the remainder of the variables are as described in Formula (I) or the twenty-third, twenty-ninth, thirtieth, thirty-first, or thirty-second, thirty-third, thirty-fourth, thirty-fifth, or thirty-sixth embodiment.

Specific examples of compounds of the invention are provided in the EXEMPLIFICATION. Pharmaceutically acceptable salts as well as the neutral forms of these compounds are included in the invention.

In certain embodiments, the present invention provides any one of the compounds in the foregoing examples, or a pharmaceutically acceptable salt thereof.

In certain embodiments, the present invention provides a method of treating a patient (e.g., a human) with a disorder mediated by RORγ comprising the step of administering to the patient an effective amount of the compound with any compound described herein, or a pharmaceutically acceptable salt or composition thereof.

4. Uses, Formulation and Administration

Pharmaceutically Acceptable Compositions

According to another embodiment, the present invention provides a method of treating a subject (e.g., a human) with a disorder mediated by RORγ using a composition comprising a compound of the invention and a pharmaceutically acceptable carrier, adjuvant, or vehicle. In certain embodiments, the amount of compound of the invention in a provided composition is such that it is effective as an inverse agonist or antagonist to RORγ in a biological sample or in a subject. In certain embodiments, a provided composition is formulated for administration to a subject in need of such composition. In some embodiments, a provided composition is formulated for oral administration to a subject.

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for the inhibition of RORγ. Thus, in some embodiments, the present invention provides a method of treating inflammatory, metabolic and autoimmune diseases or disorders mediated by RORγ, comprising administering a provided compound or composition. More particularly, the compounds and compositions described herein act as inverse agonists or antagonists of RORγ.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

Diseases and conditions treatable according to the methods of the invention include, but are not limited to, inflammatory, metabolic and autoimmune diseases or disorders mediated by RORγ. These diseases and conditions include, for example, asthma, chronic obstructive pulmonary disease (COPD), bronchitis, allergic rhinitis, atopic dermatitis, contact dermatitis, acne, urticaria, hives, angioedema, cystic fibrosis, allograft rejection, multiple sclerosis, Balo's concentric (circular) sclerosis, Balo disease, leukoencephalitis periaxialis concentrica, encephalitis periaxialis concentrica, scleroderma, limited scleroderma, CREST syndrome, arthritis, rheumatoid arthritis, juvenile rheumatoid arthritis, reactive arthritis, Reiter's syndrome, osteoarthritis, ankylosing spondylitis, systemic lupus erythematosus (SLE), psoriasis, plaque psoriasis, guttate psoriasis, inverse psoriasis, pustular psoriasis, erythrodermic psoriasis, psoriatic epidermal hyperplasia, epidermal hyperplasia, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, psoriatic arthritis (PsA), steroid resistant asthma, Graves' disease, scleritis, endometriosis, obstructive sleep apnea syndrome (OSAS), Behçet's disease, dermatomyositis, polymyositis, graft versus host disease, chronic graft versus host disease, acute graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, celiac sprue, neuromyelitis, juvenile idiopathic arthritis, systemic sclerosis, myocardial infarction, pulmonary hypertension, osteoarthritis, cutaneous leishmaniasis, sinonasal polyposis, cancer, including but not limited to lung cancer, gastric cancer, breast cancer and colon cancer, thrombocytopenic purpura, idiopathic thrombocytopenic purpura (ITP), immune thrombocytopenic purpura, cartilage inflammation, bone degradation, vasculitis, acute disseminated encephalomyelitis (ADEM), acute necrotizing hemorrhagic leukoencephalitis, Addison's disease, agammaglobulinemia, alopecia areata, amyloidosis, anti-glomerular basement membrane (GBM) nephritis, anti-tubular basement membrane (TBM) nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticaria, axonal and neuronal neuropathies, bullous pemphigoid, cardiomyopathy, Castleman disease, Chagas disease, chronic inflammatory demyelinating polyneuropathy (CIDP), chronic recurrent multifocal ostomyelitis (CRMO), Churg-Strauss syndrome, cicatricial pemphigoid, benign mucosal pemphigoid, Cogan's syndrome, cold agglutinin disease, congenital heart block, coxsackie myocarditis, essential mixed cryoglobulinemia, demyelinating neuropathies, dermatitis herpetiformis, Devic's disease, neuromyelitis optica, discoid lupus, Dressler's syndrome, eosinophilic esophagitis, eosinophilic fasciitis, erythema nodosum, experimental allergic encephalomyelitis, Evans syndrome, fibrosing alveolitis, giant cell arteritis, temporal arteritis, giant cell myocarditis, glomerulonephritis, Goodpasture's syndrome, granulomatosis with polyangiitis (GPA), Wegener's granulomatosis, Hashimoto's encephalitis, Hashimoto's thyroiditis, hemolytic anemia, Henoch-Schonlein purpura, herpes gestationis, hypogammaglobulinemia, IgA nephropathy, IgG4-related sclerosing disease, immunoregulatory lipoproteins, inclusion body myositis, interstitial cystitis, juvenile myositis, Kawasaki syndrome, Lambert-Eaton syndrome, leukocytoclastic vasculitis, lichen planus, lichen sclerosus, ligneous conjunctivitis, linear IgA disease (LAD), chronic Lyme disease, Meniere's disease, microscopic polyangiitis, mixed connective tissue disease (MCTD), Mooren's ulcer, Mucha-Habermann disease, myositis, narcolepsy, neuromyelitis optica, Devic's syndrome, neutropenia, ocular cicatricial pemphigoid, optic neuritis, palindromic rheumatism, pediatric autoimmune neuropsychiatric disorders associated with streptococcus (PANDAS), paraneoplastic cerebellar degeneration, paroxysmal nocturnal hemoglobinuria (PNH), Parry-Romberg syndrome, Parsonnage-Turner syndrome, pars planitis, peripheral uveitis, pemphigus, peripheral neuropathy, perivenous encephalomyelitis, pernicious anemia, POEMS syndrome, polyarteritis nodosa, type I autoimmune polyglandular syndrome, type II autoimmune polyglandular syndrome, type III autoimmune polyglandular syndrome, polymyalgia rheumatic, postmyocardial infarction syndrome, postpericardiotomy syndrome, progesterone dermatitis, primary biliary cirrhosis, primary sclerosing cholangitis, idiopathic pulmonary fibrosis, pyoderma gangrenosum, pure red cell aplasia, Raynaud's phenomenon, reflex sympathetic dystrophy, relapsing polychondritis, restless legs syndrome, retroperitoneal fibrosis, rheumatic fever, rheumatoid arthritis, sarcoidosis, Schmidt syndrome, sperm autoimmunity, stiff person syndrome, subacute bacterial endocarditis (SBE), Susac's syndrome, sympathetic ophthalmia, Takayasu's arteritis, temporal arteritis, giant cell arteritistesticular autoimmunity, Tolosa-Hunt syndrome, transverse myelitis, undifferentiated connective tissue disease (UCTD), vesiculobullous dermatosis, and vitiligo.

Also included are diseases or disorders which are implicated by the regulation of the circadian rhythm of individuals and include, e.g., major depression, seasonal affective disorder, post-traumatic stress disorder (PTSD), bipolar disorder, autism, epilepsy, Alzheimer's and other central nervous system (CNS) disorders associated with altered sleep and/or circadian rhythms.

In one embodiment, a human patient is treated with a compound of the invention and a pharmaceutically acceptable carrier, adjuvant, or vehicle, wherein said compound is present in an amount to treat or ameliorate one or more of the diseases and conditions recited above. In another embodiment, the diseases and conditions treated or ameliorated by a compound of the invention include, e.g., asthma, COPD, bronchitis, allergic rhinitis, atopic dermatitis, contact dermatitis, acne, urticaria, cystic fibrosis, allograft rejection, multiple sclerosis, scleroderma, arthritis, rheumatoid arthritis, juvenile rheumatoid arthritis, osteoarthritis, ankylosing spondylitis, SLE, psoriasis, Hashimoto's disease, pancreatitis, autoimmune diabetes, type I diabetes, autoimmune ocular disease, ulcerative colitis, Crohn's disease, regional enteritis, IBD, IBS, Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, PsA, steroid resistant asthma, Graves' disease, scleritis, major depression, seasonal affective disorder, PTSD, bipolar disorder, autism, epilepsy, Alzheimer's, CNS disorders associated with altered sleep and/or circadian rhythms, endometriosis, OSAS, Behçet's disease, dermatomyositis, polymyocitis, graft versus host disease, primary biliary cirrhosis, liver fibrosis, NAFLD, sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer. In an alternative embodiment, the diseases and conditions treated or ameliorated by a compound of the invention include, e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, SLE, scleroderma, psoriasis, PsA, steroid resistant asthma and rheumatoid arthritis in the patient.

The invention further relates to a combination therapy for treating or ameliorating a disease or a disorder described herein. In some embodiments, the combination therapy comprises administering at least one compound of the invention in combination with one or more agents for treating or ameliorating inflammatory, metabolic and autoimmune diseases or disorders mediated by RORγ. In some embodiments, the combination therapy comprises administering at least one compound of the invention in combination with one or more agents for treating or ameliorating a disease or a disorder described herein. In some embodiments, the combination therapy comprises administering at least one compound of the invention in combination with one or more agents for the treatment of diseases including asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, SLE, scleroderma, psoriasis, PsA, steroid resistant asthma and rheumatoid arthritis.

The compounds according to the invention may also be used in combination with immunotherapies for the treatment of a disease or disorder disclosed herein.

Combination therapy includes, e.g., co-administration of a compound of the invention and one or more other agents, sequential administration of a compound of the invention and one or more other agents, administration of a composition containing a compound of the invention and one or more other agents, or simultaneous administration of separate compositions containing a compound of the invention and one or more other agents.

The invention further provides a method of treating a subject, such as a human, suffering from one of the abovementioned disorders or diseases.

The invention further relates to the use of provided compounds for the production of pharmaceutical compositions which are employed for the treatment and/or prophylaxis and/or amelioration of the diseases and disorders mentioned herein.

Compounds or compositions described herein may be administered using any amount and any route of administration effective for treating or lessening the severity of one or more of the diseases and conditions described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

The amount of both, a provided compound and additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent.

The amount of additional therapeutic agent present in the compositions of this disclosure will be no more than the amount that would normally be administered in a composition comprising that therapeutic agent as the only active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Description of Synthesis

The compounds of the present invention can be readily prepared according to the following reaction schemes and examples, or modifications thereof, using readily available starting materials, reagents and conventional synthesis procedures. Many of the reactions can also be carried out under microwave (MW) conditions or using conventional heating or utilizing other technologies such as solid phase reagents/scavengers or flow chemistry. In these reactions, it is also possible to make use of variants which are themselves known to those of ordinary skill in the art, but are not mentioned in greater detail. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below variables have the meanings indicated above unless otherwise indicated. The abbreviations used in these experimental details are listed below and additional ones should be known to a person skilled in the art of synthesis. In addition, one can refer to the following references for suitable methods of synthesis as described in March, Advanced Organic Chemistry, 3rd edition, John Wiley & Sons, 1985, Greene and Wuts, Protective Groups in Organic Synthesis, $2^{nd}$ edition, John Wiley & Sons, 1991, and Richard Larock, Comprehensive Organic Transformations, $4^{th}$ edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Compounds were purified by various HPLC methods including those described below. Purification techniques, include HPLC methods, are know to those skilled in the art.

TFA Preparative HPLC Method A:
Mobile phase A: water with 0.1% TFA; Mobile phase B: $CH_3CN$; Flow rate: 90 mL/min; Detection: UV 220 nm/254 nm; Column: Phenomenex Synergi Max-RP C18 250*50 mm*10 μm; Column temperature: 30° C.

| Time in min | % A | % B |
|---|---|---|
| 0.00 | 80 | 20 |
| 30.00 | 50 | 50 |
| 30.20 | 0 | 100 |
| 40.00 | 0 | 100 |

Basic Preparative HPLC Method B:
Mobile phase A: water with 0.05% $NH_3$; Mobile phase B: $CH_3CN$; Flow rate: 30 mL/min; Detection: UV 220 nm/254 nm; Column: Synergi 200 mm×25 mm×5 μm; Column temperature: 30° C.

| Time in min | % A | % B |
|---|---|---|
| 0.0 | 63 | 37 |
| 8.0 | 33 | 67 |
| 8.1 | 0 | 100 |
| 10.1 | 0 | 100 |
| 10.1 | 70 | 30 |
| 12 | 70 | 30 |

Basic Preparative HPLC Method C:
Mobile phase A: water with 0.05% $NH_3$; Mobile phase B: $CH_3CN$; Flow rate: 30 mL/min; Detection: UV 220 nm/254 nm; Column: Xyridge 200*25 mm*5 μm; Column temperature: 30° C.

| Time in min | % A | % B |
|---|---|---|
| 0.00 | 99 | 1 |
| 8.00 | 70 | 30 |
| 8.20 | 0 | 100 |
| 10.00 | 0 | 100 |

HCl Preparative HPLC Method D:
Mobile phase A: water with 0.05% HCl; Mobile phase B: $CH_3CN$; Flow rate: 25 mL/min; Detection: UV 220 nm/254 nm; Column: Synergi Max-RP 150*30 mm*4 μm; Column temperature: 30° C.

| Time in min | % A | % B |
|---|---|---|
| 0.00 | 75 | 25 |
| 12.00 | 45 | 55 |
| 12.20 | 0 | 100 |
| 14.00 | 0 | 100 |

HCl Preparative HPLC Method E:
Mobile phase A: water with 0.1% HCl; Mobile phase B: $CH_3CN$; Flow rate: 25 mL/min; Detection: UV 220 nm/254 nm; Column: Agella Venusil ASB C18 150*21.2 mm*5 μm; Column temperature: 40° C.

| Time in min | % A | % B |
|---|---|---|
| 0.00 | 80 | 20 |
| 10.00 | 50 | 50 |
| 10.20 | 0 | 100 |
| 14.00 | 0 | 100 |

HCl Preparative HPLC Method F:
Mobile phase A: water with 0.05% HCl; Mobile phase B: $CH_3CN$; Flow rate: 25 mL/min; Detection: UV 220 nm/254 nm; Column: Agella Venusil ASB C18 150*21.2 mm*5 μm; Column temperature: 40° C.

| Time in min | % A | % B |
|---|---|---|
| 0.00 | 80 | 20 |
| 10.00 | 50 | 50 |
| 10.20 | 0 | 100 |
| 14.00 | 0 | 100 |

HCl Preparative HPLC Method G:
Mobile phase A: water with 0.05% HCl; Mobile phase B: $CH_3CN$; Flow rate: 25 mL/min; Detection: UV 220 nm/254 nm; Column: Agella Venusil ASB C18 150*21.2 mm*5 μm; Column temperature: 30° C.

| Time in min | % A | % B |
|---|---|---|
| 0.00 | 80 | 20 |
| 8.00 | 50 | 50 |
| 8.20 | 0 | 100 |
| 10.00 | 0 | 100 |

HCl Preparative HPLC Method H:
Mobile phase A: water with 0.05% HCl; Mobile phase B: $CH_3CN$; Flow rate: 15 mL/min; Detection: UV 220 nm/254 nm; Column: Gemini 150*25 mm*5 μm; Column temperature: 30° C.

| Time in min | % A | % B |
|---|---|---|
| 0.00 | 85 | 15 |
| 8.00 | 55 | 45 |
| 8.20 | 0 | 100 |
| 10.00 | 0 | 100 |

Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

The invention is illustrated by way of the following examples, in which the following abbreviations may be employed.

| Abbreviation | Meaning |
|---|---|
| ACN, MeCN, CH$_3$CN | acetonitrile |
| AIBN | azobisisobutyronitrile |
| aq | aqueous |
| Boc | tert-butoxycarbonyl or t-butoxycarbonyl |
| brine | saturated aqueous NaCl |
| Cbz | benzyloxy carbonyl |
| Cpd | compound |
| DCM or CH$_2$Cl$_2$ | methylene chloride |
| DIEA | diisopropyl ethyl amine |
| DMF | dimethyl formamide |
| DMS/Me$_2$S | dimethyl sulfide |
| DMSO | dimethyl sulfoxide |
| EDCI | 1-(3-dimethylaminopropyl)-3-ethylcarbodiiimide hydrochloride |
| EtI | ethyl iodide |
| Et | ethyl |
| Et$_2$O | ethyl ether |
| Et$_3$SiH | triethylsilane |
| Et$_3$N | triethylamine |
| EtOAc, EA, AcOEt | ethyl acetate |
| EtOH | ethanol |
| h, hr | hour(s) |
| HATU | O-(7-azabenzotriazol-1-yl)-N,N,N',N'-tetramethyluronium-hexafluorophosphate |
| HBTU | O-benzotriazole-1-yl-N,N,N',N'-tetramethyluronium-hexafluorophosphate |
| HCl | hydrochloric acid |
| H$_2$O$_2$ | hydrogen peroxide |
| HPLC | high performance liquid chromatography |
| i-BuOCOCl | iso-butoxycarbonyl chloride |
| ICl | iodochloride |
| K$_3$PO$_4$ | tripotassium phosphate |
| LC-MS | liquid chromatography-mass spectrometry |
| LDA | lithium diisopropylamide |
| MCPBA, m-CPBA | meta-chloroperoxybenzoic acid |
| MeOH | methanol |
| MeI | methyl iodide |
| Me | methyl |
| mg | milligram |
| min | minute(s) |
| mL | milliliters |
| mmol | millimoles |
| mp, m.p. | melting point |
| MS | mass spectrometry |
| MW, uwave | microwave |
| NBS | N-bromosuccinimide |
| n-BuLi | n-butyllithium |
| NMM | N-methyl-morpholine |
| NMP | N-methyl-pyrrolidin-2-one |
| OTf | trifluoromethanesulfonate |
| OTs | tosylate |
| PdCl$_2$dppf | [1,1-bis(diphenylphosphino)ferrocene]dichloropalladium(ii) |
| Pd$_2$(dba)$_3$ | tris(dibenzylideneacetone)dipalladium(0) |
| PE | petroleum ether |
| rt | room temperature |
| sat. | saturated |
| SFC | supercritical fluid chromatography |
| t-BuOK | potassium tert butoxide |
| t-BuLi | tert butyl lithium |
| t-BuOOH | tert butyl peroxide |
| TBAF | tetrabutylammonium fluoride |
| TFA | trifluoroacetic acid |
| THF | tetrahydrofuran |
| TLC | thin layer chromatography |
| Ti(OEt)$_4$ | titanium tetra ethoxide |

Compounds according to Formula (I), can be prepared by reacting an intermediate compound of Formula (500) with an alkyl, arylalkyl, heteroaryl or aryl halide, according to reaction Scheme 1, a reaction that is performed in a polar aprotic solvent, such as, for example, acetonitrile, in the presence of a suitable base, such as, for example, N,N-diisopropylethylamine or potassium carbonate. Alternatively, the final compounds according to Formula (I) in which m=1 or 2, can be prepared by reacting an intermediate compound of Formula (500) with an aldehyde, according to reaction Scheme 1, following art-known reductive amination procedure, in the typical solvent, such as, for example, dichloroethane, dichloromethane, or methanol; in the presence of suitable reducing reagent, such as sodium cyanoborohydride or sodium triacetoxyborohydride. In reaction Scheme 1, all variables are defined as in Formula (I) and G$^1$ is a leaving group, such as for example, bromide, chloride, mesylate (methanesulfonate), tosylate (p-toluenesulfonate), trifluorormethanesulfonate (triflate), or iodide.

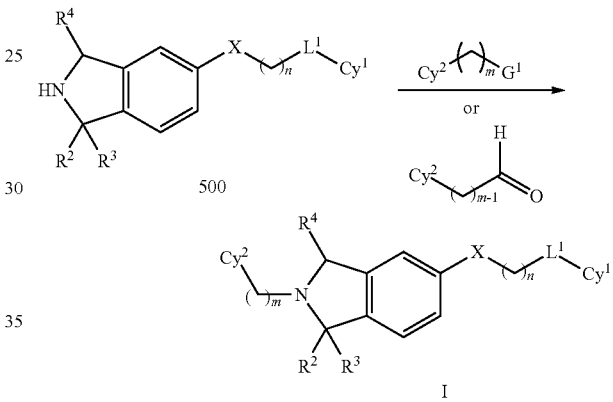

Scheme 1.

Intermediate compound of Formula (500) can be can be prepared by deprotecting an intermediate compound of Formula (501), wherein Pg is a suitable nitrogen protecting group (Greene and Wuts, Protective Groups in Organic Synthesis, 2$^{nd}$ edition, John Wiley & Sons, 1991), e.g., Pg=tert-butoxycarbonyl, removed with trifluoroacetic acid according to Scheme 2. In reaction Scheme 2, all variables are defined as in Formula (I).

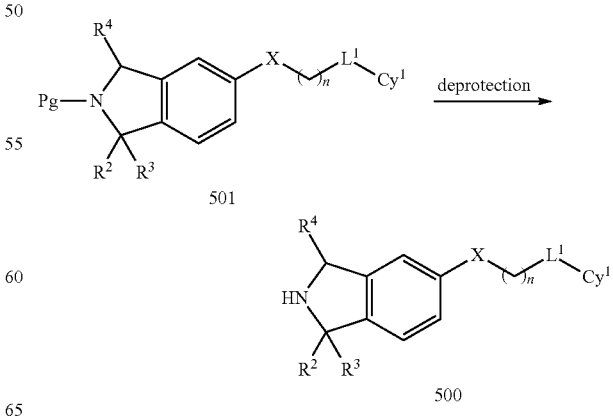

Scheme 2.

Intermediate compound of Formula (502), wherein X is C(=O)NH, can be prepared from a carboxylic acid (504)

and an amine (503), according to Scheme 3. The reaction is conveniently carried out in the presence of an activating reagent, for example, N-(3-dimethylaminopropyl)-N'-ethyl-carbodiimide hydrochloride (EDCI) or O-(7-azabenzotri-azol-1-yl)-N,N,N',N'-tetramethyluronium hexafluorophosphate (HATU), in an organic solvent, for example, N,N-dimethylformamide or dichloromethane, optionally in the presence of a base, e.g., N,N-diisopropylethylamine or triethylamine, at a temperature, for example in the range from 0 to 60° C.

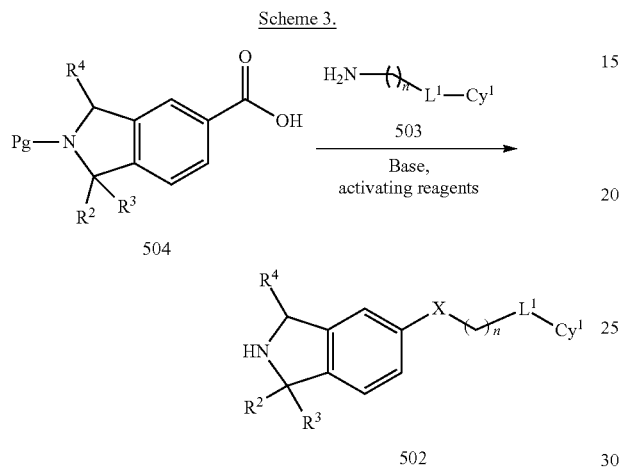

Intermediate compound of Formula (505), wherein X is NHC=O, can be prepared from an intermediate compound of Formula (506) and an amide (507), according to Scheme 4. The reaction is carried out in the presence of a catalyst, for example, tris(dibenzylideneacetone)dipalladium (0) (Pd$_2$(dba)$_3$), in an organic solvent, for example, dioxane or tert-butanol, in the presence of an additive, e.g., potassium phosphate, at a temperature, for example, in the range from 80 to 150° C.

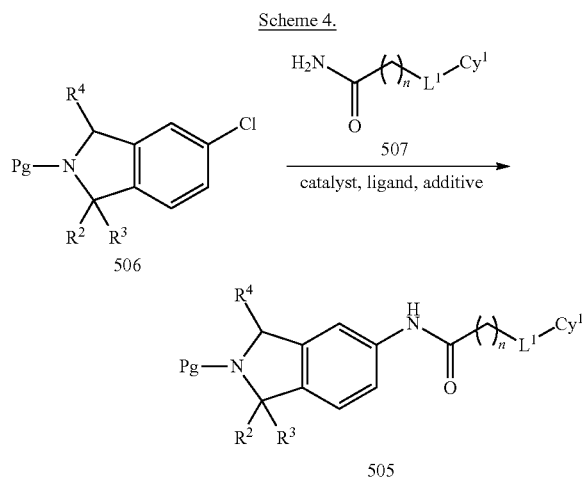

Preparation of Intermediates

As a representative example, intermediate compound of Formula (504) wherein R$^4$ is H, R$^2$ is isopropyl, R$^3$ is H and Pg is tert-butoxycarbonyl, can be prepared by following the reaction steps shown in Scheme 5. An intermediate compound of Formula (504) with variables R$^4$, R$^2$ and R$^3$ can be prepared readily according to Scheme 5, or modifications thereof, using readily available starting materials and reagents.

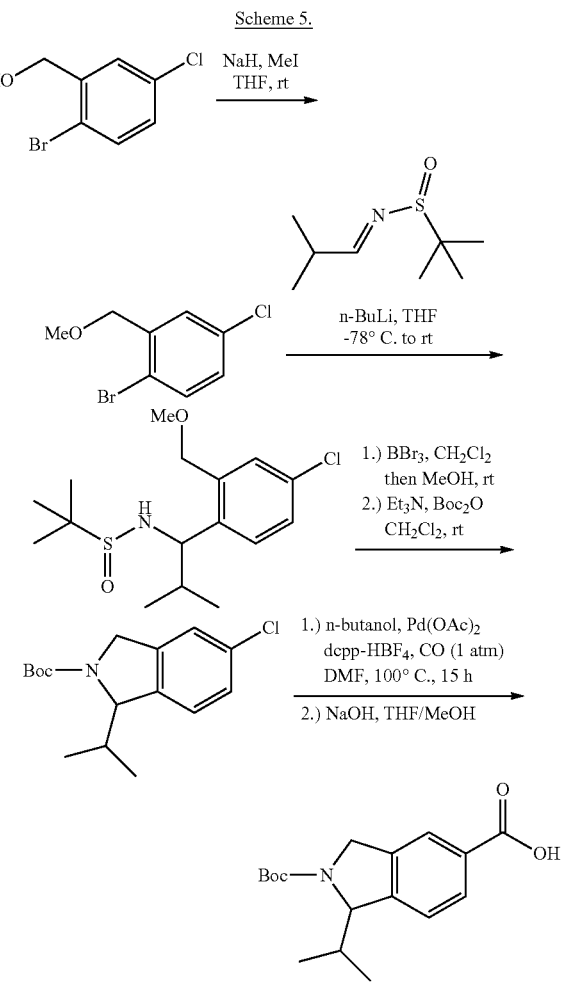

To a solution of (2-bromo-5-chlorophenyl)methanol (60 g, 0.27 mol) in dry THF (600 mL) was added NaH (14.1 g, 0.35 mol, 60% in mineral oil) in portions at 0° C. under N$_2$. The mixture was stirred at 0° C. for 1 h, and then MeI (84.9 g, 0.6 mol) was added dropwise to the reaction mixture at 0° C. The mixture was allowed to warm to rt and stirred for 1 h. The mixture was quenched with a sat. NH$_4$Cl solution (600 mL) at 0° C. and extracted with DCM (3×500 mL). The combined organic layers were dried over anhydrous Na$_2$SO$_4$, filtered and concentrated under reduced pressure. The crude residue was purified by column chromatography on silica gel (eluting with 5% ethyl acetate in petroleum ether) to afford 1-bromo-4-chloro-2-(methoxymethyl)benzene (58 g, 91%) as a colorless oil. $^1$H NMR (CDCl$_3$ 400 MHz): δ 7.54-7.43 (m, 2H), 7.13 (dd, J=2.8 Hz, 8.8 Hz, 1H), 4.48 (s, 2H), 3.49 (s, 3H). To a solution of isobutyraldehyde (77.4 g, 1.1 mol) and racemic 2-methylpropane-2-sulfinamide (86.7 g, 0.72 mol) in DCM (1 L) was added CuSO$_4$ (172 g, 1.1 mol) at rt. The mixture was stirred at rt for 3 days. The mixture was filtered and the filtrate was concentrated under reduced pressure. The residue was purified by column chromatography on silica gel (eluting with 0.50% ethyl acetate in petroleum ether) to afford (E)-2-methyl-N-(2-methylpropylidene)propane-2-sulfinamide (82.0 g, 43%) as a yellow oil.

To a solution of 1-bromo-4-chloro-2-(methoxymethyl)benzene (18 g, 0.08 mol) in anhydrous THF (400 mL) was added n-BuLi (64 mL, 0.16 mol, 2.5 M in THF) dropwise at −78° C. under $N_2$. After addition, the reaction mixture was stirred at −78° C. for 0.5 h, then a solution of (E)-2-methyl-N-(2-methylpropylidene)propane-2-sulfinamide (16 g, 0.09 mol) in THF (100 mL) was added dropwise to the reaction mixture at −78° C. under $N_2$. The reaction solution was stirred at −78° C. for 0.5 h, and the mixture was allowed to warm to rt and stirred for 1 h. The reaction mixture was quenched with a sat. $NH_4Cl$ solution (500 mL) at 0° C. and extracted with DCM (3×300 mL). The combined organic layers were washed with brine (500 mL), dried over anhydrous sodium sulfate, filtered and concentrated under reduced pressure. The residue was purified by column chromatography on silica gel (eluting with a gradient of 10% to 50% ethyl acetate in petroleum ether) to afford racemic diastereomers of N-(1-(4-chloro-2-(methoxymethyl)phenyl)-2-methylpropyl)-2-methylpropane-2-sulfinamide as white solids. The more polar diastereomer was isolated as the major product (13.0 g, 51.4%) and the less polar diastereomer was isolated as the minor product (6.4 g, 25.3%). The more polar major diastereomer was used for the subsequent reactions for the isolations of the final compounds.

To a solution of N-(1-(4-chloro-2-(methoxymethyl)phenyl)-2-methylpropyl)-2-methylpropane-2-sulfinamide/more polar diastereomer from above (3 g, 9.06 mmol) in anhydrous DCM (20 mL) was added $BBr_3$ (13 mL, 12.9 mmol, 1.0 M solution in DCM) dropwise at 0° C. under $N_2$. After addition, the reaction mixture was allowed to warm to rt and stirred for 0.5 h.

The reaction mixture was cooled to 0° C., and MeOH (10 mL) was added carefully at 0° C. After addition, the reaction solution was allowed to warm to rt and stirred for 2 h. An additional 30 mL of MeOH was added and the reaction mixture was concentrated under reduced pressure. The residue was placed under high vacuum for 1 h resulting in the formation of a foamy tan solid. To this solid was added MeOH (30 mL), followed by $Et_3N$ (4.58 g, 45.3 mmol) at rt. After 5 min of stirring, $Boc_2O$ (4.0 g, 18.3 mmol) was added at rt. The reaction mixture was stirred for 1 h at rt. The mixture was concentrated under reduced pressure to remove the MeOH. DCM (30 mL) and water (30 mL) were added to the reaction mixture. The organic layer was extracted with DCM (3×30 mL). The combined organic layers were washed with brine (50 mL), dried over anhydrous sodium sulfate, filtered and concentrated under reduced pressure. The crude residue was purified by column chromatography on silica gel (eluting with a gradient of 1% to 2% ethyl acetate in petroleum ether) to afford tert-butyl-5-chloro-1-isopropylisoindoline-2-carboxylate (1.64 g, 61%) as a pale yellow solid. $^1$H NMR ($CDCl_3$ 400 MHz): δ 7.08-7.28 (m, 3H), 4.99 (s, 0.51H), 4.89 (s, 0.56H), 4.77 (d, J=15.2 Hz, 0.62H), 4.66 (d, J=15.2 Hz, 0.61H), 4.49 (s, 0.64H), 4.45 (s, 0.48H), 2.53-2.39 (m, 0.66H), 2.35-2.19 (m, 0.65H), 1.49 (s, 9H), 0.99 (d, J=7.2 Hz, 1.47H), 0.93 (d, J=7.2 Hz, 1.60H), 0.69 (d, J=6.8 Hz, 1.64H), 0.63 (d, J=6.8 Hz, 1.5H).

$K_2CO_3$ (4.3 g, 0.03 mol) and powdered 4 A molecular sieves (4.60 g) were added to a 250 mL round bottom flask. The flask was placed under high vacuum and the contents were dried with a heat gun for about 5 min. Upon cooling to rt, $Pd(OAc)_2$ (186 mg, 0.8 mmol) and 1,3-bis(dicyclohexylphosphino)propane bis(tetrafluoroborate) (979 mg, 1.6 mmol) were added and the flask was placed under an $N_2$ atmosphere. A solution of tert-butyl-5-chloro-1-isopropylisoindoline-2-carboxylate (6.1 g, 0.02 mol) in dry DMF (70 mL) was added to the mixture, followed by addition of n-butanol (24 ml, 0.2 mol). The contents were stirred while the flask was evacuated using a vacuum line and backfilled with about 1 atm of CO (2 balloons nested inside one another, filled with CO and attached to a syringe with a needle). This evacuation and backfilling process was repeated 4 times. The flask was then kept under bubbling with CO gas (from a gas bag with a volume of 30 L) and heated to 130° C. overnight, at which point LCMS analysis showed complete consumption of starting material with ~51% of butyl ester formation along with ~41% of the corresponding carboxylic acid product. The reaction was then cooled to rt and 200 mL of 1 N aqueous NaOH solution was added. After stirring for 1 h, the mixture was washed with ethyl acetate (3×100 mL). The aqueous layer was acidified with 2 N aqueous HCl solution to pH=3. The carboxylic acid product was then extracted out using EtOAc (4×100 mL) and the combined organic layers were washed with brine (3×100 mL) before drying and evaporating. The residue was purified by column chromatography on silica gel (eluting with a gradient of 20% to 50% ethyl acetate in petroleum ether) to afford 2-(tert-butoxycarbonyl)-1-isopropylisoindoline-5-carboxylic acid (3.80 g, 62%) as a white solid. LC-MS $t_R$=5.093 min in 10-80AB_7 min chromatography (Welch Xtimate MK RP-18e 25-2 mm), MS (ESI) m/z 306.0 [M+H]$^+$. $^1$H NMR ($CDCl_3$ 400 MHz): δ 8.05-7.95 (m, 2H), 7.36 (d, J=8.0 Hz, 0.48H), 7.32 (d, J=8.0 Hz, 0.56H), 5.11 (s, 0.49H), 5.01 (s, 0.53H), 4.88 (d, J=15.2 Hz, 0.54H), 4.77 (d, J=15.6 Hz, 0.51H), 4.59 (s, 0.61H), 4.55 (s, 0.47H), 2.53-2.45 (m, 0.62H), 2.40-2.30 (m, 0.69H), 1.52 (s, 9H), 1.04 (d, J=7.2 Hz, 1.5H), 0.98 (d, J=6.8 Hz, 1.7H), 0.73 (d, J=6.8 Hz, 1.6H), 0.68 (d, J=6.8 Hz, 1.5H).

As another representative example, intermediate compound of Formula (504) wherein $R^4$ is H, $R^2$ is ethyl, $R^3$ is H and Pg is tert-butoxycarbonyl, can be prepared by following the reaction steps set forth in Scheme 5, except that (R,E)-2-methyl-N-propylidenepropane-2-sulfinamide was used (Scheme 6).

Scheme 6.

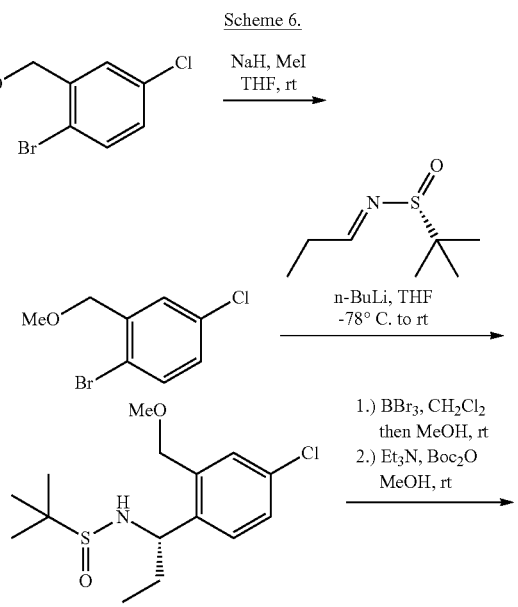

-continued

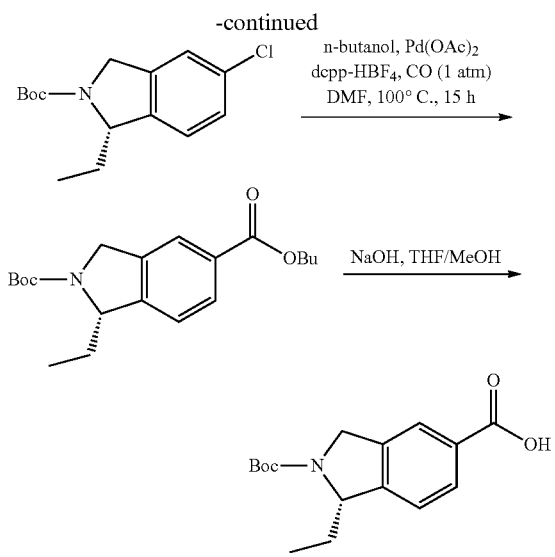

To a solution of (2-bromo-5-chlorophenyl)methanol (30.0 g, 135.4 mmol) in anhydrous THF (400 mL) was added NaH (8.1 g, 203.2 mmol, 60% in mineral oil) at 0° C. The reaction was stirred at 0° C. for 1 h. MeI (28.8 g, 203.2 mmol) was added dropwise via syringe over a 10 min period. After addition, the reaction mixture was stirred at rt for 2 h, at which point TLC analysis (petroleum ether:ethyl acetate=5: 1) showed the complete consumption of starting material. The reaction was cooled down with an ice-water bath, quenched with water (100 mL) and diluted with ethyl acetate (1 L). The organic layer was washed with brine (3×500 mL), dried over anhydrous $Na_2SO_4$, filtered and concentrated in vacuo to afford the crude residue, which was purified by column chromatography on silica gel (eluting with petroleum ether) to give 1-bromo-4-chloro-2-(methoxymethyl) benzene (30 g, 94%) as a light brown oil. $^1$H NMR ($CDCl_3$ 400 MHz): δ 7.43-7.47 (m, 2H), 7.11-7.13 (m, 1H), 4.47 (s, 2H), 3.48 (s, 3H).

To a solution of propionaldehyde (10 g, 172.2 mmol) and (R)-2-methylpropane-2-sulfinamide (23 g, 189.4 mmol) in dry $CH_2Cl_2$ (500 mL) was added $CuSO_4$ (41 g, 258.3 mmol) under a nitrogen atmosphere. The reaction was stirred for 20 h under a nitrogen atmosphere. The reaction was then filtered, washed with $CH_2Cl_2$ (3×300 mL) and concentrated in vacuo. The crude residue was purified by column chromatography on silica gel (eluting with petroleum ether:ethyl acetate=gradient of 50:1 to 15:1) to give (R,E)-2-methyl-N-propylidenepropane-2-sulfinamide (15 g, 54%) as a colorless oil. $^1$H NMR ($CDCl_3$ 400 MHz): δ 8.08 (t, J=4.4 Hz, 1H), 2.49-2.56 (m, 2H), 1.14-1.18 (m, 12H).

To a solution of 1-bromo-4-chloro-2-(methoxymethyl) benzene (6.0 g, 25.5 mmol) in anhydrous THF (50 mL) was added n-BuLi (20 mL, 51.0 mmol, 2.5 M in hexane) dropwise at −78° C. After addition, the reaction mixture was stirred at −78° C. for 30 min before adding a solution of (R,E)-2-methyl-N-propylidenepropane-2-sulfinamide (5.3 g, 33.1 mmol) in 15 mL of anhydrous THF dropwise. The reaction was stirred for 30 min at −78° C. and was slowly allowed to warm to rt. Stirring was continued at rt for 1 h, at which point TLC analysis (petroleum ether:ethyl acetate=20:1) showed complete consumption of the starting material. The reaction was cooled down to −78° C., quenched with a sat. $NH_4Cl$ solution (30 mL) then diluted with ethyl acetate (100 mL) and water (100 mL). The aqueous phase was extracted with ethyl acetate (3×80 mL). The organic layers were combined, washed with brine (3×200 mL), dried over anhydrous $Na_2SO_4$, filtered and evaporated in vacuo. The crude residue was purified by column chromatography on silica gel (eluting with petroleum ether:ethyl acetate=gradient of 20:1 to 1:1) to give the (R)—N—((R)-1-(4-chloro-2-(methoxymethyl)phenyl)propyl)-2-methylpropane-2-sulfinamide (2.0 g, 25%) and (R)—N—((S)-1-(4-chloro-2 (methoxymethyl)phenyl)propyl)-2-methylpropane-2-sulfinamide (1.2 g, 15%) as a solid. (R)—N—((R)-1-(4-chloro-2-(methoxymethyl)phenyl)propyl)-2-methylpropane-2-sulfinamide LC-MS: $t_R$=1.054 min in 10-80AB_2.0 min chromatography (Welch Xtimate C18, 2.1*30 mm, 3 μm), MS (ESI) m/z 318.1 [M+H]$^+$. (R)—N—((S)-1-(4-chloro-2-(methoxymethyl)phenyl)propyl)-2-methylpropane-2-sulfinamide LC-MS: $t_R$=0.793 min in 5-95AB_1.5 min chromatography (Welch Xtimate C18, 2.1*30 mm, 3 μm), MS (ESI) m/z 318.0 [M+H]$^+$.

To a solution of (R)—N—((S)-1-(4-chloro-2-(methoxymethyl)phenyl)propyl)-2-methylpropane-2-sulfinamide (1.2 g, 3.77 mmol) in anhydrous $CH_2Cl_2$ (10 mL) was added 5.6 mL of a 1M solution of $BBr_3$ in $CH_2Cl_2$ at 0° C. under a nitrogen atmosphere. The reaction was allowed to warm to rt and stirred for 30 min. LCMS showed no starting material left and 4 peaks were observed corresponding to (S)-1-(2-(bromomethyl)-4-chlorophenyl)propan-1-amine, N—((S)-1-(4-chloro-2-(hydroxymethyl)phenyl)propyl)-2-methylpropane-2-sulfinamide, N—((S)-1-(2-(bromomethyl)-4-chlorophenyl)propyl)-2-methylpropane-2-sulfinamide and (S)-(2-(1-aminopropyl)-5-chlorophenyl)methanol. At this point, the reaction was cooled with an ice-water bath and 10 mL of MeOH was carefully added. The reaction was warmed to rt and stirred for 2 h before removing all of the solvents. 10 mL of MeOH was added to the residue and evaporated off again under reduced pressure. The resulting crude (S)-1-(2-(bromomethyl)-4-chlorophenyl)propan-1-amine was placed under high vacuum for 30 min resulting in the formation of a foamy tan solid. To this solid was added 8 mL of MeOH followed by $Et_3N$ (2.6 mL, 18.85 mmol, d=0.726 g/mL) at rt. After 5 min of stirring at rt, $Boc_2O$ (1.6 g, 7.54 mmol) was added. After 1 h, the MeOH was removed and the workup was done using ethyl acetate with water. The residue was purified by column chromatography on silica gel (eluting with petroleum ether:ethyl acetate=10:1) to give the (S)-tert-butyl 5-chloro-1-ethylisoindoline-2-carboxylate (850 mg, 80%) as a colorless oil. LC-MS $t_R$=1.215 min in 10-80AB_2.0 min chromatography (Welch Xtimate C18, 2.1*30 mm, 3 μm), MS (ESI) m/z 226.1, 228.1 [M−55]$^+$.

$K_2CO_3$ (624 mg, 4.51 mmol) and powdered 4 Å molecular sieves (208 mg) were added to a 100 mL round bottom flask. The flask was placed under high vacuum and the contents were flamed dried for 5 min. Upon cooling to rt, $Pd(OAc)_2$ (54 mg, 0.24 mmol) and 1,3-bis(dicyclohexylphosphino)propane bis(tetrafluoroborate) (294 mg, 0.48 mmol) were added to the flask. A solution of (S)-tert-butyl 5-chloro-1-ethylisoindoline-2-carboxylate (850 mg, 3.01 mmol) in anhydrous DMF (10 mL) was added followed by the addition of n-butanol (2.7 mL, 30.10 mmol, d=0.81 g/mL). The contents were stirred while the flask was evacuated using a vacuum line and backfilled with 1 atm of CO (2 balloons nested inside one another). This evacuation and backfilling process was repeated 4 times. The flask was kept under 1 atm of CO and heated to 100° C. overnight, at which point TLC analysis (petroleum ether:ethyl acetate=10:1) showed the starting material was consumed.

To the cooled reaction mixture was added 15 mL of a 1N NaOH solution at rt. After stirring for 30 min, the aqueous phase was washed with ethyl acetate (3×15 mL), acidified to pH=2~3 with 1N HCl solution and extracted with ethyl acetate (3×30 mL). The combined organic layers were washed with brine (3×60 mL), dried over anhydrous Na$_2$SO$_4$, filtered and evaporated. The crude residue was purified by TFA preparative HPLC method A to give (S)-2-(tert-butoxycarbonyl)-1-ethylisoindoline-5-carboxylic acid (330 mg, 38%) as a brown solid and (S)-2-tert-butyl 5-butyl 1-ethylisoindoline-2,5-dicarboxylate (200 mg, 19%) as a yellow oil. LC-MS $t_R$=1.288 min in 10-80AB_2.0 min chromatography (Welch Xtimate C18, 2.1*30 mm, 3 μm), MS (ESI) m/z 292.1 [M−55]$^+$.

To a solution of (S)-2-tert-butyl 5-butyl 1-ethylisoindoline-2,5-dicarboxylate (200 mg, 0.57 mmol) in MeOH (2 mL) and THF (2 mL) was added NaOH solution (1 mL, 10% w/w in water). After addition, the reaction mixture was stirred at 20~24° C. for 16 h. The reaction mixture was then acidified to pH=2~4 with 1 N HCl solution, diluted with water (10 mL) and extracted with ethyl acetate (3×15 mL). The combined organics were washed with brine (3×30 mL), dried over anhydrous Na$_2$SO$_4$, filtered and evaporated to afford (S)-2-(tert-butoxycarbonyl)-1-ethylisoindoline-5-carboxylic acid (160 mg, 96%) as a brown solid. LC-MS $t_R$=1.021 min in 10-80AB_2.0 min chromatography (Welch Xtimate C18, 2.1*30 mm, 3 μm), MS (ESI) m/z 236.1 [M−55]$^+$.

(R)-2-(tert-butoxycarbonyl)-1-ethylisoindoline-5-carboxylic acid

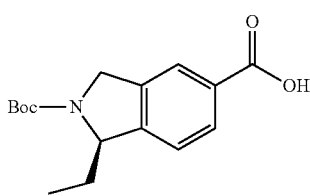

Procedure same as that for (S)-2-(tert-butoxycarbonyl)-1-ethylisoindoline-5-carboxylic acid, outlined in Scheme 6, using (R)—N—((R)-1-(4-chloro-2-(methoxymethyl)phenyl)propyl)-2-methylpropane-2-sulfinamide as the starting material. LC-MS $t_R$=1.017 min in 10-80AB_2.0 min chromatography (Welch Xtimate C18, 2.1*30 mm, 3 μm), MS (ESI) m/z 236.1 [M−55]$^+$.

(5-(ethylsulfonyl)pyridin-2-yl)methanamine was prepared following the synthetic route shown in Scheme 7.

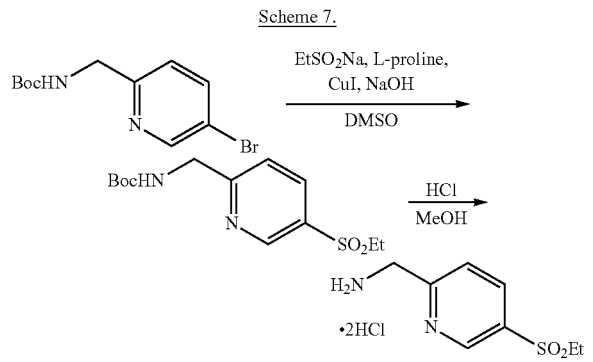

Scheme 7.

To a flame dried flask equipped with a stir bar was added tert-butyl ((5-bromopyridin-2-yl)methyl)carbamate (2.92 g, 10.2 mmol), ethane sulfinic acid sodium salt (2.36 g, 20.3 mmol), L-proline (234 mg, 2.03 mmol), copper (I) iodide (194 mg, 1.02 mmol) and sodium hydroxide (81.3 mg, 2.03 mmol). The flask was purged with N$_2$, then DMSO (35 mL) was added. The reaction mixture was heated to 110° C. and stirred for 15 h. The flask was then cooled to rt and the mixture was partitioned between EtOAc (150 mL) and saturated aqueous ammonium chloride (150 mL). The organic phase was separated, washed with brine (50 mL), dried over anhydrous MgSO$_4$, filtered and concentrated under reduced pressure. The residue was purified by silica gel chromatography (eluting with 35% EtOAc in hexanes, gradient to 60%) to afford tert-butyl((5-bromopyridin-2-yl)methyl)carbamate (1.81 g, 59%). LC-MS $t_R$=0.74 min in 1 min chromatography, MS (ESI) m/z 301.4 [M+H]$^+$. $^1$H NMR (CDCl$_3$, 400 MHz): δ 9.02 (dd, J=0.8 Hz, 2.0 Hz, 1H), 8.15 (dd, J=2.4 Hz, 8.4 Hz, 1H), 7.49 (dd, J=0.8 Hz, 8.4 Hz, 1H), 5.49 (broad s, 1H), 4.55 (d, J=7.0 Hz, 2H), 3.15 (q, J=7.2 Hz, 2H), 1.47 (s, 9H), 1.31 (t, J=7.2 Hz, 3H).

To a solution of tert-butyl ((5-bromopyridin-2-yl)methyl) carbamate (1.81 g, 6.03 mmol) in MeOH (40 mL) at 0° C. was added acetyl chloride (4.30 mL, 60.3 mmol) dropwise over 5 min. The solution was allowed to warm to rt and was stirred for 3 h. The mixture was concentrated under reduced pressure to yield 1.64 g (5-(ethylsulfonyl)pyridin-2-yl)methanamine bis-hydrochloride salt (~100%). This material was used directly for the next step without purification. LC-MS $t_R$=0.25 min in 1 min chromatography, MS (ESI) m/z 201.2 [M+H]$^+$. $^1$H NMR (CD$_3$OD, 400 MHz): δ 9.09 (d, J=1.2 Hz, 1H), 8.35 (dd, J=2.4 Hz, 8.4 Hz, 1H), 7.49 (d, J=8.4 Hz, 1H), 4.45 (s, 2H), 3.31 (q, J=7.2 Hz, 2H), 1.26 (t, J=7.2 Hz, 3H).

N-((5-(ethylsulfonyl)pyridin-2-yl)methyl)-1-isopropylisoindoline-5-carboxamide was prepared following the synthetic route shown in Scheme 8.

Scheme 8.

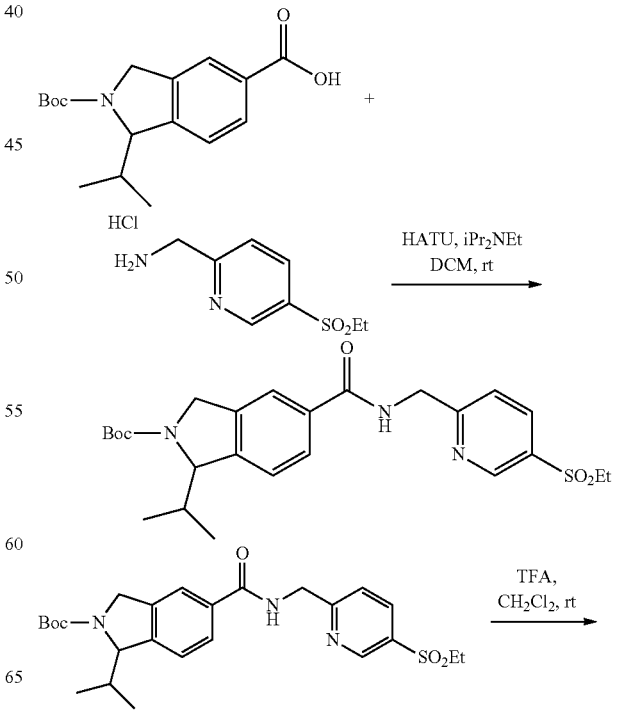

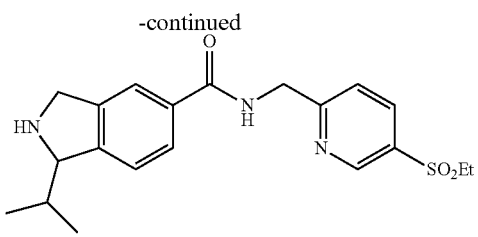

To a solution of (5-(ethylsulfonyl)pyridin-2-yl)methanamine (HCl salt, 290 mg, 1.23 mmol) in anhydrous DCM (2 mL) was added DIPEA (318 mg, 2.46 mmol), HATU (622 mg, 1.64 mmol) and 2-(tert-butoxycarbonyl)-1-isopropylisoindoline-5-carboxylic acid (250 mg, 0.82 mmol). The mixture was stirred at 25° C. for 2 h. The mixture was filtered and the filtrate was washed with $H_2O$ (5 mL) and extracted with DCM (3×5 mL). The combined organic layers were washed with $H_2O$ (5 mL) then brine (5 mL), dried over anhydrous sodium sulfate, filtered and concentrated under reduced pressure. The residue was purified by column chromatography on silica gel (eluting with 5% MeOH in DCM) to afford tert-butyl 5-(((5-(ethylsulfonyl)pyridin-2-yl)methyl)carbamoyl)-1-isopropylisoindoline-2-carboxylate (125 mg, 50%) as a white solid. A portion of this material was purified by SFC separation to afford pure enantiomers of both tert-butyl (S)-5-(((5-(ethylsulfonyl)pyridin-2-yl)methyl)carbamoyl)-1-isopropylisoindoline-2-carboxylate and tert-butyl (R)-5-(((5-(ethylsulfonyl)pyridin-2-yl)methyl)carbamoyl)-1-isopropylisoindoline-2-carboxylate.

To a solution of tert-butyl 5-((5-(ethylsulfonyl)pyridin-2-yl)methyl)carbamoyl)-1-isopropylisoindoline-2-carboxylate (50 mg, 0.102 mmol) in $CH_2Cl_2$ (2 mL) was added TFA (1 mL). The mixture was stirred at rt for 1 h. The reaction was neutralized with aqueous $NaHCO_3$ to pH=9-10. The mixture was extracted with $CH_2Cl_2$ (3×5 mL). The combined organic layers were washed with water (5 mL) then brine (5 mL), dried over anhydrous sodium sulfate, filtered and concentrated under reduced pressure to afford crude N-((5-(ethylsulfonyl)pyridin-2-yl)methyl)-1-isopropylisoindoline-5-carboxamide (50 mg, 100%) as a white solid, which was used for the next step directly without further purification. For some Examples, enantiomercially pure tert-butyl (S)-5-(((5-(ethylsulfonyl)pyridin-2-yl)methyl)carbamoyl)-1-isopropylisoindoline-2-carboxylate and tert-butyl (R)-5-(((5-(ethylsulfonyl)pyridin-2-yl)methyl)carbamoyl)-1-isopropylisoindoline-2-carboxylate were subjected to the same conditions to afford enantiomerically pure (S)—N-((5-(ethylsulfonyl)pyridin-2-yl)methyl)-1-isopropylisoindoline-5-carboxamide and (R)—N-((5-(ethylsulfonyl)pyridin-2-yl)methyl)-1-isopropylisoindoline-5-carboxamide, respectively.

(S)-1-ethyl-N-((5-(ethylsulfonyl)pyridin-2-yl)methyl)isoindoline-5-carboxamide was prepared following the synthetic route shown in Scheme 9.

Scheme 9.

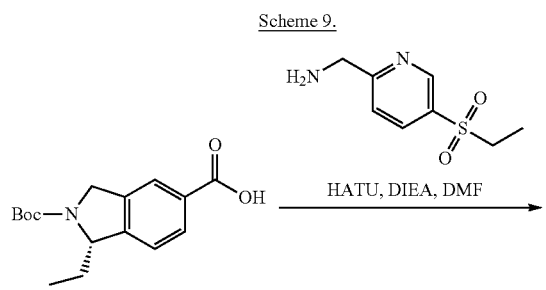

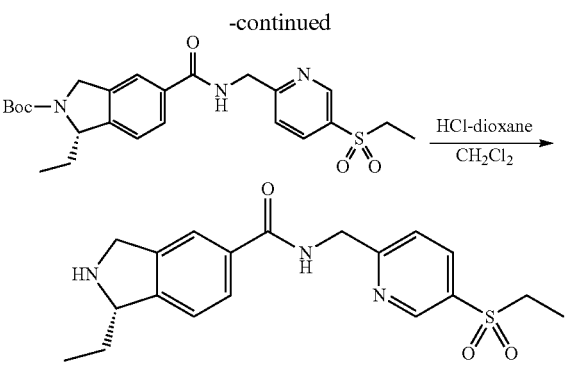

To a solution of (S)-2-(tert-butoxycarbonyl)-1-ethylisoindoline-5-carboxylic acid (40 mg, 0.14 mmol) and (5-(ethylsulfonyl)pyridin-2-yl)methanamine HCl salt (42 mg, 0.21 mmol) in DMF (1 mL) was added HATU (106 mg, 0.28 mmol) and DIEA (122 uL, 0.70 mmol, d=0.782 g/mL) under $N_2$ at rt. After addition, the reaction was stirred at rt for 16 h. The reaction mixture was then diluted with ethyl acetate (30 mL), washed with brine (20 mL), dried over anhydrous $Na_2SO_4$, filtered and evaporated. The crude residue was purified by preparative TLC (eluting with petroleum ether: ethyl acetate=1:4) to give (S)-tert-butyl 1-ethyl-5-(((5-(ethylsulfonyl)pyridin-2-yl)methyl)carbamoyl)isoindoline-2-carboxylate (30 mg, 45%) as a brown solid. LCMS $t_R$=1.110 min in 10-80AB_2.0 min chromatography (Xbridge Shield RP18 2.1*50 mm), MS (ESI) m/z 474.1 [M+H]$^+$.

To a solution of (S)-tert-butyl 1-ethyl-5-(((5-(ethylsulfonyl)pyridin-2-yl)methyl)carbamoyl)isoindoline-2-carboxylate (50 mg, 0.10 mmol) in dichloromethane (2 mL) was added HCl/dioxane (0.5 mL, 2.0 mmol, 4N) under a nitrogen atmosphere. After addition, the reaction mixture was stirred at rt for 16 h. The reaction mixture was then basified to pH=11~13 with 1 N NaOH solution. The mixture was diluted with water (10 mL) and extracted with ethyl acetate (3×15 mL). The combined organics were washed with brine (3×30 mL), dried over anhydrous $Na_2SO_4$, filtered and evaporated to afford crude (S)-1-ethyl-N-((5-(ethylsulfonyl)pyridin-2-yl)methyl)isoindoline-5-carboxamide (20 mg, 85%) as a brown solid. LC-MS $t_R$=1.249 min in 10-80CD_POS_3.0 min chromatography (Welch Xtimate C18, 2.1*30 mm, 3 μm), MS (ESI) m/z 374.1 [M+H]$^+$.

(R)-1-ethyl-N-((5-(ethylsulfonyl)pyridin-2-yl)methyl)isoindoline-5-carboxamide

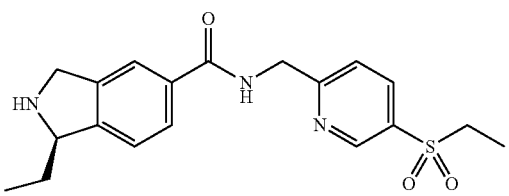 [SMILES: CC[C@H]1NCc2cc(C(=O)NCc3ccc(S(=O)(=O)CC)cn3)ccc21]

Procedure same as that for (S)-1-ethyl-N-((5-(ethylsulfonyl)pyridin-2-yl)methyl)isoindoline-5-carboxamide using (R)-2-(tert-butoxycarbonyl)-1-ethylisoindoline-5-carboxylic acid as the starting material. LC-MS $t_R$=1.253 min in 10-80CD_POS_3.0 min chromatography (Welch Xtimate C18, 2.1*30 mm, 3 μm), MS (ESI) m/z 374.1 [M+H]$^+$.

(4-(ethylsulfonyl)phenyl)methanamine was prepared following the synthetic route shown in Scheme 10.

Scheme 10.

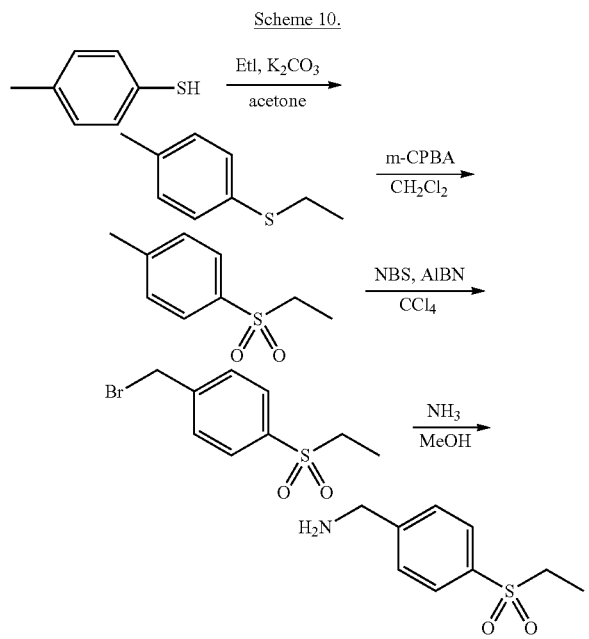

To a mixture of 4-methylbenzenethiol (100 g, 0.8 mol) in acetone (1 L) was added iodoethane (190 g, 1.2 mol) and potassium carbonate (220 g, 1.6 mol). The mixture was stirred at 60° C. overnight. The mixture was filtered and the filtrate was concentrated under reduced pressure to afford crude ethyl(p-tolyl)sulfane (120 g, 99%) as a yellow solid, which was used for the next step without further purification.

To a solution of crude ethyl(p-tolyl)sulfane (35 g, 0.23 mol) in CH$_2$Cl$_2$ (1.5 L) was added m-chloroperoxybenzoic acid (101 g, 0.59 mol) at 0° C. The mixture was stirred at rt overnight. The mixture was filtered. The filtrate was added to saturated aqueous Na$_2$SO$_3$ (500 mL) slowly and then stirred for 0.5 h. After partitioning, the organic layer was washed with saturated aqueous NaHCO$_3$ (500 mL), dried over anhydrous Na$_2$SO$_4$, filtered and concentrated under reduced pressure to afford crude 1-(ethylsulfonyl)-4-methylbenzene (42.3 g, 100%) as a pale yellow solid. This material was used for the next step without further purification.

To a solution of 1-(ethylsulfonyl)-4-methylbenzene (5 g, 25.7 mmol) in CCl$_4$ (30 mL) was added N-bromosuccinimide (5.54 g, 30.8 mmol) and azobisisobutyronitrile (0.46 g, 2.57 mmol). The mixture was stirred at 80° C. overnight. The mixture was filtered and the filtrate was concentrated under reduced pressure. The residue was added to water (50 mL) and extracted with EtOAc (3×30 mL). The combined organic layers were washed with water (2×40 mL) then brine (50 mL), dried over anhydrous Na$_2$SO$_4$, filtered and concentrated under reduced pressure to afford crude 1-(bromomethyl)-4-(ethylsulfonyl)benzene (6.62 g, 98%) as a yellow solid. This material was used for the next step without further purification.

To a solution of 1-(bromomethyl)-4-(ethylsulfonyl)benzene (6.62 g, 25.2 mmol) in MeOH (30 mL) was added a 28% aqueous ammonium hydroxide solution (30 mL). The mixture was stirred at rt overnight. The mixture was then concentrated under reduced pressure. The residue was purified by basic preparative HPLC method B separation to afford (4-(ethylsulfonyl)phenyl)methanamine (1.5 g, 30%) as a yellow solid. LC-MS t$_R$=1.747 min in 0-30CD_3 min chromatography (Durashell C18, 2.1*30 mm, 3 μm), MS (ESI) m/z 200.0 [M+H]$^+$ and 399.0 [2M+H]$^+$. $^1$H NMR (CDCl$_3$, 400 MHz): δ 7.85 (d, J=8.0 Hz, 2H), 7.53 (d, J=8.0 Hz, 2H), 3.98 (s, 2H), 3.10 (q, J=7.6 Hz, 2H), 1.26 (t, J=7.6 Hz, 3H).

Tert-butyl 5-((4-(ethylsulfonyl)benzyl)carbamoyl)-1-isopropylisoindoline-2-carboxylate

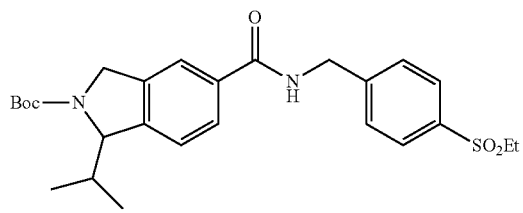

Procedure same as that for tert-butyl-5-(((5-(ethylsulfonyl)pyridin-2-yl)methyl)carbamoyl)-1-isopropylisoindoline-2-carboxylate using (4-(ethylsulfonyl)phenyl)methanamine as the starting material.

N-(4-(ethylsulfonyl)benzyl)-1-isopropylisoindoline-5-carboxamide

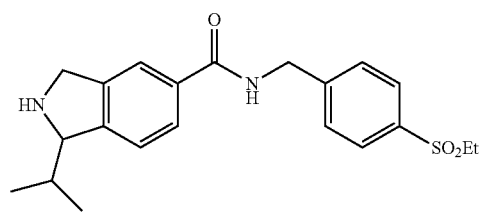

Procedure same as that for N-((5-(ethylsulfonyl)pyridin-2-yl)methyl)-1-isopropylisoindoline-5-carboxamide using tert-butyl 5-((4-(ethylsulfonyl)benzyl)carbamoyl)-1-isopropylisoindoline-2-carboxylate as the starting material. The crude product was used directly for the next step without further purification. LC-MS t$_R$=0.522 min in 5-95 AB_1.5 min chromatography (MK RP-18e 25-2 mm), MS (ESI) m/z 387.0 [M+H]$^+$.

(R)-2-amino-2-(4-(ethylsulfonyl)phenyl)ethan-1-ol (3:2 mixture of enantiomers, R:S) was prepared following the synthetic route shown in Scheme 11.

Scheme 11.

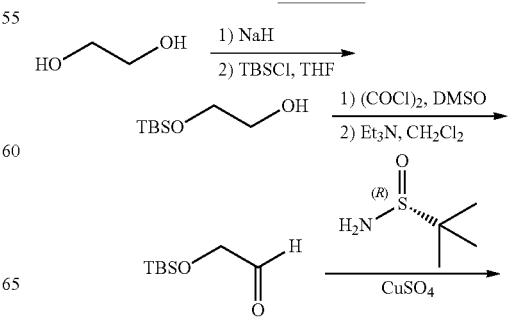

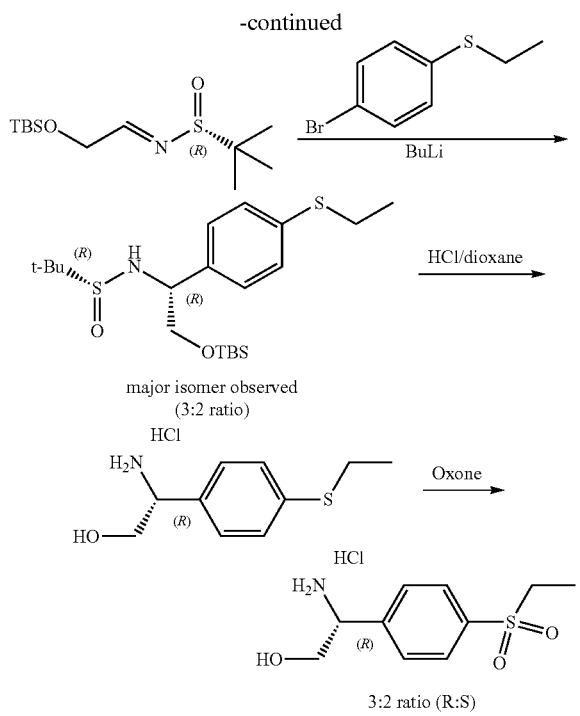

major isomer observed
(3:2 ratio)

3:2 ratio (R:S)

To a suspension of NaH (12.9 g, 0.322 mol, 60% in mineral oil) in dry THF (500 mL) was added a solution of ethane-1,2-diol (20.0 g, 0.322 mol) in dry THF (100 mL) dropwise. The mixture was stirred for 1 h at rt, then TBSCl (48.59 g, 0.322 mol) was added and the mixture was stirred for another 1 h at rt. The mixture was quenched with an aqueous $K_2CO_3$ solution (100 mL, 10%) and extracted with MTBE (3×300 mL). The combined organic layers were dried over anhydrous $Na_2SO_4$, filtered and concentrated under reduced pressure. The crude residue was purified by column chromatography on silica gel (eluting with a gradient of 1% to 33% ethyl acetate in petroleum ether) to afford 2-((tert-butyldimethylsilyl)oxy)ethanol (55.0 g, 96%) as a colorless oil.

To a solution of $(COCl)_2$ (13.7 mL, 162.2 mmol) in anhydrous $CH_2Cl_2$ (400 mL) was added DMSO (25.1 mL, 353.9 mmol) at −78° C. under $N_2$. After being stirred for 30 min, a solution of 2-((tert-butyldimethylsilyl)oxy)ethanol (26.0 g, 147.5 mmol) in anhydrous $CH_2Cl_2$ (100 mL) was added dropwise. The mixture was stirred at −78° C. for 30 min and then $Et_3N$ (102.74 mL, 737.0 mmol) was added dropwise. After being stirred at −78° C. for 30 min, the reaction was allowed to warm to rt and stirred for 1 h. The reaction mixture was acidified with 2 N aqueous HCl solution to pH=4 and then extracted with $CH_2Cl_2$ (3×400 mL). The combined organic layers were dried over anhydrous $Na_2SO_4$, filtered and concentrated under reduced pressure to afford 2-((tert-butyldimethylsilyl)oxy)acetaldehyde (34.0 g, 100%) as a colorless oil. This material was used for the next step directly without further purification.

To a solution of 2-((tert-butyldimethylsilyl)oxy)acetaldehyde (34.0 g, 147.5 mmol) and (R)-2-methylpropane-2-sulfinamide (19.6 g, 162.2 mmol) in DCM (400 mL) was added $CuSO_4$ (47.2 g, 295.0 mmol) at rt. The mixture was stirred at 25° C. for 48 h. The mixture was filtered and the filtrate was concentrated under reduced pressure. The residue was purified by column chromatography on silica gel (eluting with a gradient of 1% to 10% ethyl acetate in petroleum ether) to afford (R,E)-N-(2-((tert-butyldimethylsilyl)oxy)ethylidene)-2-methylpropane-2-sulfinamide (30.0 g, 73%) as a yellow oil. $^1$H NMR (CDCl$_3$ 400 MHz): δ 7.96 (t, J=3.2 Hz, 1H), 4.45 (d, J=3.2 Hz, 2H), 1.11 (s, 9H), 0.82 (s, 9H), 0.00 (s, 6H).

To a solution of (4-bromophenyl)(ethyl)sulfane (1.88 g, 8.65 mmol) in anhydrous THF (15 mL) was added n-BuLi (14.4 mL, 36.0 mmol, 2.5 M in THF) at −78° C. under $N_2$. The reaction mixture was stirred at −78° C. for 0.5 h, then a solution of (R,E)-N-(2-((tert-butyldimethylsilyl)oxy)ethylidene)-2-methylpropane-2-sulfinamide (2.0 g, 7.2 mmol) in THF (1 mL) was added dropwise to the mixture at −78° C. The reaction mixture was stirred at −78° C. for 0.5 h and was allowed to warm to rt. After 0.5 h at rt, the reaction mixture was quenched with water (10 mL) and extracted with ethyl acetate (3×20 mL). The combined organic layers were washed with $H_2O$ (10 mL) then brine (10 mL), dried over anhydrous sodium sulfate, filtered and concentrated under reduced pressure.

The crude residue was purified by column chromatography on silica gel (eluting with a gradient of 5% to 10% ethyl acetate in petroleum ether) to afford a 3:2 mixture of (R)—N—((R)-2-((tert-butyldimethylsilyl)oxy)-1-(4-(ethylthio)phenyl)ethyl)-2-methylpropane-2-sulfinamide and (R)—N—((S)-2-((tert-butyldimethylsilyl)oxy)-1-(4-(ethylthio)phenyl)ethyl)-2-methylpropane-2-sulfinamide (2.86 g, 47.9%) as a yellow oil. This 3:2 mixture of diastereomers was used for the subsequent reactions. $^1$H NMR (CDCl$_3$ 400 MHz): δ 7.24-7.16 (m, 4H), 4.47-4.40 (m, 1H), 4.21 (s, 1H), 3.75-3.67 (m, 1H), 3.60-3.47 (m, 1H), 2.90 (q, J=7.2 Hz, 2H), 1.27 (t, J=7.2 Hz, 3H), 1.18 (s, 9H), 0.85 (s, 9H), 0.02 (s, 3H), 0.00 (s, 3H).

To a solution of (R)—N—((R)-2-((tert-butyldimethylsilyl)oxy)-1-(4-(ethylthio)phenyl)ethyl)-2-methylpropane-2-sulfinamide (2.86 g, 6.86 mmol), as a 3:2 mixture of diastereomers from previous step, in dioxane (10 mL) was added HCl in dioxane (20 mL, 4 M) at rt. The mixture was stirred for 3 h at rt and was then concentrated under reduced pressure to afford crude (R)-2-amino-2-(4-(ethylthio)phenyl)ethan-1-ol HCl salt (3.0 g, 100%) as a white solid. This crude material was a 3:2 mixture of enantiomers (R:S) and used for the next step without further purification.

To a solution of (R)-2-amino-2-(4-(ethylthio)phenyl)ethan-1-ol HCl salt (3.0 g, 6.86 mmol), as a 3:2 mixture of enantiomers/R:S, in $H_2O$ (30 mL) was added Oxone® monopersulfate (8.4 g, 13.72 mmol) at rt. The mixture was stirred for 1.5 h at rt and was lyophilized directly. After lyophilization, the crude product was purified by flash column chromatography on silica gel (eluting with MeOH) to give crude (R)-2-amino-2-(4-(ethylsulfonyl)phenyl)ethan-1-ol HCl salt (3:2 mixture of enantiomers, R:S) (1.25 g, 80%) as a yellow solid. $^1$H NMR (CDCl$_3$ 400 MHz): δ 7.99 (d, J=8.4 Hz, 2H), 7.73 (d, J=8.0 Hz, 2H), 4.55-4.50 (m, 1H), 3.99-3.91 (m, 1H), 3.85-3.80 (m, 1H), 3.23 (q, J=7.2 Hz, 2H), 1.21 (t, J=7.2 Hz, 3H).

(S)-1-ethyl-N—((R)-1-(4-(ethylsulfonyl)phenyl)-2-hydroxyethyl)isoindoline-5-carboxamide (3:2 mixture of diastereomers) was prepared following the synthetic route shown in Scheme 12.

Scheme 12.

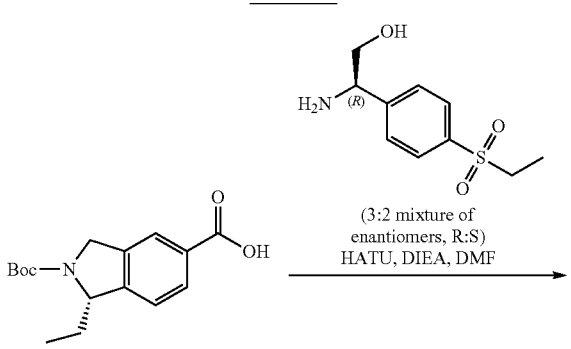

(3:2 mixture of enantiomers, R:S)
HATU, DIEA, DMF

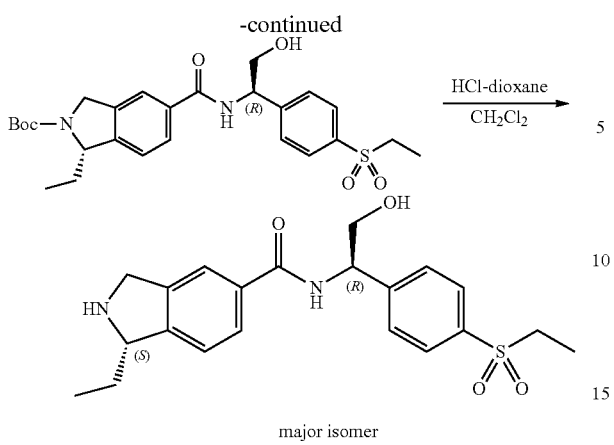

major isomer

To a solution of (S)-2-(tert-butoxycarbonyl)-1-ethylisoindoline-5-carboxylic acid (120 mg, 0.41 mmol) and (R)-2-amino-2-(4-(ethylsulfonyl)phenyl)ethanol (113 mg, 0.49 mmol), as a 3:2 mixture of enantiomers (R:S), in DMF (5 mL) was added HATU (312 mg, 0.82 mmol) and DIEA (0.36 mL, 2.05 mmol, d=0.782 g/mL) under a nitrogen atmosphere. After addition, the reaction mixture was stirred at 24~27° C. for 18 h. TLC analysis (eluting with $CH_2Cl_2$:MeOH=10:1) showed complete consumption of the starting material. The reaction mixture was diluted with ethyl acetate (30 mL), washed with brine (3×20 mL), dried over anhydrous $Na_2SO_4$, filtered and evaporated. The crude residue was purified by preparative TLC (eluting with $CH_2Cl_2$:MeOH=10:1) to give a 3:2 mixture of (S)-tert-butyl 1-ethyl-5-(((R)-1-(4-(ethylsulfonyl)phenyl)-2-hydroxyethyl)carbamoyl)isoindoline-2-carboxylate and (S)-tert-butyl 1-ethyl-5-(((S)-1-(4-(ethylsulfonyl)phenyl)-2-hydroxyethyl)carbamoyl)isoindoline-2-carboxylate (180 mg, 41%, 47% chemical purity) as a brown oil. LC-MS $t_R$=1.223 min in 10-80AB_2.0 min chromatography (Welch Xtimate C18, 2.1*30 mm, 3 μm), MS (ESI) m/z 503.2 [M+H]$^+$.

To a solution of (S)-tert-butyl 1-ethyl-5-(((R)-1-(4-(ethylsulfonyl)phenyl)-2-hydroxyethyl)carbamoyl)isoindoline-2-carboxylate and (S)-tert-butyl 1-ethyl-5-(((S)-1-(4-(ethylsulfonyl)phenyl)-2-hydroxyethyl)carbamoyl)isoindoline-2-carboxylate (180 mg, 0.17 mmol, 47% chemical purity) in dichloromethane (4.0 mL) was added HCl/dioxane (1.0 mL, 4.0 mmol, 4N) under a nitrogen atmosphere. After addition, the reaction mixture was stirred at 23~30° C. for 16 h. TLC analysis (eluting with $CH_2Cl_2$:MeOH=10:1) showed complete consumption of the starting material. The solvents were removed under reduced pressure to afford the residue which was purified by basic preparative HPLC method C to give a 3:2 mixture of (S)-1-ethyl-N—((R)-1-(4-(ethylsulfonyl)phenyl)-2-hydroxyethyl)isoindoline-5-carboxamide and (S)-1-ethyl-N—((S)-1-(4-(ethylsulfonyl)phenyl)-2-hydroxyethyl)isoindoline-5-carboxamide (70 mg, 100%) as a white solid. LC-MS $t_R$=1.276 min in 10-80CD_POS_3.0 min chromatography (Welch Xtimate C18, 2.1*30 mm, 3 μm), MS (ESI) m/z 403.1 [M+H]$^+$.

Tert-butyl (R)-1-ethyl-5-(((R)-1-(4-(ethylsulfonyl)phenyl)-2-hydroxyethyl)carbamoyl)isoindoline-2-carboxylate:

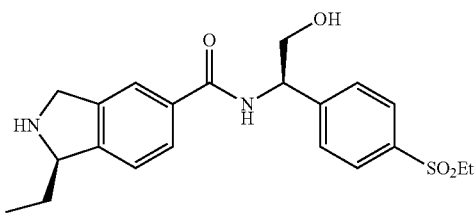

Procedure same as that for (S)-tert-butyl 1-ethyl-5-(((R)-1-(4-(ethylsulfonyl)phenyl)-2-hydroxyethyl)carbamoyl)isoindoline-2-carboxylate using (R)-2-(tert-butoxycarbonyl)-1-ethylisoindoline-5-carboxylic acid and (R)-2-amino-2-(4-(ethylsulfonyl)phenyl)ethanol (3:2 mixture of enantiomers/R:S) as the starting materials. LC-MS $t_R$=1.095 min in 10-80AB_2.0 min chromatography (Welch Xtimate C18, 2.1*30 mm, 3 μm), MS (ESI) m/z 503.1 [M+H]$^+$.

(R)-1-ethyl-N—((R)-1-(4-(ethylsulfonyl)phenyl)-2-hydroxyethyl)isoindoline-5-carboxamide

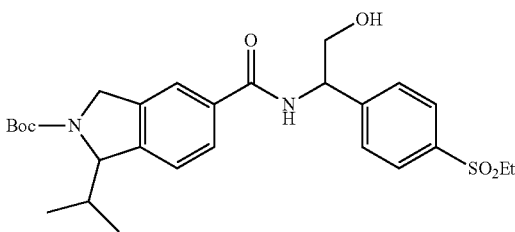

Procedure same as that for (S)-1-ethyl-N—((R)-1-(4-(ethylsulfonyl)phenyl)-2-hydroxyethyl)isoindoline-5-carboxamide using tert-butyl (R)-1-ethyl-5-(((R)-1-(4-(ethylsulfonyl)phenyl)-2-hydroxyethyl)carbamoyl)isoindoline-2-carboxylate (3:2 mixture of diastereomers) as the starting material. LC-MS $t_R$=1.252 min in 10-80CD_POS_3.0 min chromatography (Welch Xtimate C18, 2.1*30 mm, 3 μm), MS (ESI) m/z 403.1 [M+H]$^+$.

Tert-butyl 5-((1-(4-(ethylsulfonyl)phenyl)-2-hydroxyethyl)carbamoyl)-1-isopropylisoindoline-2-carboxylate

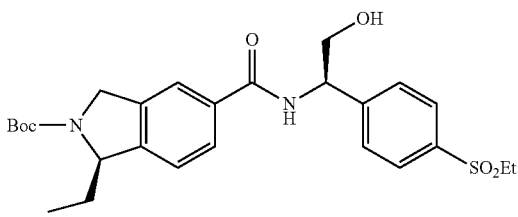

Procedure same as that for (S)-tert-butyl 1-ethyl-5-(((R)-1-(4-(ethylsulfonyl)phenyl)-2-hydroxyethyl)carbamoyl)isoindoline-2-carboxylate using 2-(tert-butoxycarbonyl)-1-isopropylisoindoline-5-carboxylic acid and (R)-2-amino-2-(4-(ethylsulfonyl)phenyl)ethanol (3:2 mixture of enantiomers/R:S) as the starting materials. Most of this intermediate was used for the subsequent reactions as a mixture of 4 diastereomers which was ultimately subjected to SFC separation after the final step of the sequence. However, a portion of this intermediate was purified by SFC separation at this stage to afford pure diastereomers of tert-butyl (S)-5-(((R)-1-(4-(ethylsulfonyl)phenyl)-2-hydroxyethyl)carbamoyl)-1-isopropylisoindoline-2-carboxylate and tert-butyl (R)-5-(((R)-1-(4-(ethylsulfonyl)phenyl)-2-hydroxyethyl)carbamoyl)-1-isopropylisoindoline-2-carboxylate. In some Examples, these enantiomercially pure intermediates were used in subsequent reactions to isolate final compounds. LC-MS $t_R$=0.777 min in 5-95 AB_1.5 min chromatography (Welch MERCK RP-18e 25-2 mm), MS (ESI) m/z 539.0 [M+Na]$^+$.

N-(1-(4-(ethylsulfonyl)phenyl)-2-hydroxyethyl)-1-isopropylisoindoline-5-carboxamide

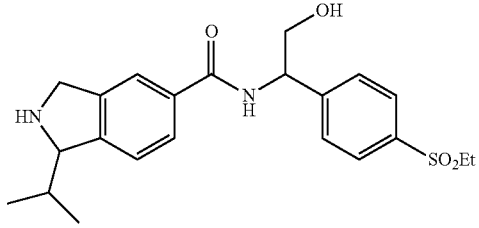

Procedure same as that for (S)-1-ethyl-N—((R)-1-(4-(ethylsulfonyl)phenyl)-2-hydroxyethyl)isoindoline-5-carboxamide using tert-butyl 5-((1-(4-(ethylsulfonyl)phenyl)-2-hydroxyethyl)carbamoyl)-1-isopropylisoindoline-2-carboxylate as the starting material. The crude product was used directly for the next step without further purification. For some Examples, tert-butyl (S)-5-(((R)-1-(4-(ethylsulfonyl)phenyl)-2-hydroxyethyl)carbamoyl)-1-isopropylisoindoline-2-carboxylate and tert-butyl (R)-5-(((R)-1-(4-(ethylsulfonyl)phenyl)-2-hydroxyethyl)carbamoyl)-1-isopropylisoindoline-2-carboxylate were subjected to the same conditions to afford enantiomercially pure (S)—N—((R)-1-(4-(ethylsulfonyl)phenyl)-2-hydroxyethyl)-1-isopropylisoindoline-5-carboxamide and (R)—N—((R)-1-(4-(ethylsulfonyl)phenyl)-2-hydroxyethyl)-1-isopropylisoindoline-5-carboxamide, respectively. In some Examples, these enantiomercially pure intermediates were used in subsequent reactions to isolate final compounds.

(R)-2-amino-2-(5-(ethylsulfonyl)pyridin-2-yl)ethan-1-ol (3:2 mixture of enantiomers, R:S) was prepared following the synthetic route shown in Scheme 13.

Scheme 13.

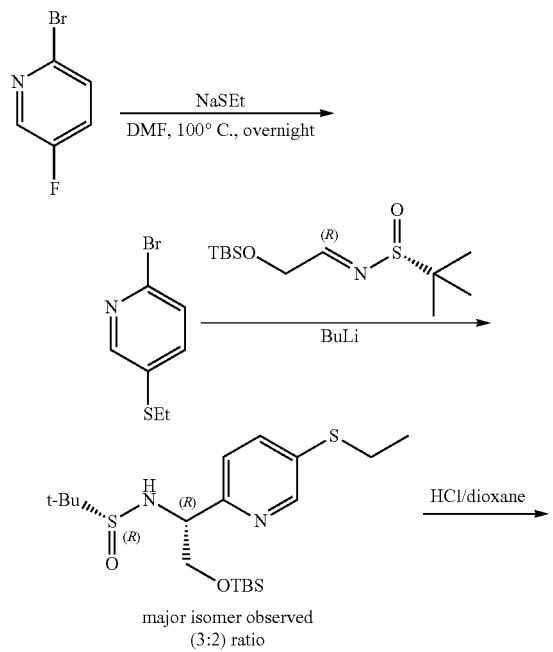

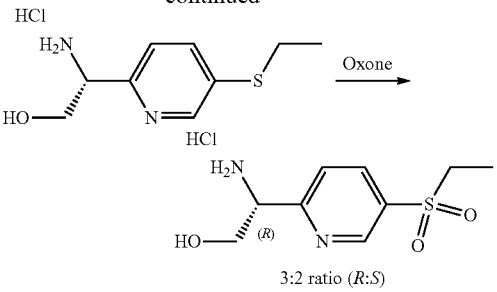

3:2 ratio (R:S)

To a mixture of 2-bromo-5-fluoropyridine (6.28 g, 35.66 mmol) in anhydrous DMF (60 mL) was added NaSEt (3 g, 35.66 mmol). The mixture was stirred at 100° C. for 3 h under $N_2$. TLC analysis (eluting with 10% ethyl acetate in petroleum ether) showed that the starting material was not consumed completely, therefore additional NaSEt (0.9 g, 9.56 mmol) was added to the mixture. The mixture was stirred at 100° C. for another 12 h under $N_2$. The mixture was added to $H_2O$ (150 mL) and extracted with ethyl acetate (3×150 mL). The combined organic layers were washed with brine (400 mL), dried over anhydrous sodium sulfate, filtered and concentrated under reduced pressure. The residue was purified by column chromatography on silica gel (eluting with 2% ethyl acetate in petroleum ether) to afford 2-bromo-5-(ethylthio)pyridine (7.0 g, 90%) as a colorless oil. LC-MS $t_R$=0.717 min in 5-95AB_1.5 min chromatography (Welch Merck RP-18e 25-2 mm), MS (ESI) m/z 217.6 [M+H]$^+$.

To a solution of toluene (60 mL) was added n-BuLi (10.6 mL, 26.48 mmol, 2.5 M in hexane) dropwise at −78° C. under $N_2$ such that the internal temperature did not exceed −50° C. Then a solution of 2-bromo-5-(ethylthio)pyridine (3.85 g, 17.65 mmol) in toluene (10 mL) was added to the reaction mixture at −78° C. such that the internal temperature did not exceed −65° C. The mixture was stirred at −78° C. for 1 h under $N_2$. A solution of (R,E)-N-(2-((tert-butyldimethylsilyl)oxy)ethylidene)-2-methylpropane-2-sulfinamide (4.90 g, 17.65 mmol) in toluene (10 mL) was added to the reaction mixture at −78° C. such that the internal temperature did not exceed −60° C. The mixture was stirred at −78° C. for another 2 h under $N_2$. The mixture was quenched with brine (150 mL) at −78° C. and extracted with ethyl acetate (3×150 mL). The combined organic layers were washed with brine (400 mL), dried over anhydrous sodium sulfate, filtered and concentrated under reduced pressure. The residue was purified by column chromatography on silica gel (eluting with a gradient of 10% to 33% ethyl acetate in petroleum ether) to afford a 3:2 mixture of (R)—N—((R)-2-((tert-butyldimethylsilyl)oxy)-1-(5-(ethylthio)pyridin-2-yl)ethyl)-2-methylpropane-2-sulfinamide and (R)—N—((S)-2-((tert-butyldimethylsilyl)oxy)-1-(5-(ethylthio)pyridin-2-yl)ethyl)-2-methylpropane-2-sulfinamide (3.0 g, 41%) as a pale yellow oil. This 3:2 mixture of diastereomers was used for the subsequent reactions. LC-MS $t_R$=1.014 min in 5-95AB_1.5 min chromatography (Welch Merck RP-18e 25-2 mm), MS (ESI) m/z 417.2 [M+H]$^+$.

(R)—N—((R)-2-((tert-butyldimethylsilyl)oxy)-1-(5-(ethylthio)pyridin-2-yl)ethyl)-2-methylpropane-2-sulfinamide (4.9 g, 11.76 mmol), as a 3:2 mixture of diastereomers from the previous step, in 1,4-dioxane (30 mL) was added HCl/dioxane (12 mL, 4 N) at 0° C. The mixture was stirred at rt for 2 h. The mixture was concentrated under reduced pressure to afford crude (R)-2-amino-2-(5-(ethylthio)pyridin-2-yl)ethan-1-ol HCl salt (2.5 g, 91%) as a yellow solid. This material was a 3:2 mixture of enantiomers (R:S) and was used for the next step directly without further purification.

To a mixture of (R)-2-amino-2-(5-(ethylthio)pyridin-2-yl)ethan-1-ol HCl salt (2.5 g, 10.66 mmol) in H$_2$O (40 mL) was added Oxone® monopersulfate (13.1 g, 21.32 mmol). The mixture was stirred at rt for 2 h. CH$_3$CN (15 mL) was added and the reaction mixture was lyophilized. After lyophilization, the crude product was purified by flash column chromatography on silica gel (eluting with MeOH). After concentration, the residue was purified again by column chromatography on silica gel (eluting with 10% MeOH in DCM) to afford (R)-2-amino-2-(5-(ethylsulfonyl)pyridin-2-yl)ethan-1-ol (3:2 mixture of enantiomers/R:S) (1.9 g, 67%) as a black solid. $^1$H NMR (CD$_3$OD 400 MHz): δ 9.08 (s, 1H), 8.35 (dd, J=2.0, 8.4 Hz, 1H), 7.79 (d, J=8.4 Hz, 1H), 4.70 (t, J=5.6 Hz, 1H), 4.03 (dd, J=4.8, 12.0 Hz, 1H), 3.91 (dd, J=4.8, 11.6 Hz, 1H), 3.29 (q, J=7.2 Hz, 2H), 1.25 (t, J=7.2 Hz, 3H).

Tert-butyl 5-(((R)-1-(5-(ethylsulfonyl)pyridin-2-yl)-2-hydroxyethyl)carbamoyl)-1-isopropylisoindoline-2-carboxylate

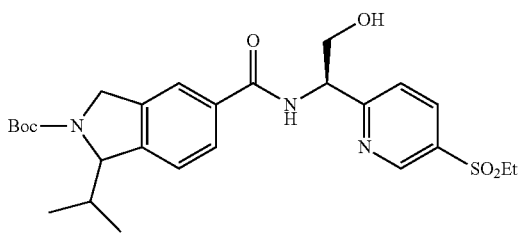

Procedure same as that for (S)-tert-butyl 1-ethyl-5-(((R)-1-(4-(ethylsulfonyl)phenyl)-2-hydroxyethyl)carbamoyl)isoindoline-2-carboxylate using 2-(tert-butoxycarbonyl)-1-isopropylisoindoline-5-carboxylic acid and (R)-2-amino-2-(5-(ethylsulfonyl)pyridin-2-yl)ethan-1-ol (3:2 mixture of enantiomers, R:S) as the starting materials. LC-MS t$_R$=0.778 min in 5-95AB_1.5 min chromatography (Welch MERCK RP-18e 25-2 mm), MS (ESI) m/z 518.0 [M+H]$^+$.

N—((R)-1-(5-(ethylsulfonyl)pyridin-2-yl)-2-hydroxyethyl)-1-isopropylisoindoline-5-carboxamide

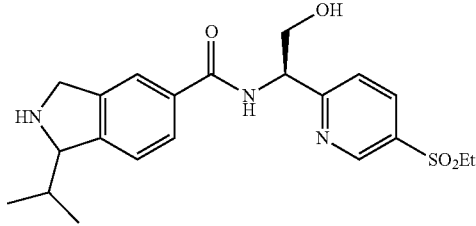

Procedure same as that for (S)-1-ethyl-N— ((R)-1-(4-(ethylsulfonyl)phenyl)-2-hydroxyethyl)isoindoline-5-carboxamide using tert-butyl 5-(((R)-1-(5-(ethylsulfonyl)pyridin-2-yl)-2-hydroxyethyl)carbamoyl)-1-isopropylisoindoline-2-carboxylate as the starting material.

Tert-butyl (S)-1-ethyl-5-(((R)-1-(5-(ethylsulfonyl)pyridin-2-yl)-2-hydroxyethyl)carbamoyl)isoindoline-2-carboxylate

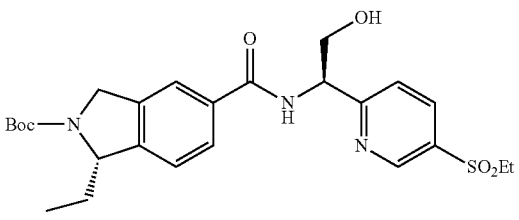

Procedure same as that for (S)-tert-butyl 1-ethyl-5-(((R)-1-(4-(ethylsulfonyl)phenyl)-2-hydroxyethyl)carbamoyl)isoindoline-2-carboxylate using (R)-2-amino-2-(5-(ethylsulfonyl)pyridin-2-yl)ethan-1-ol (3:2 mixture of enantiomers, R:S) as the starting material. LCMS t$_R$=0.711 min in 5-95AB_1.5 min chromatography (MK RP18e 25-2 mm), MS (ESI) m/z 504.1 [M+H]$^+$.

(S)-1-ethyl-N—((R)-1-(5-(ethylsulfonyl)pyridin-2-yl)-2-hydroxyethyl)isoindoline-5-carboxamide

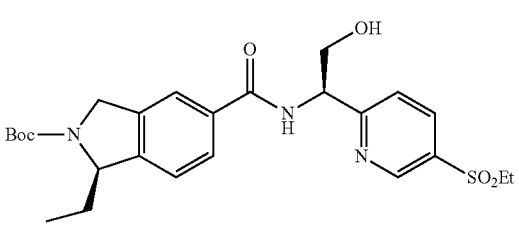

Procedure same as that for (S)-1-ethyl-N— ((R)-1-(4-(ethylsulfonyl)phenyl)-2-hydroxyethyl)isoindoline-5-carboxamide using tert-butyl (S)-1-ethyl-5-(((R)-1-(5-(ethylsulfonyl)pyridin-2-yl)-2-hydroxyethyl)carbamoyl)isoindoline-2-carboxylate as the starting material.

Tert-butyl (R)-1-ethyl-5-(((R)-1-(5-(ethylsulfonyl)pyridin-2-yl)-2-hydroxyethyl)carbamoyl)isoindoline-2-carboxylate Procedure same as that for (S)-tert-butyl 1-ethyl-5-(((R)-1-(4-(ethylsulfonyl)phenyl)-2-hydroxyethyl)carbamoyl)isoindoline-2-carboxylate using (R)-2-(tert-butoxycarbonyl)-1-ethylisoindoline-5-carboxylic acid and (R)-2-amino-2-(5-(ethylsulfonyl)pyridin-2-yl)ethan-1-ol (3:2 mixture of enantiomers, R:S) as the starting materials. LCMS t$_R$=0.715 min in 5-95AB_1.5 min chromatography (MK RP18e 25-2 mm), MS (ESI) m/z 504.2 [M+H]$^+$.

(R)-1-ethyl-N—((R)-1-(5-(ethylsulfonyl)pyridin-2-yl)-2-hydroxyethyl)isoindoline-5-carboxamide

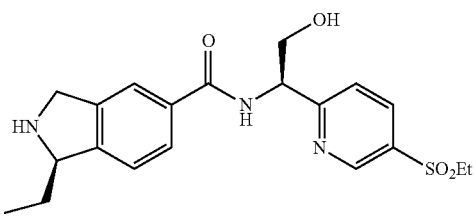

Procedure same as that for (S)-1-ethyl-N—((R)-1-(4-(ethylsulfonyl)phenyl)-2-hydroxyethyl)isoindoline-5-carboxamide using tert-butyl (R)-1-ethyl-5-(((R)-1-(5-(ethylsulfonyl)pyridin-2-yl)-2-hydroxyethyl)carbamoyl)isoindoline-2-carboxylate as the starting material.

(1-(methylsulfonyl)piperidin-4-yl)methanamine was prepared following the synthetic route shown in Scheme 14.

Scheme 14.

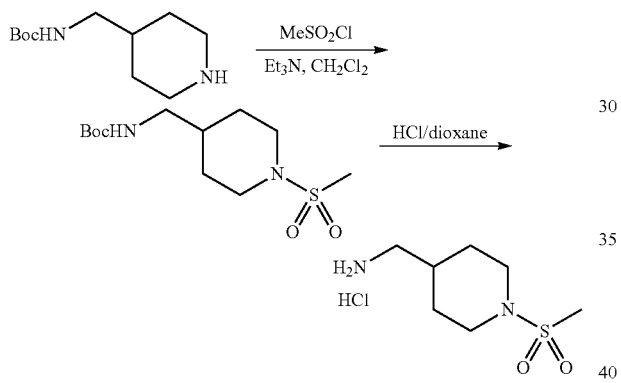

To a mixture of tert-butyl (piperidin-4-ylmethyl)carbamate (500 mg, 2.34 mmol) and Et$_3$N (1.18 g, 1.63 mL, 11.7 mmol) in CH$_2$Cl$_2$ (8 mL) was added MsCl (536 mg, 4.68 mmol) at 0° C. The mixture was stirred at rt overnight. TLC (CH$_2$Cl$_2$:MeOH=2:1) showed that the tert-butyl(piperidin-4-ylmethyl)carbamate was consumed. The mixture was added with CH$_2$Cl$_2$ (30 mL), washed with 1 N HCl (3×20 mL) and then brine (20 mL). The organic layer was dried over anhydrous sodium sulfate, filtered and concentrated under reduced pressure to give tert-butyl ((1-(methylsulfonyl)piperidin-4-yl)methyl)carbamate (650 mg, 95%) as a yellow solid, which was used for the next step directly without further purification. $^1$H NMR (CDCl$_3$ 400 MHz): δ 4.65 (brs, 1H), 3.81 (d, J=12.4 Hz, 2H), 3.05 (t, J=6.4 Hz, 2H), 2.77 (s, 3H), 2.65 (t, J=11.6 Hz, 2H), 1.81 (d, J=12.4 Hz, 2H), 1.62-1.57 (m, 1H), 1.44 (s, 9H), 1.37-1.30 (m, 2H).

To a mixture of tert-butyl-((1-(methylsulfonyl)piperidin-4-yl)methyl)carbamate (650 mg, 2.22 mmol) in dioxane (5 mL) was added HCl/dioxane (5 mL, 4N). The mixture was stirred at rt for 3 h. The mixture was concentrated under reduced pressure to give (1-(methylsulfonyl)piperidin-4-yl)methanamine HCl salt (500 mg, 98%) as a white solid, which was used for the next step directly without further purification. $^1$H NMR (DMSO-d$_6$ 400 MHz): δ 7.93 (brs, 3H), 3.55-3.53 (m, 2H), 2.85 (s, 3H), 2.74-2.65 (m, 4H), 1.80 (d, J=13.2 Hz, 2H), 1.70-1.60 (m, 1H), 1.25-1.17 (m, 2H).

Tert-butyl 1-isopropyl-5-(((1-(methylsulfonyl)piperidin-4-yl)methyl)carbamoyl)isoindoline-2-carboxylate

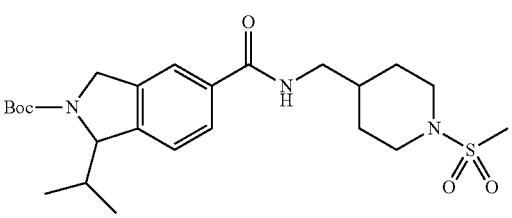 [SMILES: CC(C)C1c2ccc(C(=O)NCC3CCN(S(C)(=O)=O)CC3)cc2CN1C(=O)OC(C)(C)C]

Procedure same as that for tert-butyl-5-(((5-(ethylsulfonyl)pyridin-2-yl)methyl)carbamoyl)-1-isopropylisoindoline-2-carboxylate using (1-(methylsulfonyl)piperidin-4-yl)methanamine HCl salt as the starting material. Most of this intermediate was used for the subsequent reactions as a mixture of enantiomers which was ultimately subjected to SFC separation after the final step of the sequence. However, a portion of this intermediate was purified by SFC separation at this stage to afford pure enantiomers of tert-butyl (S)-1-isopropyl-5-(((1-(methylsulfonyl)piperidin-4-yl)methyl)carbamoyl)isoindoline-2-carboxylate and tert-butyl (R)-1-isopropyl-5-(((1-(methylsulfonyl)piperidin-4-yl)methyl)carbamoyl)isoindoline-2-carboxylate. LCMS t$_R$=0.786 min in 5-95AB_1.5 min chromatography (MK RP18e 25-2 mm), MS (ESI) m/z 480.0 [M+H]$^+$.

1-isopropyl-N-((1-(methylsulfonyl)piperidin-4-yl)methyl)isoindoline-5-carboxamide

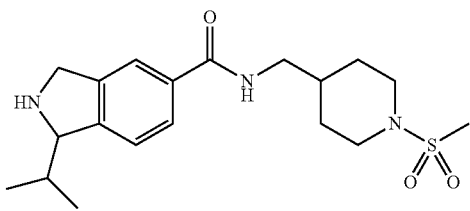 [SMILES: CC(C)C1NCc2cc(C(=O)NCC3CCN(S(C)(=O)=O)CC3)ccc21]

Procedure same as that for N-((5-(ethylsulfonyl)pyridin-2-yl)methyl)-1-isopropylisoindoline-5-carboxamide using tert-butyl 1-isopropyl-5-(((1-(methylsulfonyl)piperidin-4-yl)methyl)carbamoyl)isoindoline-2-carboxylate as the starting material. For some Examples, enantiomercially pure tert-butyl (S)-1-isopropyl-5-(((1-(methylsulfonyl)piperidin-4-yl)methyl)carbamoyl)isoindoline-2-carboxylate and tert-butyl (R)-1-isopropyl-5-(((1-(methylsulfonyl)piperidin-4-yl)methyl)carbamoyl)isoindoline-2-carboxylate were subjected to the same conditions to afford (S)-1-isopropyl-N-((1-(methylsulfonyl)piperidin-4-yl)methyl)isoindoline-5-carboxamide, respectively.

(1-(ethylsulfonyl)piperidin-4-yl)methanamine was prepared following the synthetic route shown in Scheme 15.

Scheme 15.

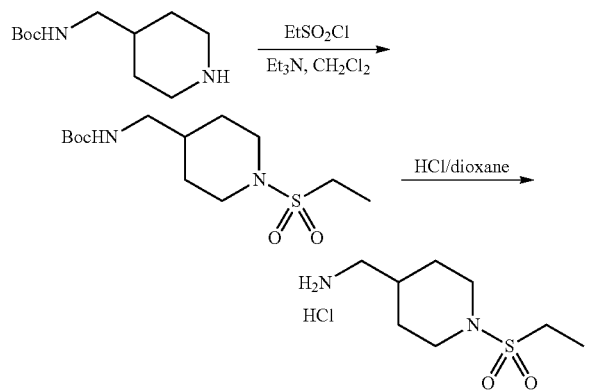

To a mixture of tert-butyl-(piperidin-4-ylmethyl)carbamate (500 mg, 2.34 mmol) and Et$_3$N (1.18 g, 1.63 mL, 11.7 mmol) in CH$_2$Cl$_2$ (8 mL) was added EtSO$_2$Cl (602 mg, 4.68 mmol) at 0° C. The mixture was stirred at rt overnight. The mixture was added with CH$_2$Cl$_2$ (30 mL), washed with 1 N HCl (3×20 mL) and brine (20 mL). The organic layer was dried over anhydrous sodium sulfate, filtered and concentrated under reduced pressure to give tert-butyl ((1-(ethylsulfonyl)piperidin-4-yl)methyl)carbamate (700 mg, 98%) as a brown oil, which was used for the next step directly without further purification. $^1$H NMR (CDCl$_3$ 400 MHz): δ 4.64 (brs, 1H), 3.82 (d, J=12.4 Hz, 2H), 3.04 (t, J=6.4 Hz, 2H), 2.94 (q, J=7.6 Hz, 2H), 2.78 (t, J=10.0 Hz, 2H), 1.78 (d, J=12.8 Hz, 2H), 1.65-1.55 (m, 1H), 1.44 (s, 9H), 1.35 (t, J=7.6 Hz, 3H), 1.30-1.26 (m, 2H).

To a mixture of tert-butyl ((1-(ethylsulfonyl)piperidin-4-yl)methyl)carbamate (700 mg, 2.28 mmol) in dioxane (5 mL) was added HCl/dioxane (5 mL, 4N). The mixture was stirred at rt for 3 h. The mixture was concentrated under reduced pressure to give (1-(ethylsulfonyl)piperidin-4-yl)methanamine HCl salt (530 mg, 96%) as a slight yellow solid, which was used for the next step directly without further purification. $^1$H NMR (DMSO-d$_6$ 400 MHz): δ 8.05 (brs, 3H), 3.60-3.55 (m, 2H), 3.02 (q, J=7.6 Hz, 2H), 2.75-2.71 (m, 4H), 1.80-1.71 (m, 3H), 1.21-1.16 (m, 5H).

Tert-butyl 5-(((1-(ethylsulfonyl)piperidin-4-yl)methyl)carbamoyl)-1-isopropylisoindoline-2-carboxylate

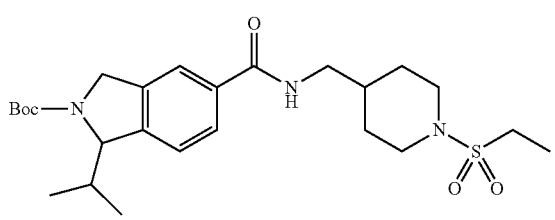 [SMILES: CCS(=O)(=O)N1CCC(CNC(=O)c2ccc3c(c2)CN(C(=O)OC(C)(C)C)C3C(C)C)CC1]

Procedure same as that for tert-butyl-5-(((5-(ethylsulfonyl)pyridin-2-yl)methyl)carbamoyl)-1-isopropylisoindoline-2-carboxylate using (1-(ethylsulfonyl)piperidin-4-yl)methanamine HCl salt as the starting material.

N-((1-(ethylsulfonyl)piperidin-4-yl)methyl)-1-isopropylisoindoline-5-carboxamide

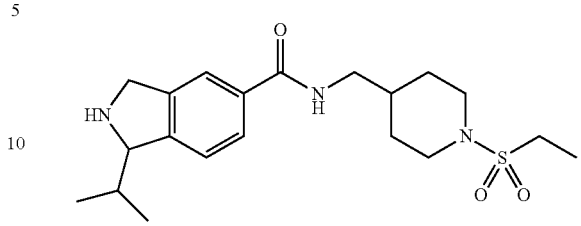

Procedure same as that for N-((5-(ethylsulfonyl)pyridin-2-yl)methyl)-1-isopropylisoindoline-5-carboxamide using tert-butyl 5-(((1-(ethylsulfonyl)piperidin-4-yl)methyl)carbamoyl)-1-isopropylisoindoline-2-carboxylate as the starting material.

(S)-3-amino-3-(4-(ethylsulfonyl)phenyl)propan-1-ol was prepared following the synthetic route shown in Scheme 16.

Scheme 16.

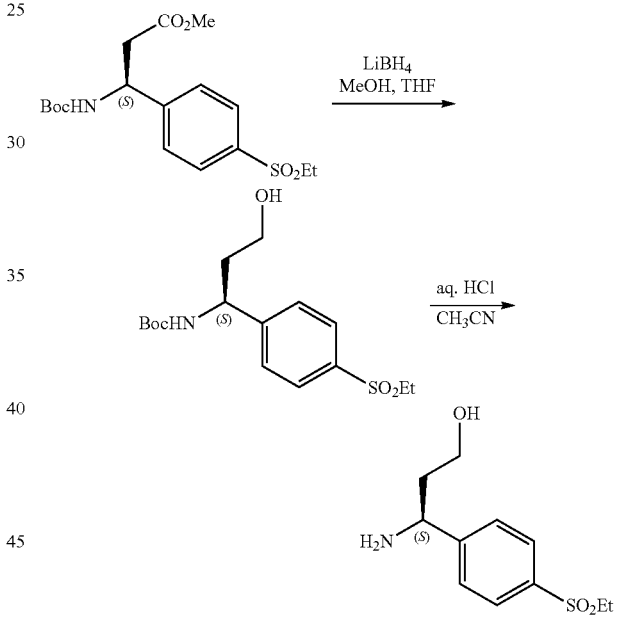

To a solution of (S)-methyl 3-((tert-butoxycarbonyl)amino)-3-(4-(ethylsulfonyl)phenyl)propanoate (650 mg, 1.75 mmol) in anhydrous MeOH/THF (1:3, 12 mL) was added LiBH$_4$ (367 mg, 17.5 mmol). The mixture was stirred at rt overnight. The mixture was concentrated under reduced pressure and the residue was added to water (10 mL) and extracted with ethyl acetate (3×10 mL). The combined organic layers were washed with water (20 mL) then brine (20 mL), dried over anhydrous Na$_2$SO$_4$, filtered, concentrated and purified by preparative TLC (eluting with 75% ethyl acetate in petroleum ether) to afford (S)-tert-butyl (1-(4-(ethylsulfonyl)phenyl)-3-hydroxypropyl)carbamate (500 mg, 83%) as a white solid. LC-MS t$_R$=0.610 min in 5-95 AB_1.5 min chromatography (MK RP-18e 25-2 mm), MS (ESI) m/z 365.9 [M+Na]$^+$.

To a solution of (S)-tert-butyl (1-(4-(ethylsulfonyl)phenyl)-3-hydroxypropyl)carbamate (200 mg, 0.58 mmol) in CH$_3$CN (1 mL), was added aq. 10% HCl (1 mL). The mixture was stirred at rt overnight. The mixture was concentrated under reduced pressure. To the crude residue was added a sat. K₂CO₃ solution to adjust to pH=9 and the product was extracted with ethyl acetate (3×5 mL). The combined organic layers were dried over anhydrous Na₂SO₄, filtered and concentrated to afford (S)-3-amino-3-(4-(ethylsulfonyl)phenyl)propan-1-ol (25 mg, 15%) as a yellow oil. The aqueous layer was lyophilized to afford a white solid, which was added to ethyl acetate (20 mL) and the mixture was stirred for 15 min. The mixture was then filtered and the filtrate was concentrated under reduced pressure to afford (S)-3-amino-3-(4-(ethylsulfonyl)phenyl)propan-1-ol (130 mg, 69%) as a yellow oil, which was used for the next step directly without further purification.

Tert-butyl 5-(((S)-1-(4-(ethylsulfonyl)phenyl)-3-hydroxypropyl)carbamoyl)-1-isopropylisoindoline-2-carboxylate

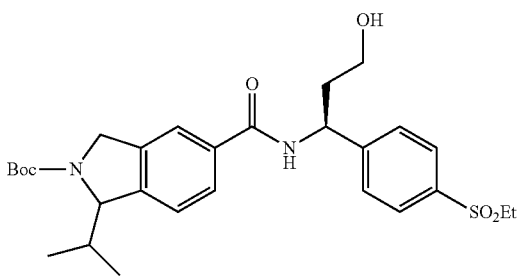

Procedure same as that for tert-butyl-5-(((5-(ethylsulfonyl)pyridin-2-yl)methyl)carbamoyl)-1-isopropylisoindoline-2-carboxylate using (S)-3-amino-3-(4-(ethylsulfonyl)phenyl)propan-1-ol as the starting material. Purification by preparative TLC afforded tert-butyl 5-(((S)-1-(4-(ethylsulfonyl)phenyl)-3-hydroxypropyl)carbamoyl)-1-isopropylisoindoline-2-carboxylate as a yellow oil. A portion of this material was purified by SFC separation to afford pure enantiomers of tert-butyl (S)-5-(((S)-1-(4-(ethylsulfonyl)phenyl)-3-hydroxypropyl)carbamoyl)-1-isopropylisoindoline-2-carboxylate and tert-butyl (R)-5-(((S)-1-(4-(ethylsulfonyl)phenyl)-3-hydroxypropyl)carbamoyl)-1-isopropylisoindoline-2-carboxylate.

N—((S)-1-(4-(ethylsulfonyl)phenyl)-3-hydroxypropyl)-1-isopropylisoindoline-5-carboxamide

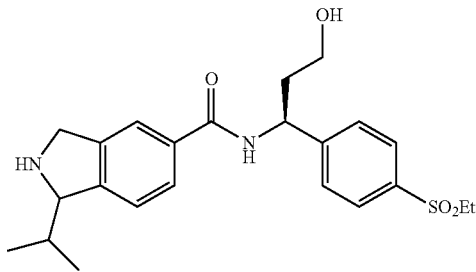

Procedure same as that for N-((5-(ethylsulfonyl)pyridin-2-yl)methyl)-1-isopropylisoindoline-5-carboxamide, using tert-butyl 5-(((S)-1-(4-(ethylsulfonyl)phenyl)-3-hydroxypropyl)carbamoyl)-1-isopropylisoindoline-2-carboxylate as the starting material. The crude product was used directly for the next step without further purification. For some Examples, pure enantiomers of both (S)-5-(((S)-1-(4-(ethylsulfonyl)phenyl)-3-hydroxypropyl)carbamoyl)-1-isopropylisoindoline-2-carboxylate and tert-butyl (R)-5-(((S)-1-(4-(ethylsulfonyl)phenyl)-3-hydroxypropyl)carbamoyl)-1-isopropylisoindoline-2-carboxylate were subjected to the same conditions to give (S)—N—((S)-1-(4-(ethylsulfonyl)phenyl)-3-hydroxypropyl)-1-isopropylisoindoline-5-carboxamide and (R)—N—((S)-1-(4-(ethylsulfonyl)phenyl)-3-hydroxypropyl)-1-isopropylisoindoline-5-carboxamide, respectively.

(S)-3-amino-3-(5-(ethylsulfonyl)pyridin-2-yl)propan-1-ol (3:1 mixture of enantiomers S:R) was prepared following the synthetic route shown in Scheme 17.

Scheme 17.

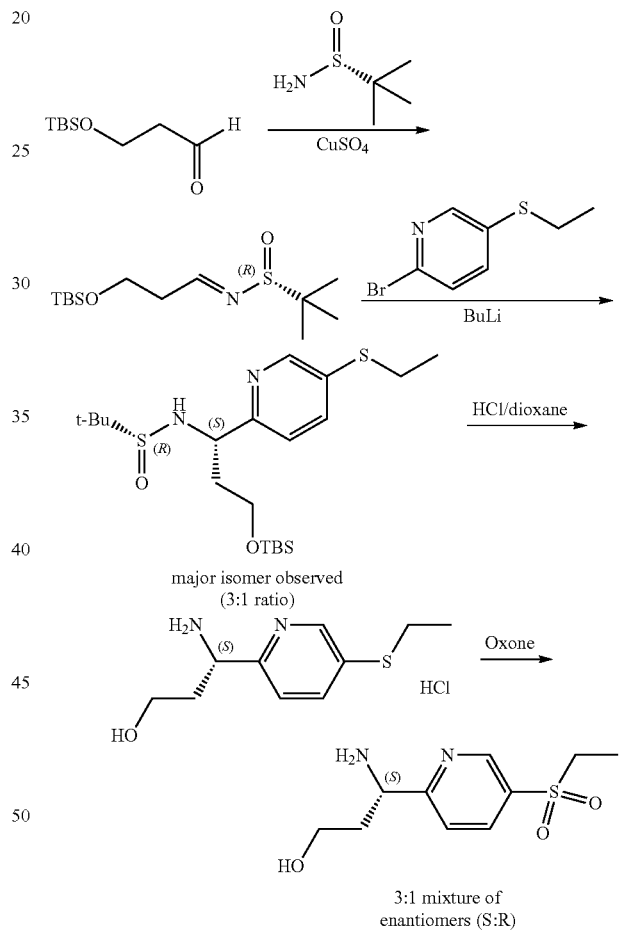

A mixture of 3-((tert-butyldimethylsilyl)oxy)propanal (10 g, 53.1 mmol), (R)-2-methylpropane-2-sulfinamide (7.72 g, 63.7 mmol) and CuSO₄ (21.2 g, 13.3 mmol) in CH₂Cl₂ (100 mL) was stirred at rt for 17 h. The mixture was filtered and the filtrate was concentrated under reduced pressure. The residue was purified by column chromatography on silica gel (eluting with petroleum ether:ethyl acetate=20:1) to give (R,E)-N-(3-((tert-butyldimethylsilyl)oxy)propylidene)-2-methylpropane-2-sulfinamide (7.2 g, 48%) as a yellow oil. LC-MS $t_R$=0.900 min in 5-95AB_1.5 min chromatography (RP-18e, 25-2 mm), MS (ESI) m/z 292.1 [M+H]⁺.

To toluene (120 mL) was added n-BuLi (10 mL, 24.0 mmol) at −70° C. under a N₂ atmosphere, followed by the dropwise addition of a solution of 2-bromo-5-(ethylthio) pyridine (5.8 g, 26.4 mmol) in toluene (15 mL). After being stirred for 30 min, a solution of (R,E)-N-(3-((tert-butyldimethylsilyl)oxy)propylidene)-2-methylpropane-2-sulfinamide (7.0 g, 24.0 mmol) in toluene (15 mL) was added dropwise at −70° C. The resulting mixture was stirred at −70° C. for 2 h and slowly allowed to warm to rt, at which point the stirring was continued for an additional 18 h. To the mixture was added a sat. aq. NH₄Cl solution (20 mL) slowly below −40° C. and the product was extracted with ethyl acetate (3×50 mL). The combined organic layers were washed with brine (50 mL), dried over anhydrous sodium sulfate, filtered and concentrated under reduced pressure. The residue was purified by column chromatography on silica gel (eluting with petroleum ether:ethyl acetate=gradient from 10:1 to 3:1) to give a 3:1 mixture of (R)—N—((S)-3-((tert-butyldimethylsilyl)oxy)-1-(5-(ethylthio)pyridine-2-yl)propyl)-2-methylpropane-2-sulfinamide and (R)—N—((R)-3-((tert-butyldimethylsilyl)oxy)-1-(5-(ethylthio)pyridine-2-yl) propyl)-2-methylpropane-2-sulfinamide, respectively, (5.1 g, 49%) as a yellow oil. This 3:1 mixture of diastereomers was used for the subsequent reactions. LC-MS $t_R$=1.313 min in 10-80AB_2.0 min chromatography (Xtimate 3 um, C18, 2.1*30 mm), MS (ESI) m/z 431.5 [M+H]⁺.

To a solution of (R)—N—((S)-3-((tert-butyldimethylsilyl)oxy)-1-(5-(ethylthio)pyridine-2-yl)propyl)-2-methylpropane-2-sulfinamide (5.1 g, 11.84 mmol), as a 3:1 mixture of diastereomers from the previous step, in CH₂Cl₂ (40 mL) was added HCl/dioxane (10 mL, 4N) at 0° C. The mixture was stirred at 21-24° C. for 17 h. The residue was concentrated under reduced pressure to afford (S)-3-amino-3-(5-(ethylthio)pyridin-2-yl)propan-1-ol (2.5 g, crude) as a 3:1 mixture of enantiomers (S:R), which was used for the next step directly without further purification.

To a solution of (S)-3-amino-3-(5-(ethylthio)pyridin-2-yl) propan-1-ol (2.5 g, 11.8 mmol), as a 3:1 mixture of enantiomers (S:R), in MeOH (10 mL) was added dropwise Oxone® monopersulfate (1.5 g, 2.47 mmol) in H₂O (10 mL) at 0° C. The mixture was stirred at 22-25° C. for 2 h at which point LCMS analysis showed complete consumption of the starting material. The mixture was filtered and concentrated under reduced pressure to remove MeOH. The residue was purified by basic preparative HPLC method to give (S)-3-amino-3-(5-(ethylsulfonyl)pyridin-2-yl)propan-1-ol (300 mg, 10%) as a 3:1 mixture of enantiomers (S:R). This 3:1 mixture of enantiomers was used for the subsequent reactions. LC-MS $t_R$=1.289 min in 0-30CD_3.0 min chromatography (Xtimate ODS 2.1*30 mm, 3 um), MS (ESI) m/z 245.0 [M+1]⁺. ¹H NMR (CDCl₃ 400 MHz): δ 9.05 (d, J=2.0 Hz, 1H), 8.16 (dd, J=8.0, 2.4 Hz, 1H), 7.49 (d, J=8.0 Hz, 1H), 4.33-4.36 (m, 2H), 3.83-3.92 (m, 2H), 3.17 (q, J=7.2 Hz, 2H), 1.91-1.94 (m, 2H), 1.33 (t, J=7.6 Hz, 3H).

Tert-butyl (S)-1-ethyl-5-(((S)-1-(5-(ethylsulfonyl) pyridin-2-yl)-3-hydroxypropyl)carbamoyl)isoindoline-2-carboxylate

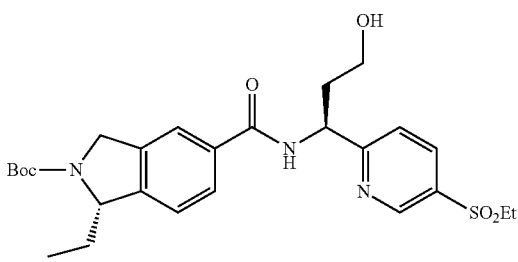

Procedure same as that for (S)-tert-butyl 1-ethyl-5-(((R)-1-(4-(ethylsulfonyl)phenyl)-2-hydroxyethyl)carbamoyl) isoindoline-2-carboxylate using (S)-3-amino-3-(5-(ethylsulfonyl)pyridin-2-yl)propan-1-ol (3:1 mixture of enantiomers) as the starting material. LCMS $t_R$=1.061 min in 10-80AB_2.0 min chromatography (Xtimate 3 um, C18, 2.1*30 mm), MS (ESI) m/z 518.1 [M+H]⁺.

(S)-1-ethyl-N—((S)-1-(5-(ethylsulfonyl)pyridin-2-yl)-3-hydroxypropyl)isoindoline-5-carboxamide

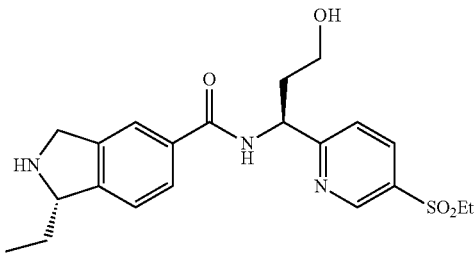

Procedure same as that for (S)-1-ethyl-N—((R)-1-(4-(ethylsulfonyl)phenyl)-2-hydroxyethyl)isoindoline-5-carboxamide using tert-butyl (S)-1-ethyl-5-(((S)-1-(5-(ethylsulfonyl)pyridin-2-yl)-3-hydroxypropyl)carbamoyl) isoindoline-2-carboxylate as the starting material.

4-(aminomethyl)-N-methylbenzenesulfonamide was prepared following the synthetic route shown in Scheme 18.

Scheme 18

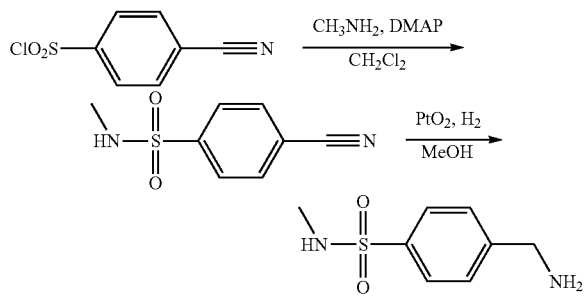

To a solution of MeNH₂ (2M, 25.3 mL, 50 mmol) and DMAP (0.5 g, 4.0 mmol) in dichloromethane (50 mL) was added 4-cyanobenzene-1-sulfonyl chloride (4.0 g, 20 mmol) at 0° C. The mixture was stirred at rt for 2 h. TLC analysis (eluting with petroleum ether:ethyl acetate=1:1) showed the reaction was complete. The mixture was acidified to pH=1 with HCl (2N) and extracted with dichloromethane (2×50 mL). The combined organic layers were dried over anhydrous Na₂SO₄, filtered and concentrated in vacuo to give 4-cyano-N-methylbenzenesulfonamide (3.8 g, 97%) as a white solid. ¹H NMR (CDCl3 400 MHz): δ 7.98 (d, J=8.4 Hz, 2H), 7.84 (d, J=8.4 Hz, 2H), 4.51-4.60 (m, 1H), 2.71 (d, J=5.2 Hz, 3H).

To a solution of 4-cyano-N-methylbenzenesulfonamide (3.8 g, 19.4 mmol) in CH₃OH (60 mL) was added PtO₂ (1.2 g, w/w 30%). The mixture was stirred under H₂ (30 psi) at rt for 16 h. The mixture was filtered and the filtrate was concentrated under reduced pressure to give 4-(aminomethyl)-N-methylbenzenesulfonamide (3.7 g, 95%) as oil. ¹H NMR (CD$_3$OD 400 MHz): δ 7.78 (d, J=8.0 Hz, 2H), 7.54 (t, J=8.4 Hz, 2H), 3.85 (d, J=7.2 Hz, 2H), 2.48-2.51 (m, 3H).

Tert-butyl (S)-1-ethyl-5-((4-(N-methylsulfamoyl)benzyl)carbamoyl)isoindoline-2-carboxylate

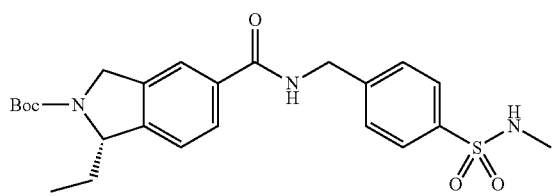 [SMILES: CC[C@H]1c2ccc(C(=O)NCc3ccc(S(=O)(=O)NC)cc3)cc2CN1C(=O)OC(C)(C)C]

Procedure same as that for (S)-tert-butyl 1-ethyl-5-(((5-(ethylsulfonyl)pyridin-2-yl)methyl)carbamoyl)isoindoline-2-carboxylate using (S)-2-(tert-butoxycarbonyl)-1-ethyl-isoindoline-5-carboxylic acid and 4-(aminomethyl)-N-methylbenzenesulfonamide as the starting materials.

(S)-1-ethyl-N-(4-(N-methylsulfamoyl)benzyl)isoindoline-5-carboxamide

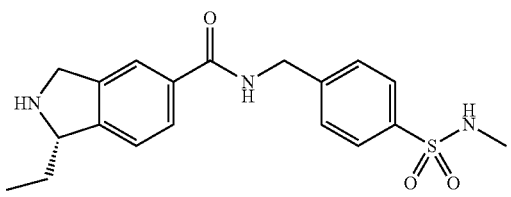 [SMILES: CC[C@@H]1NCc2cc(C(=O)NCc3ccc(S(=O)(=O)NC)cc3)ccc21]

Procedure same as that for (S)-1-ethyl-N-((5-(ethylsulfonyl)pyridin-2-yl)methyl)isoindoline-5-carboxamide using tert-butyl (S)-1-ethyl-5-((4-(N-methylsulfamoyl)benzyl)carbamoyl)isoindoline-2-carboxylate as the starting material.

6-(aminomethyl)-N-methylpyridine-3-sulfonamide was prepared following the synthetic route shown in Scheme 19.

Scheme 19

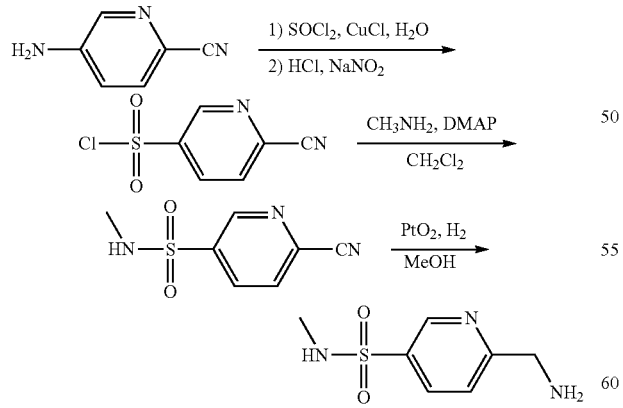

To 9 mL of H$_2$O was added SOCl$_2$ (2.7 mL, 23.1 mmol) at 0° C. Then the mixture was stirred at rt overnight. To the above mixture was added CuCl (8 mg, 0.08 mmol) and the resulting mixture was cooled to −5° C. To a mixture of 5-aminopicolinonitrile (500 mg, 4.2 mmol) in HCl (conc., 5 mL) was added a solution of NaNO$_2$ (410 mg, 6.3 mmol) in H$_2$O (3 mL) dropwise at −5° C. and the mixture was stirred at −5° C. for 1 h. Then, the mixture was added to the above SOCl$_2$/H$_2$O/CuCl mixture and stirred for 1 h. A red solid precipitated during addition. The precipitate was collected by filtration, washed with cold water and dried in vacuo to give 6-cyanopyridine-3-sulfonyl chloride (800 mg, 94%) as a red solid, which was used directly for the next step without further purification. LCMS $t_R$=1.354 min in 0-30AB_2.0 min chromatography (Xtimate C18, 2.1*30 mm, 3 um), MS (ESI) m/z 202.9 [M+H]$^+$.

To a solution of MeNH$_2$ (2M, 2.5 mL, 5 mmol) and DMAP (50 mg, 0.4 mmol) in dichloromethane (5 mL) was added 6-cyanopyridine-3-sulfonyl chloride (0.4 g, 2.0 mmol) at 0° C. The mixture was stirred at rt for 2 h. TLC analysis (eluting petroleum ether:ethyl acetate=1:1) showed the reaction was complete. The mixture was acidified to pH=1 with HCl (2N) and extracted with dichloromethane (2×5 mL). The combined organic layers were dried over anhydrous Na$_2$SO$_4$, filtered and concentrated in vacuo to give 6-cyano-N-methylpyridine-3-sulfonamide (290 mg, 74%) as a red solid. LCMS $t_R$=0.426 min in 5-95AB_1.5 min chromatography (MK RP18e 25-2 mm), MS (ESI) m/z 197.9 [M+H]$^+$.

To a solution of 6-cyano-N-methylpyridine-3-sulfonamide (200 mg, 1.0 mmol) in CH$_3$OH (5 mL) was added PtO$_2$ (50 mg, w/w 25%). The mixture was stirred under H$_2$ (30 psi) at rt overnight. The mixture was filtered and the filtrate was concentrated under reduced pressure to give 6-(aminomethyl)-N-methylpyridine-3-sulfonamide (200 mg, 100%) as an oil. $^1$H NMR (CDCl$_3$ 400 MHz): δ 9.00 (d, J=2.4 Hz, 1H), 8.10 (dd, J=8.0, 2.4 Hz, 1H), 7.50 (d, J=8.4 Hz, 1H), 4.10 (s, 2H), 2.71 (s, 3H).

Tert-butyl (S)-1-ethyl-5-(((5-(N-methylsulfamoyl)pyridin-2-yl)methyl)carbamoyl)isoindoline-2-carboxylate

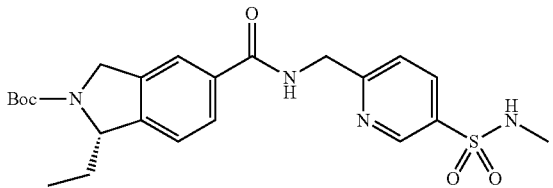 [SMILES: CC[C@H]1c2ccc(C(=O)NCc3ccc(S(=O)(=O)NC)cn3)cc2CN1C(=O)OC(C)(C)C]

Procedure same as that for (S)-tert-butyl 1-ethyl-5-(((5-(ethylsulfonyl)pyridin-2-yl)methyl)carbamoyl)isoindoline-2-carboxylate using (S)-2-(tert-butoxycarbonyl)-1-ethyl-isoindoline-5-carboxylic acid and 6-(aminomethyl)-N-methylpyridine-3-sulfonamide as the starting materials. LCMS $t_R$=0.779 min in 5-95AB_1.5 min chromatography (RP-18e,25-2 mm), MS (ESI) m/z 475.0 [M+H]$^+$.

(S)-1-ethyl-N-((5-(N-methylsulfamoyl)pyridin-2-yl)methyl)isoindoline-5-carboxamide

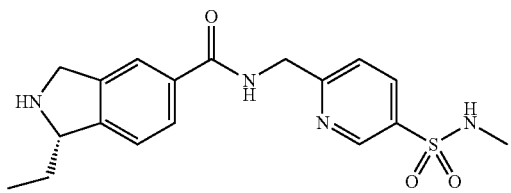 [SMILES: CC[C@@H]1NCc2cc(C(=O)NCc3ccc(S(=O)(=O)NC)cn3)ccc21]

Procedure same as that for (S)-1-ethyl-N-((5-(ethylsulfonyl)pyridin-2-yl)methyl)isoindoline-5-carboxamide using tert-butyl (S)-1-ethyl-5-(((5-(N-methylsulfamoyl)pyridin-2-yl)methyl)carbamoyl)isoindoline-2-carboxylate as the starting material.

Preparation of Compounds of Formula I

Trans-4-(trifluoromethyl)cyclohexane-1-carbaldehyde (was prepared following the synthetic route shown in Scheme 20.

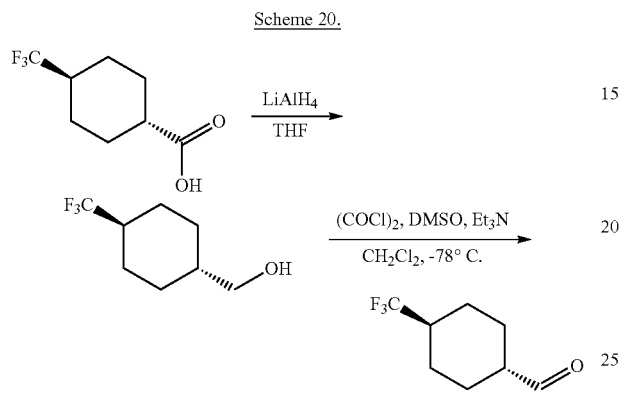

To a solution of trans-4-(trifluoromethyl)cyclohexane carboxylic acid (789 mg, 4.02 mmol) in THF (12 mL) at rt was added lithium aluminum hydride (1.0 M in THF, 4.02 mL). The mixture was heated to reflux and stirred for 3 h. It was then cooled to 0° C. and quenched successively with water (152 μL), 15% aqueous sodium hydroxide (152 μL), and water (456 μL). The mixture was then filtered through Celite and concentrated under reduced pressure. The crude liquid (trans-4-(trifluoromethyl)cyclohexyl)methanol was carried forward without any purification and without placing under high vacuum due to its volatility.

To a solution of oxalyl chloride (6.2 mL, 87.4 mmol) in anhydrous CH$_2$Cl$_2$ (300 mL) was added dropwise DMSO (12.5 mL, 0.17 mol) at −78° C. under N$_2$. After the mixture was stirred at −78° C. for 30 min., a solution of (trans-4-(trifluoromethyl)cyclohexyl)methanol (5.3 g, 29.1 mmol) in CH$_2$Cl$_2$ (40 mL) was added dropwise while keeping the internal temperature below −65° C. After being stirred for 30 min., a solution of Et$_3$N (40.5 mL, 0.29 mol) in CH$_2$Cl$_2$ (60 mL) was added dropwise slowly, keeping the internal temperature below −65° C. The reaction mixture was stirred at −78° C. for 1 h, and warmed to rt overnight. The mixture was washed with water (3×300 mL) and brine (300 mL), dried over anhydrous Na$_2$SO$_4$, filtered and concentrated under reduced pressure. The residue was purified by column chromatography on silica (eluting with 15% EtOAc in petroleum ether) to give trans-4-(trifluoromethyl)cyclohexane-1-carbaldehyde (4.6 g, 87%) as a yellow oil.

Examples 1a and 1b

N-((5-(ethylsulfonyl)pyridin-2-yl)methyl)-1-isopropyl-2-((trans-4-(trifluoromethyl)cyclohexyl)methyl)isoindoline-5-carboxamide (1a) and (1b)

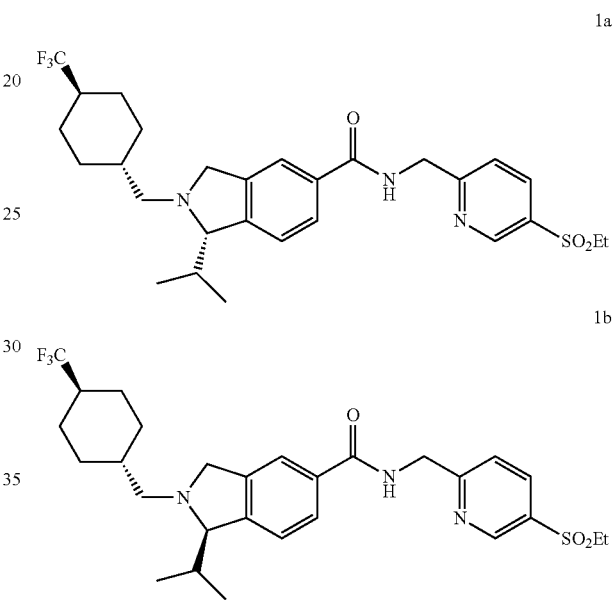

Examples 1a and 1b were prepared according to General Procedure A outlined below.

General Procedure A:

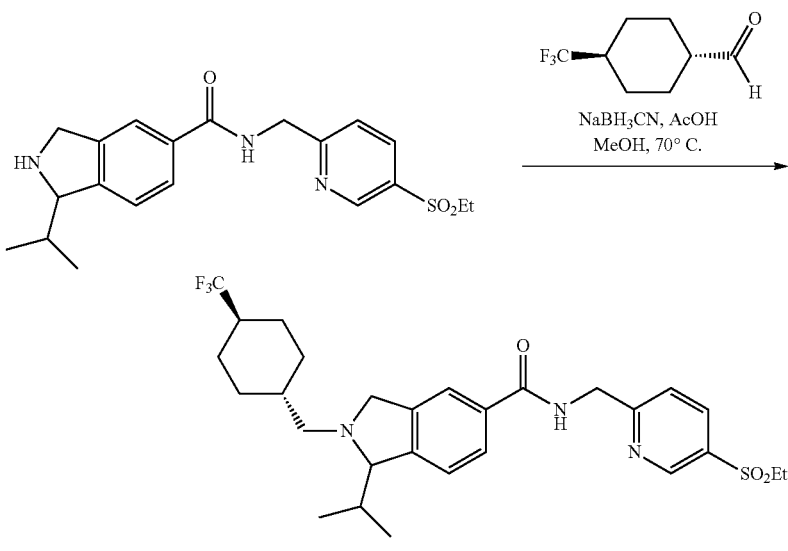

A mixture of trans-4-(trifluoromethyl)cyclohexanecarbaldehyde (1.3 g, 7.235 mmol) and N-((5-(ethylsulfonyl)pyridin-2-yl)methyl)-1-isopropylisoindoline-5-carboxamide (560 mg, 1.447 mmol) in anhydrous MeOH (10 mL) was adjusted to pH=6 with AcOH. NaBH$_3$CN (273 mg, 4.341 mmol) was added. The mixture was stirred at 70° C. for 4.5 h before being concentrated under reduced pressure. Water (15 mL) was added and the aqueous layer was extracted with ethyl acetate (3×15 mL). The combined organic layers were washed with brine (45 mL), dried over anhydrous Na$_2$SO$_4$, filtered and concentrated under reduced pressure. The residue was purified by column chromatography on silica gel (eluting with 25% ethyl acetate in petroleum ether followed by SFC separation (AD-3) and HCl preparative HPLC method D separation to afford HCl salts of isomer 1 (1a) (175.9 mg, 21%) and isomer 2 (1b) (188.8 mg, 22%) as white solids.

Isomer 1 (1a) HCl salt (175.90 mg, 21%) LC-MS $t_R$=0.693 min in 5-95AB_1.5 min chromatography (Welch MK RP-18e 25-2 mm), MS (ESI) m/z 552.1 [M+H]$^+$. $^1$H NMR (CD$_3$OD 400 MHz): δ 9.08 (d, J=2.0 Hz, 1H), 8.33 (dd, J=2.4, 8.4 Hz, 1H), 8.00 (d, J=8.0 Hz, 1H), 7.98 (s, 1H), 7.72 (d, J=8.4 Hz, 1H), 7.58 (d, J=8.0 Hz, 1H), 5.11 (d, J=15.2 Hz, 1H), 4.99 (d, J=4.8 Hz, 1H), 4.83 (s, 2H), 4.65 (d, J=15.2 Hz, 1H), 3.20 (q, J=7.2 Hz, 2H), 3.26-3.15 (m, 2H), 2.48-2.34 (m, 1H), 2.25-1.90 (m, 6H), 1.50-1.35 (m, 2H), 1.33-1.28 (m, 2H), 1.26 (t, J=7.2 Hz, 3H), 1.21 (d, J=6.8 Hz, 3H), 1.04 (d, J=6.8 Hz, 3H). Isomer SFC $t_R$=6.938 min in 12 min chromatography (ee=100%).

Isomer 2 (1b) HCl salt (188.80 mg, 22%) LC-MS $t_R$=0.631 min in 5-95AB_1.5 min chromatography (Welch MK RP-18e 25-2 mm), MS (ESI) m/z 552.1 [M+H]$^+$. $^1$H NMR (CD$_3$OD 400 MHz): δ 9.08 (d, J=2.0 Hz, 1H), 8.33 (dd, J=2.0, 8.0 Hz, 1H), 8.02 (d, J=8.0 Hz, 1H), 7.99 (s, 1H), 7.70 (d, J=8.4 Hz, 1H), 7.60 (d, J=8.0 Hz, 1H), 5.11 (dd, J=4.0, 15.6 Hz, 1H), 4.99 (d, J=4.4 Hz, 1H), 4.83 (s, 2H), 4.67 (dd, J=5.2, 15.2 Hz, 1H), 3.31 (q, J=7.2 Hz, 2H), 3.26-3.15 (m, 2H), 2.48-2.38 (m, 1H), 2.25-1.90 (m, 6H), 1.52-1.35 (m, 2H), 1.33-1.29 (m, 2H), 1.27 (t, J=7.2 Hz, 3H), 1.23 (d, J=6.8 Hz, 3H), 1.06 (d, J=6.8 Hz, 3H). Isomer SFC $t_R$=9.651 min in 12 min chromatography (ee=97.96%).

The following compounds in Table 1 were prepared using General Procedure A described above with trans-4-(trifluoromethyl)cyclohexane-1-carbaldehyde and the appropriate intermediates described herein.

TABLE 1

| Ex. No. | Structure | LCMS | $^1$H-NMR |
|---|---|---|---|
| 2a | (structure with F$_3$C-cyclohexyl-CH$_2$-N-isoindoline (S)-isopropyl, carboxamide to (R)-CH(CH$_2$OH)-pyridine-SO$_2$Et) | 582.0 [M + H]$^+$ | (CD$_3$OD 400 MHz): δ 9.07 (d, J = 2.0 Hz, 1H), 8.51 (dd, J = 2.0, 8.4 Hz, 1H), 7.99-7.92 (m, 3H), 7.51 (d, J = 8.4 Hz, 1H), 5.33 (t, J = 6.4 Hz, 1H), 5.10-5.05 (m, 1H), 4.97-4.92 (m, 1H), 4.58-4.53 (m, 1H), 4.07-4.02 (m, 2H), 3.31 (q, J = 7.2 Hz, 2H), 3.20-3.10 (m, 2H), 2.40-2.30 (m, 1H), 2.20-1.90 (m, 6H), 1.44-1.28 (m, 2H), 1.23 (t, J = 7.2 Hz, 3H), 1.25-1.16 (m, 2H), 1.15 (d, J = 6.8 Hz, 3H), 0.98 (d, J = 6.8 Hz, 3H) |
| 2b | (structure with F$_3$C-cyclohexyl-CH$_2$-N-isoindoline (R)-isopropyl, carboxamide to (R)-CH(CH$_2$OH)-pyridine-SO$_2$Et) | 582.0 [M + H]$^+$ | (CD$_3$OD 400 MHz): δ 9.07 (s, 1H), 8.54 (d, J = 8.0 Hz, 1H), 8.03-7.87 (m, 3H), 7.49 (d, J = 7.6 Hz, 1H), 5.32 (t, J = 5.6 Hz, 1H), 5.10-5.05 (m, 1H), 4.97-4.92 (m, 1H), 4.58-4.53 (m, 1H), 4.07-4.00 (m, 2H), 3.30 (q, J = 7.2 Hz, 2H), 3.20-3-10 (m, 2H), 2.40-2.30 (m, 1H), 2.20-1.85 (m, 6H), 1.42-1.30 (m, 2H), 1.21 (t, J = 7.2 Hz, 3H), 1.20-1.14 (m, 2H), 1.13 (d, J = 6.8 Hz, 3H), 0.96 (d, J = 6.8 Hz, 3H) |
| 2c | (structure with F$_3$C-cyclohexyl-CH$_2$-N-isoindoline (S)-isopropyl, carboxamide to (S)-CH(CH$_2$OH)-pyridine-SO$_2$Et) | 582.0 [M + H]$^+$ | (CD$_3$OD 400 MHz): δ 9.04 (s, 1H), 8.55-8.45 (m, 1H), 8.01-7.90 (m, 3H), 7.47 (d, J = 8.4 Hz, 1H), 5.30 (t, J = 5.6 Hz, 1H), 5.08-5.02 (m, 1H), 4.97-1.92 (m, 1H), 4.58-1.53 (m, 1H), 4.07-4.00 (m, 2H), 3.27 (q, J = 7.2 Hz, 2H), 3.17-3.10 (m, 2H), 2.41-2.30 (m, 1H), 2.13-1.81 (m, 6H), 1.40-1.30 (m, 2H), 1.18 (t, J = 7.2 Hz, 3H), 1.17-1.13 (m, 2H), 1.11 (d, J = 6.8 Hz, 3H), 0.94 (d, J = 6.8 Hz, 3H) |

TABLE 1-continued

| Ex. No. | Structure | LCMS | ¹H-NMR |
|---|---|---|---|
| 2d | 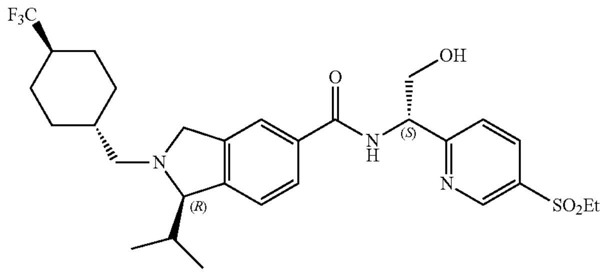 | 582.0 [M + H]⁺ | (CD$_3$OD 400 MHz): δ 9.01 (s, 1H), 8.60-8.45 (m, 1H), 8.04-7.85 (m, 3H), 7.41 (d, J = 8.0 Hz, 1H), 5.25 (t, J = 5.6 Hz, 1H), 5.08-4.98 (m, 1H), 4.97-4.92 (m, 1H), 4.55-4.48 (m, 1H), 4.03-3.95 (m, 2H), 3.30-3.20 (m, 2H), 3.15-3.08 (m, 2H), 2.35-2.20 (m, 1H), 2.13-1.81 (m, 6H), 1.40-1.20 (m, 2H), 1.13 (t, J = 7.2 Hz, 3H), 1.12-1.08 (m, 2H), 1.05 (d, J = 6.8 Hz, 3H), 0.89 (d, J = 6.8 Hz, 3H). |
| 3a | 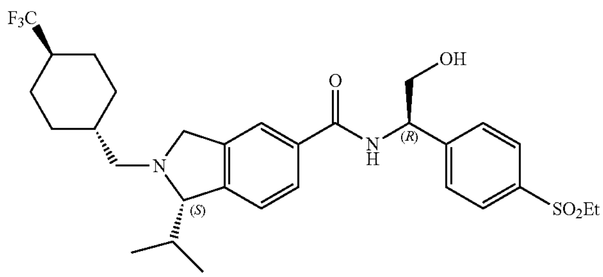 | 581.1 (M + H)⁺ | (CD$_3$OD 400 MHz): δ 8.99 (d, J = 8.0 Hz, 1H), 8.00 (d, J = 7.6 Hz, 1H), 7.97 (s, 1H), 7.92 (d, J = 8.4 Hz, 2H), 7.71 (d, J = 8.8 Hz, 2H), 7.57 (d, J = 8.0 Hz, 1H), 5.30 (q, J = 6.8 Hz, 1H), 5.15-5.07 (m, 1H), 5.05-4.98 (m, 1H), 4.68-4.59 (m, 1H), 3.94 (d, J = 6.4 Hz, 2H), 3.25-3.16 (m, 4H), 2.50-2.30 (m, 1H), 2.25-1.95 (m, 6H), 1.55-1.35 (m, 2H), 1.35-1.23 (m, 6H), 1.23 (t, J = 7.2 Hz, 3H), 1.05 (d, J = 6.8 Hz, 3H). |
| 3b | 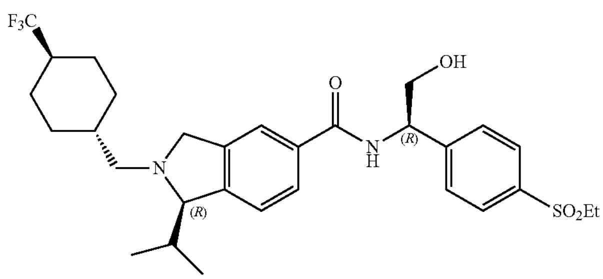 | 581.1 (M + H)⁺ | (CD$_3$OD 400 MHz): δ 8.98 (d, J = 7.6 Hz, 1H), 8.02 (d, J = 8.0 Hz, 1H), 7.96 (s, 1H), 7.92 (d, J = 8.4 Hz, 2H), 7.71 (d, J = 8.4 Hz, 2H), 7.58 (d, J = 7.2 Hz, 1H), 5.30 (q, J = 6.8 Hz, 1H), 5.15-5.07 (m, 1H), 5.05-4.98 (m, 1H), 4.68-4.59 (m, 1H), 3.93 (d, J = 6.8 Hz, 2H), 3.25-3.15 (m, 4H), 2.50-2.35 (m, 1H), 2.25-1.90 (m, 6H), 1.55-1.36 (m, 2H), 1.35-1.23 (m, 6H), 1.23 (t, J = 7.2 Hz, 3H), 1.05 (d, J = 6.4 Hz, 3H). |
| 3c | 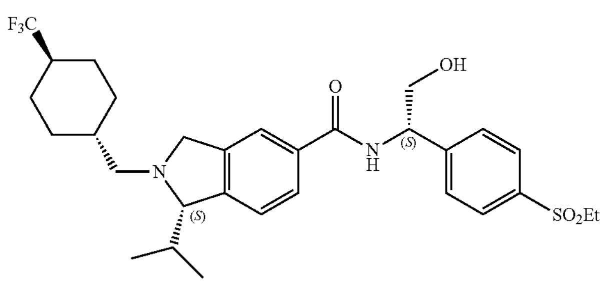 | 581.1 (M + H)⁺ | (CD$_3$OD 400 MHz): δ 7.99 (d, J = 8.4 Hz, 1H), 7.92 (s, 1H), 7.89 (d, J = 8.0 Hz, 2H), 7.68 (d, J = 8.4 Hz, 2H), 7.56 (d, J = 6.8 Hz, 1H), 5.27 (t, J = 6.8 Hz, 1H), 5.12-5.04 (m, 1H), 5.02-4.98 (m, 1H), 4.65-4.58 (m, 1H), 3.93-3.86 (m, 2H), 3.25-3.15 (m, 2H), 3.19 (q, J = 7.2 Hz, 2H), 2.38-2.35 (m, 1H), 2.20-1.90 (m, 6H), 1.55-1.36 (m, 2H), 1.35-1.23 (m, 6H), 1.23 (t, J = 7.2 Hz, 3H), 1.02 (d, J = 6.4 Hz, 3H). |
| 3d | 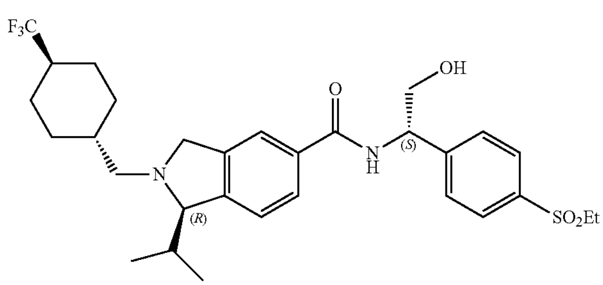 | 581.1 (M + H)⁺ | (OD$_3$OD 400 MHz): δ 9.00-8.97 (m, 1H), 8.00 (d, J = 8.0 Hz, 1H), 7.96 (s, 1H), 7.92 (d, J = 8.4 Hz, 2H), 7.71 (d, J = 8.4 Hz, 2H), 7.58 (d, J = 8.0 Hz, 1H), 5.30 (t, J = 6.5 Hz, 1H), 5.12-5.07 (m, 1H), 5.03-4.99 (m, 1H), 4.68-4.62 (m, 1H), 3.95-3.90 (m, 2H), 3.26-3.19 (m, 2H), 3.22 (q, J = 7.2 Hz, 4H), 2.45-2.38 (m, 1H), 2.20-1.90 (m, 6H), 1.51-1.36 (m, 2H), 1.35-1.23 (m, 6H), 1.23 (t, J = 7.2 Hz, 3H), 1.05 (d, J = 6.8 Hz, 3H). |

TABLE 1-continued

| Ex. No. | Structure | LCMS | ¹H-NMR |
|---|---|---|---|
| 4a | 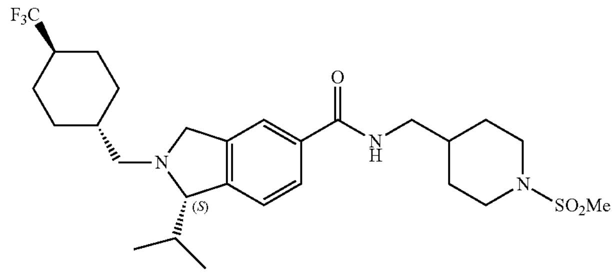 | 544.1 (M + H)⁺ | (CD₃OD 400 MHz): δ 7.91 (d, J = 7.6 Hz, 1H), 7.90 (s, 1H), 7.55 (d, J = 8.4 Hz, 1H), 5.09 (d, J = 15.2 Hz, 1H), 5.05-4.95 (m, 3H), 4.63 (d, J = 15.2 Hz, 1H), 3.74 (d, J = 11.6 Hz, 2H), 3.40-3.36 (m, 2H), 3.30-3.15 (m, 2H), 2.82 (s, 3H), 2.75-2.65 (m, 2H), 2.45-2.33 (m, 1H), 2.25-1.70 (m, 8H), 1.50-1.25 (m, 5H), 1.21 (d, J = 6.8 Hz, 3H), 1.03 (d, J = 6.4 Hz, 3H). |
| 4b | 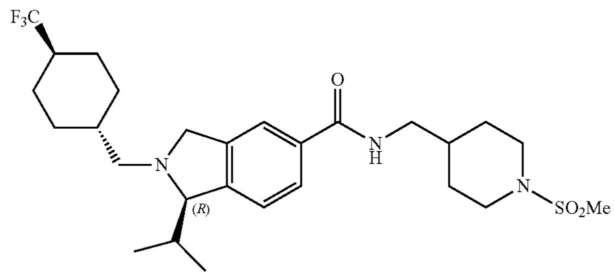 | 544.1 (M + H)⁺ | (CD₃OD 400 MHz): δ 8.68 (brs, 1H), 7.88 (s, 2H), 7.53 (d, J = 7.6 Hz, 1H), 5.07 (d, J = 15.2 Hz, 1H), 5.02-4.95 (m, 3H), 4.61 (d, J = 15.2 Hz, 1H), 3.73 (d, J = 12.0 Hz, 2H), 3.40-3.36 (m, 2H), 3.27-3.13 (m, 2H), 2.81 (s, 3H), 2.77-2.65 (m, 2H), 2.45-2.33 (m, 1H), 2.25-1.70 (m, 8H), 1.50-1.20 (m, 5H), 1.19 (d, J = 6.4 Hz, 3H), 1.02 (d, J = 6.41 Hz, 3H). |
| 5a | 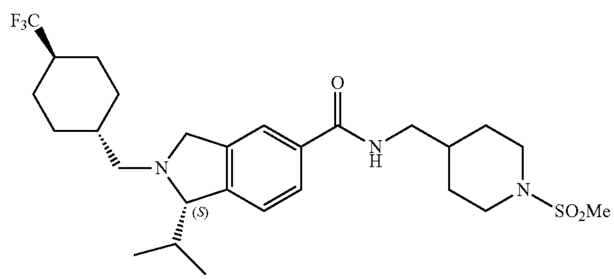 | 558.1 (M + H)⁺ | (CD₃OD 400 MHz): δ 8.69 (brs, 1H), 7.88 (s, 2H), 7.53 (d, J = 7.6 Hz, 1H), 5.07 (d, J = 15.2 Hz, 1H), 5.03-4.95 (m, 3H), 4.61 (d, J = 14.8 Hz, 1H), 3.75 (d, J = 12.0 Hz, 2H), 3.45-3.35 (m, 2H), 3.30-3.15 (m, 2H), 3.01 (q, J = 7.2 Hz, 2H), 2.83 (t, J = 10.8 Hz, 2H), 2.45-2.33 (m, 1H), 2.25-1.75 (m, 8H), 1.50-1.40 (m, 3H), 1.30 (t, J = 7.2 Hz, 3H), 1.28-1.22 (m, 2H), 1.19 (d, J = 6.8 Hz, 3H), 1.02 (d, J = 6.4 Hz, 3H). |
| 5b | 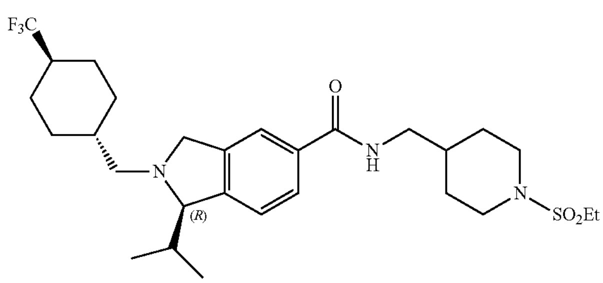 | 558.1 (M + H)⁺ | (CD₃OD 400 MHz): δ 8.69 (brs, 1H), 7.88 (s, 2H), 7.53 (d, J = 8.0 Hz, 1H), 5.07 (d, J = 15.6 Hz, 1H), 5.03-4.93 (m, 3H), 4.61 (d, J = 15.6 Hz, 1H), 3.76 (d, J = 12.4 Hz, 2H), 3.45-3.34 (m, 2H), 3.30-3.15 (m, 2H), 3.01 (q, J = 7.2 Hz, 2H), 2.83 (t, J = 11.6 Hz, 2H), 2.45-2.32 (m, 1H), 2.25-1.75 (m, 8H), 1.45-1.35 (m, 3H), 1.30 (t, J = 7.2 Hz, 3H), 1.28-1.22 (m, 2H), 1.19 (d, J = 6.4 Hz, 3H). 1.02 (d, J = 6.4 Hz, 3H). |
| 6a | 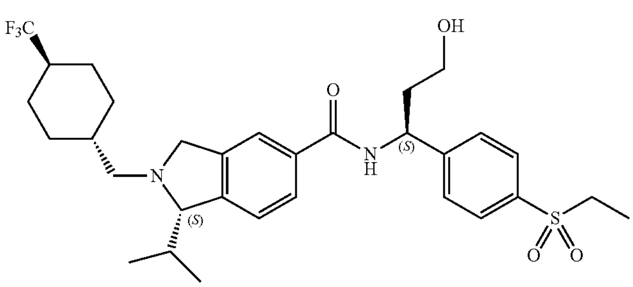 | 595.2 (M + H)⁺ | (CD₃OD 400 MHz): δ 9.06 (d, J = 7.6 Hz, 1H), 7.93 (d, J = 8.0 Hz, 1H), 7.89 (s, 1H), 7.88 (d, J = 8.0 Hz, 2H), 7.67 (d, J = 8.4 Hz, 2H), 7.54 (d, J = 8.0 Hz, 1H ), 5.39-5.34 (m, 1H), 5.06 (d, J = 15.2 Hz, 1H), 4.95 (d, J = 4.8 Hz, 1H), 4.60 (d, J = 15.2 Hz, 1H), 3.67-3.61 (m, 2H), 3.22-3.18 (m, 2H), 3.19 (q, J = 7.2 Hz, 2H), 2.38-2.36 (m, 1H), 2.17-1.98 (m, 8H), 1.42-1.39 (m, 2H), 1.23-1.19 (m, 2H), 1.20 (t, J = 7.2 Hz, 3H), 1.19 (d, J = 7.2 Hz, 3H), 1.01 (d, J = 6.4 Hz, 3H) |

TABLE 1-continued

| Ex. No. | Structure | LCMS | ¹H-NMR |
|---|---|---|---|
| 6b | [Structure: F₃C-cyclohexyl-CH₂-N(isoindoline with isopropyl)-C(O)NH-CH(S)-CH₂CH₂OH with phenyl-SO₂Et] | 595.2 (M + H)⁺ | (CD₃OD 400 MHz): δ 7.92 (d, J = 8.0 Hz, 1H), 7.89 (s, 1H), 7.87 (d, J = 8.4 Hz, 2H), 7.67 (d, J = 8.4 Hz, 2H), 7.54 (d, J = 8.0 Hz, 1H), 5.38-5.35 (m, 1H), 5.06 (d, J = 15.2 Hz, 1H), 4.95 (d, J = 4.8 Hz, 1H), 4.60 (d, J = 15.2 Hz, 1H), 3.67-3.60 (m, 2H), 3.23-3.19 (m, 2H), 3.18 (q, J = 7.2 Hz, 2H), 2.38-2.36 (m, 1H), 2.16-1.94 (m, 8H), 1.42-1.39 (m, 2H), 1.23-1.19 (m, 2H), 1.20 (t, J = 7.2 Hz, 3H), 1.18 (d, J = 7.2 Hz, 3H), 1.01 (d, J = 6.8 Hz, 3H). |

Examples 7a and 7b 2-((trans-4-ethoxycyclohexyl)methyl)-N-((5-(ethylsulfonyl)pyridin-2-yl)methyl)-1-isopropylisoindoline-5-carboxamide (7a) and (7b)

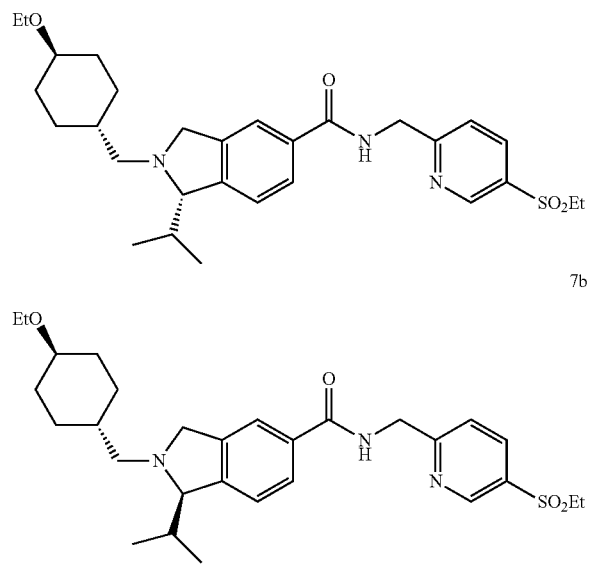

To a solution of trans-methyl 4-hydroxycyclohexanecarboxylate (1.0 g, 6.32 mmol) in anhydrous DMF (10 mL) was added NaH (759 mg, 18.96 mmol, 60% in mineral oil) in portions at 0° C. under N₂. The mixture was stirred at 0° C. for 30 min and EtI (4.93 g, 31.6 mmol) was then added at 0° C. The mixture was allowed to warm to rt and stirred for another 1.5 h. TLC analysis (petroleum ether:ethyl acetate=5:1) showed the starting material was consumed. The mixture was quenched with a sat. NH₄Cl solution (50 mL) at 0° C. and extracted with MTBE (3×20 mL). The combined organic layers were washed with H₂O (15 mL) then brine (15 mL), dried over anhydrous sodium sulfate, filtered and concentrated under reduced pressure to afford trans-methyl 4-ethoxycyclohexanecarboxylate (680 mg, 58%) as a colorless liquid, which was used for next step directly without purification.

To a solution of trans-methyl 4-ethoxycyclohexanecarboxylate (680 mg, 3.65 mmol) in anhydrous THF (10 mL) was added LiAlH₄ (5.5 mL, 10.95 mmol, 2 M in THF) dropwise at 0° C. The mixture was stirred at rt for 2 h. TLC analysis (petroleum ether:ethyl acetate=2:1) showed the starting material was consumed. The mixture was quenched with water (0.4 mL) slowly followed by a 10% aqueous NaOH solution (0.4 mL) at 0° C. The mixture was filtered and the filtrate was concentrated under reduced pressure. The residue was purified by chromatography column on silica gel to afford (trans-4-ethoxycyclohexyl)methanol (210 mg, 36%) as a colorless oil. ¹H NMR (CDCl₃ 400 MHz): δ 3.51 (q, J=7.2 Hz, 2H), 3.45 (d, J=6.8 Hz, 2H), 3.20-3.15 (m, 1H), 2.10-2.06 (m, 2H), 1.86-1.83 (m, 2H), 1.45-1.25 (m, 3H), 1.20 (t, J=6.8 Hz, 3H), 1.00-0.96 (m, 2H).

To a solution of (trans-4-ethoxycyclohexyl)methanol (60 mg, 0.38 mmol) in CH₂Cl₂ (2 mL) was added PCC (163 mg, 0.76 mmol). The mixture was stirred at rt for 1.5 h. TLC analysis (petroleum ether:ethyl acetate=3:1) showed the starting material was consumed. Water (15 mL) was added to the mixture and the product was extracted with CH₂Cl₂ (3×15 mL). The combined organic layers were washed with water (3×10 mL) then brine (10 mL), dried over anhydrous sodium sulfate, filtered and concentrated under reduced pressure to afford crude trans-4-ethoxycyclohexanecarbaldehyde (crude 60 mg, 100%) as a pink oil, which was used for the next step directly without further purification.

Isomer 1 (7a) was made according to General Procedure A using trans-4-ethoxycyclohexane-1-carbaldehyde and (S)—N-((5-(ethylsulfonyl)pyridin-2-yl)methyl)-1-isopropylisoindoline-5-carboxamide as the starting materials. The crude material was purified by HCl preparative HPLC method E separation to afford isomer 1 HCl salt (7a) (3.10 mg, 9%) as a white solid. LC-MS $t_R$=1.207 min in 0-60AB_2 min chromatography (Xtimate C18 2.1*30 mm), MS (ESI) m/z 528.1 [M+H]⁺. ¹H NMR (CD₃OD 400 MHz): δ 9.05 (s, 1H), 8.43 (d, J=8.4 Hz, 1H), 8.00 (d, J=9.2 Hz, 1H), 7.99 (s, 1H), 7.81 (d, J=8.4 Hz, 1H), 7.58 (d, J=8.0 Hz, 1H), 5.10 (d, J=15.2 Hz, 1H), 4.98 (d, J=5.2 Hz, 1H), 4.86 (s, 2H), 4.64 (d, J=15.6 Hz, 1H), 3.56 (q, J=7.2 Hz, 2H), 3.36-3.34 (m, 2H), 3.23-3.21 (m, 3H), 2.43-2.39 (m, 1H), 2.15-2.13 (m, 2H), 2.14-2.01 (m, 1H), 1.93-1.90 (m, 2H), 1.29-1.16 (m, 13H), 1.04 (d, J=6.8 Hz, 3H). Isomer SFC $t_R$=4.350 min in 12 min chromatography (ee=98.2%).

Isomer 2 (7b) was made according to General Procedure A using trans-4-ethoxycyclohexane-1-carbaldehyde and (R)—N-((5-(ethylsulfonyl)pyridin-2-yl)methyl)-1-isopropylisoindoline-5-carboxamide as the starting materials. The crude material was purified by HCl preparative HPLC Method E separation to afford the HCl salt of isomer 2 (7b) (8.10 mg, 23%) as a white solid. LC-MS $t_R$=0.686 min in 5-95AB_1.5 min chromatography (MK RP Xtimate C18 2.1*30 mm), MS (ESI) m/z 528.1 [M+H]⁺. ¹H NMR (CD₃OD 400 MHz): δ 9.06 (s, 1H), 8.44 (d, J=8.0 Hz, 1H), 8.00 (d, J=9.2 Hz, 1H), 7.99 (s, 1H), 7.83 (d, J=8.4 Hz, 1H), 7.57 (d, J=7.6 Hz, 1H), 5.11 (d, J=14.8 Hz, 1H), 4.99 (d, J=4.4 Hz, 1H), 4.86 (s, 3H), 4.64 (d, J=15.6 Hz, 1H), 3.56 (q, J=6.8 Hz, 2H), 3.36-3.33 (m, 2H), 3.23-3.20 (m, 2H), 2.43-2.35 (m, 1H), 2.12-2.02 (m, 3H), 1.95-1.93 (m, 2H), 1.30-1.20 (m, 12H), 1.04 (d, J=7.2 Hz, 3H).

Examples 8a and 8b (S)-2-((-4-ethoxycyclohexyl)methyl)-N—((R)-1-(4-(ethylsulfonyl)phenyl)-2-hydroxyethyl)-1-isopropylisoindoline-5-carboxamide (8a) and (8b)

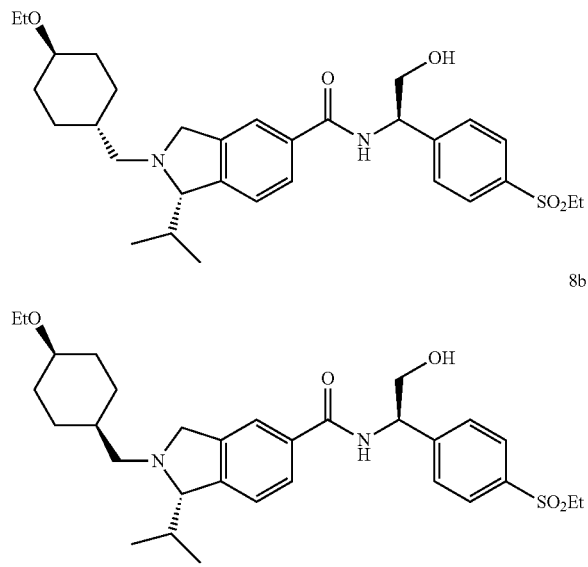

Isomers 1 and 2 (8a and 8b) was made according to General Procedure A using trans-4-ethoxycyclohexane-1-carbaldehyde and (S)—N—((R)-1-(4-(ethylsulfonyl)phenyl)-2-hydroxyethyl)-1-isopropylisoindoline-5-carboxamide as the starting materials. The crude residue was purified by HCl preparative HPLC Method E separation to afford the HCl salts of isomer 1 (8a) (6.90 mg, 10%) and isomer 2 (8b) (6.80 mg, 10%) as white solids.

Isomer 1 (8a) (6.90 mg, 10%). LC-MS $t_R$=0.652 min in 5-95AB_1.5 min chromatography (Welch MERCK RP-18e 25-2 mm), MS (ESI) m/z 557.1 [M+H]$^+$. $^1$H NMR (CD$_3$OD 400 MHz): δ 8.04 (d, J=8.0 Hz, 1H), 8.00 (s, 1H), 7.95 (d, J=8.0 Hz, 2H), 7.75 (d, J=8.4 Hz, 2H), 7.60 (d, J=8.0 Hz, 1H), 5.34 (t, J=6.4 Hz, 1H), 5.17-5.10 (m, 1H), 5.05-5.01 (m, 1H), 4.71-4.64 (m, 1H), 3.98 (d, J=6.4 Hz, 2H), 3.61 (q, J=7.2 Hz, 2H), 3.37-3.31 (m, 1H), 3.30-3.22 (m, 2H), 3.25 (q, J=7.2 Hz, 2H), 2.51-2.40 (m, 1H), 2.25-1.94 (m, 5H), 1.45-1.20 (m, 13H), 1.09 (d, J=6.8 Hz, 3H). Isomer SFC $t_R$=2.113 min in 3 min chromatography (ee=97.92%). Isomer 2 (8b) (6.80 mg, 10%). LC-MS $t_R$=0.661 min in 5-95AB_1.5 min chromatography (Welch MERCK RP-18e 25-2 mm), MS (ESI) m/z 557.1 [M+H]$^+$. $^1$H NMR (CD$_3$OD 400 MHz): δ 8.03 (d, J=7.6 Hz, 1H), 7.98 (s, 1H), 7.93 (d, J=8.4 Hz, 2H), 7.73 (d, J=8.4 Hz, 2H), 7.58 (d, J=7.6 Hz, 1H), 5.31 (t, J=6.0 Hz, 1H), 5.14-5.09 (m, 1H), 5.04-5.00 (m, 1H), 4.69-4.63 (m, 1H), 3.95 (d, J=6.4 Hz, 2H), 3.66-3.60 (m, 1H), 3.52 (q, J=7.2 Hz, 2H), 3.28-3.21 (m, 2H), 3.25 (q, J=7.2 Hz, 2H), 2.46-2.38 (m, 1H), 2.10-1.93 (m, 3H), 1.80-1.45 (m, 6H), 1.30-1.20 (m, 9H), 1.06 (d, J=6.8 Hz, 3H). Isomer SFC $t_R$=1.741 min in 3 min chromatography (ee=91.90%).

Example 9

(R)-2-((trans-4-ethoxycyclohexyl)methyl)-N—((R)-1-(4-(ethylsulfonyl)phenyl)-2-hydroxyethyl)-1-isopropylisoindoline-5-carboxamide (9)

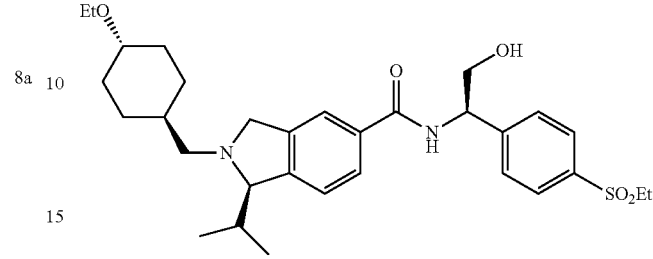

(R)-2-((trans-4-ethoxycyclohexyl)methyl)-N—((R)-1-(4-(ethylsulfonyl)phenyl)-2-hydroxyethyl)-1-isopropylisoindoline-5-carboxamide (9) was prepared according to General Procedure A using trans-4-ethoxycyclohexane-1-carbaldehyde and (R)—N—((R)-1-(4-(ethylsulfonyl)phenyl)-2-hydroxyethyl)-1-isopropylisoindoline-5-carboxamide as the starting materials. The crude residue was purified by HCl preparative HPLC Method F separation to afford the HCl salt of (R)-2-((trans-4-ethoxycyclohexyl)methyl)-N—((R)-1-(4-(ethylsulfonyl)phenyl)-2-hydroxyethyl)-1-isopropylisoindoline-5-carboxamide (9) (3.40 mg, 17%) as a white solid. LC-MS $t_R$=0.590 min in 5-95AB_1.5 min chromatography (Welch MK RP-18e 25-2 mm), MS (ESI) m/z 557.1 [M+H]$^+$. $^1$H NMR (CD$_3$OD 400 MHz): δ 7.98 (d, J=8.0 Hz, 1H), 7.95 (s, 1H), 7.89 (d, J=8.4 Hz, 2H), 7.69 (d, J=8.4 Hz, 2H), 7.55 (d, J=8.0 Hz, 1H), 5.28 (t, J=6.4 Hz, 1H), 5.13-5.07 (m, 1H), 5.03-4.97 (m, 1H), 4.64-4.60 (m, 1H), 3.92 (d, J=6.4 Hz, 2H), 3.61-3.54 (m, 3H), 3.35 (d, J=6.4 Hz, 2H), 3.23-3.19 (m, 4H), 2.45-2.35 (m, 1H), 2.23-2.00 (m, 5H), 1.97-1.80 (m, 4H), 1.26-1.17 (m, 9H), 1.03 (d, J=6.8 Hz, 3H). Isomer SFC $t_R$=2.653 min in 3 min chromatography (ee=97.5%).

Example 10a and 10b 2-((trans-4-ethoxycyclohexyl)methyl)-N—((S)-1-(4-(ethylsulfonyl)phenyl)-3-hydroxypropyl)-1-isopropylisoindoline-5-carboxamide (10a) and (10b)

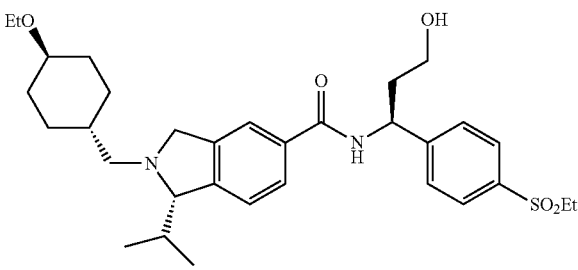

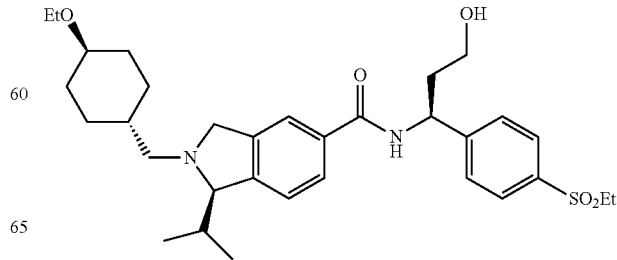

Isomer 1 (10a) was prepared according to General Procedure A using trans-4-ethoxycyclohexane-1-carbaldehyde and (S)—N—((S)-1-(4-(ethylsulfonyl)phenyl)-3-hydroxypropyl)-1-isopropylisoindoline-5-carboxamide as the starting materials. The crude residue was purified by preparative TLC (petroleum ether:ethyl acetate/1:6) and HCl preparative HPLC Method G separation to afford the HCl salt of isomer 1 (10a) (4.30 mg, 13%) as a white solid. LC-MS $t_R$=0.601 min in 5-95 AB_1.5 min chromatography (MK RP-18e 25-2 mm), MS (ESI) m/z 571.1 [M+H]$^+$. $^1$H NMR (CD$_3$OD 400 MHz): δ 9.08 (d, J=6.8 Hz, 1H), 7.96 (d, J=8.0 Hz, 1H), 7.92 (d, J=8.4 Hz, 2H), 7.90 (s, 1H), 7.70 (d, J=8.4 Hz, 2H), 7.57 (d, J=8.0 Hz, 1H), 5.41-5.39 (m, 1H), 5.08 (d, J=15.2 Hz, 1H), 4.98 (d, J=5.2 Hz, 1H), 4.88-4.86 (m, 1H), 4.63 (d, J=12.8 Hz, 1H), 3.66-3.62 (m, 2H), 3.58 (q, J=7.2 Hz, 2H), 3.27-3.26 (m, 1H), 3.25-3.21 (m, 2H), 3.22 (q, J=7.2 Hz, 2H), 2.42-2.38 (m, 1H), 2.20-2.18 (m, 4H), 2.16-2.10 (m, 1H), 1.96-1.92 (m, 2H), 1.32-1.28 (m, 2H), 1.25-1.20 (m, 11H), 1.04 (d, J=6.8 Hz, 3H). Isomer SFC $t_R$=3.298 min in 8 min chromatography (ee=100%).

Isomer 2 (10b) was prepared in accordance with General Procedure A using trans-4-ethoxycyclohexane-1-carbaldehyde and (R)—N—((S)-1-(4-(ethylsulfonyl)phenyl)-3-hydroxypropyl)-1-isopropylisoindoline-5-carboxamide as the starting materials. The crude residue was purified by preparative TLC (petroleum ether:ethyl acetate/1:6) and HCl preparative HPLC Method G separation to afford the HCl salt of isomer 2 (10b) (4.70 mg, 12%) as a white solid. LC-MS $t_R$=0.605 min in 5-95 AB_1.5 min chromatography (YMC-Pack ODS-AQ), MS (ESI) m/z 571.1 [M+H]$^+$. $^1$H NMR (CD$_3$OD 400 MHz): δ 9.08 (d, J=8.0 Hz, 1H), 7.95 (d, J=8.0 Hz, 1H), 7.93-7.90 (m, 3H), 7.70 (d, J=8.0 Hz, 2H), 7.57 (d, J=8.0 Hz, 1H), 5.41-5.39 (m, 1H), 5.08 (d, J=15.2 Hz, 1H), 4.98 (d, J=4.8 Hz, 1H), 4.90-4.88 (m, 1H), 4.63 (d, J=15.6 Hz, 1H), 3.66-3.62 (m, 2H), 3.58 (q, J=7.2 Hz, 2H), 3.37-3.34 (m, 1H), 3.34-3.32 (m, 2H), 3.22 (q, J=7.2 Hz, 2H), 2.42-2.38 (m, 1H), 2.20-2.15 (m, 4H), 2.13-1.87 (m, 3H), 1.32-1.28 (m, 2H), 1.25-1.20 (m, 11H), 1.04 (d, J=6.8 Hz, 3H). Isomer SFC $t_R$=3.479 min in 8 min chromatography (ee=98%).

Examples 11a, 11b, 11c and 11d

N-((5-(ethylsulfonyl)pyridin-2-yl)methyl)-2-(4-hydroxy-4-(trifluoromethyl)cyclohexyl)methyl)-1-isopropylisoindoline-5-carboxamide Isomers

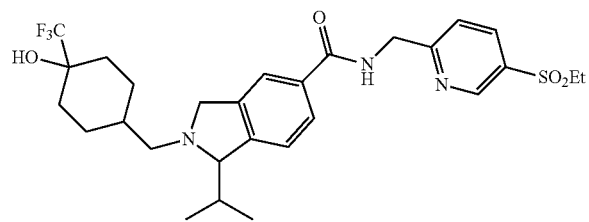

To a mixture of LiAlH$_4$ (200 mg, 5.26 mmol) in anhydrous THF (15 mL) was added a solution of 4-hydroxy-4-(trifluoromethyl)cyclohexanecarboxylic acid (500 mg, 2.36 mmol) in anhydrous THF (5 mL) at 0° C. under N$_2$. The mixture was stirred at rt for 2 h. To the mixture was added water (0.2 mL) slowly followed by 10% NaOH solution (0.2 mL) at 0° C. The mixture was filtered and the filtrate was dried over anhydrous Na$_2$SO$_4$, filtered and concentrated under reduced pressure to afford crude 4-(hydroxymethyl)-1-(trifluoromethyl)cyclohexanol (480 mg, 100%) as a white solid, which was used for the next step directly without further purification. $^1$H NMR (CDCl$_3$ 400 MHz): δ 3.60 (d, J=6.4 Hz, 1H), 3.50 (d, J=6.4 Hz, 1H), 1.89-1.77 (m, 5H), 1.75-1.65 (m, 1H), 1.64-1.56 (m, 2H), 1.38-1.34 (m, 2H).

To a solution of (COCl)$_2$ (0.35 mL, 3.84 mmol) in anhydrous CH$_2$Cl$_2$ (18 mL) was added DMSO (0.55 mL, 7.68 mmol) at −78° C. under N$_2$. After being stirred for 30 min, a solution of 4-(hydroxymethyl)-1-(trifluoromethyl)cyclohexanol (380 mg, 1.92 mmol) in anhydrous CH$_2$Cl$_2$ (5 mL) was added dropwise. The mixture was stirred at −78° C. for 30 min and solution of Et$_3$N (1.6 mL, 11.52 mmol) in anhydrous CH$_2$Cl$_2$ (5 mL) was added dropwise. After being stirred at −78° C. for 1 h, the mixture was warmed to rt and stirred overnight. CH$_2$Cl$_2$ (10 mL) was added and the organic layer was washed with water (3×20 mL) then brine (20 mL), dried over anhydrous Na$_2$SO$_4$, filtered and concentrated under reduced pressure. The crude residue was purified by column chromatography on silica gel (eluting with 33% ethyl acetate in petroleum ether) to afford 4-hydroxy-4-(trifluoromethyl)cyclohexanecarbaldehyde (280 mg, 74%) as a yellow oil.

N-((5-(ethylsulfonyl)pyridin-2-yl)methyl)-2-(4-hydroxy-4-(trifluoromethyl)cyclohexyl)methyl)-1-isopropylisoindoline-5-carboxamide was prepared according to General Procedure A using 4-hydroxy-4-(trifluoromethyl)cyclohexanecarbaldehyde described above as the starting material to afford 4 isomers (11a to 11d). The crude product was purified by preparative TLC (eluting with 75% ethyl acetate in petroleum ether) to afford two isomers. The less polar isomeric material was separated by SFC (OJ-3) and HCl preparative HPLC Method H separation to afford HCl salts of isomer 1 (11a) (11.90 mg, 17%) and isomer 2 (11b) (10.90 mg, 16%) as white solids. The more polar isomeric material was separated by SFC (OJ-3) and HCl preparative HPLC Method H separation to afford HCl salts of isomer 3 (11c) (5.10 mg, 10%) and isomer 4 (11d) (5.00 mg, 10%) as white solids.

Isomer 1 (11a) HCl salt (11.90 mg, 17%). LC-MS $t_R$=0.631 min in 5-95 AB_1.5 min chromatography (MK RP-18e 25-2 mm), MS (ESI) m/z 568.1 [M+H]$^+$. $^1$H NMR (CD$_3$OD 400 MHz): δ 9.13 (d, J=1.6 Hz, 1H), 8.60 (dd, J=2.0, 8.4 Hz, 1H), 8.01 (d, J=8.0 Hz, 1H), 8.00 (s, 1H), 7.97 (d, J=8.0 Hz, 1H), 7.57 (d, J=8.0 Hz, 1H), 5.12 (d, J=15.2 Hz, 1H), 5.00 (d, J=4.4 Hz, 1H), 4.89 (s, 2H), 4.66 (d, J=15.2 Hz, 1H), 3.37 (q, J=7.2 Hz, 2H), 3.25-3.20 (m, 2H), 2.43-2.40 (m, 1H), 2.03-1.91 (m, 1H), 1.90-1.87 (m, 3H), 1.86-1.85 (m, 1H), 1.69-1.65 (m, 2H), 1.57-1.51 (m, 2H), 1.28 (t, J=7.2 Hz, 3H), 1.20 (d, J=6.8 Hz, 3H), 1.03 (d, J=6.8 Hz, 3H). Isomer SFC $t_R$=4.355 min in 12 min chromatography (ee=99%).

Isomer 2 (11b) HCl salt (10.90 mg, 16%). LC-MS $t_R$=0.636 min in 5-95 AB_1.5 min chromatography (MK RP-18e 25-2 mm), MS (ESI) m/z 568.1 [M+H]$^+$. $^1$H NMR (CD3OD 400 MHz): δ 8.99 (s, 1H), 8.31 (dd, J=1.6, 8.4 Hz, 1H), 7.99 (d, J=8.4 Hz, 1H), 7.96 (s, 1H), 7.70 (d, J=8.4 Hz, 1H), 7.56 (d, J=8.4 Hz, 1H), 5.10 (d, J=15.2 Hz, 1H), 4.98 (d, J=4.4 Hz, 1H), 4.81 (s, 2H), 4.64 (d, J=15.2 Hz, 1H), 3.32-3.30 (m, 1H), 3.24 (q, J=7.2 Hz, 2H), 3.22-3.20 (m, 1H), 2.42-2.39 (m, 1H), 1.98-1.97 (m, 1H), 1.88-1.85 (m, 3H), 1.70-1.69 (m, 1H), 1.68-1.66 (m, 2H), 1.55-1.51 (m, 2H), 1.24 (t, J=7.2 Hz, 3H), 1.20 (d, J=6.8 Hz, 3H), 1.03 (d, J=6.8 Hz, 3H). Isomer SFC $t_R$=4.811 min in 12 min chromatography (ee=99%).

Isomer 3 (11c) HCl salt (5.10 mg, 10%). LC-MS $t_R$=0.576 min in 5-95 AB_1.5 min chromatography (YMC-Pack ODS-AQ), MS (ESI) m/z 568.1 [M+H]$^+$. $^1$H NMR (CD$_3$OD 400 MHz): δ 9.03 (s, 1H), 8.38 (dd, J=2.0, 8.0 Hz, 1H), 8.00 (d, J=8.4 Hz, 1H), 7.98 (s, 1H), 7.76 (d, J=8.4 Hz, 1H), 7.57 (d, J=8.0 Hz, 1H), 5.10 (d, J=15.2 Hz, 1H), 5.00 (d, J=4.0 Hz, 1H), 4.84 (s, 2H), 4.68 (d, J=15.6 Hz, 1H), 3.46-3.41 (m, 1H), 3.36-3.32 (m, 1H), 3.34 (q, J=7.2 Hz, 2H), 2.40-2.39 (m, 1H), 2.31-2.29 (m, 1H), 1.93-1.90 (m, 2H), 1.80-1.76 (m, 2H), 1.72-1.69 (m, 3H), 1.68-1.66 (m, 1H), 1.25 (t, J=7.2 Hz, 3H), 1.20 (d, J=6.8 Hz, 3H), 1.03 (d, J=6.8 Hz, 3H). Isomer SFC $t_R$=4.528 min in 12 min chromatography (ee=99.7%).

Isomer 4 (11d) HCl salt (5.00 mg, 10%). LC-MS $t_R$=0.573 min in 5-95 AB_1.5 min chromatography (YMC-Pack ODS-AQ), MS (ESI) m/z 568.1 [M+H]$^+$. $^1$H NMR (CD$_3$OD 400 MHz): δ 9.05 (d, J=1.6 Hz, 1H), 8.43 (dd, J=2.0, 8.0 Hz, 1H), 8.00 (d, J=8.4 Hz, 1H), 7.98 (s, 1H), 7.80 (d, J=8.0 Hz, 1H), 7.57 (d, J=8.0 Hz, 1H), 5.11 (d, J=15.6 Hz, 1H), 5.01 (d, J=4.8 Hz, 1H), 4.85 (s, 2H), 4.68 (d, J=15.6 Hz, 1H), 3.46-3.41 (m, 1H), 3.36-3.32 (m, 1H), 3.32 (q, J=7.2 Hz, 2H), 2.40-2.39 (m, 1H), 2.30-2.28 (m, 1H), 2.05-2.01 (m, 2H), 1.99-1.77 (m, 2H), 1.72-1.69 (m, 3H), 1.68-1.66 (m, 1H), 1.26 (t, J=7.2 Hz, 3H), 1.20 (d, J=6.8 Hz, 3H), 1.03 (d, J=6.8 Hz, 3H). Isomer SFC $t_R$=4.837 min in 12 min chromatography (ee=95%).

Examples 12a, 12b, 12c and 12d

N-(4-(ethylsulfonyl)benzyl)-2-((4-hydroxy-4-(trifluoromethyl)cyclohexyl)methyl)-1-isopropylisoindoline-5-carboxamide Isomers

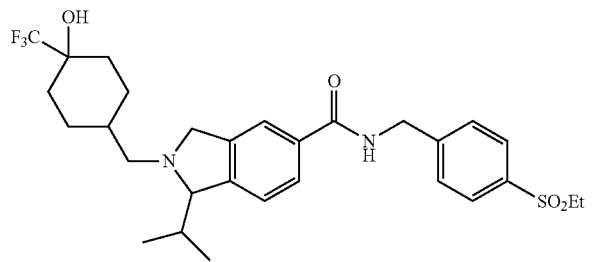

N-(4-(ethylsulfonyl)benzyl)-2-((4-hydroxy-4-(trifluoromethyl)cyclohexyl)methyl)-1-isopropylisoindoline-5-carboxamide was prepared according to General Procedure A, using N-(4-(ethylsulfonyl)benzyl)-1-isopropylisoindoline-5-carboxamide and 4-hydroxy-4-(trifluoromethyl)cyclohexanecarbaldehyde as the starting materials to afford 4 isomers (12a to 12d). The crude product was purified by preparative TLC (eluting with 70% ethyl acetate in petroleum ether) followed by SFC then HCl preparative HPLC method H separation to afford HCl salts of isomer 1 (12a) (8.20 mg, 7%), isomer 2 (12b) (6.90 mg, 6%), isomer 3 (12c) (13.40 mg, 11%), and isomer 4 (12d) (15.80 mg, 13%) as white solids.

Isomer 1 (12a) HCl salt (8.20 mg, 7%). LC-MS $t_R$=0.612 min in 5-95 AB_1.5 min chromatography (MK RP-18e 25-2 mm), MS (ESI) m/z 567.1 [M+H]$^+$. $^1$H NMR (CD$_3$OD 400 MHz): δ 7.98 (d, J=8.8 Hz, 1H), 7.97 (s, 1H), 7.90 (d, J=8.4 Hz, 2H), 7.65 (d, J=8.4 Hz, 2H), 7.58 (d, J=8.0 Hz, 1H), 5.12 (d, J=14.8 Hz, 1H), 5.01 (d, J=5.2 Hz, 1H), 4.72 (s, 2H), 4.70 (d, J=12.4 Hz, 1H), 3.45-3.42 (m, 1H), 3.38-3.35 (m, 1H), 3.22 (q, J=7.2 Hz, 2H), 2.42-2.41 (m, 1H), 2.33-2.31 (m, 1H), 2.05-2.03 (m, 2H), 1.91-1.83 (m, 2H), 1.72-1.70 (m, 3H), 1.65-1.60 (m, 1H), 1.22 (t, J=7.2 Hz, 3H), 1.22 (d, J=6.8 Hz, 3H), 1.05 (d, J=6.8 Hz, 3H). Isomer SFC $t_R$=8.782 min in 15 min chromatography (ee=100%).

Isomer 2 (12b) HCl salt (6.90 mg, 6%). LC-MS $t_R$=0.607 min in 5-95 AB_1.5 min chromatography (MK RP-18e 25-2 mm), MS (ESI) m/z 567.1 [M+H]$^+$. $^1$H NMR (CD$_3$OD 400 MHz): δ 7.98 (d, J=9.2 Hz, 1H), 7.97 (s, 1H), 7.90 (d, J=8.0 Hz, 2H), 7.65 (d, J=8.0 Hz, 2H), 7.58 (d, J=7.6 Hz, 1H), 5.12 (d, J=15.2 Hz, 1H), 5.01 (d, J=5.2 Hz, 1H), 4.72 (s, 2H), 4.70 (d, J=18.4 Hz, 1H), 3.47-3.42 (m, 1H), 3.38-3.37 (m, 1H), 3.21 (q, J=7.2 Hz, 2H), 2.42-2.41 (m, 1H), 2.33-2.31 (m, 1H), 2.05-2.03 (m, 2H), 1.91-1.82 (m, 2H), 1.73-1.70 (m, 3H), 1.62-1.58 (m, 1H), 1.22 (t, J=7.2 Hz, 3H), 1.22 (d, J=6.8 Hz, 3H), 1.05 (d, J=6.8 Hz, 3H). Isomer SFC $t_R$=9.378 min in 15 min chromatography (ee=98%).

Isomer 3 (12c) HCl salt (13.40 mg, 11%). LC-MS $t_R$=0.622 min in 5-95 AB_1.5 min chromatography (MK RP-18e 25-2 mm), MS (ESI) m/z 567.1 [M+H]$^+$. $^1$H NMR (CD$_3$OD 400 MHz): δ 7.98 (d, J=9.2 Hz, 1H), 7.97 (s, 1H), 7.90 (d, J=8.0 Hz, 2H), 7.65 (d, J=8.0 Hz, 2H), 7.58 (d, J=7.6 Hz, 1H), 5.12 (d, J=14.8 Hz, 1H), 5.00 (d, J=4.4 Hz, 1H), 4.72 (s, 2H), 4.66 (d, J=15.6 Hz, 1H), 3.28-3.25 (m, 2H), 3.22 (q, J=7.2 Hz, 2H), 2.45-2.42 (m, 1H), 2.01-1.99 (m, 1H), 1.94-1.88 (m, 3H), 1.73-1.67 (m, 3H), 1.56-1.53 (m, 2H), 1.23 (d, J=7.2 Hz, 3H), 1.22 (t, J=7.2 Hz, 3H), 1.05 (d, J=6.8 Hz, 3H). Isomer SFC $t_R$=9.717 min in 15 min chromatography (ee=96%).

Isomer 4 (12d) HCl salt (15.80 mg, 13%). LC-MS $t_R$=0.626 min in 5-95 AB_1.5 min chromatography (MK RP-18e 25-2 mm), MS (ESI) m/z 567.1 [M+H]$^+$. $^1$H NMR (CD$_3$OD 400 MHz): δ 7.98 (d, J=9.2 Hz, 1H), 7.97 (s, 1H), 7.90 (d, J=8.4 Hz, 2H), 7.65 (d, J=8.4 Hz, 2H), 7.58 (d, J=8.0 Hz, 1H), 5.12 (d, J=15.2 Hz, 1H), 5.00 (d, J=3.2 Hz, 1H), 4.72 (s, 2H), 4.66 (d, J=15.2 Hz, 1H), 3.30-3.26 (m, 2H), 3.22 (q, J=7.2 Hz, 2H), 2.43-2.42 (m, 1H), 2.06-2.05 (m, 1H), 1.94-1.88 (m, 3H), 1.71-1.68 (m, 3H), 1.57-1.53 (m, 2H), 1.23 (d, J=7.2 Hz, 3H), 1.22 (t, J=7.2 Hz, 3H), 1.05 (d, J=6.8 Hz, 3H). Isomer SFC $t_R$=10.327 min in 15 min chromatography (ee=98%).

Examples 13a, 13b, 13c, and 13d

N-((1-(ethylsulfonyl)piperidin-4-yl)methyl)-1-isopropyl-2-((4-methoxy-4-(trifluoromethyl)cyclohexyl)methyl)isoindoline-5-carboxamide Isomers

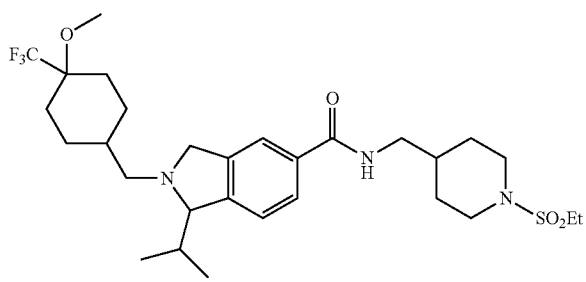

Scheme 21.

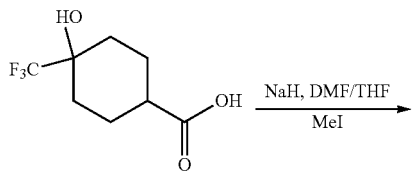

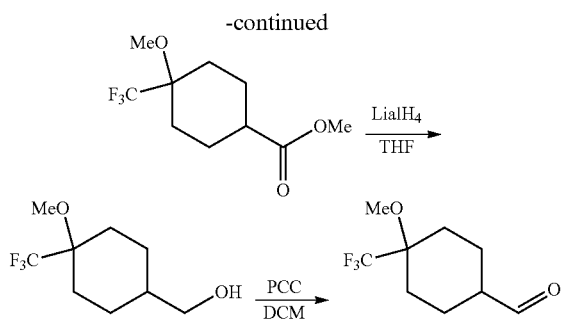

To a solution of 4-hydroxy-4-(trifluoromethyl)cyclohexanecarboxylic acid (500 mg, 2.36 mmol) in a solution of dry THF/DMF (6 mL, v/v=1:1) was added NaH (278 mg, 6.94 mmol, 60% in mineral oil) in portions at 0° C. under $N_2$. The mixture was stirred at 0° C. for 30 min, then MeI (2.38 g, 16.76 mmol) was added dropwise to the reaction mixture at 0° C. under $N_2$. The mixture was stirred at 30° C. for 3.5 h. TLC analysis (eluting with petroleum ether:ethyl acetate=3:1) showed that the reaction was complete. The mixture was quenched with a sat. $NH_4Cl$ solution (40 mL) at 0° C. and extracted with ethyl acetate (3×10 mL). The combined organic layers were washed with brine (30 mL), dried over anhydrous $Na_2SO_4$, filtered and concentrated under reduced pressure to afford crude methyl 4-methoxy-4-(trifluoromethyl)cyclohexanecarboxylate (crude 560 mg, 100%) as a yellow oil, which was used for the next step directly without further purification.

To a solution of methyl 4-methoxy-4-(trifluoromethyl)cyclohexanecarboxylate (560 mg, 2.36 mmol) in anhydrous THF (10 mL) was added $LiAlH_4$ (4.67 mL, 4.67 mmol, 1 M in THF) dropwise at 0° C. under $N_2$. The mixture was stirred at 0° C. for 1.5 h. TLC analysis (eluting with petroleum ether:ethyl acetate=3:1) showed that the starting material was consumed completely. The mixture was quenched with water (0.18 mL) slowly followed by 10% aqueous NaOH solution (0.18 mL) at 0° C. The mixture was filtered and the filtrate was concentrated under reduced pressure to afford crude (4-methoxy-4-(trifluoromethyl)cyclohexyl)methanol (500 mg, 100%) as a colorless oil, which was used for the next step directly without further purification.

To a solution of (4-methoxy-4-(trifluoromethyl)cyclohexyl)methanol (100 mg, 0.47 mmol) in anhydrous $CH_2Cl_2$ (3 mL) was added PCC (200 mg, 0.94 mmol). The mixture was stirred at rt for 2 h. TLC analysis (eluting with petroleum ether:ethyl acetate=3:1) showed that the starting material was consumed completely. The reaction mixture was quenched with water (20 mL) and extracted with $CH_2Cl_2$ (2×15 mL). The combined organic layers were dried over anhydrous $MgSO_4$, filtered and concentrated under reduced pressure to afford crude 4-methoxy-4-(trifluoromethyl)cyclohexanecarbaldehyde (100 mg, 100%) as a brown oil. This material was used for next step directly without further purification.

N-((1-(ethylsulfonyl)piperidin-4-yl)methyl)-1-isopropyl-2-((4-methoxy-4-(trifluoromethyl)cyclohexyl)methyl)isoindoline-5-carboxamide was prepared according to General Procedure A, using N-((1-(ethylsulfonyl)piperidin-4-yl)methyl)-1-isopropylisoindoline-5-carboxamide and 4-methoxy-4-(trifluoromethyl)cyclohexane carbaldehyde as the starting materials to afford 4 isomers (13a to 13d). The crude residue was purified by column chromatography on silica gel (eluting with a gradient of 33% to 75% EtOAc in petroleum ether) to give the crude free base. This crude free base was taken up in ethyl acetate (20 mL) and HCl/dioxane (1 mL, 4M) was added. The solution was then concentrated under reduced pressure to afford the crude product as the HCl salt (100 mg, 66%). This mixture was purified by SFC separation followed by HCl preparative HPLC method separation to afford HCl salts of isomer 1 (13a) (4.10 mg, 4%), isomer 2 (13b) (13.70 mg, 14%), and an inseparable mixture of isomers 3 and 4 (13c and 13d) (24.70 mg, 25%) as white solids.

Isomer 1 (13a) (4.10 mg, 4%) LC-MS $t_R$=0.643 min in 5-95AB_1.5 min chromatography (Welch Sepax-Pack ODS-AQ), MS (ESI) m/z 588.2 $[M+H]^+$. $^1H$ NMR ($CD_3OD$ 400 MHz): δ 8.70 (brs, 1H), 7.95-7.83 (m, 2H), 7.53 (d, J=7.2 Hz, 1H), 5.15-5.00 (m, 3H), 4.70-4.60 (m, 1H), 3.76 (d, J=12.4 Hz, 2H), 3.41 (s, 3H), 3.42-3.35 (m, 2H), 3.02 (q, J=7.6 Hz, 2H), 2.83 (t, J=12.0 Hz, 2H), 2.48-2.18 (m, 2H), 2.02-1.78 (m, 8H), 1.78-1.52 (m, 3H), 1.40-1.34 (m, 3H), 1.31 (t, J=7.6 Hz, 3H), 1.19 (d, J=6.0 Hz, 3H), 1.02 (d, J=6.0 Hz, 3H). Isomer SFC $t_R$=7.713 min in 15 min chromatography (ee=92%).

HCl salt of isomer 2 (13b) (13.70 mg, 14%). LC-MS $t_R$=0.639 min in 5-95AB_1.5 min chromatography (Welch Sepax-Pack ODS-AQ), MS (ESI) m/z 588.2 $[M+H]^+$. $^1H$ NMR ($CD_3OD$ 400 MHz): δ 8.70 (brs, 1H), 7.95-7.83 (m, 2H), 7.54 (d, J=7.6 Hz, 1H), 5.12-5.04 (m, 1H), 5.00-4.94 (m, 2H), 4.66-4.58 (m, 1H), 3.77 (d, J=12.4 Hz, 2H), 3.40 (s, 3H), 3.36-3.32 (m, 2H), 3.27-3.15 (m, 1H), 3.02 (q, J=7.6 Hz, 2H), 2.83 (t, J=12.0 Hz, 2H), 2.45-2.32 (m, 1H), 2.14-1.92 (m, 3H), 1.90-1.72 (m, 5H), 1.70-1.57 (m, 2H), 1.50-1.30 (m, 4H), 1.31 (t, J=7.6 Hz, 3H), 1.21 (d, J=6.8 Hz, 3H), 1.02 (d, J=6.8 Hz, 3H). Isomer SFC $t_R$=7.976 min in 15 min chromatography (ee=89%).

HCl salt mixture of isomers 3 and 4 (13c and 13d) (24.70 mg, 25%). LC-MS $t_R$=0.637 min in 5-95AB_1.5 min chromatography (Welch MK RP-18e 25-2 mm), MS (ESI) m/z 588.2 $[M+H]^+$. $^1H$ NMR ($CD_3OD$ 400 MHz): δ 8.68 (brs, 1H), 7.95-7.81 (m, 2H), 7.54 (d, J=7.2 Hz, 1H), 5.15-5.04 (m, 1H), 5.02-4.93 (m, 1H), 4.70-4.60 (m, 1H), 3.77 (d, J=12.0 Hz, 2H), 3.41 (s, 3H), 3.40-3.34 (m, 2H), 3.27-3.15 (m, 1H), 3.02 (q, J=7.2 Hz, 2H), 2.83 (t, J=12.0 Hz, 2H), 2.45-2.25 (m, 2H), 2.14-2.02 (m, 2H), 2.00-1.72 (m, 6H), 1.70-1.53 (m, 2H), 1.50-1.30 (m, 3H), 1.31 (t, J=7.2 Hz, 3H), 1.21 (d, J=5.6 Hz, 3H), 1.02 (d, J=5.6 Hz, 3H). Isomer SFC $t_R$=8.310 and 8.680 min in 15 min chromatography (ee=36%, racemic).

Examples 14a and 14b (S)-1-isopropyl-2-((4-methoxy-4-(trifluoromethyl)cyclohexyl)methyl)-N-((1-(methylsulfonyl)piperidin-4-yl)methyl)isoindoline-5-carboxamide Isomers

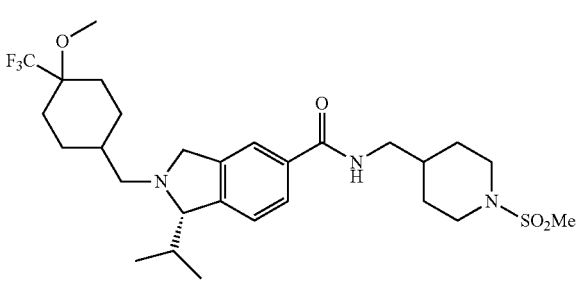 [SMILES: COC1(C(F)(F)F)CCC(CN2Cc3cc(C(=O)NCC4CCN(S(C)(=O)=O)CC4)ccc3[C@@H]2C(C)C)CC1]

(S)-1-isopropyl-2-((4-methoxy-4-(trifluoromethyl)cyclohexyl)methyl)-N-((1-(methylsulfonyl)piperidin-4-yl)methyl)isoindoline-5-carboxamide was prepared according to General Procedure A, using (S)-1-isopropyl-N-((1-(methylsulfonyl)piperidin-4-yl)methyl)isoindoline-5-carboxamide and 4-methoxy-4-(trifluoromethyl)cyclohexane carbaldehyde as the starting materials to afford 2 isomers (14a and 14b). The crude free base was taken up in ethyl acetate (20 mL) and HCl/dioxane (1 mL, 4M) was added. The solution was then concentrated under reduced pressure to afford the crude product as the HCl salt (66 mg, 100%). This mixture was purified by SFC separation followed by HCl preparative HPLC method separation to afford isomer 1 (14a) HCl salt (4.00 mg, 12%) and isomer 2 (14b) HCl salt (4.00 mg, 12%) as white solids.

HCl salt of isomer 1 (14a) (4.00 mg, 12%). LC-MS: $t_R$=0.776 min in 5-95AB_1.5 min chromatography (MK RP-18e 25-2 mm), MS (ESI) m/z 574.2 [M+H]$^+$. $^1$H NMR (CD$_3$OD 400 MHz): δ 8.65 (s, 1H), 7.86 (s, 2H), 7.51 (d, J=6.8 Hz, 1H), 5.15-5.00 (m, 3H), 4.65-4.55 (m, 1H), 3.72 (d, J=12.0 Hz, 2H), 3.39 (s, 3H), 3.38-3.31 (m, 2H), 2.80 (s, 3H), 2.72 (t, J=10.8 Hz, 2H), 2.40-2.30 (m, 2H), 2.10-1.70 (m, 9H), 1.64 (q, J=14.0 Hz, 2H), 1.45-1.32 (m, 3H), 1.18 (d, J=6.4 Hz, 3H), 1.00 (d, J=6.4 Hz, 3H). Isomer SFC $t_R$=5.415 min in 12 min chromatography (ee=100.00%).

HCl salt of isomer 2 (14b) (4.00 mg, 12%) LC-MS: $t_R$=0.772 min in 5-95AB_1.5 min chromatography (MK RP-18e 25-2 mm), MS (ESI) m/z 574.1 [M+H]$^+$. $^1$H NMR (CD$_3$OD 400 MHz): δ 8.63 (s, 1H), 7.85 (s, 2H), 7.49 (s, 1H), 5.15-5.00 (m, 3H), 4.70-4.55 (m, 1H), 3.72 (d, J=11.6 Hz, 2H), 3.39 (s, 3H), 3.35-3.30 (m, 2H), 2.80 (s, 3H), 2.72 (t, J=10.8 Hz, 2H), 2.40-2.15 (m, 2H), 2.10-1.70 (m, 8H), 1.70-1.55 (m, 3H), 1.40-1.25 (m, 3H), 1.16 (s, 3H), 0.99 (s, 3H). Isomer SFC $t_R$=5.685 min in 12 min chromatography (ee=100.00%).

Examples 15a, 15b, 15c and 15d

N-((5-(ethylsulfonyl)pyridin-2-yl)methyl)-1-isopropyl-2-((2-methyl-4,5,6,7-tetrahydrobenzo[d]oxazol-6-yl)methyl)isoindoline-5-carboxamide Isomers

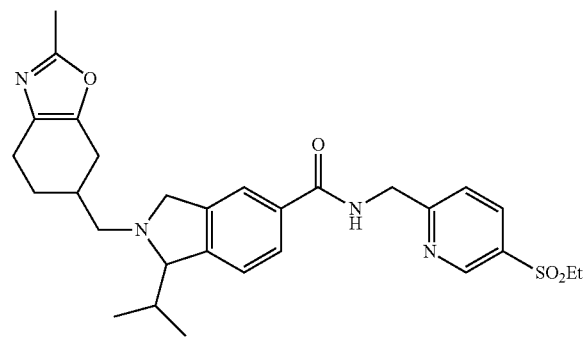

Scheme 22.

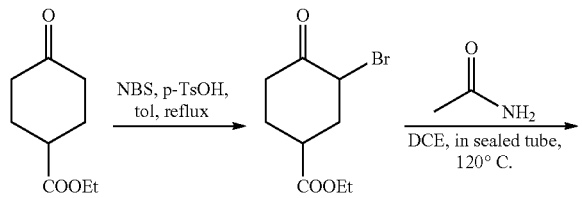

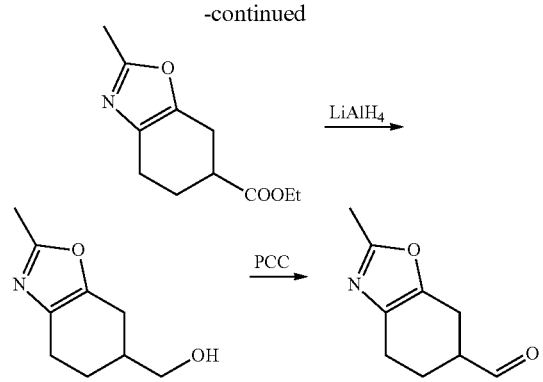

To a solution of ethyl 4-oxocyclohexanecarboxylate (5.0 g, 29 mmol) in anhydrous toluene (75 mL) was added NBS (5.5 g, 31 mmol), followed by p-TsOH (450 mg, 3.0 mmol). The mixture was stirred at 110° C. for 5 h under N$_2$. The toluene was evaporated under reduced pressure and the residue was partitioned between water (250 mL) and EtOAc (250 mL). After separation, the organic layers were washed with a saturated sodium bicarbonate solution, followed by brine (100 mL), dried over anhydrous Na$_2$SO$_4$ and filtered. The crude residue was purified by column chromatography on silica gel (eluting with 20% ethyl acetate in petroleum ether) to give ethyl 3-bromo-4-oxocyclohexanecarboxylate (4.0 g, 55%) as a yellow oil.

To a mixture of ethyl 3-bromo-4-oxocyclohexanecarboxylate (500 mg, 2.02 mmol) in DCE (5 mL) was added acetamide (596 mg, 10.1 mmol). The mixture was stirred at 120° C. in a sealed tube overnight. Water (10 mL) was added and the product was extracted with ethyl acetate (3×15 mL). The combined organic layers were dried over anhydrous sodium sulfate, filtered and concentrated under reduced pressure. The residue was purified by preparative TLC (eluting with 50% ethyl acetate in petroleum ether) to afford ethyl 2-methyl-4,5,6,7-tetrahydrobenzo[d]oxazole-6-carboxylate (130 mg, 31%) as a yellow solid. LC-MS $t_R$=0.603 min in 5-95AB_1.5 min chromatography (MK RP-18e 25-2 mm, UM8505/148), MS (ESI) m/z 209.9 [M+H]$^+$.

To a mixture of ethyl 2-methyl-4,5,6,7-tetrahydrobenzo[d]oxazole-6-carboxylate (130 mg, 0.62 mmol) in anhydrous THF (3 mL) was added LiAlH$_4$ (71 mg, 1.86 mmol) at 0° C. The mixture was stirred at 0° C. under N$_2$ for 3 h. 0.1 mL of H$_2$O and 0.1 mL of a 10% aqueous NaOH solution were carefully added to the reaction mixture at 0° C. The mixture was filtered and the filtrate was concentrated under reduced pressure to afford crude (2-methyl-4,5,6,7-tetrahydrobenzo[d]oxazol-6-yl)methanol (100 mg, 96%) as a yellow oil which was used for the next step directly without further purification.

To a solution of (2-methyl-4,5,6,7-tetrahydrobenzo[d]oxazol-6-yl)methanol (100 mg, 0.60 mmol) in anhydrous DCM (5 mL) was added PCC (389 mg, 1.80 mmol) at rt. The mixture was stirred for 4 h. The reaction was quenched with water (10 mL) and extracted with ethyl acetate (3×10 mL). The combined organic layers were dried over anhydrous Na$_2$SO$_4$, filtered and concentrated under reduced pressure to afford crude 2-methyl-4,5,6,7-tetrahydrobenzo[d]oxazole-6- carbaldehyde (75 mg, 76%) as a yellow oil, which was used for next step directly without further purification.

N-((5-(ethylsulfonyl)pyridin-2-yl)methyl)-1-isopropyl-2-((2-methyl-4,5,6,7-tetrahydrobenzo[d]oxazol-6-yl)methyl)isoindoline-5-carboxamide was prepared according to General Procedure A, using 2-methyl-4,5,6,7-tetrahydrobenzo[d]oxazole-6-carbaldehyde as the starting material to afford 4 isomers (15a-15d). The crude residue was purified by preparative TLC (eluting with 50% ethyl acetate in petroleum ether) followed by SFC (AD-H) then HCl preparative HPLC to afford isomer 1 (15a) HCl salt (5.90 mg, 7%), isomer 2 (15b) HCl salt (8.40 mg, 9%), isomer 3 (15c) HCl salt (9.60 mg, 11%) and isomer 4 (15d) HCl salt (4.00 mg, 4%) as white solids.

HCl salt of isomer 1 (15a) (5.90 mg, HCl salt, 7%). LC-MS $t_R$=0.596 min in 5-95AB_1.5 min chromatography (MK RP-18e 25-2 mm, μm 8505/148), MS (ESI) m/z 537.1 [M+H]$^+$. $^1$H NMR (CD$_3$OD 400 MHz): δ 9.06 (d, J=2.0 Hz, 1H), 8.45 (dd, J=2.4, 8.4 Hz, 1H), 8.03-8.01 (m, 2H), 7.83 (d, J=8.4 Hz, 1H), 7.59 (d, J=8.4 Hz, 1H), 5.19 (d, J=14.8 Hz, 1H), 5.07 (d, J=4.0 Hz, 1H), 4.87 (s, 2H), 4.77-4.73 (m, 1H), 3.55-3.45 (m, 2H), 3.31 (q, J=6.8 Hz, 2H), 3.20-3.10 (m, 1H), 2.80-2.65 (m, 7H), 2.55-2.45 (m, 1H), 2.35-2.30 (m, 1H), 1.83-1.80 (m, 1H), 1.29-1.22 (m, 6H), 1.06 (d, J=6.8 Hz, 3H). Isomer SFC $t_R$=4.130 min in 10 min chromatography (ee=94%).

HCl salt of isomer 2 (15b) (8.40 mg, HCl salt, 9%). LC-MS $t_R$=0.599 min in 5-95AB_1.5 min chromatography (MK RP-18e 25-2 mm, UM8505/148), MS (ESI) m/z 537.1 [M+H]$^+$. $^1$H NMR (CD$_3$OD 400 MHz): δ 9.06 (d, J=2.0 Hz, 1H), 8.46 (dd, J=2.4, 8.4 Hz, 1H), 8.03-8.01 (m, 2H), 7.85 (d, J=8.4 Hz, 1H), 7.59 (d, J=8.4 Hz, 1H), 5.20 (d, J=15.6 Hz, 1H), 5.09 (d, J=4.0 Hz, 1H), 4.87 (s, 2H), 4.72 (d, J=15.2 Hz, 1H), 3.51 (d, J=4.8 Hz, 1H), 3.32 (q, J=7.2 Hz, 2H), 3.20-3.10 (m, 1H), 2.79 (s, 3H), 2.75-2.60 (m, 4H), 2.55-2.45 (m, 1H), 2.30-2.20 (m, 1H), 1.80-1.70 (m, 1H), 1.29-1.24 (m, 6H), 1.07 (d, J=6.4 Hz, 3H). Isomer SFC $t_R$=4.872 min in 10 min chromatography (ee=98%).

HCl salt of isomer 3 (15c) (9.60 mg, HCl salt, 11%). LC-MS $t_R$=0.593 min in 5-95AB_1.5 min chromatography (MK RP-18e 25-2 mm, UM8505/148), MS (ESI) m/z 537.1 [M+H]$^+$. $^1$H NMR (CD$_3$OD 400 MHz): δ 9.07 (d, J=2.0 Hz, 1H), 8.49 (dd, J=2.0, 8.4 Hz, 1H), 8.03-8.01 (m, 2H), 7.74 (d, J=8.4 Hz, 1H), 7.59 (d, J=8.8 Hz, 1H), 5.20 (d, J=14.8 Hz, 1H), 5.10 (d, J=4.0 Hz, 1H), 4.88 (s, 2H), 4.72 (d, J=15.2 Hz, 1H), 3.51 (d, J=4.8 Hz, 1H), 3.31 (q, J=7.6 Hz, 2H), 3.20-3.10 (m, 1H), 2.80 (s, 3H), 2.75-2.65 (m, 4H), 2.55-2.45 (m, 1H), 2.30-2.25 (m, 1H), 1.80-1.70 (m, 1H), 1.29-1.24 (m, 6H), 1.07 (d, J=6.4 Hz, 3H). Isomer SFC $t_R$=7.005 min in 10 min chromatography (ee=100%).

HCl salt of isomer 4 (15d) (4.00 mg, 4%). LC-MS $t_R$=0.598 min in 5-95AB_1.5 min chromatography (MK RP-18e 25-2 mm, UM8505/148), MS (ESI) m/z 537.0 [M+H]$^+$. $^1$H NMR (CD$_3$OD 400 MHz): δ 9.02 (d, J=2.0 Hz, 1H), 8.35 (dd, J=2.0 and 8.0 Hz, 1H), 8.02-8.00 (m, 2H), 7.74 (d, J=8.4 Hz, 1H), 7.59 (d, J=8.0 Hz, 1H), 5.20 (d, J=14.8 Hz, 1H), 5.06-5.05 (m, 1H), 4.84 (s, 2H), 4.76-4.70 (m, 1H), 3.55-3.45 (m, 2H), 3.32 (q, J=7.2 Hz, 2H), 3.20-3.10 (m, 1H), 2.71 (s, 3H), 2.73-2.60 (m, 4H), 2.55-2.45 (m, 1H), 2.30-2.25 (m, 1H), 1.85-1.75 (m, 1H), 1.29-1.23 (m, 6H), 1.06 (d, J=6.4 Hz, 3H). Isomer SFC $t_R$=5.149 min in 10 min chromatography (ee=100%).

Examples 16a and 16b (S)—N-((5-(ethylsulfonyl)pyridin-2-yl)methyl)-1-isopropyl-2-((-6-(trifluoromethyl)tetrahydro-2H-pyran-3-yl)methyl)isoindoline-5-carboxamide Isomers

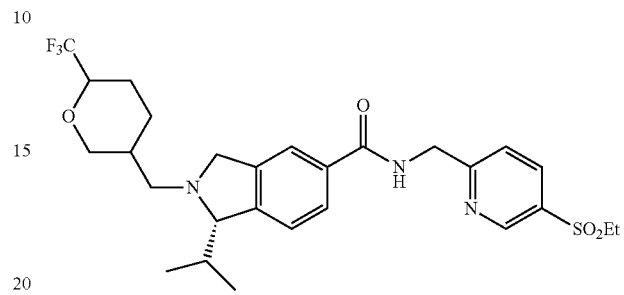

Scheme 23

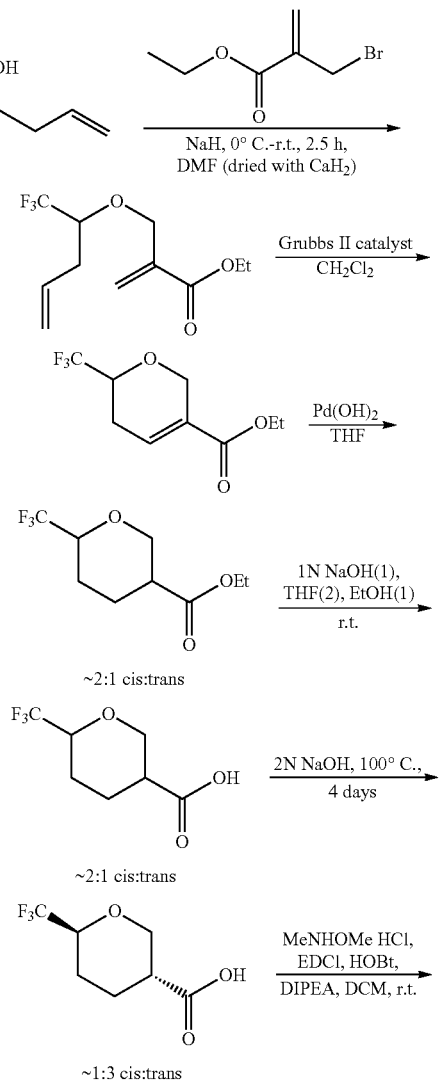

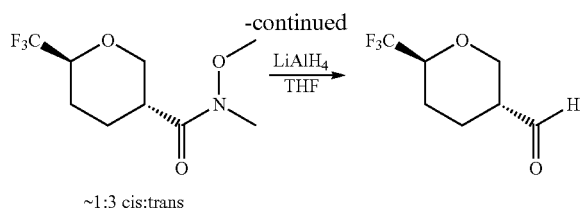

~1:3 cis:trans

To a solution of 1,1,1-trifluoropent-4-en-2-ol (6.7 g, 48 mmol) in anhydrous DMF (85 mL) (dried with CaH$_2$) was added NaH (2.3 g, 57 mmol, 60% in mineral oil) in portions at 0° C. The mixture was stirred at 0° C. for 30 min and ethyl 2-(bromomethyl)acrylate (9.2 g, 48 mmol) was added dropwise to the resulting mixture via syringe at 0° C. After addition, the mixture was stirred at rt for 2 h. TLC analysis (eluting with petroleum ether:ethyl acetate=10:1) showed that the starting material was consumed. The reaction was quenched with water (50 mL) at 0° C. and the aqueous layer was extracted with ethyl acetate (3×50 mL). The combined organic layers were washed successively with water (3×50 mL), brine (50 mL), dried over anhydrous sodium sulfate, filtered and concentrated under reduced pressure. The crude residue was purified by column chromatography on silica gel (eluting with petroleum ether/ethyl acetate:gradient from 100/1 to 50/1) to afford ethyl 2-(((1,1,1-trifluoropent-4-en-2-yl)oxy)methyl)acrylate (6.6 g, 55%) as a pale yellow oil. $^1$H NMR (CDCl$_3$ 400 MHz): δ 6.31 (s, 1H), 5.89 (s, 1H), 5.85-5.74 (m, 1H), 5.23-5.07 (m, 2H), 4.52-4.43 (m, 1H), 4.38-4.15 (m, 3H), 3.82-3.68 (m, 1H), 2.50-2.35 (m, 2H), 1.38-1.20 (m, 3H).

To a solution of ethyl 2-(((1,1,1-trifluoropent-4-en-2-yl)oxy)methyl)acrylate (6.6 g, 26.2 mmol) in anhydrous CH$_2$Cl$_2$ (2.6 L) was added Grubbs II catalyst (2.2 g, 2.62 mmol) under N$_2$. The mixture was stirred at rt for 3 h. TLC analysis (eluting with petroleum ether:ethyl acetate=10:1) showed that the reaction was complete. Water (2 L) was added to the mixture to quench the reaction. After partition, the organic layer was washed successively with water (3×2 L) then brine (2 L), dried over anhydrous sodium sulfate, filtered and concentrated under reduced pressure. The residue was purified by column chromatography on silica gel (eluting with petroleum ether/ethyl acetate: gradient from 100/1 to 80/1) to afford ethyl 6-(trifluoromethyl)-5,6-dihydro-2H-pyran-3-carboxylate (4.83 g, 82%) as a pale yellow oil. $^1$H NMR (CDCl$_3$ 400 MHz): δ 7.01 (d, J=2.8 Hz, 1H), 4.63-4.58 (m, 1H), 4.40-4.33 (m, 1H), 4.20 (q, J=7.2 Hz, 2H), 3.95-3.84 (m, 1H), 2.57-2.46 (m, 1H), 2.41-2.32 (m, 1H), 1.28 (t, J=7.2 Hz, 3H).

To a solution of ethyl 6-(trifluoromethyl)-5,6-dihydro-2H-pyran-3-carboxylate (4.83 g, 22 mmol) in anhydrous THF (130 mL) was added dry Pd(OH)$_2$ on carbon (2.7 g, 10% w/w). The mixture was stirred at rt for 16 h under H$_2$ (30 psi). TLC analysis (eluting with petroleum ether/ethyl acetate=10/1) showed that most of the starting material was not consumed. The mixture was filtered, then the filtrate was concentrated under reduced pressure and dissolved into anhydrous THF (60 mL). Dry Pd(OH)$_2$ on carbon (2.7 g, 10% w/w) was added to the mixture. The mixture was stirred at rt for 28 h under H$_2$ (30 psi). TLC analysis (eluting with petroleum ether/ethyl acetate=10/1) showed that the starting material was consumed. The mixture was filtered and the filtrate was concentrated under reduced pressure to afford crude ethyl 6-(trifluoromethyl)tetrahydro-2H-pyran-3-carboxylate (3.4 g, 70%) as a colorless oil, which was used for the next step directly without further purification. $^1$H NMR (CDCl$_3$ 400 MHz): δ 4.50 (d, J=11.6 Hz, 1H), 4.18 (q, J=7.2 Hz, 2H), 3.80-3.68 (m, 1H), 3.66 (d, J=3.2, 11.6 Hz, 1H), 2.55-2.49 (m, 1H), 2.43-2.35 (m, 1H), 1.95-1.81 (m, 1H), 1.75-1.65 (m, 2H), 1.25 (t, J=7.2 Hz, 3H).

To a solution of crude ethyl 6-(trifluoromethyl)tetrahydro-2H-pyran-3-carboxylate (2.0 g, 8.8 mmol) in THF (24 mL), EtOH (12 mL) was added 1 N aqueous NaOH solution (12 mL). The mixture was stirred at rt for 3 h. TLC analysis (eluting with petroleum ether:ethyl acetate=10:1) showed that the reaction was complete. The mixture was added to water (20 mL) and concentrated under reduced pressure to remove the organic solvent. The residue was washed with MTBE (20 mL) and adjusted to pH=4-5 with 1 N HCl solution. Then, the aqueous layer was extracted with EtOAc (3×20 mL). The combined organic layers were washed successively with brine (20 mL), dried over anhydrous sodium sulfate, filtered and concentrated under reduced pressure to afford crude 6-(trifluoromethyl)tetrahydro-2H-pyran-3-carboxylic acid (1.72 g, 98%) as a pale yellow oil, which was used for the next step directly without further purification. The ratio of cis:trans isomers was ~2:1 based on $^1$H NMR and $^{19}$F NMR analysis.

To a solution of crude 6-(trifluoromethyl)tetrahydro-2H-pyran-3-carboxylic acid (1.72 g, 8.69 mmol) was added a 2 N aqueous NaOH solution (76 mL). The mixture was stirred in sealed tube at 100° C. for 84 h. The mixture was added to water (20 mL) and washed with MTBE (50 mL). The aqueous layer was adjusted to pH=4-5 with 1 N HCl solution and extracted with EtOAc (3×50 mL). The combined organic layers were washed successively with brine (50 mL), dried over anhydrous sodium sulfate, filtered and concentrated under reduced pressure to afford crude 6-(trifluoromethyl)tetrahydro-2H-pyran-3-carboxylic acid (1.60 g, 93%) as a pale yellow oil, which was used for the next step directly without further purification. The ratio of cis:trans was 1:3 based on $^1$H NMR and $^{19}$F NMR analysis.

To a solution of crude 6-(trifluoromethyl)tetrahydro-2H-pyran-3-carboxylic acid (1.0 g, 5.01 mmol) (~1:3 cis:trans ratio of isomers) in anhydrous CH$_2$Cl$_2$ (60 mL) was added N,O-dimethylhydroxylamine hydrochloride (980 mg, 10.10 mmol), EDCI (1.93 g, 10.10 mmol), HOBt (1.36 g, 10.10 mmol), and DIPEA (1.95 g, 15.15 mmol). The mixture was stirred at rt for 16 h. The mixture was added to water (60 mL) and extracted with CH$_2$Cl$_2$ (3×60 mL). The combined organic layers were washed successively with brine (60 mL), dried over anhydrous sodium sulfate, filtered and concentrated under reduced pressure. The residue was purified by column chromatography on silica gel (eluting with petroleum ether/ethyl acetate: gradient from 30/1 to 15/1) to afford N-methoxy-N-methyl-6-(trifluoromethyl)tetrahydro-2H-pyran-3-carboxamide (1.05 g, 87%) as a pale yellow oil. The ratio of cis:trans was 1:3 based on $^1$H NMR and $^{19}$F NMR analysis. $^1$H NMR (CDCl$_3$ 400 MHz): δ 4.30-4.24 (m, 0.25H), 4.22-4.15 (m, 0.75H), 3.90-3.68 (m, 4H), 3.62-3.52 (m, 1H), 3.24-3.14 (m, 2H), 3.10-2.98 (m, 1H), 2.14-2.04 (m, 1H), 1.95-1.80 (m, 2H), 1.80-1.65 (m, 2H).

To a solution of N-methoxy-N-methyl-6-(trifluoromethyl)tetrahydro-2H-pyran-3-carboxamide (90 mg, 0.373 mmol) (~1:3 cis:trans ratio of isomers) in anhydrous THF (5 mL) was added LiAlH$_4$ (0.75 mL, 0.746 mmol, 1 M in THF) dropwise at 0° C. under N$_2$. The mixture was stirred at 0° C. for 1 h. TLC analysis (eluting with petroleum ether/ethyl acetate: 5/1) showed that the reaction was complete. The mixture was quenched with a sat. Na$_2$SO$_4$ solution (1 mL) and filtered. The filtrate was diluted with DCM (60 mL) and washed with water (60 mL), a 10% HCl solution (0.5 M, 60 mL), a sat. NaHCO$_3$ solution (60 mL) and then water (60 mL), respectively. The organic layer was dried over anhydrous sodium sulfate, filtered and concentrated under reduced pressure to afford crude 6-(trifluoromethyl)tetrahydro-2H-pyran-3-carbaldehyde (60 mg, 88%) as a pale yellow oil, which was used for the next step directly without further purification. The ratio of cis:trans was 1:3 based on $^1$H NMR and $^{19}$F NMR analysis.

(S)—N-((5-(ethylsulfonyl)pyridin-2-yl)methyl)-1-isopropyl-2-((-6-(trifluoromethyl)tetrahydro-2H-pyran-3-yl)

methyl)isoindoline-5-carboxamide was prepared according to General Procedure A using (S)—N-((5-(ethylsulfonyl)pyridin-2-yl)methyl)-1-isopropylisoindoline-5-carboxamide and 6-(trifluoromethyl)tetrahydro-2H-pyran-3-carbaldehyde (~1:3 ratio of cis:trans isomers) as the starting materials. The crude material was separated by SFC (IC-3) to give two crude isomer products (16a and 16b), which were purified by HCl preparative HPLC separation, then lyophilized directly to afford isomer 1 (16a) HCl salt (30.10 mg, 23%) and isomer 2 (16b) HCl salt (17.80 mg, 14%) as white solids.

HCl salt of isomer 1 (16a) (30.10 mg, 23%). LC-MS $t_R$=0.642 min in 5-95AB_1.5 min chromatography (Welch MK RP-18e 25-2 mm), MS (ESI) m/z 554.1 [M+H]$^+$. Isomer SFC $t_R$=6.705 min in 15 min chromatography (ee=100.00%). $^1$H NMR (CD$_3$OD 400 MHz): δ 9.01 (s, 1H), 8.34 (d, J=8.0 Hz, 1H), 7.99 (d, J=8.4 Hz, 1H), 7.97 (s, 1H), 7.73 (d, J=8.0 Hz, 1H), 7.57 (d, J=8.4 Hz, 1H), 5.10 (d, J=15.2 Hz, 1H), 5.00 (d, J=4.4 Hz, 1H), 4.96-4.90 (m, 1H), 4.82 (s, 2H), 4.62 (d, J=15.2 Hz, 1H), 4.28 (d, J=10.8 Hz, 1H), 3.93-3.83 (m, 1H), 3.34 (q, J=7.2 Hz, 2H), 3.21 (d, J=6.0 Hz, 2H), 2.50-2.38 (m, 1H), 2.33-2.10 (m, 2H), 1.95-1.87 (m, 1H), 1.74-1.63 (m, 1H), 1.50-1.37 (m, 1H), 1.25 (t, J=7.2 Hz, 3H), 1.20 (d, J=6.8 Hz, 3H), 1.03 (d, J=6.8 Hz, 3H).

Isomer 2 (16b) (17.80 mg, 14%) LC-MS $t_R$=0.639 min in 5-95AB_1.5 min chromatography (Welch MK RP-18e 25-2 mm), MS (ESI) m/z 554.0 [M+H]$^+$. Isomer SFC $t_R$=8.160 min in 15 min chromatography (ee=100.00%). $^1$H NMR (CD$_3$OD 400 MHz): δ 9.00 (s, 1H), 8.33 (d, J=8.0 Hz, 1H), 7.99 (d, J=8.4 Hz, 1H), 7.97 (s, 1H), 7.72 (d, J=8.4 Hz, 1H), 7.56 (d, J=8.0 Hz, 1H), 5.10 (d, J=15.2 Hz, 1H), 5.03-4.93 (m, 2H), 4.82 (s, 2H), 4.65 (d, J=15.2 Hz, 1H), 4.19 (d, J=10.8 Hz, 1H), 3.93-3.83 (m, 1H), 3.40-3.32 (m, 2H), 3.25-3.13 (m, 2H), 2.50-2.38 (m, 1H), 2.33-2.16 (m, 2H), 1.96-1.87 (m, 1H), 1.74-1.60 (m, 1H), 1.56-1.47 (m, 1H), 1.25 (t, J=7.2 Hz, 3H), 1.20 (d, J=6.8 Hz, 3H), 1.01 (d, J=6.8 Hz, 3H).

Example 17

(S)-1-ethyl-N—((R)-1-(5-(ethylsulfonyl)pyridin-2-yl)-2-hydroxyethyl)-2-((trans-4-(trifluoromethyl)cyclohexyl)methyl)isoindoline-5-carboxamide (17)

General Procedure B: (S)-1-ethyl-N—((R)-1-(5-(ethylsulfonyl)pyridin-2-yl)-2-hydroxyethyl)-2-((trans-4-(trifluoromethyl)cyclohexyl)methyl)isoindoline-5-carboxamide A mixture of (S)-1-ethyl-N—((R)-1-(5-(ethylsulfonyl)pyridin-2-yl)-2-hydroxyethyl)isoindoline-5-carboxamide (40 mg, 0.1 mmol), trans-4-(trifluoromethyl)cyclohexanecarbaldehyde (27 mg, 0.15 mmol), NaBH$_3$CN (24 mg, 0.4 mmol) and HOAc (50 μL) (pH=6-7) in MeOH (4 mL) was stirred at 70° C. for 1 h. LCMS showed no starting material remained. The mixture was concentrated under reduced pressure. The residue was basified to pH=8 with saturated NaHCO$_3$ solution and extracted with ethyl acetate (3×30 mL). The combined organic layers were dried over anhydrous Na$_2$SO$_4$, filtered and concentrated under reduced pressure. The crude residue was purified by preparative TLC (ethyl acetate) to give the product (20 mg, 36%) as an oil, which was purified by SFC separation (AD-H) followed by acidic (HCl) preparative HPLC to afford (S)-1-ethyl-N—((R)-1-(5-(ethylsulfonyl)pyridin-2-yl)-2-hydroxyethyl)-2-((trans-4-(trifluoromethyl)cyclohexyl)methyl)isoindoline-5-carboxamide (17) HCl salt (2.3 mg, 12%) as a white solid. LC-MS $t_R$=0.623 min in 5-95AB_1.5 min chromatography (MK RP-18e 25-2 mm), MS (ESI) m/z 568.2 [M+H]$^+$. $^1$H NMR (CD$_3$OD 400 MHz): δ 9.04 (d, J=1.6 Hz, 1H), 8.31 (dd, J=8.0, 2.0 Hz, 1H), 8.03 (d, J=8.0 Hz, 1H), 7.97 (s, 1H), 7.76 (d, J=8.0 Hz, 1H), 7.59 (d, J=8.0 Hz, 1H), 5.39 (t, J=6.8 Hz, 1H), 4.92-4.93 (m, 1H), 4.68-4.85 (m, 2H), 4.06-4.08 (m, 2H), 3.33-3.34 (m, 2H), 3.23 (q, J=7.2 Hz, 2H), 2.00-2.22 (m, 8H), 1.46-1.47 (m, 2H), 1.07-1.30 (m, 8H). $^{19}$F NMR (CD$_3$OD 400 MHz): δ −75.41. Isomer SFC $t_R$=2.307 min in 3 min chromatography (Column: AD-H_3 UM_4_5_40_4ML), ee=100%.

The following compounds in Table 2 were prepared using General Procedure B with trans-4-(trifluoromethyl)cyclohexane-1-carbaldehyde and intermediates derived from 2-(tert-butoxycarbonyl)-1-ethylisoindoline-5-carboxylic acid, and the appropriate intermediates described herein.

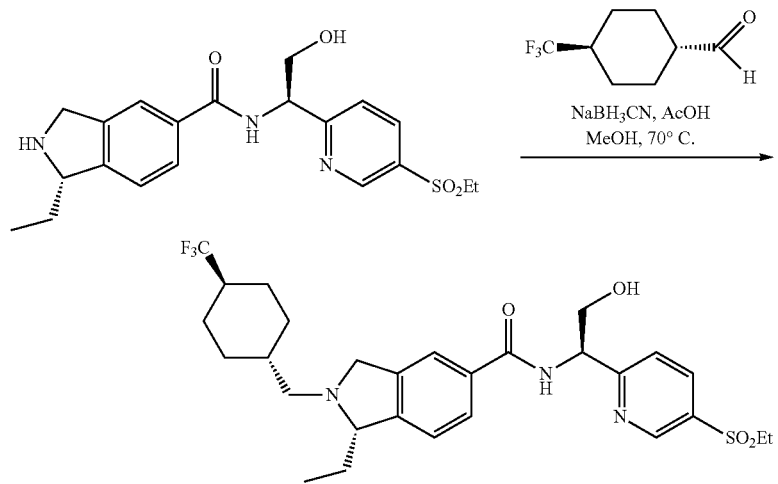

TABLE 2

| Ex. No. | Structure | LCMS | ¹H-NMR |
|---|---|---|---|
| 18 | 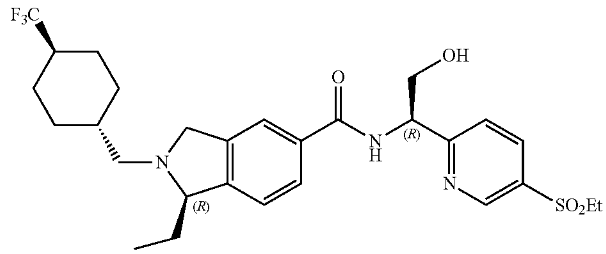 | 568.2 [M + H]⁺ | (CD₃OD 400 MHz): δ 9.04 (d, J = 2.0 Hz, 1H), 8.30 (dd, J = 8.0, 2.0 Hz, 1H), 8.03 (d, J = 7.6 Hz, 1H), 7.96 (s, 1H), 7.75 (d, J = 8.4 Hz, 1H), 7.59 (d, J = 8.0 Hz, 1H), 5.40 (t, J = 6.8 Hz, 1H), 4.92-4.93 (m, 1H), 4.79-4.87 (m, 2H), 4.05-4.07 (m, 2H), 3.33-3.34 (m, 2H), 3.23 (q, J = 7.2 Hz, 2H), 2.04-2.22 (m, 8H), 1.46-1.47 (m, 2H), 1.24-1.31 (m, 8H) |
| 19a | 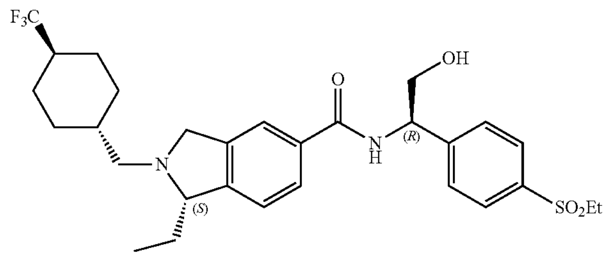 | 567.1 [M + H]⁺ | (CD₃OD 400 MHz): δ 7.97-8.01 (m, 2H), 7.91 (d, J = 8.4 Hz, 2H), 7.72 (d, J = 8.4 Hz, 2H), 7.56 (d, J = 8.4 Hz, 1H), 5.29 (t, J = 6.0 Hz, 1H), 5.08 (d, J = 14.8 Hz, 1H), 4.91-4.97 (m, 1H), 4.65 (d, J = 14.8 Hz, 1H), 3.94 (d, J = 6.4 Hz, 2H), 3.34-3.43 (m, 1H), 3.26-3.32 (m, 1H), 3.22 (dd, J = 14.8, 7.6 Hz, 2H), 1.85-2.32 (m, 8H), 1.37-1.57 (m, 2H), 1.01-1.30 (m, 8H) |
| 19b | 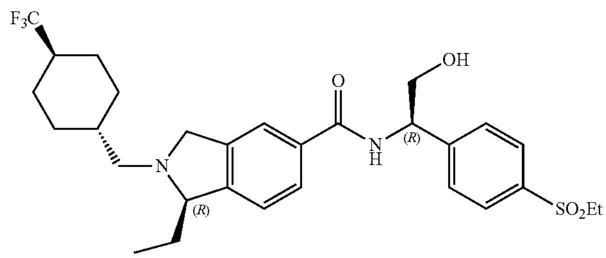 | 567.1 [M + H]⁺ | (CD₃OD 400 MHz): δ 7.90-7.97 (m, 4H), 7.71 (d, J = 8.0 Hz, 2H), 7.52 (d, J = 6.8 Hz, 1H), 5.29 (t, J = 6.4 Hz, 1H), 4.31-4.85 (m, 3H), 3.93 (d, J = 6.4 Hz, 2H), 3.22 (dd, J = 14.8, 7.6 Hz, 3H), 1.77-2.26 (m, 9H), 1.35-1.52 (m, 2H), 1.05-1.25 (m, 8H) |
| 20a | 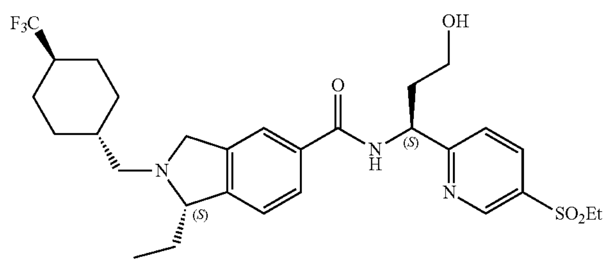 | 582.2 [M + H]⁺ | (CD₃OD 400 MHz): δ 8.99 (d, J = 2.0 Hz, 1H), 8.27 (d, J = 8.8 Hz, 1H), 7.95 (d, J = 8.0 Hz, 1H), 7.90 (s, 1H), 7.72 (d, J = 8.0 Hz, 1H), 7.53-7.55 (d, J = 8.0 Hz, 1H), 5.42-5.46 (m, 1H), 5.01-5.05 (m, 2H), 4.59-4.63 (m, 1H), 3.65-3.70 (m, 2H), 3.32-3.34 (m, 1H), 3.28-3.29 (m, 1H), 2.12-2.26 (m, 11H), 2.00-2.03 (m, 2H), 1.19-1.25 (m, 9H) |
| 20b | 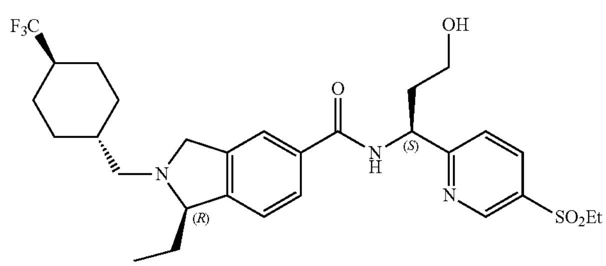 | 582.2 [M + H]⁺ | (CD₃OD 400 MHz): δ 9.03 (d, J = 2.0 Hz, 1H), 8.36 (d, J = 8.0 Hz, 1H), 7.92-7.97 (m, 2H), 7.81 (d, J = 8.4 Hz, 1H), 7.55 (d, J = 8.4 Hz, 1H), 5.44-5.47 (m, 1H), 5.02-5.08 (m, 2H), 4.61-4.67 (m, 1H), 3.66-3.74 (m, 2H), 3.38-3.47 (m, 1H), 3.28-3.29 (m, 1H), 2.16-2.25 (m, 12H), 2.01-2.04 (m, 2H), 1.17-1.27 (m, 8H) |
| 21a | 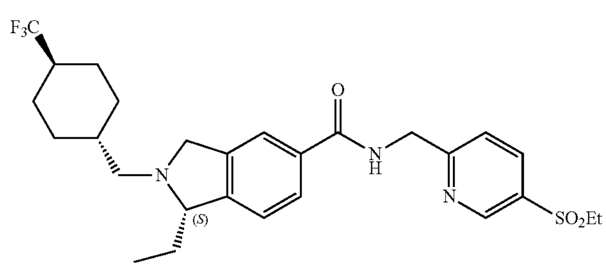 | 538.1 (M + H)⁺ | (CD₃OD 400 MHz): δ 9.00 (d, J = 2.0 Hz, 1H), 8.30 (dd, J = 8.4, 2.0 Hz, 1H), 7.93-8.04 (m, 2H), 7.69 (d, J = 8.4 Hz, 1H), 7.60 (d, J = 8.0 Hz, 1H), 5.08 (d, J = 14.0 Hz, 1H), 4.81-4.83 (m, 2H), 4.66 (d, J = 14.0 Hz, 1H), 3.27-3.31 (m, 2H), 2.15-2.28 (m, 6H), 1.99-2.13 (m, 4H), 1.39-1.54 (m, 2H), 1.32 (s, 2H), 1.18-1.30 (m, 7H). |

TABLE 2-continued

| Ex. No. | Structure | LCMS | ¹H-NMR |
|---|---|---|---|
| 21b | 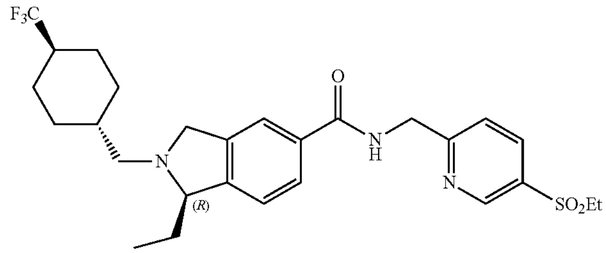 | 538.1 (M + H)⁺ | (CD₃OD 400 MHz): δ 8.98 (d, J = 2.0 Hz, 1H), 8.36 (dd, J = 8.4, 2.0 Hz, 1H), 7.94-8.04 (m, 2H), 7.77 (d, J = 8.4 Hz, 1H), 7.59 (d, J = 8.0 Hz, 1H), 5.10 (d, J = 15.2 Hz, 1H), 4.84 (s, 2H), 4.67 (d, J = 14.8 Hz, 1H), 3.28-3.32 (m, 2H), 2.11-2.31 (m, 5H), 1.92-2.11 (m, 5H), 1.39-1.53 (m, 2H), 1.10-1.34 (m, 9H). |
| 22 | 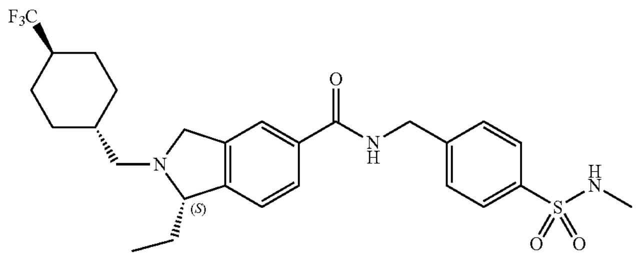 | 538.2 (M + H)⁺ | (CD₃OD 400 MHz): δ 7.90-8.00 (m, 2H), 7.79-7.85 (m, 2H), 7.52-7.61 (m, 3H), 4.96-5.14 (m, 2H), 4.69 (s, 3H), 3.34-3.41 (m, 1H), 3.23-3.31 (m, 1H), 2.53 (s, 3H), 1.82-2.27 (m, 8H), 1.37-1.53 (m, 2H), 1.06-1.32 (m, 5H). |
| 23a | 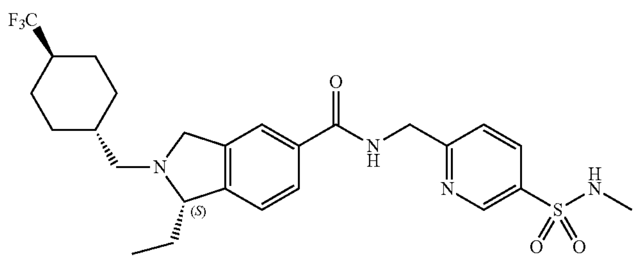 | 539.0 [M + H]⁺ | (CD₃OD 400 MHz): δ 8.98 (d, J = 2.0 Hz, 1H), 8.35 (dd, J = 8.0, 2.0 Hz, 1H), 7.99-8.03 (m, 2H), 7.77 (d, J = 8.4 Hz, 1H), 7.59 (d, J = 8.4 Hz, 1H), 5.09 (d, J = 15.2 Hz, 1H), 4.92-4.94 (m, 1H), 4.85-4.89 (m, 3H), 4.67 (d, J = 14.8 Hz, 1H), 3.36-3.39 (m, 1H), 2.61 (s, 3H), 2.01-2.23 (m, 8H), 1.45-1.48 (m, 2H), 1.07-1.27 (m, 5H) |
| 23b | 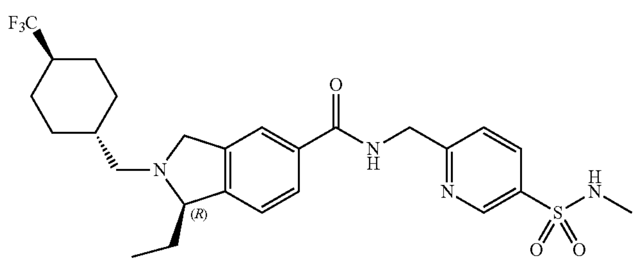 | 539.0 [M + H]⁺ | (CD₃OD 400 MHz): δ 8.98 (d, J = 1.6 Hz, 1H), 8.32 (dd, J = 8.4, 2.4 Hz, 1H), 8.03-7.98 (m, 2H), 7.75 (d, J = 8.4 Hz, 1H), 7.59 (d, J = 8.0 Hz, 1H), 5.09 (d, J = 14.8 Hz, 1H), 4.92-4.94 (m, 1H), 4.86-4.89 (m, 3H), 4.67 (d, J = 15.2 Hz, 1H), 3.39-3.42 (m, 1H), 2.60 (s, 3H), 2.01-2.24 (m, 8H), 1.45-1.48 (m, 2H), 1.05-1.27 (m, 5H). |

Example 24a (R)-2-(-1-ethyl-2-((trans-4-(trifluoromethyl)cyclohexyl)methyl)isoindoline-5-carboxamido)-2-(4-(ethylsulfonyl)phenyl)ethyl carbamate (24a and 24b)

Scheme 24

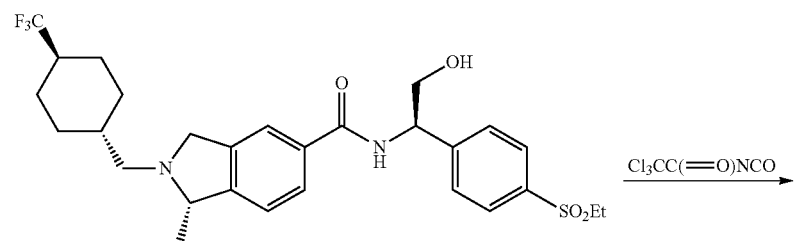

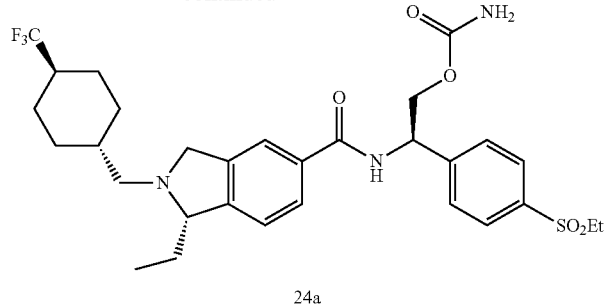

24a

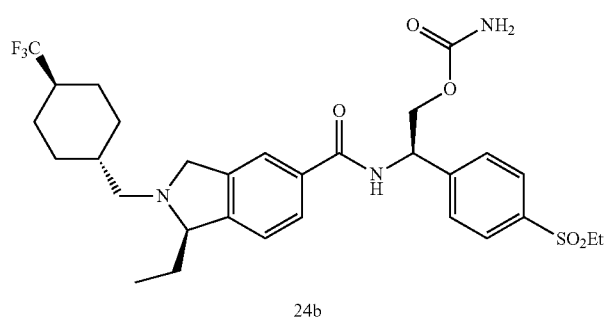

24b

To a solution of (19a) (20 mg, 0.033 mmol) in anhydrous CH₂Cl₂ (2 mL) was added 2,2,2-trichloroacetyl isocyanate (31 mg, 0.165 mmol) at 0° C. under a nitrogen atmosphere. Then the reaction was stirred at 24-31° C. for 1 h. The reaction mixture was checked by LCMS, which showed that the starting material was consumed. The reaction was quenched with MeOH (5 mL) and the solvents were removed under reduced pressure to afford the crude residue which was redissolved in MeOH (2 mL). Solid K₂CO₃ (14 mg, 0.099 mmol) was then added and the reaction mixture stirred at 24-31° C. for 1 h. The solvents were removed under reduced pressure to afford the crude residue which was purified by preparative HPLC (HCl) to give isomer 1 (24a) (15.00 mg, 73%) as a white solid. LC-MS $t_R$=0.819 min in 10-80AB_2.0 min chromatography (Welch Xtimate C18, 2.1*30 mm, 3 μm), MS (ESI) m/z 610.2 [M+H]⁺. ¹H NMR (CD₃OD 400 MH): δ 7.92-7.99 (m, 4H), 7.74 (d, J=8.4 Hz, 2H), 7.57 (d, J=8.0 Hz, 1H), 5.47-5.55 (m, 1H), 4.94-5.13 (m, 2H), 4.60-4.71 (m, 1H), 4.43 (d, J=6.8 Hz, 2H), 3.33-3.42 (m, 1.5H), 3.27-3.31 (m, 0.5H), 3.22 (dd, J=14.8, 7.6 Hz, 2H), 1.90-2.29 (m, 8H), 1.38-1.54 (m, 2H), 0.96-1.32 (m, 8H). ¹⁹F NMR (CD₃OD 400 MHz): δ −75.35. Isomer SFC $t_R$=11.935 min in 18.0 min chromatography (AD-H_5_5_40_2, 35 mL, ee=96.97%).

Isomer 2 (24b) was prepared in accordance with Scheme 24 using (19b) as the starting material. LC-MS $t_R$=0.827 min in 10-80AB_2.0 min chromatography (Welch Xtimate C18, 2.1*30 mm, 3 μm), MS (ESI) m/z 610.2 [M+H]⁺. ¹H NMR (CD₃OD 400 MHz): δ 7.92-7.99 (m, 4H), 7.74 (d, J=8.4 Hz, 2H), 7.57 (d, J=8.4 Hz, 1H), 5.51 (t, J=6.4 Hz, 1H), 4.92-5.14 (m, 2H), 4.57-4.75 (m, 1H), 4.43 (d, J=6.8 Hz, 2H), 3.34-3.54 (m, 1.5H), 3.27-3.32 (m, 0.5H), 3.22 (dd, J=14.8, 7.6 Hz, 2H), 1.64-2.37 (m, 9H), 1.36-1.55 (m, 2H), 1.15-1.30 (m, 7H). ¹⁹F NMR (CD₃OD 400 MHz): δ −75.35. Isomer SFC $t_R$=11.104 min in 18.0 min chromatography (AD-H_5_5_40_2, 35 mL, ee=64.23%).

Examples 25a and 25b 1-ethyl-N—((S)-1-(4-(ethylsulfonyl)phenyl)-3-hydroxypropyl)-2-((trans-4-(trifluoromethyl)cyclohexyl)methyl)isoindoline-5-carboxamide (25a and 25b)

Scheme 25

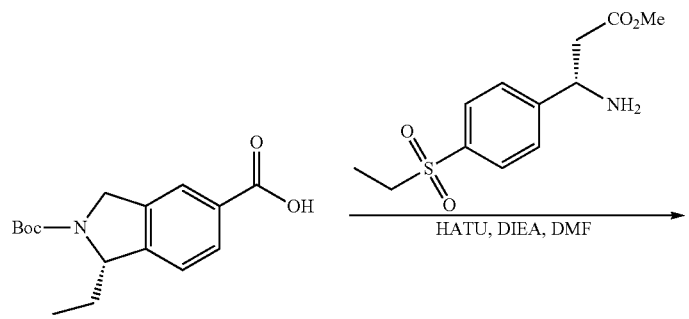

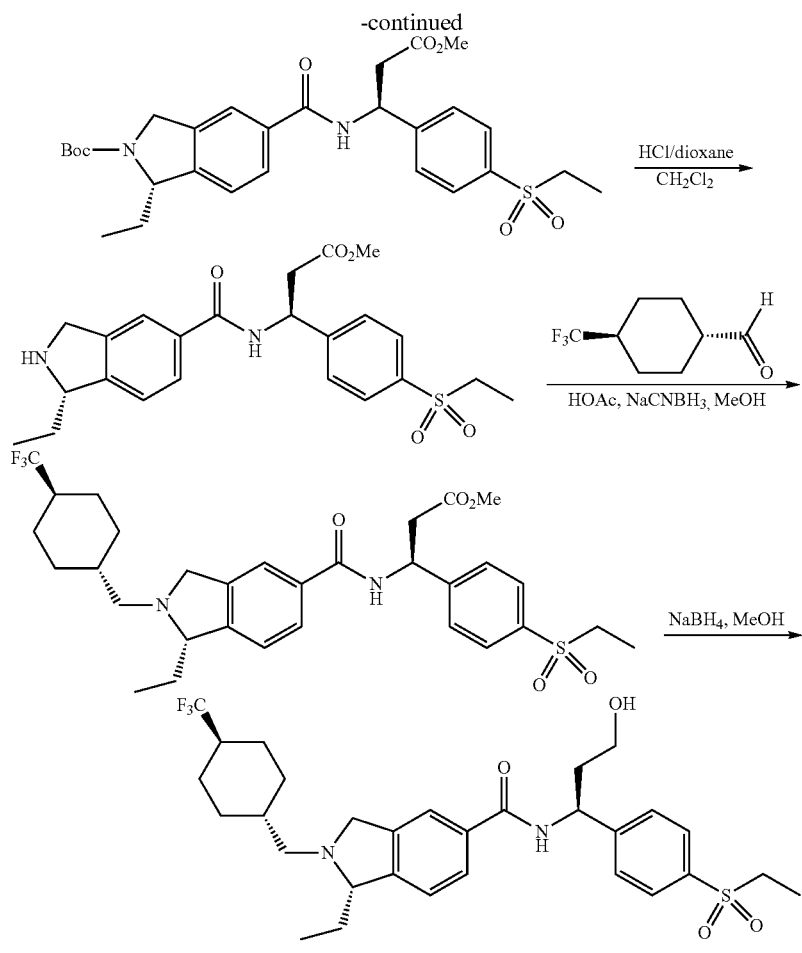

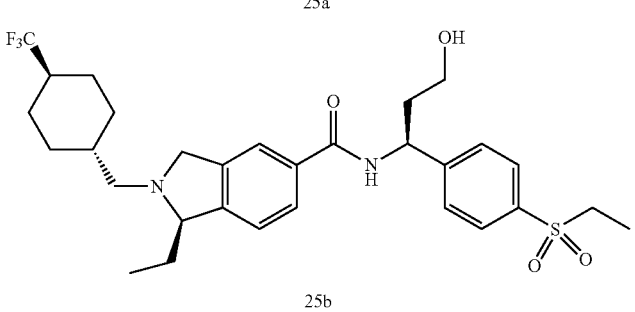

To a solution of (S)-2-(tert-butoxycarbonyl)-1-ethylisoindoline-5-carboxylic acid (150 mg, 0.50 mmol) and (S)-methyl 3-amino-3-(4-(ethylsulfonyl)phenyl)propanoate (136 mg, 0.50 mmol) in DMF (5 mL) was added HATU (286 mg, 0.75 mmol) and DIEA (0.4 mL, 2.50 mmol, d=0.782 g/mL) under a nitrogen atmosphere. After addition, the reaction mixture was stirred at 27~30° C. for 2 h. The reaction mixture was checked by LCMS, which showed that the starting material was consumed. The reaction mixture was diluted with ethyl acetate (40 mL), washed with brine (3×30 mL), dried over anhydrous $Na_2SO_4$, filtered and concentrated by rotary evaporation. The crude residue was purified by column chromatography on silica gel (eluting with petroleum ether:ethyl acetate=gradient from 2:1 to 1:2) to afford (S)-tert-butyl 1-ethyl-5-(((S)-1-(4-(ethylsulfonyl)phenyl)-3-methoxy-3-oxopropyl)carbamoyl)isoindoline-2-carboxylate (100 mg, 71%) as a brown solid. LC-MS $t_R$=1.155 min in 10-80AB_2.0 min chromatography (Welch Xtimate C18, 2.1*30 mm, 3 μm), MS (ESI) m/z 545.3 $[M+H]^+$.

To a solution of (S)-tert-butyl 1-ethyl-5-(((S)-1-(4-(ethylsulfonyl)phenyl)-3-methoxy-3-oxopropyl)carbamoyl)isoindoline-2-carboxylate (200 mg, 0.36 mmol) in anhydrous dichloromethane (4.0 mL) was added an HCl in dioxane solution (1.0 mL, 4.0 mmol, 4N). The reaction mixture was stirred at 27~34° C. for 16 h. TLC analysis (eluting with petroleum ether:ethyl acetate=1:2) showed that the starting material was consumed. The reaction was cooled down with an ice-water bath for 5 min, basified to pH=12~14 with 1 N NaOH solution, diluted with water (10 mL) and extracted with ethyl acetate (3×20 mL). The combined organics were washed with brine (3×50 mL), dried over anhydrous Na₂SO₄, filtered and concentrated by rotary evaporation to afford (S)-methyl 3-((S)-1-ethylisoindoline-5-carboxamido)-3-(4-(ethylsulfonyl)phenyl)propanoate (100 mg, 61%) as a brown oil. This material was used directly for the next step without further purification.

To a solution of (S)-methyl 3-((S)-1-ethylisoindoline-5-carboxamido)-3-(4-(ethylsulfonyl)phenyl)propanoate (100 mg, 0.22 mmol) in anhydrous MeOH (5 mL) and HOAc (0.05 mL) was added trans-4-(trifluoromethyl)cyclohexanecarbaldehyde (60 mg, 0.33 mmol) and NaBH₃CN (28 mg, 0.44 mmol) under a nitrogen atmosphere. After addition, the reaction mixture was heated to 40° C. for 1 h. LCMS analysis showed that the starting material was consumed. After cooling to rt, the reaction basified to pH=10-11 with 1N NaOH solution, diluted with water (20 mL) and extracted with ethyl acetate (3×20 mL). The combined organics were washed with brine (3×40 mL), dried over anhydrous Na₂SO₄, filtered and concentrated by rotary evaporation. The crude residue was purified by preparative TLC (eluting with petroleum ether:ethyl acetate=1:1) to give (S)-methyl 3-((S)-1-ethyl-2-((trans-4-(trifluoromethyl)cyclohexyl)methyl)isoindoline-5-carboxamido)-3-(4-(ethylsulfonyl)phenyl)propanoate (100 mg, 68%) as a brown solid. LC-MS $t_R$=0.946 min in 10-80AB_2.0 min chromatography (Welch Xtimate C18, 2.1*30 mm, 3 μm), MS (ESI) m/z 609.3 [M+H]⁺.

To a solution of (S)-methyl 3-((S)-1-ethyl-2-((trans-4-(trifluoromethyl)cyclohexyl)methyl)isoindoline-5-carboxamido)-3-(4-(ethylsulfonyl)phenyl)propanoate (100 mg, 0.15 mmol) in anhydrous MeOH (5 mL) was added NaBH₄ (114 mg, 3.00 mmol) under a nitrogen atmosphere. After addition, the reaction mixture was stirred at 27~34° C. for 16 h. The reaction mixture was checked by LCMS, which showed that the starting material was nearly consumed. The reaction was quenched with water (20 mL) and extracted with ethyl acetate (3×20 mL). The combined organics were washed with brine (3×50 mL), dried over anhydrous Na₂SO₄, filtered and concentrated by rotary evaporation to afford the crude residue which was purified by preparative TLC (petroleum ether:ethyl acetate=1:2) to give (S)-1-ethyl-N—((S)-1-(4-(ethylsulfonyl)phenyl)-3-hydroxypropyl)-2-((trans-4-(trifluoromethyl)cyclohexyl)methyl)isoindoline-5-carboxamide (12 mg, 13%) as a brown solid.

This product was then purified by SFC (AD-H) followed preparative HPLC (HCl) to give the HCl salt of isomer 1 (25a) (4.40 mg, 37%) as a white solid. LC-MS $t_R$=0.918 min in 10-80AB_2.0 min chromatography (Welch Xtimate C18, 2.1*30 mm, 3 μm), MS (ESI) m/z 581.3 [M+H]⁺. ¹H NMR (CD₃OD 400 MHz): δ 9.08 (d, J=7.6 Hz, 1H), 7.96 (d, J=8.4 Hz, 1H), 7.89-7.93 (m, 3H), 7.68-7.72 (m, 2H), 7.57 (d, J=7.6 Hz, 1H), 5.37-5.43 (m, 1H), 5.06 (d, J=16.0 Hz, 1H), 4.90-4.93 (m, 1H), 4.65 (d, J=11.6 Hz, 1H), 3.60-3.74 (m, 2H), 3.34-3.42 (m, 1H), 3.22 (dd, J=14.8, 7.6 Hz, 2H), 3.19-3.26 (m, 2H), 1.88-2.27 (m, 10H), 1.39-1.54 (m, 2H), 1.15-1.28 (m, 8H). ¹⁹F NMR (CD₃OD 400 MHz): δ −75.40. Isomer SFC $t_R$=1.860 min in 3.0 min chromatography (AD-H_3 UM_3_5_40_4 mL, ee=95.93%).

Isomer 2 (25b) was prepared according to Scheme 25 using (R)-2-(tert-butoxycarbonyl)-1-ethylisoindoline-5-carboxylic acid as the starting material. LC-MS $t_R$=0.814 min in 10-80AB_2.0 min chromatography (Welch Xtimate C18, 2.1*30 mm, 3 μm), MS (ESI) m/z 581.2 [M+H]⁺. ¹H NMR (CD₃OD 400 MHz): δ 7.94-7.98 (m, 1H), 7.88-7.93 (m, 3H), 7.68-7.73 (m, 2H), 7.54-7.59 (m, 1H), 5.35-5.44 (m, 1H), 5.01-5.10 (m, 1H), 4.91-4.95 (m, 1H), 4.60-4.68 (m, 1H), 3.60-3.74 (m, 2H), 3.34-3.41 (m, 1H), 3.26-3.32 (m, 1H), 3.22 (dd, J=14.8, 7.6 Hz, 2H), 1.95-2.27 (m, 10H), 1.38-1.55 (m, 2H), 1.03-1.32 (m, 8H). ¹⁹F NMR (CD₃OD 400 MHz): δ −75.39. Isomer SFC $t_R$=1.860 min in 3.0 min chromatography (AD-H_3 UM_3_5_4 mL, ee=98.71%).

Examples 26a and 26b

N-(4-(ethylsulfonyl)benzyl)-1-isopropyl-3-oxo-2-(4-(trifluoromethyl)benzyl)isoindoline-5-carboxamide Isomers

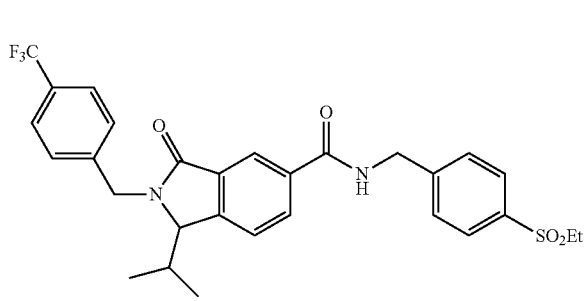

Scheme 26

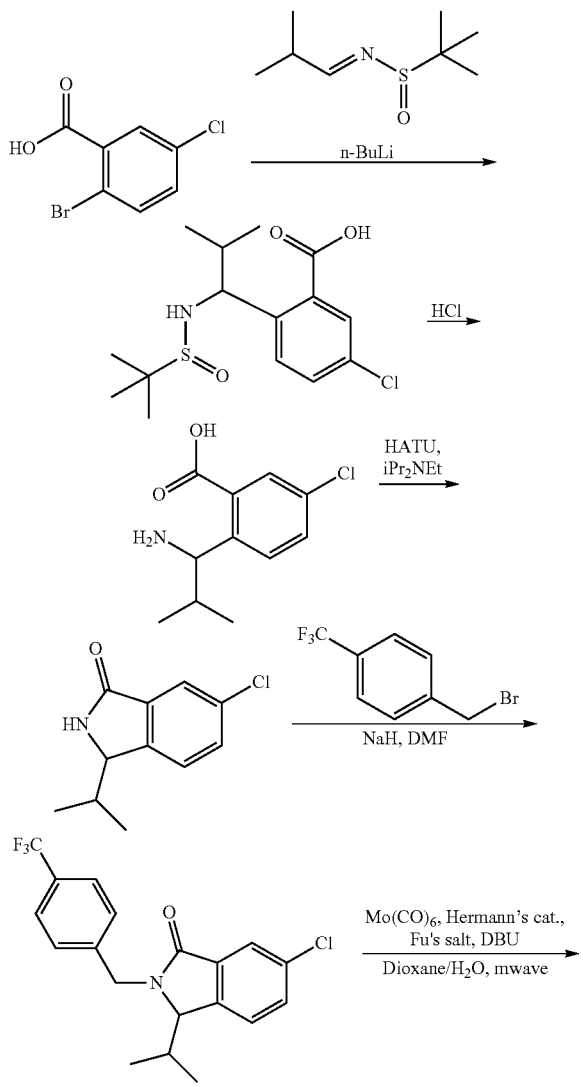

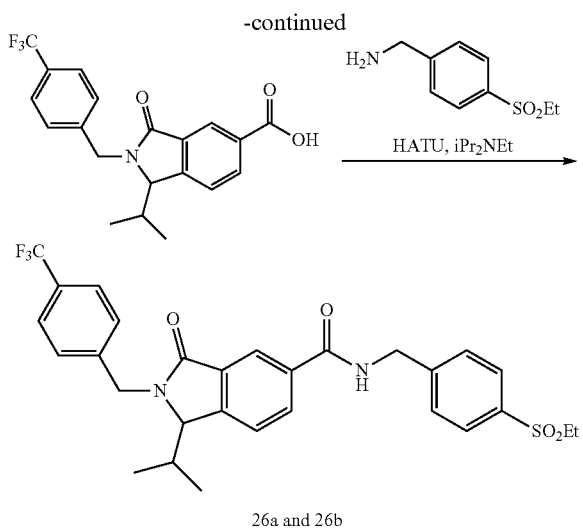

26a and 26b

To a suspension of 2-methylpropane-2-sulfinamide (758 mg, 6.25 mmol) in DCM (15 mL) was added CuSO$_4$ (2.2 g, 13.75 mmol) followed by isobutyraldehyde (497 mg, 6.9 mmol) in one portion at rt. The mixture was allowed to stir for 10 h at rt. Vacuum filtration was used to remove the solid and the filtrate was dried over Na$_2$SO$_4$, filtered and concentrated under reduced pressure to afford crude (E)-2-methyl-N-(2-methylpropylidene)propane-2-sulfinamide as a white solid, which was used directly for the next step without further purification.

To a solution of 2-bromo-5-chlorobenzoic acid (505 mg, 2.15 mmol) in dry THF (20 mL) was added a 2.5 M solution of n-BuLi in THF (2.2 mL, 5.4 mmol) slowly under N$_2$ at −78° C. The mixture was allowed to stir for 10 min at −78° C. then a solution of the above crude (E)-2-methyl-N-(2-methylpropylidene)propane-2-sulfinamide (395 mg, 2.26 mmol) in THF (5 mL) was introduced to the reaction mixture. The reaction was allowed to stir for 10 min at −78° C. then slowly allowed to warm to rt. H$_2$O (20 mL) was added at rt and the mixture was washed with EtOAc (30 mL). The aqueous phase was acidified with 1 N HCl solution to pH=3 and extracted with EtOAc (2×30 mL). The organic layers were combined, dried over Na$_2$SO$_4$ and evaporated to afford crude product. Purification using flash chromatography over silica gel (eluting with 5% MeOH in DCM) gave 200 mg of 2-(1-((tert-butylsulfinyl)amino)-2-methylpropyl)-5-chlorobenzoic acid as a colorless oil (30% yield). LC-MS $t_R$=1.45 min in 2 min chromatography, MS (ESI) m/z 332.1 [M+H]$^+$.

To a solution of compound 2-(1-((tert-butylsulfinyl)amino)-2-methylpropyl)-5-chlorobenzoic acid (200 mg, 0.6 mmol) in CH$_2$Cl$_2$ (2 mL) was added HCl in methanol (0.5 M, 3 mL, 1.5 mmol) at 0° C. The mixture was stirred at 0° C. for 2 h. Et$_3$N was added and the mixture was concentrated under reduced pressure to afford crude 2-(1-amino-2-methylpropyl)-5-chlorobenzoic acid, which was used for the next step directly without further purification.

To a solution of crude 2-(1-amino-2-methylpropyl)-5-chlorobenzoic acid (0.6 mmol) and iPr$_2$NEt (420 μL, 2.4 mmol) in THF (3 mL) was added HATU (340 mg, 0.9 mmol) at rt. The reaction was stirred for 1 h before adding a sat. NH$_4$Cl solution (10 mL). The mixture was extracted with EtOAc (2×10 mL). The organic layers were combined, washed with brine (10 mL), dried over Na$_2$SO$_4$, filtered and concentrated under reduced pressure. The crude material was purified by flash chromatography over silica gel (eluting with 30% EtOAc in hexanes) to afford 108 mg of 6-chloro-3-isopropylisoindolin-1-one as a colorless oil (86% yield). LC-MS $t_R$=1.23 min in 2 min chromatography, MS (ESI) m/z 210.1 [M+H]$^+$. $^1$H NMR (CD$_3$OD) δ 7.72 (s, 1H), 7.62 (d, J=8 Hz, 1H), 7.55 (d, J=8 Hz, 1H), 4.61 (d, J=2.8 Hz, 1H), 2.32-2.28 (m, 1H), 1.05 (d, J=6.8 Hz, 1H), 0.69 (d, J=6.8 Hz, 1H).

To a solution of 6-chloro-3-isopropylisoindolin-1-one (91 mg, 0.44 mmol) in DMF (3 mL) was added NaH (35 mg, 0.87 mmol) at 0° C. and the mixture was stirred at 0° C. for 15 mins. 1-(Bromomethyl)-4-(trifluoromethyl)benzene was added in one portion and the resulting mixture was allowed to stir at 0° C. for 30 min. A saturated NH$_4$Cl solution (10 mL) was then added and the mixture was extracted with EtOAc (2×10 mL). The organic layers were combined, washed with brine (10 mL), dried over Na$_2$SO$_4$, filtered and concentrated under reduced pressure. The crude mixture was purified by flash chromatography over silica gel (eluting with 30% EtOAc in hexanes) to afford 90 mg of 6-chloro-3-isopropyl-2-(4-(trifluoromethyl)benzyl)isoindolin-1-one as a colorless oil (56% yield). LC-MS $t_R$=1.87 min in 2 min chromatography, MS (ESI) m/z 368.1 [M+H]$^+$.

To a solution of 6-chloro-3-isopropyl-2-(4-(trifluoromethyl)benzyl)isoindolin-1-one (95 mg, 260 μmol) in dioxane/H$_2$O (2/0.2 mL) was added molybdenum hexacarbonyl (42 mg, 156 μmol) and 1,8-diazabicyclo[5.4.0]undec-7-ene (102 μL, 780 μmol) in a microwave tube. The mixture was degassed with N$_2$ for 5 min, at which point trans-bis(acetato)bis[o-(di-o-tolylphosphino)benzyl]dipalladium(II) (13 mg, 13 μmol) and tri-tert-butylphosphonium tetrafluoroborate (8 mg, 26 zμmol) were added. The mixture was degassed again with N$_2$ for 10 min then heated in a CEM microwave reactor at 160° C. for 20 min. After cooling to rt, the mixture was diluted with H$_2$O (20 mL) and washed with EtOAc (20 mL). The aqueous phase was acidified with 1 N HCl solution to pH=3 and extracted with EtOAc (3×20 mL). The organic layer was washed with brine, dried over Na$_2$SO$_4$, and concentrated to afford crude 1-isopropyl-3-oxo-2-(4-(trifluoromethyl)benzyl)isoindoline-5-carboxylic acid (670 mg, 70%) as a light yellow solid. This material was used for the next step without further purification.

To a solution of 1-isopropyl-3-oxo-2-(4-(trifluoromethyl)benzyl)isoindoline-5-carboxylic acid (30 mg, 100 μmol) in DMF (2 mL) was added (4-(ethylsulfonyl)phenyl)methanamine HCl salt (30 mg, 100 μmol), HATU (57 mg, 100 μmol) and DIEA (70 μL, 400 μmol). The mixture was stirred at rt for 4 h. Ethyl acetate (20 mL) and water (20 mL) were added to the mixture. After partition, the aqueous layer was extracted with ethyl acetate (2×20 mL). The combined organic layers were washed with brine, dried over anhydrous Na$_2$SO$_4$, filtered and concentrated under reduced pressure. The solvent was removed in vacuo to give the crude product which was purified by Gilson-HPLC to afford N-(4-(ethylsulfonyl)benzyl)-1-isopropyl-3-oxo-2-(4-(trifluoromethyl)benzyl)isoindoline-5-carboxamide. The racemic mixture was purified by SFC separation followed by basic preparative HPLC separation to afford isomer two isomers (26a and 26b) as white solids.

Isomer 1 (26a) SFC $t_R$=1.916 min in 3 min chromatography (ee=92%); LC-MS $t_R$=0.774 min in 5-95AB_1.5 min chromatography (Welch MK RP-18e 25-2 mm), MS (ESI) m/z 559.0 [M+H]$^+$; $^1$H NMR (CDCl$_3$, 400 MHz): δ 8.24 (s, 1H), 8.17 (d, J=8.0 Hz, 1H), 7.90 (d, J=8.4 Hz, 2H), 7.61-7.55 (m, 5H), 7.38 (d, J=8.0 Hz, 2H), 6.84 (t, J=6.0 Hz, 1H), 5.43 (d, J=15.6 Hz, 1H), 4.78 (d, J=6.4 Hz, 2H), 4.35 (d, J=3.6 Hz, 1H), 4.25 (d, J=15.6 Hz, 1H), 3.13 (q, J=7.6 Hz, 2H), 2.48-2.39 (m, 1H), 1.29 (t, J=7.6 Hz, 3H), 1.20 (d, J=6.8 Hz, 3H), 0.51 (d, J=6.8 Hz, 3H).

Isomer 2 (26b) SFC $t_R$=0.542 min in 3 min chromatography (ee=88%); LC-MS $t_R$=0.772 min in 5-95AB_1.5 min chromatography (Welch MK RP-18e 25-2 mm), MS (ESI)

m/z 559.0 [M+H]⁺; ¹H NMR (CDCl₃, 400 MHz): δ 8.24 (s, 1H), 8.17 (d, J=8.4 Hz, 1H), 7.90 (d, J=8.4 Hz, 2H), 7.61-7.55 (m, 5H), 7.38 (d, J=8.0 Hz, 2H), 6.84 (t, J=6.0 Hz, 1H), 5.43 (d, J=15.6 Hz, 1H), 4.78 (d, J=6.0 Hz, 2H), 4.35 (d, J=3.2 Hz, 1H), 4.25 (d, J=15.6 Hz, 1H), 3.13 (q, J=7.6 Hz, 2H), 2.48-2.39 (m, 1H), 1.29 (t, J=7.6 Hz, 3H), 1.20 (d, J=6.8 Hz, 3H), 0.51 (d, J=6.8 Hz, 3H).

The following compounds in Table 3 were prepared using the methods described in Scheme 26 with 1-isopropyl-3-oxo-2-(4-(trifluoromethyl)benzyl)isoindoline-5-carboxylic acid and the appropriate ethylsulfonyl amine.

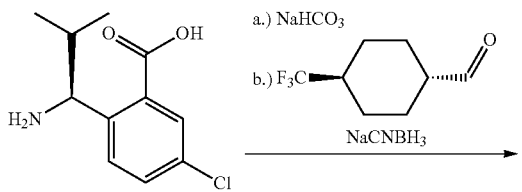

TABLE 3

| Ex. No. | Structure | LCMS | 1H-NMR |
|---|---|---|---|
| 27 | 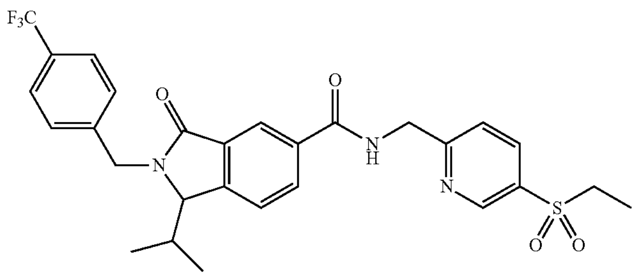 [SMILES: CCS(=O)(=O)c1ccc(CNC(=O)c2ccc3c(c2)C(=O)N(Cc2ccc(C(F)(F)F)cc2)C3C(C)C)nc1] | 560.3 [M + H]⁺ | (CD₃OD, 400 MHz): δ 8.99 (s, 1H), 8.36 (s, 1H), 8.26 (d, J = 8.4 Hz, 1H), 8.16 (d, J = 8.4 Hz, 1H), 7.72-7.65 (m, 5H), 7.51 (d, J = 8.4 Hz, 2H), 5.28 (d, J = 15.6 Hz, 1H), 4.80 (s, 2H), 4.56-4.53 (m, 2H), 3.29 (q, J = 7.6 Hz, 2H), 2.54-2.51 (m, 1H), 1.25 (t, J = 6.8 Hz, 3H), 1.22 (t, J = 6.8 Hz, 3H), 0.48 (d, J = 6.8 Hz, 3H). |
| 28 | 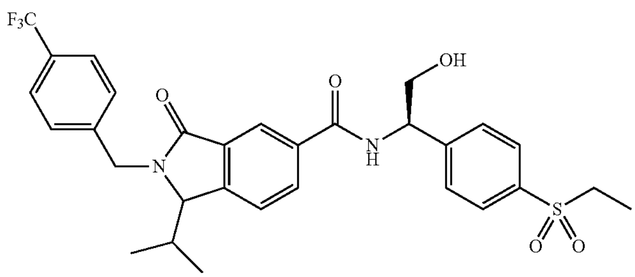 [SMILES: CCS(=O)(=O)c1ccc([C@H](CO)NC(=O)c2ccc3c(c2)C(=O)N(Cc2ccc(C(F)(F)F)cc2)C3C(C)C)cc1] | 589.3 [M + H]⁺ | (CD₃OD, 400 MHz): δ 8.36 (s, 1H), 8.13 (d, J = 8.4 Hz, 1H), 7.90 (d, J = 8.0 Hz, 2H), 7.72-7.65 (m, 5H), 7.51 (d, J = 8.4 Hz, 2H), 5.28 (d, J = 15.6 Hz, 1H), 4.54 (t, J = 8.0 Hz, 2H), 3.93 (d, J = 6.4 Hz, 2H), 3.19 (q, J = 7.6 Hz, 2H), 2.55-2.50 (m, 1H), 1.27-1.19 (m, 6H), 0.47 (d, J = 6.8 Hz, 3H). |

Example 29

(S)—N-(4-(ethylsulfonyl)benzyl)-1-isopropyl-3-oxo-2-((trans-4-(trifluoromethyl)cyclohexyl)methyl)isoindoline-5-carboxamide (29)

Scheme 27.

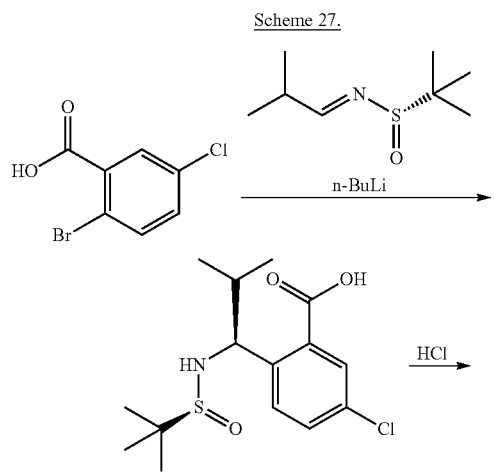

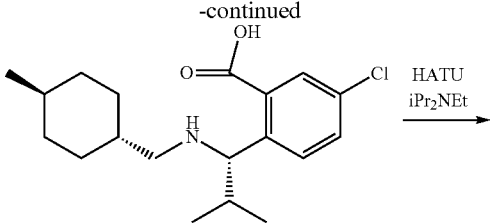

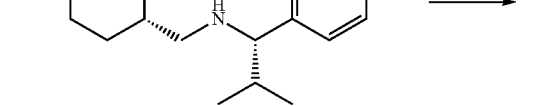

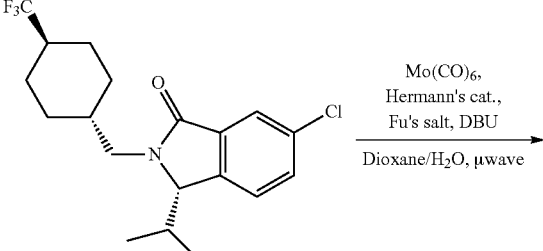

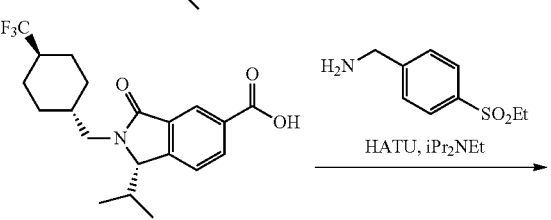

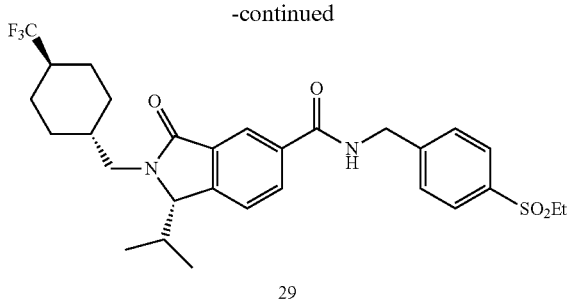

29

To a solution of 2-bromo-5-chlorobenzoic acid (3.33 g, 14 mmol) in dry THF (100 mL) was added a 2.5 M solution of n-BuLi in THF (14 mL, 35.5 mmol) slowly under $N_2$ at −78° C. The mixture was allowed to stir for 10 min at −78° C. then a solution of (S)-2-methyl-N-(2-methylpropylidene)propane-2-sulfinamide (2.48 g, 14 mmol) in THF (10 mL) was added. The reaction was allowed to stir for 10 min at −78° C. then slowly warmed to rt. The reaction was quenched by adding $H_2O$ (50 mL) and the mixture was washed with EtOAc (50 mL). The aqueous phase was acidified with 1 N HCl solution to pH=3 and extracted with EtOAc (2×50 mL). The organic layers were combined, dried over $Na_2SO_4$ and evaporated to afford crude product, which was purified by flash chromatography over silica gel (eluting with 5% MeOH in DCM) to afford 925 mg of 2-((S)-1-(((S)-tert-butylsulfinyl)amino)-2-methylpropyl)-5-chlorobenzoic acid as an off-white solid (20% yield). LC-MS $t_R$=2.87 min in 5 min chromatography, MS (ESI) m/z 332.4 [M+H]$^+$.

To a solution of 2-((S)-1-(((S)-tert-butylsulfinyl)amino)-2-methylpropyl)-5-chlorobenzoic acid (25 mg, 76 μmol) in $CH_2Cl_2$ (0.5 mL) was added HCl in methanol (0.5 M, 0.3 mL, 150 μmol) at 0° C. The mixture was stirred at 0° C. for 1 h. The mixture was concentrated under reduced pressure to afford crude (S)-2-(1-amino-2-methylpropyl)-5-chlorobenzoic acid HCl salt, which was used for the next step directly without further purification. LC-MS $t_R$=0.70 min in 2 min chromatography, MS (ESI) m/z 228.2 [M+H]$^+$.

To a solution of (S)-2-(1-amino-2-methylpropyl)-5-chlorobenzoic acid HCl salt (76 μmol) in dichloromethane (0.5 mL) was added solid $NaHCO_3$ (10 mg) and the mixture was stirred for 5 min at rt. Trans-4-(trifluoromethyl)cyclohexane-1-carbaldehyde (22 mg, 110 μmol) was added followed by $NaCNBH_3$ (12 mg, 190 μmol). The mixture was stirred at rt for 1 h. Ethyl acetate (5 mL) and water (5 mL) were added to the mixture. After partition, the aqueous layer was extracted with ethyl acetate (2×5 mL). The combined organic layers were washed with brine, dried over anhydrous $Na_2SO_4$, filtered and concentrated under reduced pressure. The solvent was removed in vacuo to give crude 5-chloro-2-((S)-2-methyl-1-(((trans-4-(trifluoromethyl)cyclohexyl)methyl)amino)propyl)benzoic acid which was used for the next step directly without further purification. LCMS $t_R$=1.29 min in 2 min chromatography, MS (ESI) m/z 392.2 [M+H]$^+$.

To a solution of 5-chloro-2-(((S)-2-methyl-1-(((trans-4-(trifluoromethyl)cyclohexyl)methyl)amino)propyl)benzoic acid (76 μmol) in THF (0.5 mL) was added HATU (42 mg, 110 μmol) and DIEA (40 μL, 200 μmol). The mixture was stirred at rt for 2 h. Ethyl acetate (5 mL) and water (5 mL) were added to the mixture. After partition, the aqueous layer was extracted with ethyl acetate (2×5 mL). The combined organic layers were washed with brine, dried over anhydrous $Na_2SO_4$, filtered and concentrated under reduced pressure. The solvent was removed in vacuo to give the crude product which was purified by flash chromatography over silica gel (eluting with 20% EtOAc in hexanes) to afford 5 mg of (S)-6-chloro-3-isopropyl-2-((trans-4-(trifluoromethyl)cyclohexyl)methyl)isoindolin-1-one as a colorless oil. LC-MS $t_R$=1.90 min in 2 min chromatography, MS (ESI) m/z 374.3 [M+H]$^+$.

To a solution of (S)-6-chloro-3-isopropyl-2-((trans-4-(trifluoromethyl)cyclohexyl)methyl)isoindolin-1-one (5 mg, 13 μmol) in dioxane/$H_2O$ (200/20 μL) was added molybdenum hexacarbonyl (3 mg, 10 μmol) and 1,8-diazabicyclo[5.4.0]undec-7-ene (6 μL, 39 μmol) in a microwave tube. The mixture was degassed with $N_2$ for 5 min, at which point trans-Bis(acetato)bis[o-(di-o-tolylphosphino)benzyl]dipalladium(II) (3 mg, 2.6 μmol) and tri-tert-butylphosphonium tetrafluoroborate (2 mg, 5.2 μmol) were added. The mixture was degassed again with $N_2$ for 10 min then heated in a CEM microwave reactor at 160° C. for 20 min. After cooling to rt, the mixture was diluted with $H_2O$ (5 mL) and washed with EtOAc (5 mL). The aqueous phase was acidified with 1 N HCl solution to pH=3 and extracted with EtOAc (3×5 mL). The organic layer was washed with brine, dried over $Na_2SO_4$, and concentrated to afford (S)-1-isopropyl-3-oxo-2-((trans-4-(trifluoromethyl)cyclohexyl)methyl)isoindoline-5-carboxylic acid as a colorless oil. This material was used for the next step directly without further purification. LC-MS $t_R$=1.61 min in 2 min chromatography, MS (ESI) m/z 384.2 [M+H]$^+$.

To a solution of (S)-1-isopropyl-3-oxo-2-((trans-4-(trifluoromethyl)cyclohexyl)methyl)isoindoline-5-carboxylic acid (5 mg, 13 μmol) in DMF (0.2 mL) was added (4-(ethylsulfonyl)phenyl)methanamine (4 mg, 20 μmol), HATU (8 mg, 20 μmol) and DIEA (7 μL, 40 μmol). The mixture was stirred at rt for 4 h. Ethyl acetate (3 mL) and water (3 mL) were added to the mixture. After partition, the aqueous layer was extracted with ethyl acetate (2×3 mL). The combined organic layers were washed with brine, dried over anhydrous $Na_2SO_4$, filtered and concentrated under reduced pressure. The solvent was removed in vacuo to give the crude product which was purified on Gilson-HPLC to afford (S)—N-(4-(ethylsulfonyl)benzyl)-1-isopropyl-3-oxo-2-((trans-4-(trifluoromethyl)cyclohexyl)methyl)isoindoline-5-carboxamide (29). LC-MS $t_R$=1.62 min in 2 min chromatography, MS (ESI) m/z 565.4 [M+H]$^+$. $^1$H NMR (CD$_3$OD, 400 MHz): δ 9.32 (m, 1H), 8.25 (s, 1H), 8.25 (s, 1H), 8.12 (d, J=7.6 Hz, 1H), 7.88 (d, J=8.8 Hz, 2H), 7.74 (d, J=8.0 Hz, 1H), 7.64 (d, J=8.8 Hz, 2H), 4.74-4.71 (m, 4H), 3.88-3.82 (m, 1H), 3.21 (q, J=7.6 Hz, 2H), 3.14-3.09 (m, 1H), 2.55-2.53 (m, 1H), 2.52-1.67 (m, 9H), 1.28 (d, J=6.8 Hz, 3H), 1.23 (t, J=6.8 Hz, 3H), 0.47 (d, J=6.8 Hz, 3H).

Example 30

N-(4-(ethylsulfonyl)benzyl)-1,1-dimethyl-3-oxo-2-((4-(trifluoromethyl)cyclohexyl)methyl)isoindoline-5-carboxamide (30)

Scheme 28

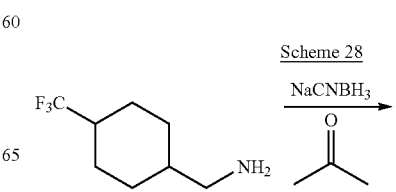

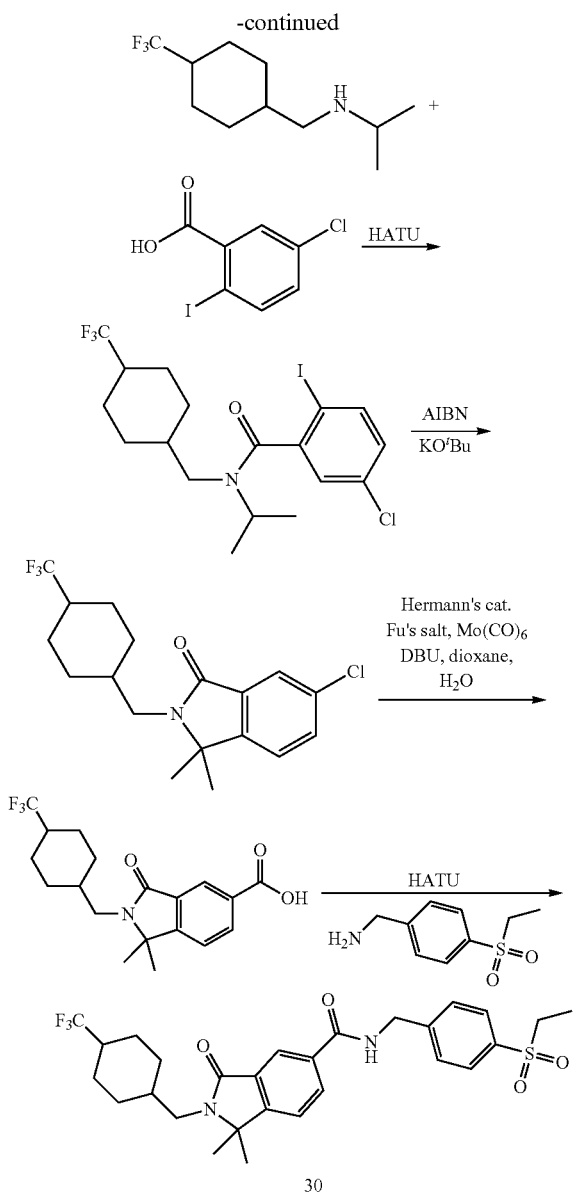

30

To a solution of (4-(trifluoromethyl)cyclohexyl)methanamine (340 mg, 1.88 mmol) in dichloromethane (5 mL) was added acetone (165 μL, 2.25 mmol) followed by NaCNBH$_3$ (240 mg, 3.76 mmol). The resulting mixture was stirred at rt for 8 h. The reaction was quenched with a saturated NaHCO$_3$ solution (5 mL) and extracted with DCM (6×10 mL). The combined organic layers were dried over anhydrous Na$_2$SO$_4$, filtered and concentrated under reduced pressure to afford N-((4-(trifluoromethyl)cyclohexyl)methyl)propan-2-amine (250 mg) as a clear oil which was used for the next step directly without further purification. LC-MS t$_R$=0.73 min in 2 min chromatography, MS (ESI) m/z 224.2 [M+H]$^+$.

To a solution of N-((4-(trifluoromethyl)cyclohexyl)methyl)propan-2-amine (250 mg, 1.07 mmol) in DMF (4 mL) was added 5-chloro-2-iodobenzoic acid (395 mg, 1.4 mmol), HATU (610 mg, 1.6 mmol) and DIEA (480 μL, 2.7 mmol). The mixture was stirred at rt for 3 h. Ethyl acetate (10 mL) and water (10 mL) were added to the mixture. After partition, the aqueous layer was extracted with ethyl acetate (2×10 mL). The combined organic layers were washed with brine, dried over anhydrous Na$_2$SO$_4$, filtered and concentrated under reduced pressure. The solvent was removed in vacuo to give the crude product which was purified by flash chromatography over silica gel (eluting with 15% EtOAc in hexanes) to afford 420 mg of 5-chloro-2-iodo-N-isopropyl-N-((4-(trifluoromethyl)cyclohexyl)methyl)benzamide as a clear oil (86% yield). LC-MS t$_R$=1.99 min in 2 min chromatography, MS (ESI) m/z 488.2 [M+H]$^+$.

To a solution of 5-chloro-2-iodo-N-isopropyl-N-((4-(trifluoromethyl)cyclohexyl)methyl)benzamide (130 mg, 0.27 mmol) in benzene (3 mL) was added AIBN (25 mg, 27 μmol) followed by potassium tert-butoxide (91 mg, 0.81 mmol). The resulting solution was heated to 80° C. for 8 h. After cooling down to rt, water (10 mL) was added to the reaction mixture. The resulting solution was extracted with ethyl acetate (2×10 mL). The combined organic layers were washed with brine, dried over anhydrous Na$_2$SO$_4$, filtered and concentrated under reduced pressure. The resulting crude reaction mixture was purified by flash chromatography over silica gel (eluting with 15% EtOAc in hexanes) to afford 70 mg of 6-chloro-3,3-dimethyl-2-((4-(trifluoromethyl)cyclohexyl)methyl)isoindolin-1-one as a clear oil (70% yield). LC-MS t$_R$=1.83, 1.89 min in 2 min chromatography, MS (ESI) m/z 360.2 [M+H]$^+$.

To a solution of 6-chloro-3,3-dimethyl-2-((4-(trifluoromethyl)cyclohexyl)methyl)isoindolin-1-one (70 mg, 190 μmol) in dioxane/H$_2$O (2/0.2 mL) was added molybdenum hexacarbonyl (40 mg, 152 μmol) and 1,8-diazabicyclo[5.4.0]undec-7-ene (75 μL, 570 μmol) in a microwave tube. The mixture was degassed with N$_2$ for 5 min, at which point trans-Bis(acetato)bis[o-(di-o-tolylphosphino)benzyl]dipalladium(II) (18 mg, 19 μmol) and tri-tert-butylphosphonium tetrafluoroborate (22 mg, 38 μmol) were added. The tube was degassed with N$_2$ again for 10 min then heated in a CEM microwave reactor at 160° C. for 20 min. After cooling to rt, the mixture was diluted with H$_2$O (5 mL) and washed with EtOAc (5 mL). The aqueous phase was acidified with 1 N HCl solution to pH=3 and extracted with EtOAc (3×5 mL). The organic layer was washed with brine, dried over Na$_2$SO$_4$, and concentrated to afford crude 1,1-dimethyl-3-oxo-2-((4-(trifluoromethyl)cyclohexyl)methyl)isoindoline-5-carboxylic acid as a colorless oil. This material was used for the next step without further purification.

To a solution of 1,1-dimethyl-3-oxo-2-((4-(trifluoromethyl)cyclohexyl)methyl)isoindoline-5-carboxylic acid (10 mg, 27 μmol) in DMF (0.25 mL) was added (4-(ethylsulfonyl)phenyl)methanamine (7 mg, 35 μmol), HATU (16 mg, 41 μmol) and DIEA (12 μL, 68 μmol). The mixture was stirred at rt for 4 h. Ethyl acetate (3 mL) and water (3 mL) were added to the mixture. After partition, the aqueous layer was extracted with ethyl acetate (2×3 mL). The combined organic layers were washed with brine, dried over anhydrous Na$_2$SO$_4$, filtered and concentrated under reduced pressure. The solvent was removed in vacuo to give the crude product which was purified on Gilson-HPLC to afford N-(4-(ethylsulfonyl)benzyl)-1,1-dimethyl-3-oxo-2-((4-(trifluoromethyl)cyclohexyl)methyl)isoindoline-5-carboxamide (30). LC-MS t$_R$=1.52 min in 2 min chromatography, MS (ESI) m/z 551.4 [M+H]$^+$. $^1$H NMR (CD$_3$OD, 400 MHz): δ 9.18 (m, 1H), 7.91 (d, J=8.8 Hz, 2H), 7.85 (d, J=7.6 Hz, 1H), 7.70-7.62 (m, 3H), 7.58 (t, J=7.6 Hz, 1H), 4.91-4.89 (m, 1H), 4.80-4.77 (m, 1H), 4.70-4.66 (m, 2H), 3.52 (m, 1H), 3.40-3.35 (m, 1H), 3.21 (q, J=7.6 Hz, 2H), 2.20-2.18 (m, 1H), 1.97-1.68 (m, 7H), 1.59 (s, 6H), 1.30-1.27 (m, 1H), 1.21 (t, J=6.8 Hz, 3H).

Example 31

1-ethyl-N-(4-(ethylsulfonyl)benzyl)-1-methyl-3-oxo-2-((4-(trifluoromethyl)cyclohexyl)methyl)isoindoline-5-carboxamide (31)

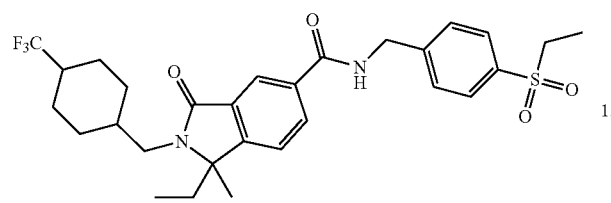

1-ethyl-N-(4-(ethylsulfonyl)benzyl)-1-methyl-3-oxo-2-((4-(trifluoromethyl)cyclohexyl)methyl)isoindoline-5-carboxamide (31) was prepared in accordance with Scheme 28, using 1,1-dimethyl-3-oxo-2-((4-(trifluoromethyl)cyclohexyl)methyl)isoindoline-5-carboxylic acid. LCMS 565.4 [M+H]+; 1H-NMR (CD3OD, 400 MHz): δ 9.18 (m, 1H), 7.91 (d, J=8.4 Hz, 2H), 7.86 (d, J=7.6 Hz, 1H), 7.70-7.61 (m, 3H), 7.59 (t, J=7.6 Hz, 1H), 4.91-4.89 (m, 1H), 4.83-4.81 (m, 1H), 4.70-4.60 (m, 2H), 3.65-3.60 (m, 1H), 3.31-3.27 (m, 1H), 3.21 (q, J=7.6 Hz, 2H), 2.39-2.32 (m, 1H), 2.20-2.12 (m, 2H), 2.01-1.90 (m, 4H), 1.71-1.68 (m, 2H), 1.59 (s, 3H), 1.55 (m, 2H), 1.16 (t, J=6.8 Hz, 3H), 0.28 (m, 3H).

Examples 32a and 32b (S)—N-((5-(ethylsulfonyl)pyridin-2-yl)methyl)-1-isopropyl-2-((2-(trifluoromethyl)-1,3-dioxan-5-yl)methyl)isoindoline-5-carboxamide (32a and 32b)

32a

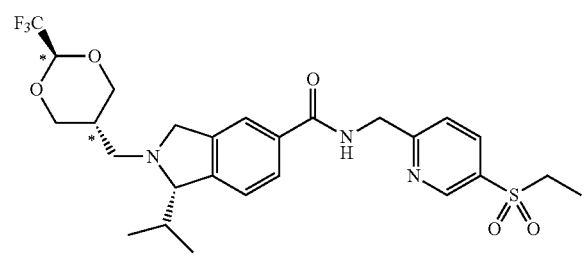

32b

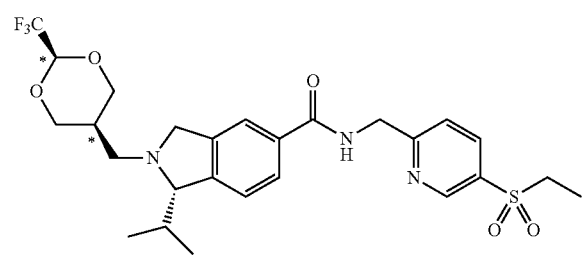

Scheme 29.

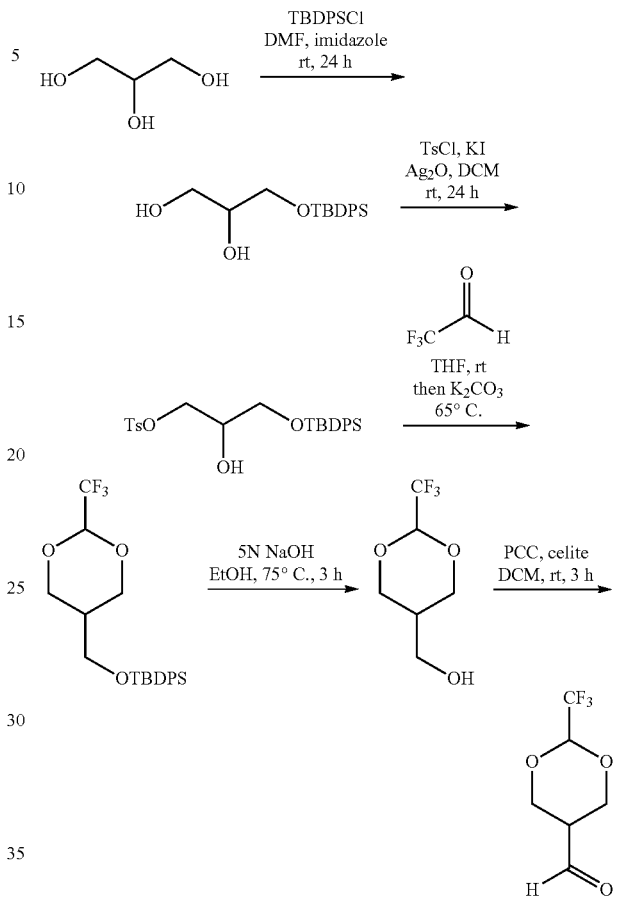

To a solution of propane-1,2,3-triol (1.0 g, 9.43 mmol) and imidazole (565 mg, 8.31 mmol) in dry DMF (7 mL) was added TBDPSCl (1 mL, 3.86 mmol) at rt. The reaction was stirred for 24 h at rt. Water (10 mL) and EtOAc (30 mL) were added after 24 h. The water layer was separated and extracted twice with EtOAc (2×15 mL). The EtOAc layers were combined, dried using Na2SO4, and evaporated. The crude residue was purified by ISCO flash column chromatography (eluting with a gradient of 0% to 50% EtOAc in hexanes) to afford 3-((tert-butyldiphenylsilyl)oxy)propane-1,2-diol (950 mg, 72%) as a clear colorless oil. LC-MS $t_R$=1.728 min in 2 min chromatography, MS (ESI) m/z 345.36 [M+H]+.

To a suspension of 3-((tert-butyldiphenylsilyl)oxy)propane-1,2-diol (500 mg, 1.45 mmol), KI (60 mg, 0.36 mmol) and Ag2O (673 mg, 2.90 mmol) in DCM (6 mL) was added TsCl (277 mg, 1.45 mmol) at rt. The reaction was stirred at rt for 24 h. Filtration through Celite® and evaporation gave the crude product. Purification using ISCO flash column chromatography (eluting with a gradient of 0% to 50% EtOAc in hexanes) gave 3-((tert-butyldiphenylsilyl)oxy)-2-hydroxypropyl 4-methylbenzenesulfonate (560 mg, 78%). LC-MS $t_R$=2.089 min in 2 min chromatography, MS (ESI) m/z 499.39 [M+H]+.

Gaseous 2,2,2-trifluoroacetaldehyde was bubbled into a solution of 3-((tert-butyldiphenylsilyl)oxy)-2-hydroxypropyl 4-methylbenzenesulfonate (192 mg, 0.39 mmol) in dry THF (6 mL) at rt. The gaseous 2,2,2-trifluoroacetaldehyde was generated in a separated flask by the dropwise addition of 2,2,2-trifluoro-1-methoxyethan-1-ol (1 mL) into polyphosphoric acid at 90° C. One end of a Teflon® tubing was placed inside of the sealed flask, while the other end was placed into the solution of 3-((tert-butyldiphenylsilyl)oxy)-2-hydroxypropyl 4-methylbenzenesulfonate in THF at rt. When the bubbling subsided in the reaction, the mixture was stirred at rt for 15 h, at which point LCMS analysis showed complete consumption of the 3-((tert-butyldiphenylsilyl)oxy)-2-hydroxypropyl 4-methylbenzenesulfonate and formation of 3-((tert-butyldiphenylsilyl)oxy)-2-((2,2,2-trifluoro-1-hydroxyethoxy)methyl)propyl 4-methylbenzenesulfonate (structure not shown; LC-MS $t_R$=2.170 min in 2 min chromatography, MS (ESI) m/z 597.45 $[M+H]^+$). Solid $K_2CO_3$ was then added and the reaction was stirred at 70° C. for 6 h, at which point LCMS analysis showed consumption of the 3-((tert-butyldiphenylsilyl)oxy)-2-((2,2,2-trifluoro-1-hydroxyethoxy)methyl)propyl 4-methylbenzenesulfonate and formation of a new, less polar product, which was observed on the LCMS from the UV-vis spectrum (wavelength=220 nM), but showed no ionization peak.

Water (10 mL) and EtOAc (20 mL) were added after cooling the reaction to rt. The water layer was extracted with EtOAc (10 mL). The EtOAc layers were combined and washed with sat. $NH_4Cl$ (5 mL), then sat. $NaHCO_3$ (5 mL). The EtOAc solution was then dried using $Na_2SO_4$ and evaporated to give crude tert-butyldiphenyl((2-(trifluoromethyl)-1,3-dioxan-5-yl)methoxy)silane (190 mg), which was used directly for the next step without purification. LC-MS $t_R$=2.214 min in 2 min chromatography, no ionization peak (only UV-vis peak was observed at 220 nM).

To a solution of tert-butyldiphenyl((2-(trifluoromethyl)-1,3-dioxan-5-yl)methoxy)silane (crude 190 mg from previous step) in EtOH (2.5 mL) was added 5N NaOH (0.50 mL). The reaction was heated to 75° C. for 3 h. The EtOH was removed by rotovap and DCM (10 mL) was added, followed by 1N HCl (3 mL). The aqueous layer was separated and extracted using DCM (2×5 mL). The DCM layers were combined, dried using $Na_2SO_4$, and evaporated to give crude (2-(trifluoromethyl)-1,3-dioxan-5-yl)methanol containing TBDPS-OH, from LCMS analysis. This material was used directly for the next step without further purification. LC-MS $t_R$=1.168 min in 2 min chromatography, MS (ESI) m/z 187.13 $[M+H]^+$.

To a solution of crude (2-(trifluoromethyl)-1,3-dioxan-5-yl)methanol (23 mg, from previous step) in DCM (2 mL) was added a solid mixture of PCC (53 mg, 0.25 mmol) and Celite® (50 mg). The suspension was stirred at rt for 3 h. $Et_2O$ (5 mL) was added to the mixture at rt and stirring continued for 30 min. The suspension was then filtered through a pad of Celite® and evaporated to give crude 2-(trifluoromethyl)-1,3-dioxane-5-carbaldehyde, which was used for the next step without purification. $^{19}F$ NMR showed a 4:1 mixture of acetal isomers from the 2 doublet signals of the $CF_3$ group. LC-MS (no ionizable or UV-vis peak detected on the LCMS). $^{19}F$ NMR ($CDCl_3$, 400 MHz): δ −82.90 ppm (major isomer), −82.37 ppm (minor isomer).

Isomers 1 and 2 (32a and 32b) were prepared according to General Procedure A, using (S)—N-((5-(ethylsulfonyl)pyridin-2-yl)methyl)-1-isopropylisoindoline-5-carboxamide and 2-(trifluoromethyl)-1,3-dioxane-5-carbaldehyde (4:1 mixture of acetal isomers) as the starting materials. The crude material was separated by SFC (IC-3) to give two crude products, which were purified by HCl preparative HPLC separation, then lyophilized directly to Isomer 2 (32b) HCl salt (major isomer from 4:1 $CF_3$-acetal mixture) and isomer 1 (32a) HCl salt (minor isomer from 4:1 $CF_3$-acetal mixture) as white solids. Based on the biological activity of the two isomers it was determined that isomer 2 was the major product from the 4:1 mixture of 2-(trifluoromethyl)-1,3-dioxane-5-carbaldehyde.

Isomer 2 (32b) HCl salt (major isomer from 4:1 acetal mixture). LC-MS $t_R$=0.632 min in 5-95AB_1.5 min chromatography (Welch MK RP-18e 25-2 mm), MS (ESI) m/z 556.1 $[M+H]^+$. $^1H$ NMR ($CD_3OD$ 400 MHz): δ 9.08 (d, J=2.0 Hz, 1H), 8.47 (dd, J=2.4, 8.4 Hz, 1H), 8.04 (d, J=8.4 Hz, 1H), 8.02 (s, 1H), 7.85 (d, J=8.0 Hz, 1H), 7.60 (d, J=8.4 Hz, 1H), 5.18 (d, J=2.8 Hz, 1H), 5.15 (s, 1H), 5.09 (d, J=4.8 Hz, 1H), 4.89 (s, 2H), 4.80-4.75 (m, 1H), 4.39-4.23 (m, 4H), 3.80 (d, J=6.0 Hz, 2H), 3.36 (q, J=7.6 Hz, 2H), 2.50 (bs, 1H), 2.32 (bs, 1H), 1.29 (t, J=7.6 Hz, 3H), 1.23 (d, J=6.8 Hz, 3H), 1.08 (d, J=6.8 Hz, 3H). Isomer 1 (32a) HCl salt (minor isomer from 4:1 acetal mixture). LC-MS $t_R$=0.638 min in 5-95AB_1.5 min chromatography (Welch MK RP-18e 25-2 mm), MS (ESI) m/z 556.1 $[M+H]^+$. $^1H$ NMR ($CD_3OD$ 400 MHz): δ 9.02 (d, J=2.0 Hz, 1H), 8.33 (dd, J=2.4, 8.4 Hz, 1H), 8.03 (d, J=8.4 Hz, 1H), 8.00 (s, 1H), 7.72 (d, J=8.0 Hz, 1H), 7.60 (d, J=8.4 Hz, 1H), 5.15-5.01 (m, 3H), 4.84 (s, 2H), 4.68-4.64 (m, 1H), 4.48-4.40 (m, 2H), 3.79-3.68 (m, 2H), 3.36 (q, J=7.6 Hz, 2H), 3.29-3.22 (m, 2H), 2.68 (bs, 1H), 2.47 (bs, 1H), 1.27 (t, J=7.6 Hz, 3H), 1.23 (d, J=6.8 Hz, 3H), 1.03 (d, J=6.8 Hz, 3H).

For the above example, it will be understood that the "*" indicates that although a single diastereomer was isolated, the absolute configuration about these positions was not fully characterized, however the relative stereochemistry at one of the designated positions to the other designated position is as shown. Accordingly, in each of compounds 32a and 32b, a single diastereomer was isolated and tested, but the absolute stereochemistry about the "*" is arbitrarily defined.

BIOLOGICAL ASSAYS

Radio-Ligand RORγ Binding Assay (Assay 1)

Compounds of the present invention were tested for ability to bind to RORγ in a cell-free competition assay with commercially available radio-ligand (RL), 25-hydroxy[26,27-$^3$H]-cholesterol (PerkinElmer, Cat. #NET674250UC), for a ligand binding site on a recombinant RORγ Ligand Binding Domain (LBD) protein expressed as a 6×His-Glutathione-S-Transferase (GST) fusion. The assay was performed in 96-well SPA plates (PerkinElmer, Cat. #1450-401) in 50 mM HEPES buffer, pH 7.4, containing 150 mM NaCl, 5 mM $MgCl_2$, 10% (v/v) glycerol, 2 mM CHAPS, 0.5 mM β-octylglucopyranoside and 5 mM DTT. Tested compounds were dissolved in DMSO, and semi-log (3.162×) serial dilutions of the compounds were prepared in the same solvent. Two μL of the DMSO solutions were mixed with 28 μL of 8.6 nM 25-hydroxy[26,27-$^3$H]-cholesterol and 50 μL of 24 nM RORγ LBD. The plate was shaken at 700 rpm for 20 min and incubated for 10 min at rt, after which 40 μL of poly-Lys YSi SPA beads (PerkinElmer, Cat. #RPNQ0010) were added to achieve 50 μg of the beads per well. The plate was incubated on an orbital shaker for 20 min and then for 10 min without agitation at rt. SPA signal for tritium beta radiation was registered on PerkinElmer Microbeta plate reader. Percent inhibition values were calculated based on the high signal obtained with DMSO control and the low signal observed with 10 μM standard RORγ inverse agonist T0901317 (SigmaAldrich, Cat. #T2320). The percent inhibition vs. concentration data were fit into a four-parameter model, and IC50 values were calculated from the fit as the concentrations corresponding to the inflection points on the dose-response curves. Inhibitory constants (Ki) were calculated using the following equation, where [RL] is the concentration in the assay and $K_D$ is a dissociation constant of 25-hydroxy[26,27-$^3$H]-cholesterol:

$$K_i = \frac{IC_{50}}{\left(1 + \frac{[RL]}{K_D}\right)}.$$

RORγt 5×RORE Assay in Jurkat Cells (Assay 2)

Compounds of the present invention were tested for RORγ inverse agonist activity in a cell-based, transcriptional activity assay. Secreted Nanoluc® luciferase was used as a reporter for transcriptional activity of the full-length RORγt in Jurkat cells (ATCC, Cat. #TIB-152). A reporter plasmid was constructed by inserting 5 repeats of the ROR Response Element (RORE) AAAGTAGGTCA (SEQ ID NO:1) into a commercially available promoterless plasmid pNL1.3[secNluc] (Promega, Cat. #N1021) using KpnI and HindIII restriction sites. The expression plasmid for RORγt was purchased (GeneCopoeia, Cat. #EX-T6988-M02). Jurkat cells (30 million cells) were transfected with 11 µg of EX-T6988-MO2 and 26 µg of the reporter plasmid in OptiMEM® media using Lipofectamine® LTX and Plus™ reagents (Life Technologies, Cat. #15338-100). After 5-6 hr incubation at 37° C./5% $CO_2$, the cells were collected, resuspended in phenol-red free RPMI media containing 10% (v/v) delipidated FBS (Hyclone, Cat. #SH30855.03) and dispensed into 96-well clear bottom tissue culture plates (CoStar, Cat. #3603), at 80,000 cells per well. Tested compounds were added to the cells in the same media (final concentration of DMSO was 0.1% (v/v)), and the plates were incubated at 37° C./5% $CO_2$ for 16-18 hrs. Luciferase activity in the conditioned supernatants was determined with NanoGlo® assay reagents (Promega, Cat.#N1130). Percent inhibition values were calculated based on the fully inhibited and non-inhibited (DMSO) controls, and the values were regressed against concentrations of the tested compounds to derive IC50 values using a four-parameter non-linear fitting model.

The results of assays 1 and 2 are shown in Table 4.

TABLE 4

| Compound Number | RORγ Binding Ki Range* (nM) (Assay 1) | RORγ t5X IC50 Range* (nM) (Assay 2) |
| --- | --- | --- |
| 1a | +++ | +++ |
| 1b | ++ | ++ |
| 2a | +++ | +++ |
| 2b | +++ | + |
| 2c | +++ | +++ |
| 2d | ++ | |
| 3a | +++ | +++ |
| 3b | +++ | ++ |
| 3c | +++ | +++ |
| 3d | +++ | + |
| 4a | +++ | +++ |
| 4b | ++ | |
| 5a | +++ | +++ |
| 5b | ++ | |
| 6a | +++ | +++ |
| 6b | +++ | ++ |
| 7a | +++ | +++ |
| 7b | + | |
| 8a | +++ | +++ |
| 8b | +++ | + |
| 9 | ++ | |
| 10a | +++ | +++ |
| 10b | ++ | |
| 11a | +++ | +++ |
| 11b | ++ | |
| 11c | +++ | |
| 11d | + | |
| 12a | +++ | +++ |
| 12b | +++ | + |
| 12c | +++ | ++ |
| 12d | +++ | +++ |
| 13a | +++ | ++ |
| 13b | +++ | +++ |
| 13c and 13d | ++ | |
| 14a | ++ | |
| 14b | +++ | + |
| 15a | ++ | |
| 15b | ++ | |
| 15c | +++ | +++ |
| 15d | +++ | +++ |
| 16a | +++ | +++ |
| 16b | +++ | +++ |
| 17 | +++ | +++ |
| 18 | ++ | |
| 19a | +++ | +++ |
| 19b | +++ | ++ |
| 20a | +++ | +++ |
| 20b | ++ | |
| 21a | +++ | +++ |
| 21b | +++ | ++ |
| 22 | +++ | +++ |
| 23a | +++ | +++ |
| 23b | +++ | ++ |
| 24a | +++ | +++ |
| 24b | +++ | + |
| 25a | +++ | +++ |
| 25b | ++ | + |
| 26a | +++ | +++ |
| 26b | +++ | ++ |
| 27 | +++ | ++ |
| 28 | +++ | +++ |
| 29 | +++ | +++ |
| 30 | ++ | |
| 31 | + | |
| 32a | +++ | +++ |
| 32b | +++ | + |

*+ means >1000 nM; ++ means 100 nM-1000 nM; +++ means <100 nM.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound of the Formula:

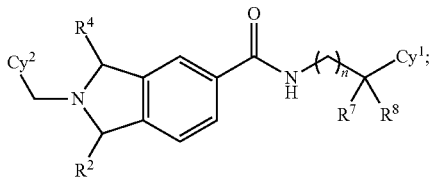

or a pharmaceutically acceptable salt thereof, wherein
$R^2$ is $(C_1-C_3)$alkyl;
$R^3$ is hydrogen, monocyclic cycloalkyl, monocyclic heterocyclyl, or $(C_1-C_6)$alkyl, wherein the $(C_1-C_6)$alkyl is optionally substituted with 1 to 2 groups independently selected from hydroxy, halo, and cyano;
$R^4$ is hydrogen, $(C_1-C_3)$alkyl, or =O;
X is —C(O)NH— or —NHC(O)—;
m is 0, 1, or 2;
n is 0, 1, 2, or 3;
$Cy^1$ is phenyl or pyridinyl, each of which is optionally substituted with 1 to 2 groups independently selected from $R^5$;
$Cy^2$ is cyclohexyl or phenyl, each of which is optionally substituted with 1 to 2 groups independently selected from $R^6$;
$R^5$ is $(C_1-C_3)$alkylsulfonyl;
$R^6$ is selected from $(C_1-C_3)$alkyl, halo$(C_1-C_3)$alkyl, hydroxy, and $(C_1-C_3)$alkoxy; and
$R^7$ and $R^8$ are each independently hydrogen, hydroxy, $(C_1-C_3)$alkyl, hydroxy$(C_1-C_3)$alkyl, $(C_1-C_3)$alkoxy$(C_1-C_3)$alkyl, aminocarbonyl-O$(C_1-C_3)$alkyl, hydroxycarbonyl$(C_1-C_3)$alkoxy$(C_1-C_3)$alkyl, $(C_1-C_3)$alkylcarbonylamino$(C_1-C_3)$alkyl, $(C_1-C_3)$alkoxycarbonylamino$(C_1-C_3)$alkyl, di$(C_1-C_3)$alkylamino$(C_1-C_3)$alkyl, di$(C_1-C_3)$alkylaminocarbonyl$(C_1-C_3)$alkyl, $(C_1-C_3)$alkylaminocarbonyl$(C_1-C_3)$alkyl, aminocarbonyl$(C_1-C_3)$alkyl, aminocarbonyl, mono$(C_1-C_3)$alkylamino, di$(C_1-C_3)$alkylamino, $CO_2H$, $(CH_2)_{1-3}COOH$, moncyclic heterocyclyl, $(C_1-C_3)$alkoxycarbonyl, halophenyl, halophenyl$(C_1-C_3)$alkyl, or quinolin-2(1H)one-4yl-methyl; or
$R^7$ and $R^8$, together with the carbon atom to which they are attached, form a 3- to 6-membered cycloalkyl or heterocyclyl.

2. The compound of claim 1, wherein the compound is of the Formula:

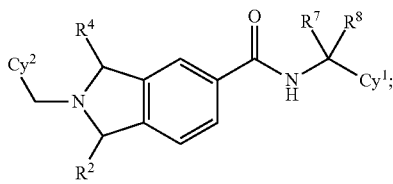

or a pharmaceutically acceptable salt thereof.

3. The compound of claim 2, wherein the compound is of the Formula:

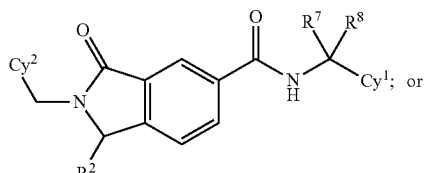

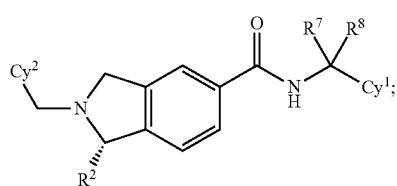

or a pharmaceutically acceptable salt thereof.

4. The compound of claim 3, wherein $R^7$ is hydrogen; and $R^8$ is hydrogen, hydroxy$(C_1-C_3)$alkyl, $(C_1-C_3)$alkoxy$(C_1-C_3)$alkyl, aminocarbonyl-O$(C_1-C_3)$alkyl, hydroxycarbonyl$(C_1-C_3)$alkoxy$(C_1-C_3)$alkyl, $(C_1-C_3)$alkylcarbonylamino$(C_1-C_3)$alkyl, $(C_1-C_3)$alkoxycarbonylamino$(C_1-C_3)$alkyl, di$(C_1-C_3)$alkylamino$(C_1-C_3)$alkyl, di$(C_1-C_3)$alkylaminocarbonyl$(C_1-C_3)$alkyl, $(C_1-C_3)$alkylaminocarbonyl$(C_1-C_3)$alkyl, aminocarbonyl$(C_1-C_3)$alkyl, or aminocarbonyl.

5. The compound of claim 4, wherein $R^7$ is hydrogen; and $R^8$ is hydrogen, —$CH_2OH$, —$(CH_2)_2OH$, —$CH_2OCH_3$, —$CH_2OC(O)NH_2$, —$CH_2OCH_2COOH$, —$CH_2NHC(O)CH_3$, —$CH_2NHC(O)OCH_3$, —$(CH_2)_2N(CH_3)_2$, —$CH_2C(O)N(CH_3)_2$, —$CH_2C(O)NHCH_3$, —$CH_2C(O)NH_2$, or $CONH_2$.

6. The compound of claim 5, wherein $R^7$ is hydrogen; and $R^8$ is hydrogen, —$CH_2OH$, —$(CH_2)_2OH$, or —$CH_2OCH_3$.

7. The compound of claim 6, wherein $R^5$ is —$SO_2CH_2CH_3$ or —$SO_2CH_3$.

8. The compound of claim 7, wherein $R^6$ is $CF_3$.

9. The compound of claim 8, wherein $R^2$ is ethyl or isopropyl.

10. A compound selected from:

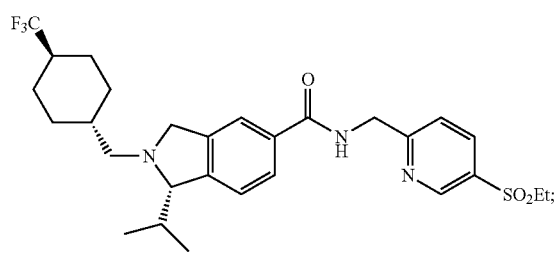

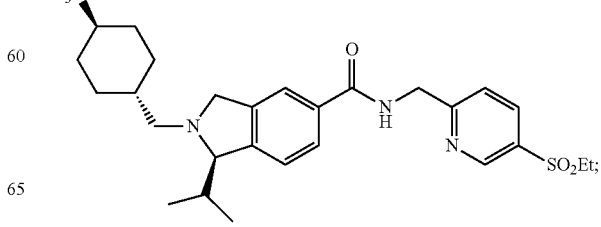

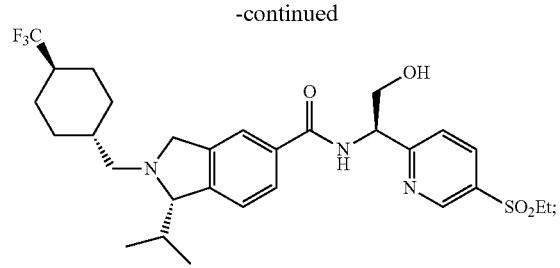
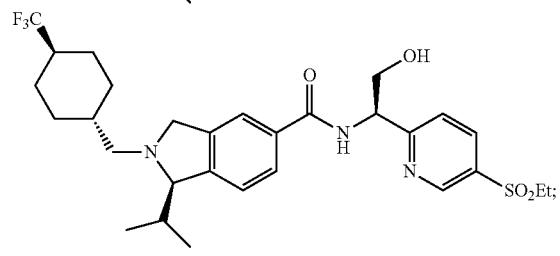
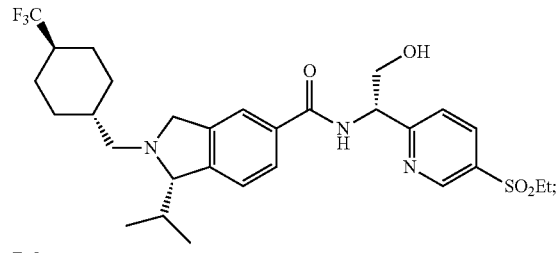
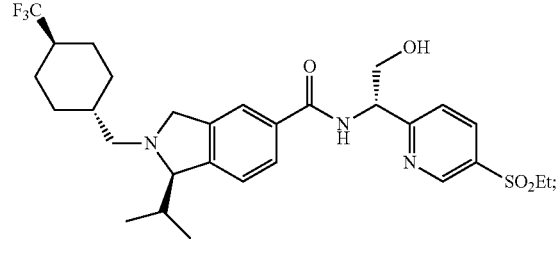
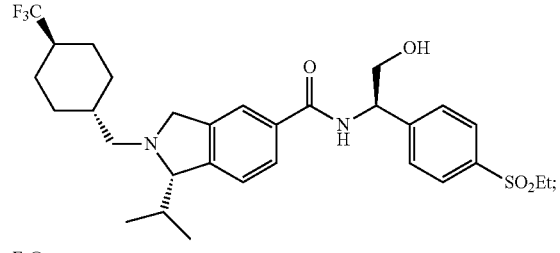
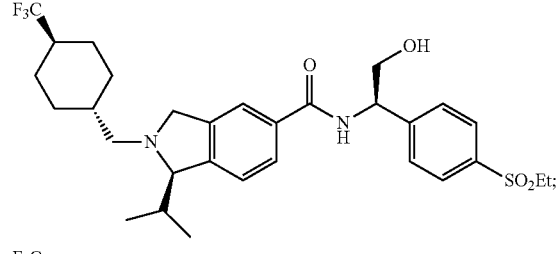
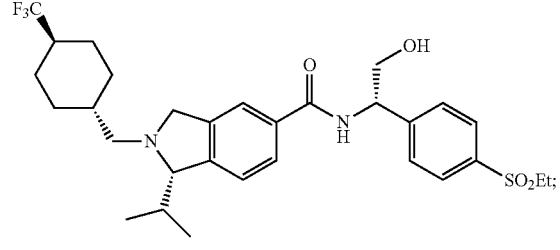
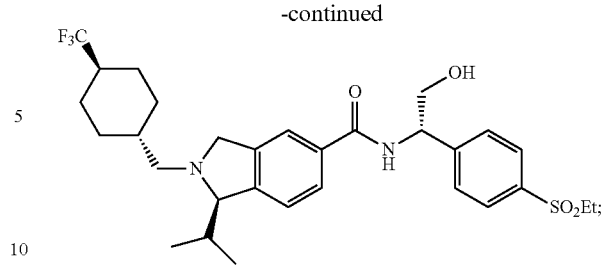
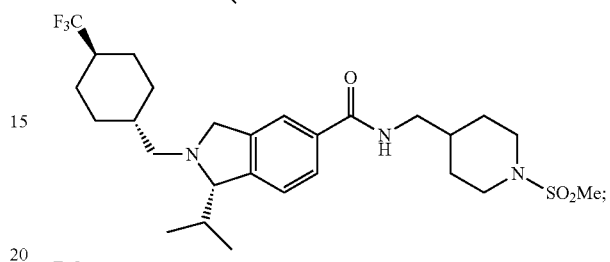
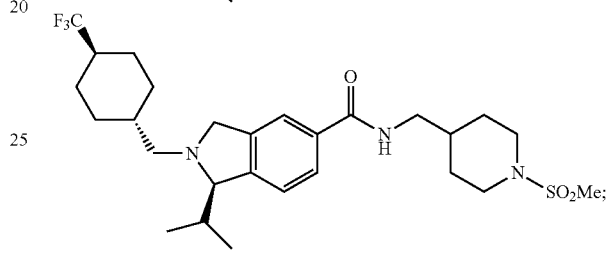
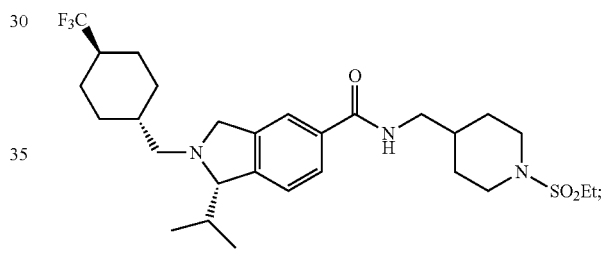
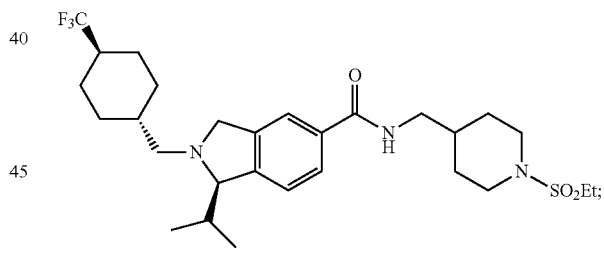
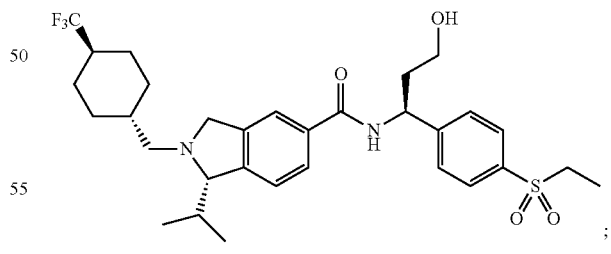
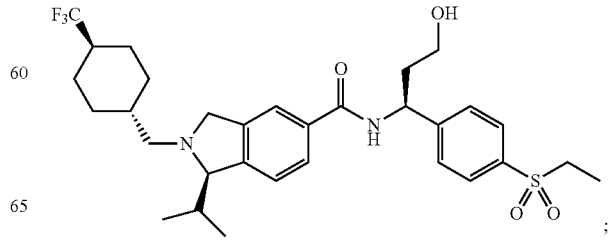

111
-continued
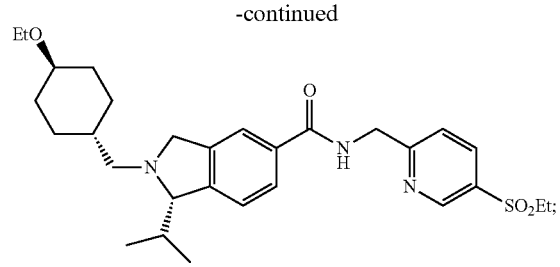
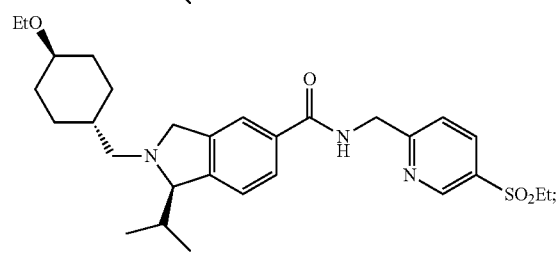
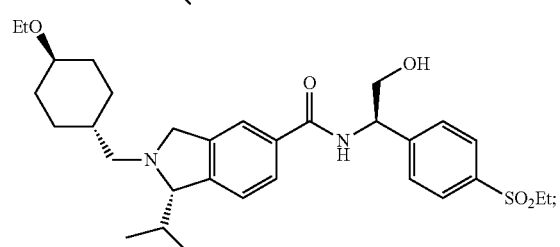
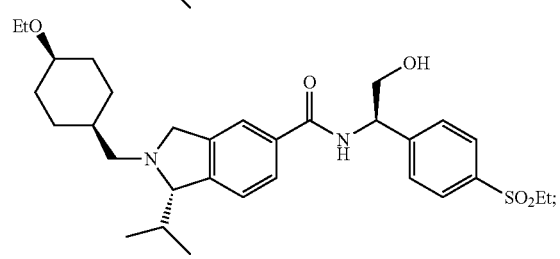
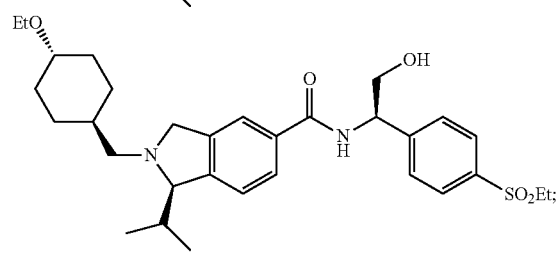
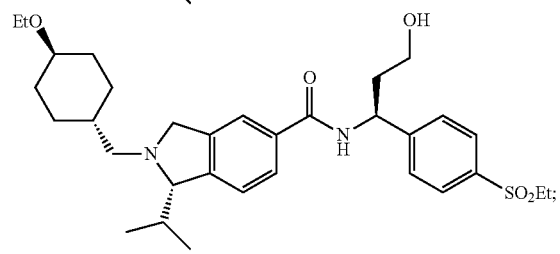
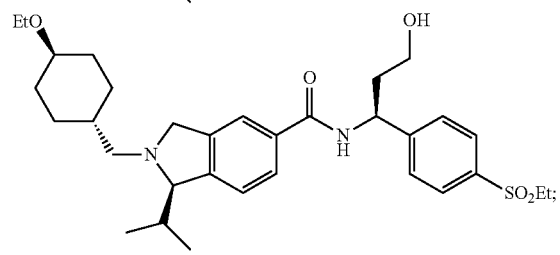
112
-continued
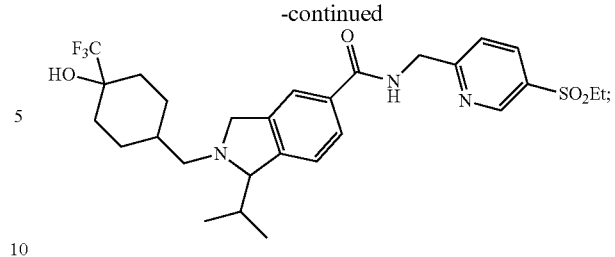
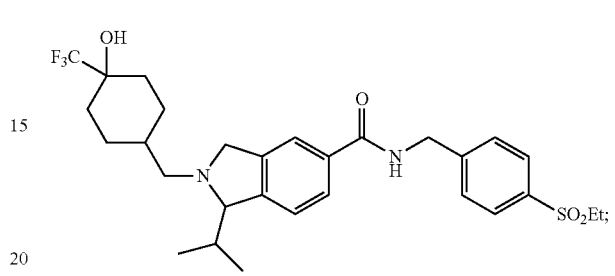
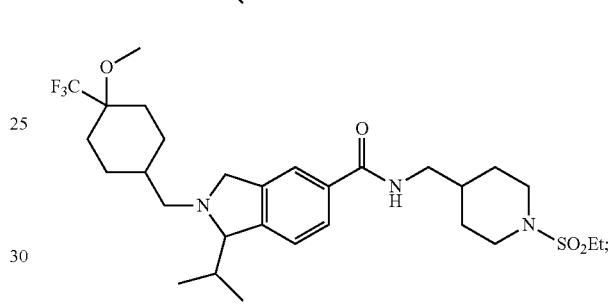
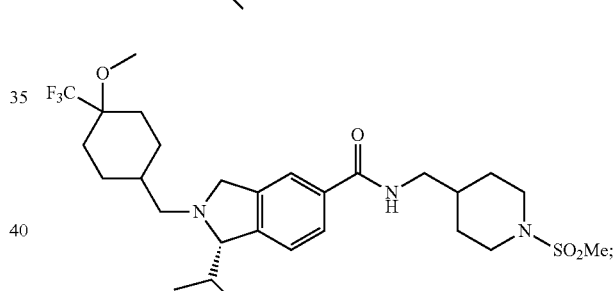
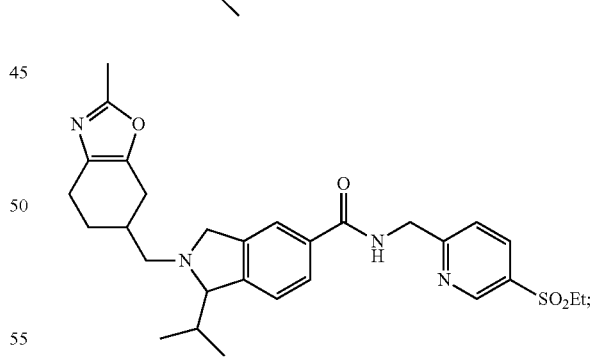
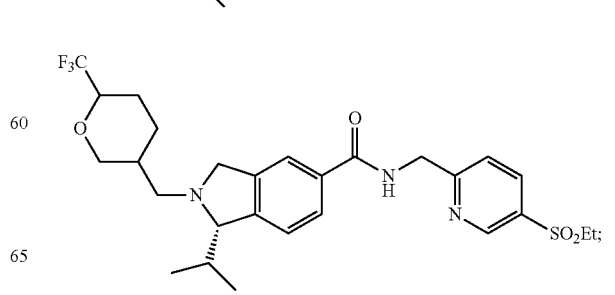

113
-continued
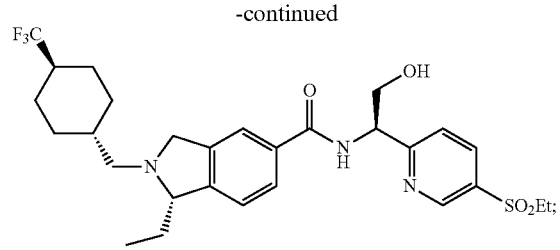
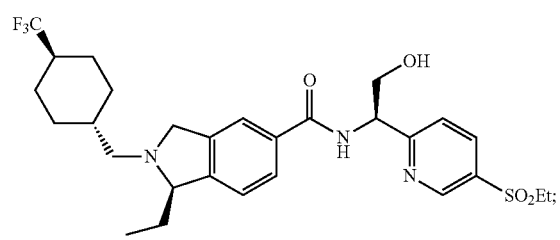
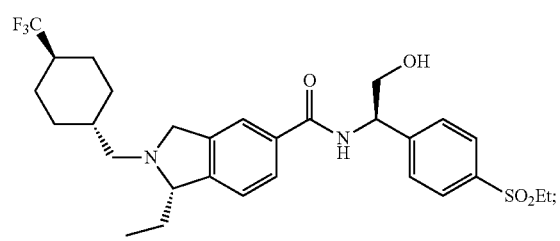
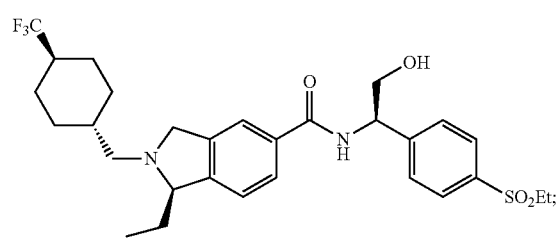
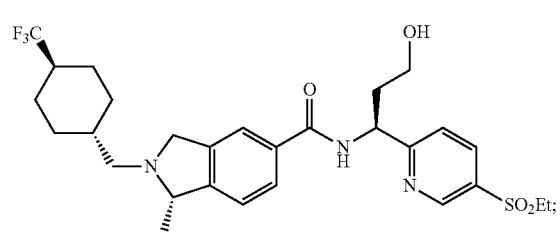
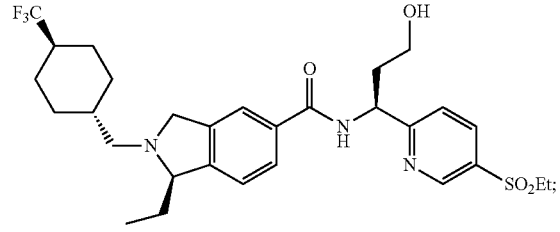
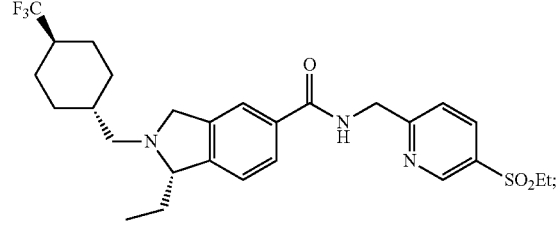
114
-continued
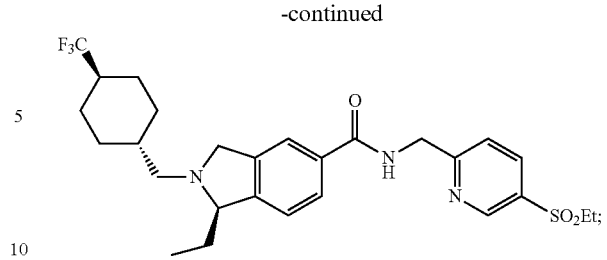
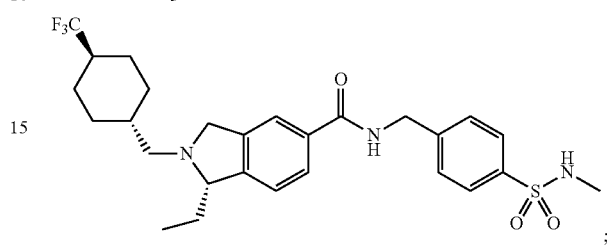
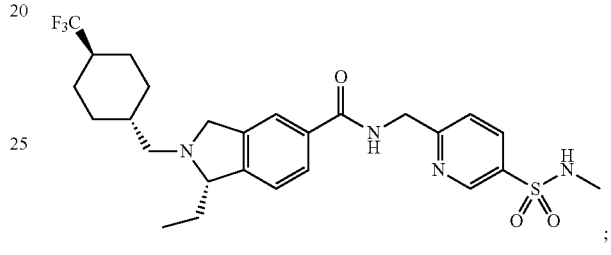
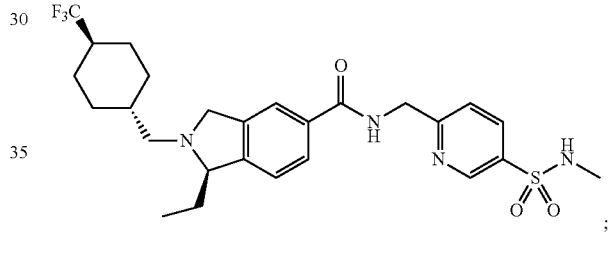
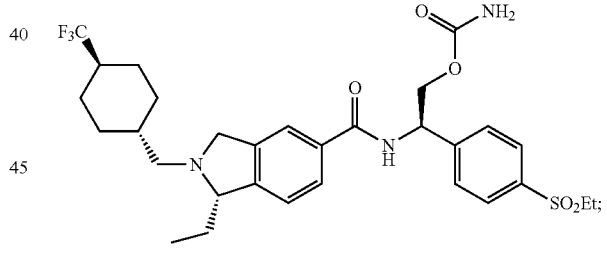
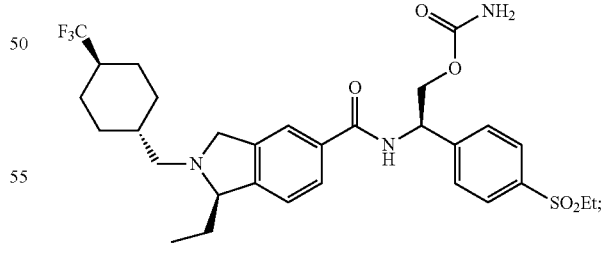
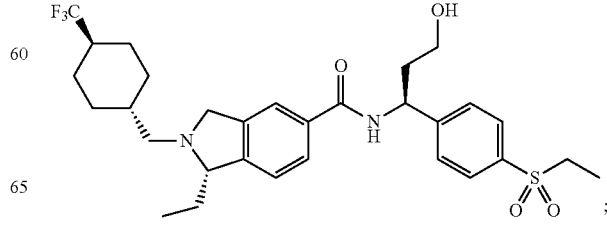

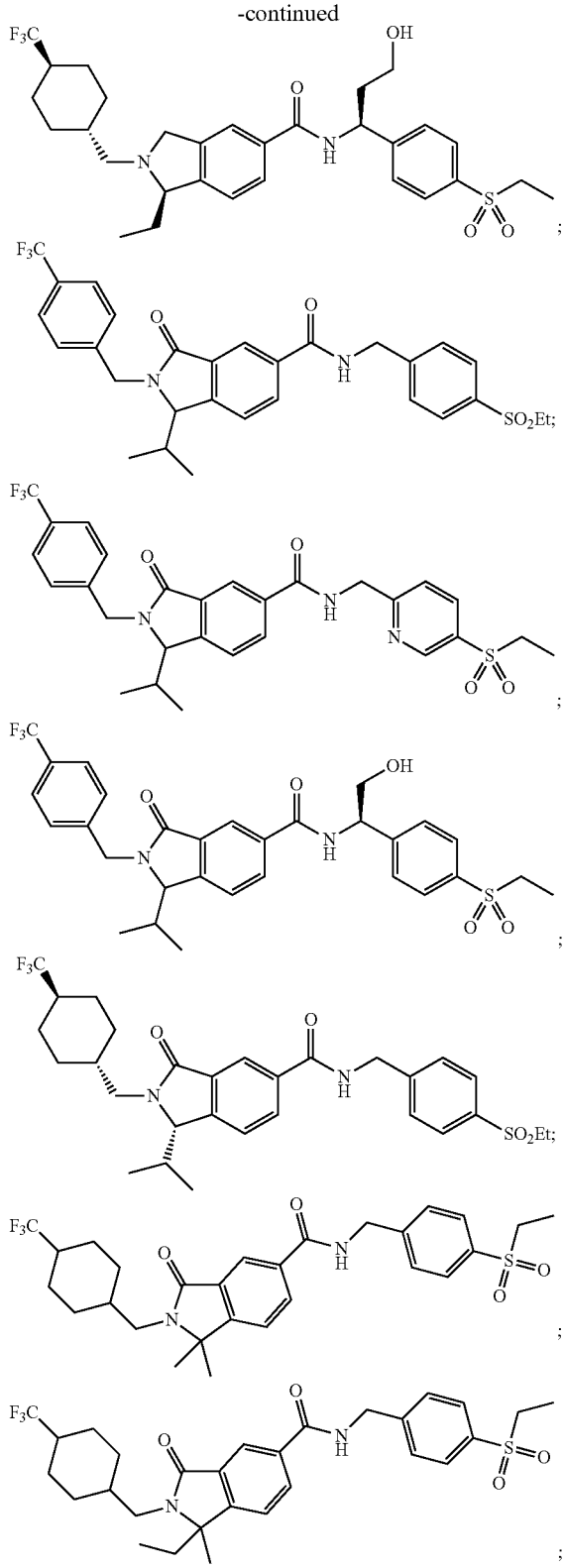

or a pharmaceutically acceptable salt thereof.

11. A pharmaceutical composition comprising a compound of claim 1, or a pharmaceutically acceptable salt thereof; and a pharmaceutically acceptable carrier.

12. A method of treating one or more diseases or disorders selected from asthma, chronic obstructive pulmonary disease (COPD), allergic rhinitis, atopic dermatitis, contact dermatitis, acne, urticaria, cystic fibrosis, allograft rejection, multiple sclerosis, scleroderma, arthritis, rheumatoid arthritis, juvenile rheumatoid arthritis, osteoarthritis, ankylosing spondylitis, systemic lupus erythematosus (SLE), psoriasis, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, obesity, hepatosteatosis, adipose tissue-associated inflammation, insulin resistance, type II diabetes, neuromyelitis optica, myasthenia gravis, dry eye, uveitis, Guillain-Barré syndrome, psoriasis, psoriatic arthritis (PsA), steroid resistant asthma, Graves' disease, scleritis, major depression, seasonal affective disorder, bipolar disorder, autism, epilepsy, Alzheimer's, endometriosis, obstructive sleep apnea syndrome (OSAS), Behçet's disease, dermatomyositis, polymyocitis, graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer in a subject, comprising administering to the subject a therapeutically effective amount of a compound according to claim 1, or a pharmaceutically acceptable salt thereof.

* * * * *